US008865419B2

(12) United States Patent (10) Patent No.: US 8,865,419 B2
Corrales et al. (45) Date of Patent: Oct. 21, 2014

(54) METHOD FOR THE SCREENING OF CONSERVED SECRETED PROTEINS

(75) Inventors: Rosa Milagros Corrales, Montpellier (FR); Françoise Mathieu-Daude, Saint Clement de Riviere (FR); Denis Sereno, Poussan (FR)

(73) Assignee: Institut de Recherche pour le Developpement (I.R.D.), Marseille (FR)

( * ) Notice: Subject to any disclaimer, the term of this patent is extended or adjusted under 35 U.S.C. 154(b) by 749 days.

(21) Appl. No.: 13/002,446

(22) PCT Filed: Jul. 3, 2009

(86) PCT No.: PCT/EP2009/058443
§ 371 (c)(1),
(2), (4) Date: Mar. 24, 2011

(87) PCT Pub. No.: WO2010/000849
PCT Pub. Date: Jan. 7, 2010

(65) Prior Publication Data
US 2011/0165597 A1    Jul. 7, 2011

(30) Foreign Application Priority Data
Jul. 4, 2008    (FR) .................. 08 290657

(51) Int. Cl.
*G01N 33/569* (2006.01)
*G01N 33/53* (2006.01)
*C07K 14/44* (2006.01)
*A61K 39/00* (2006.01)

(52) U.S. Cl.
CPC .......... *G01N 33/56905* (2013.01); *A61K 39/00* (2013.01); *C07K 14/44* (2013.01)
USPC .............................. 435/7.22; 435/7.2; 435/7.9

(58) Field of Classification Search
None
See application file for complete search history.

(56) References Cited

U.S. PATENT DOCUMENTS 5,916,572 A    6/1999  Reed et al.

FOREIGN PATENT DOCUMENTS

| WO | 9951264 A2 | 10/1999 |
| WO | 0219960 A2 | 3/2002 |
| WO | 2006108720 A | 10/2006 |

OTHER PUBLICATIONS

El-Sayed et al Science 309:409-415(2005).*
Bowie et al (Science, 1990, 247:1306-1310).*
Stolf et al Infect. Immun. 1983, 39(3): 1175-1179 abstract.*
Database UniProt [Online]—EMBL-EBI; El-Sayed Najib M et al: "Putative uncharacterized protein", May 20, 2008, XP002549121.
Database UniProt [Online] EMBL-EBI; Ivens et al: "Putative uncharacterized protein", Jun. 10, 2008, XP002549122.
Database UniProt [Online] EMBL-EBI; Peacock et al: "Putative uncharacterized protein", May 20, 2008, XP002549123.
Database UniProt [Online]; EMBL-EBI; Ghedin et al: "Putative uncharacterized protein", Jun. 10, 2008, XP002549124.
Database Genbank [Online]; Ivens et al. "*Leishmania major* strain Friedlin chromosome 29, complete sequence", Sep. 23, 2005, XP002549125.
Database Genbank [Online] ; Peacock et al. "*Leishmania infantum* chromosome 29", Jun. 28, 2007, XP002549126.
Database Genbank [Online]; Ghedin et al: "Trypasoma brucei chromosome 3 clone RPCI-28C22, complete sequence", Apr. 2, 2005, XP002549127.
Database UniProt [Online] EMBL-EBI; El-Sayed et al.: "Putative uncharacterized protein", May 20, 2008, XP002559237.
Database UniProt [Online] EMBL-EBI; Ivens et al.: "Putative uncharacterized protein", Jun. 10, 2008, XP002559238.
Database UniProt [Online] EMBL-EBI, Peacock et al.: "Putative uncharacterized protei " May 20, 2008, XP002559239.
Database UniProt [Online] EMBL-EBI. Ghedin et al.: "Putative uncharacterized protein", Jun. 10, 2008, XP002559240.
Database UniProt [Online] EMBL-EBI; Hamlin et al.: "Putative uncharacterized protein", May 20, 2008, XP002559241.
Database UniProt [Online] EMBL~EBI; Ivens et. al.: "Putative uncharacterized protein", Jun. 10, 2006, XP002559242.
Database Genbank [Online] NLM-NIH; Ivens et al.: "*Leishmania major* strain Friedlin", Dec. 1, 2005, XP002559243.
Database Genbank [Online] NLM-NIH; Peacock et al.: "*Leishmania infantum* chromosome 9", Jun. 28, 2007, XP002559244.
Database Genbank [Online] NLM-NIH; Ghedin et al.: "*Trypanosoma brucei* chromosome 8 clone RPCI93-30KI", Apr. 7, 2005, XP002559245.
Database Genbank ;[Online] NLM-NIH; Hamlin et al.: "*Trypanosoma brucei* chromosome 11", Jul. 14, 2005, XP002559246.
Chenik Met al: "Approaches for the identification of potential excreted/secreted proteins of *Leishmania major* parasites", Parasitology Apr. 2006, Apr. 2006; pp. 493-509. vol. 132. No. Pt 4, XP008097898.
Bhatia Vandanajay et al: "Utility of the *Trypanosoma cruzi* sequence database for identification of potential vaccine candidates by in silico and in vitro screening." Infection and Immunity Nov. 2004, pp. 6245-6254, vol, 72, No. 11, XP002549128.
Silverman J Maxwell et al: "Proteomic analysis of the secretome of *Leishmania donovani*", Genome Biology, Feb. 18, 2008, p. R35, vol. 9, No. 2, Biomed Central Ltd., London, GB XP021041579.
International Search Report, Dated Dec. 30, 2009, in PCT/EP2009/058443.
Van Ooij Christiaan et al: "The malaria secretome: from algorithms to essential function in blood stage infection", PLOS Pathogens, Jun. 2008, p. e1000084, vol. 4, No. 6, XP002501660.
Emanuelsson Olof et al: "Locating proteins in the cell using TargetP, SignalP and related tools" Nature Protocols, 2007, pp. 953-971, vol. 2, No. 4, XP008097990.
European Search Report; dated Oct. 30, 2008, in EP 08 29 0657.

* cited by examiner

*Primary Examiner* — Padma V Baskar
(74) *Attorney, Agent, or Firm* — Young & Thompson

(57) ABSTRACT

Conserved polypeptides from protozoan parasitic species which are secreted through the endoplasmic reticulum/Golgi dependent secretory pathway, their identification and their use.

1 Claim, 12 Drawing Sheets

FIGURE 1

Figure 4:
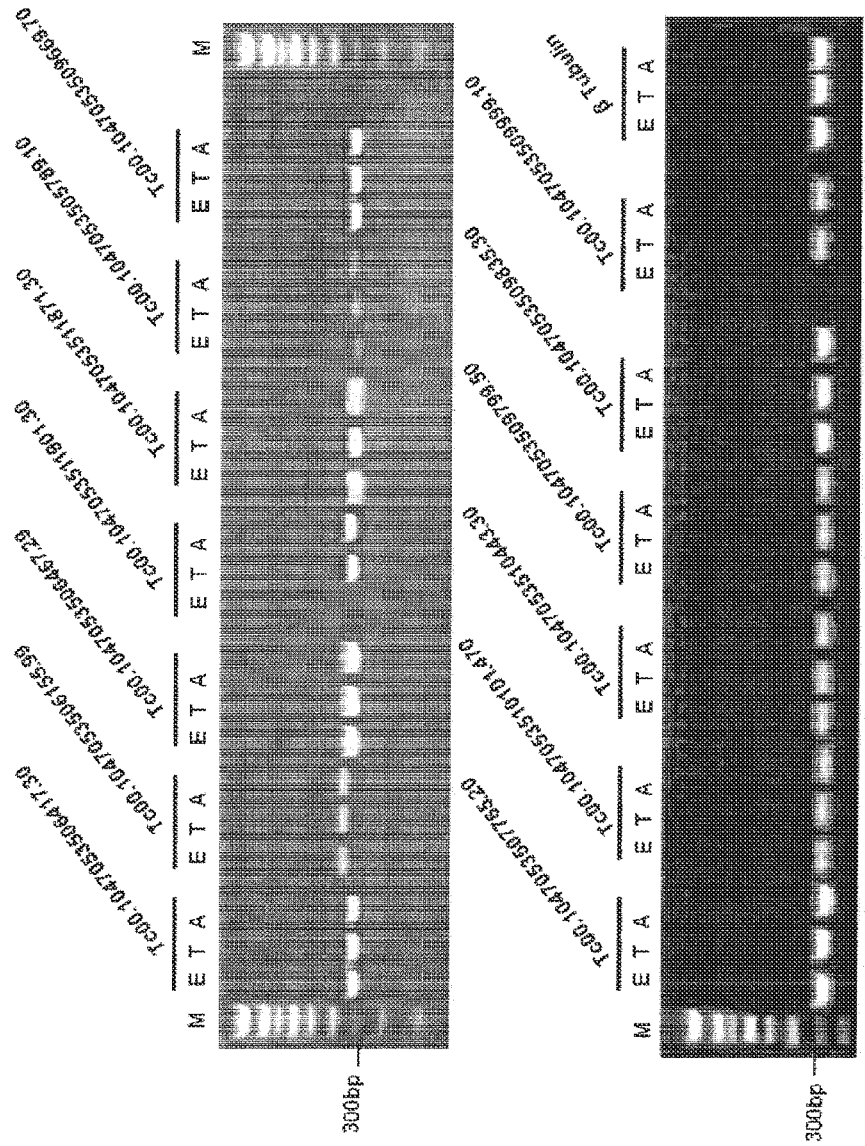

*T. cruzi* genes selected by *in silico* analysis

| *T. cruzi* GeneDB Accession No. | Orthologous Accession N° | | | P value | | Signal Peptide Sequence |
|---|---|---|---|---|---|---|
| | *L. major* | *L. infantum* | *T. brucei* | SPP | CSP | |
| Tc00.1047053506417.30 SEQ ID NO 1 | LmjF22.0225 SEQ ID NO 3 | LinJ23.0260 SEQ ID NO 5 | Tb927.8.2180 SEQ ID NO 7 | 0.937 | 0.917 | MISLAEVCLCCPAVRGV SEQ ID NO 111 |
| Tc00.1047053506155.99 SEQ ID NO 105 | LmjF36.5220 SEQ ID NO 105 | LinJ36.5780 SEQ ID NO 107 | Tb11.01.2470 SEQ ID NO 109 | 0.934 | 0.962 | MRWIFLLAVLSVLKPTDAT SEQ ID NO 112 |
| Tc00.1047053506467.29 SEQ ID NO 9 | LmjF26.2000 SEQ ID NO 11 | LinJ26.1970 SEQ ID NO 13 | Tb09.160.1070 SEQ ID NO 15 | 0.811 | 0.7711 | MIVLNGISEEQKKLAVGAAAAFFSSAVIAA SEQ ID NO 113 |
| Tc00.1047053511901.30 SEQ ID NO 17 | LmjF24.2160 SEQ ID NO 19 | LinJ24.1550 SEQ ID NO 21 | Tb927.8.6080 SEQ ID NO 23 | 0.989 | 0.898 | MFPAQEFLRYSMKSILASSLAVAAGWAY SEQ ID NO 114 |
| Tc00.1047053511871.30 SEQ ID NO 25 | LmjF25.1010 SEQ ID NO 27 | LinJ25.1040 SEQ ID NO 29 | Tb927.3.950 SEQ ID NO 31 | 0.979 | 0.958 | MRRTLFCLSTLVKIGRGA SEQ ID NO 115 |
| Tc00.1047053505789.10 SEQ ID NO 93 | LmjF19.0540 SEQ ID NO 172 LmjF19.0570 SEQ ID NO 95 | LinJ19.0410 SEQ ID NO 97 | Tb927.8.6700 SEQ ID NO 99 Tb11.39.0005 SEQ ID NO 101 | 1.000 | 0.768 | MPSGKATALAAATLALLVVAPAVASAQ SEQ ID NO 116 |
| Tc00.1047053509669.70 SEQ ID NO 33 | LmjF29.1600 SEQ ID NO 35 | LinJ29.1910 SEQ ID NO 37 | Tb927.3.4190 SEQ ID NO 39 | 0.999 | 0.980 | MRTSSAVSFLLAVAAVLFSPFVADAF SEQ ID NO 117 |
| Tc00.1047053507765.20 SEQ ID NO 41 | LmjF11.0720 SEQ ID NO 43 | LinJ11.0730 SEQ ID NO 45 | Tb11.02.4400 SEQ ID NO 47 | 0.993 | 0.986 | MSAKASRRCNRLIVLFSSINGVTAW SEQ ID NO 118 |
| Tc00.1047053510101.470 SEQ ID NO 49 | LmjF11.0720 SEQ ID NO 51 | LinJ11.0730 SEQ ID NO 53 | Tb11.02.4400 SEQ ID NO 55 | 0.931 | 0.919 | MSVKASRRCNRLJVLFSSINDVTAW SEQ ID NO 119 |
| Tc00.1047053510443.30 SEQ ID NO 57 | LmjF30.3150 SEQ ID NO 59 | LinJ30.4200 SEQ ID NO 61 | Tb927.6.4500 SEQ ID NO 63 | 0.903 | 0.838 | MIHTARKKQFGLSALALFVLLLFLLVCIILGL SEQ ID NO 120 |
| Tc00.1047053509799.50 SEQ ID NO 65 | LmjF36.5570 SEQ ID NO 67 | LinJ36.6969 SEQ ID NO 69 | Tb10.6k15.1130 SEQ ID NO 71 | 0.981 | 0.931 | MKQKMRRKFCDVLFPLLVFLLTTMEPVTAE SEQ ID NO 121 |
| Tc00.1047053509835.30 SEQ ID NO 73 | LmjF19.0540 SEQ ID NO 172 LmjF19.0570 SEQ ID NO 75 | LinJ19.0410 SEQ ID NO 77 | Tb927.8.6700 SEQ ID NO 79 Tb11.39.0005 SEQ ID NO 81 | 0.866 | 0.803 | MYSCLSLRLLVGGGMGFASRRRAAMVLSLLVFLLVPCGVFSQ SEQ ID NO 122 |
| Tc00.1047053509999.10 SEQ ID NO 85 | LmjF29.1200 SEQ ID NO 87 | LinJ29.1440 SEQ ID NO 89 | Tb927.3.3820 SEQ ID NO 91 | 1.000 | 0.952 | MYVVLFVLLLSVLGVDAE SEQ ID NO 123 |

FIGURE 2

Primer design of the 13 *T. cruzi* putative secreted proteins conserved in trypanosomatids and *T. cruzi* Tubulin

| *T. cruzi* GeneDB Accession N° | Primer sequences | F/Rint and F/R product sizes (bp) | MW (kDa) |
|---|---|---|---|
| Tc00.1047053506417.30 SEQ ID NO 1 | F CATGAGCTT*ACTAGT*ATGTTGTCTCTCGGCAGAAGTGTGT (SEQ ID NO 124)<br>Rint ACGGTGCCAAAGGCGTGTA (SEQ ID NO 125)<br>R CACACGA*AGCTT*CAATGATGATGATGATGGGACCAAACCTAGCCATAAG (SEQ ID NO 126) | 311<br>705 | 25.7 |
| Tc00.1047053506155.99 SEQ ID NO 103 | F CTGGGG*AATTC*ATGGGGTGGATTTTTTGTTACTTGCC (SEQ ID NO 127)<br>Rint CCGATACGTCCACCACCCTC (SEQ ID NO 128)<br>R CGTCGG*AAGCTT*CTAGTGATGGTGGTGGTGATGGTGGTGACAAGTTCGTGGCATGTAATTG (SEQ ID NO 129) | 336<br>735 | 28.1 |
| Tc00.1047053506467.29 SEQ ID NO 9 | F ACACGG*ACTAGT*ATGATTGTATTGAATGGAATTTCTGAG (SEQ ID NO 130)<br>Rint CTAATAGTCCGAAGTCGTTGCG (SEQ ID NO 131)<br>R CTACACA*AGCTT*TAGTGATGGTGATGGCGTCGCCTCCACACCGTGC (SEQ ID NO 132) | 309<br>1065 | 39.7 |
| Tc00.1047053511901.30 SEQ ID NO 17 | F CTGATAGGC*ACTAGT*ATGTTTCCGGCGCAGGAATTCCT (SEQ ID NO 133)<br>Rint CCCCTTTCAGGTGACCATTACAAGAG (SEQ ID NO 134)<br>R GCCGTC*AAGCTT*TTTAGTCGTGGTCGTGGTGATGCTCCGCTCCCAACTTCAAACGA (SEQ ID NO 135) | 316<br>1041 | 39.8 |
| Tc00.1047053511871.30 SEQ ID NO 25 | F CTGATAGGC*ACTAGT*ATGCGTCCACTTTATTTGTCTG (SEQ ID NO 136)<br>Rint CTCTCCAACTCGTACGGCGA (SEQ ID NO 137)<br>R CTGCAGGC*AAGCTT*CTAATGGTGGTGATGGTGATGTATGATACCGGCATCAAGTCCC (SEQ ID NO 138) | 305<br>1269 | 47.0 |
| Tc00.1047053505789.10 SEQ ID NO 93 | F CGGACTC*ACTAGT*ATGCCCTCTGGCAAAGCAAACTG (SEQ ID NO 139)<br>Rint TCACTGCTCCGCCCTGGTTTC (SEQ ID NO 140)<br>R CGCTCCCTCG*AGCTT*AGTGGTGATGGTGGTGATGGCAGCATTACCGACCCTGA (SEQ ID NO 141) | 308<br>1488 | 53.6 |

FIGURE 2 (cont'd)

| T. cruzi GeneDB Accession N° | Primer sequences | F/Rint and F/R product sizes (bp) | MW (kDa) |
|---|---|---|---|
| Tc00.1047053509669.70 SEQ ID NO 33 | F: GCTCAGCCAAGCTTATGCCACTTCTTCTGCCGTGT (SEQ ID NO 142)<br>Rint: ATCGGGAGTTTTGTGCAGGTTGAG (SEQ ID NO 143)<br>R: GTGGTCTTCTCGAGTTAGTGATGGTGGTGTGGTGATGGTGACTTTAATGCTCGCGTATA (SEQ ID NO 144) | 322<br>1944 | 73.1 |
| Tc00.1047053507765.20 SEQ ID NO 41 | F: CTGCCCAGTACTAGTATGTCTGCTAAAGCCTCACGGC (SEQ ID NO 145)<br>Rint: TCCAGGTAGTCACCCATTCCGTG (SEQ ID NO 146)<br>R: CTCAGCCAAGCTTTAATGATGATGATGATGGTGTCGCTCACAGTGCT (SEQ ID NO 147) | 318<br>1521 | 57.2 |
| Tc00.1047053510101.470 SEQ ID NO 49 | F: CTCGCTGACTAGTATGTCTGTTAAAGCCTCACGCG (SEQ ID NO 148)<br>Rint: CCATTCCGTGACCGCGTAGAC (SEQ ID NO 149)<br>R: CTCGGTAAGCTTTTAATGATGATGATGATGCGTCGTCGCCTCACAGTGCT (SEQ ID NO 150) | 302<br>1518 | 57.3 |
| Tc00.1047053510443.30 SEQ ID NO 57 | F: CTCGCTGGAATTCATCGGGTGGGTGATAGTTGTATTGC (SEQ ID NO 151)<br>Rint: CGCCAACAACGTAGTTGCCAAG (SEQ ID NO 152)<br>R: ACGGACCTCGAGTTAGTGATGGTGGTGATGCGTTGTTGAGTTTGGAGCGGGCG (SEQ ID NO 153) | 313<br>612 | 23.0 |
| Tc00.1047053509799.50 SEQ ID NO 65 | F: CGGGGACTAGTATGAAACAAAAAATGCGACGCAAATTG (SEQ ID NO 154)<br>Rint: GTGAGGATGGGGAACCAAAAGAGTC (SEQ ID NO 155)<br>R: CAGCCAAGCTTCTAGTGATGATGGTGATGATGATGGACATTCTTCTTGTAAAGTAG (SEQ ID NO 156) | 297<br>687 | 26.5 |
| Tc00.1047053509835.30 SEQ ID NO 73 | F: CGGGGACTAGTATGATTCATGTTGTCGCTGAGGC (SEQ ID NO 157)<br>Rint: GCAGCAACGGCAACAACAAAGAGC (SEQ ID NO 158)<br>R: CATGGCAAGCTTAGTGATGGTGGTGATGCTCCTCTCTGGTTTCCTTCG (SEQ ID NO 159) | 324<br>2031 | 71.6 |
| Tc00.1047053509999.10 SEQ ID NO 85 | F: CCGGCCACTAGTATGTACGTCGTGCTTTTTTCGTTT (SEQ ID NO 160)<br>Rint: CGCATATTCCGTCCGTCC (SEQ ID NO 161)<br>R: AGCAGTCCAAGCTTTAGTCATGGTGATGATGATGGCCGCACCAGGCTCCAGAA (SEQ ID NO 162) | 305<br>1227 | 46.6 |
| Tc00.1047053506363.40 SEQ ID NO 83 | F: GGGTGCCACTAGTATGCGTGAGATTGTGTCGTTCAG (SEQ ID NO 163)<br>Rint: GGGCGGAAGATCTGCCGTATG (SEQ ID NO 164)<br>R: AGCCGCTCAAGCTTTAGTGATGGTGGTGGTGATGGTACTGCTCCTCCTCGTCGAACT (SEQ ID NO 165) | 259<br>1329 | 49.6 |

FIGURE 3

Gene ID of *L. infantum* orthologous genes and primers used for cloning

| Gene ID | Primer sequences | F/R product sizes (bp) | MW (kDa) |
|---|---|---|---|
| LinJ19.0410 SEQ ID NO 77 | F CATGACCACTAGTATGGCC Expression analysis of potentially secreted proteins during the life cycle of *T. cruzi*

Protein expression in *L. infantum* episomally transfected promastigotes during the exponential phase of development

SEQUENCE LISTING

<160> NUMBER OF SEQ ID NOS: 173

<210> SEQ ID NO 1
<211> LENGTH: 705
<212> TYPE: DNA
<213> ORGANISM: Trypanosoma cruzi
<220> FEATURE:
<221> NAME/KEY: CDS
<222> LOCATION: (1)..(705)

<400> SEQUENCE: 1

```
atg ttg tct ctg gca gaa gtg tgt ttg tgt tgc cct gcc gtg cgt ggt      48
Met Leu Ser Leu Ala Glu Val Cys Leu Cys Cys Pro Ala Val Arg Gly
1               5                   10                  15 gtg ccc gag tcc act tcc tct ggc cgc cac aaa acc tgt tgc tct tcc      96
Val Pro Glu Ser Thr Ser Ser Gly Arg His Lys Thr Cys Cys Ser Ser
                20                  25                  30 acc atg gac ttt tct tgg gaa gca aag aag aag aag tgt ggg tgc tgg     144
Thr Met Asp Phe Ser Trp Glu Ala Lys Lys Lys Lys Cys Gly Cys Trp
            35                  40                  45 ggg aat tat agg cag gaa ggt ggc agc tac tca atg cgg cgg tgt ggc     192
Gly Asn Tyr Arg Gln Glu Gly Gly Ser Tyr Ser Met Arg Arg Cys Gly
        50                  55                  60 tgt gcc tcg gca att ttt tct ttg gaa gtt ggt gac atg atg gca ggt     240
Cys Ala Ser Ala Ile Phe Ser Leu Glu Val Gly Asp Met Met Ala Gly
65                  70                  75                  80 gga gcc gtg ggc aat gga gtg tcg tgg cga tca ttt gca cgt ggc cga     288
Gly Ala Val Gly Asn Gly Val Ser Trp Arg Ser Phe Ala Arg Gly Arg
                85                  90                  95 ccg tac acg cct ttg ggc acc gtt cag gac ttc acg gca tca ccg cat     336
Pro Tyr Thr Pro Leu Gly Thr Val Gln Asp Phe Thr Ala Ser Pro His
                100                 105                 110 cac ata cgt ctt gct gag atg cag cgc gaa ctg gac gaa atg agc ggt     384
His Ile Arg Leu Ala Glu Met Gln Arg Glu Leu Asp Glu Met Ser Gly
            115                 120                 125 cgt tca ccg acg cac ctc tac gag ggg cca act gtc acc act gcg cag     432
Arg Ser Pro Thr His Leu Tyr Glu Gly Pro Thr Val Thr Thr Ala Gln
        130                 135                 140 ggc cct cgg cct ctc ttc gag gct gac ttg cgg gat gat cct gca aat     480
Gly Pro Arg Pro Leu Phe Glu Ala Asp Leu Arg Asp Asp Pro Ala Asn
145                 150                 155                 160 gac aac atg ccg gag cac ttc gtt gcc gca cgt caa cgt ctg atg act     528
Asp Asn Met Pro Glu His Phe Val Ala Ala Arg Gln Arg Leu Met Thr
                165                 170                 175 ttg cag agt gac agt tac ggg gag tcc att cgc ggt gtt gtc tcc ccg     576
Leu Gln Ser Asp Ser Tyr Gly Glu Ser Ile Arg Gly Val Val Ser Pro
                180                 185                 190 ccc cca ccg ccg gat gcg aac gcc cct cga gca tat gag cag ccc cga     624
Pro Pro Pro Pro Asp Ala Asn Ala Pro Arg Ala Tyr Glu Gln Pro Arg
            195                 200                 205 gtg cag ctg ggc aat att tgg tgg acg gct atg aca tta ata ata gta     672
Val Gln Leu Gly Asn Ile Trp Trp Thr Ala Met Thr Leu Ile Ile Val
        210                 215                 220 tcg ttc ttt ctt atg gct agg ttt ggt cgc tag                         705
Ser Phe Phe Leu Met Ala Arg Phe Gly Arg
225                 230
```

<210> SEQ ID NO 2
<211> LENGTH: 234
<212> TYPE: PRT
<213> ORGANISM: Trypanosoma cruzi

<400> SEQUENCE: 2

```
Met Leu Ser Leu Ala Glu Val Cys Leu Cys Cys Pro Ala Val Arg Gly
1               5                   10                  15

Val Pro Glu Ser Thr Ser Ser Gly Arg His Lys Thr Cys Cys Ser Ser
            20                  25                  30

Thr Met Asp Phe Ser Trp Glu Ala Lys Lys Lys Cys Gly Cys Trp
        35                  40                  45

Gly Asn Tyr Arg Gln Glu Gly Gly Ser Tyr Ser Met Arg Arg Cys Gly
    50                  55                  60

Cys Ala Ser Ala Ile Phe Ser Leu Glu Val Gly Asp Met Met Ala Gly
65                  70                  75                  80

Gly Ala Val Gly Asn Gly Val Ser Trp Arg Ser Phe Ala Arg Gly Arg
                85                  90                  95

Pro Tyr Thr Pro Leu Gly Thr Val Gln Asp Phe Thr Ala Ser Pro His
            100                 105                 110

His Ile Arg Leu Ala Glu Met Gln Arg Glu Leu Asp Glu Met Ser Gly
        115                 120                 125

Arg Ser Pro Thr His Leu Tyr Glu Gly Pro Thr Val Thr Thr Ala Gln
    130                 135                 140

Gly Pro Arg Pro Leu Phe Glu Ala Asp Leu Arg Asp Asp Pro Ala Asn
145                 150                 155                 160

Asp Asn Met Pro Glu His Phe Val Ala Ala Arg Gln Arg Leu Met Thr
                165                 170                 175

Leu Gln Ser Asp Ser Tyr Gly Glu Ser Ile Arg Gly Val Val Ser Pro
            180                 185                 190

Pro Pro Pro Pro Asp Ala Asn Ala Pro Arg Ala Tyr Glu Gln Pro Arg
        195                 200                 205

Val Gln Leu Gly Asn Ile Trp Trp Thr Ala Met Thr Leu Ile Ile Val
    210                 215                 220

Ser Phe Phe Leu Met Ala Arg Phe Gly Arg
225                 230
```

<210> SEQ ID NO 3
<211> LENGTH: 666
<212> TYPE: DNA
<213> ORGANISM: Leishmania major
<220> FEATURE:
<221> NAME/KEY: CDS
<222> LOCATION: (1)..(666)

<400> SEQUENCE: 3

```
atg cgc caa gga gcc gcc agg gga tgc gcg tgt gta gcc gcg cac agc    48
Met Arg Gln Gly Ala Ala Arg Gly Cys Ala Cys Val Ala Ala His Ser
1               5                   10                  15 ggt ggt ctc tgc ggg tgc atc gcc agt gcc aac acg acc acc gct gtg    96
Gly Gly Leu Cys Gly Cys Ile Ala Ser Ala Asn Thr Thr Thr Ala Val
            20                  25                  30 cgc ggt tac aca cgc ggc atc ccc tac act ccc caa ggg acc att cag   144
Arg Gly Tyr Thr Arg Gly Ile Pro Tyr Thr Pro Gln Gly Thr Ile Gln
        35                  40                  45 gat tac acg tcc tct ccg cgg cac gta agg ttg gct gag atg cag cgc   192
Asp Tyr Thr Ser Ser Pro Arg His Val Arg Leu Ala Glu Met Gln Arg
    50                  55                  60
```

-continued

```
aat atc gac cgg gag gcg aga agg gcg ccg acc gga ctc tat gaa ggc      240
Asn Ile Asp Arg Glu Ala Arg Arg Ala Pro Thr Gly Leu Tyr Glu Gly
 65                  70                  75                  80 ccg acc atc acc acc aag gac ggt gcg aga ccg ctc ttt cct ccc gaa      288
Pro Thr Ile Thr Thr Lys Asp Gly Ala Arg Pro Leu Phe Pro Pro Glu
                 85                  90                  95 aaa gcg cgt cac cca aac cgc ggc ccg ccc cca cgt gga gcg aca ccg      336
Lys Ala Arg His Pro Asn Arg Gly Pro Pro Arg Gly Ala Thr Pro
            100                 105                 110 ccg acg tat gcc ccg cag ttc gtt gca ccg gct gcg acg cgc gag gac      384
Pro Thr Tyr Ala Pro Gln Phe Val Ala Pro Ala Ala Thr Arg Glu Asp
        115                 120                 125 atg atg ccg ccg cag tct gat tcc tac cag cgc gac ctc cgc agc gac      432
Met Met Pro Pro Gln Ser Asp Ser Tyr Gln Arg Asp Leu Arg Ser Asp
130                 135                 140 ccc gcg tac gct gat gat cca gag cat att gtg gcg gca cgt cag cgg      480
Pro Ala Tyr Ala Asp Asp Pro Glu His Ile Val Ala Ala Arg Gln Arg
145                 150                 155                 160 att atg act atg cag agc gac tct tac ggc gag gcg atg cgc ggg atg      528
Ile Met Thr Met Gln Ser Asp Ser Tyr Gly Glu Ala Met Arg Gly Met
                165                 170                 175 gtg gct ccg ccg cca ccg ctg gat cct gac gcg ccg cag gcg tac cgg      576
Val Ala Pro Pro Pro Leu Asp Pro Asp Ala Pro Gln Ala Tyr Arg
            180                 185                 190 cag cct cgg gtg cag ctg gat gac aac tgg tgg att ctg atg tgg tcc      624
Gln Pro Arg Val Gln Leu Asp Asp Asn Trp Trp Ile Leu Met Trp Ser
        195                 200                 205 ttc gca gcc ctg ttc gta gtg atg gcc atg tat gga aag tag              666
Phe Ala Ala Leu Phe Val Val Met Ala Met Tyr Gly Lys
210                 215                 220
```

<210> SEQ ID NO 4
<211> LENGTH: 221
<212> TYPE: PRT
<213> ORGANISM: Leishmania major

<400> SEQUENCE: 4

```
Met Arg Gln Gly Ala Ala Arg Gly Cys Ala Cys Val Ala Ala His Ser
 1               5                   10                  15

Gly Gly Leu Cys Gly Cys Ile Ala Ser Ala Asn Thr Thr Thr Ala Val
            20                  25                  30

Arg Gly Tyr Thr Arg Gly Ile Pro Tyr Thr Pro Gln Gly Thr Ile Gln
        35                  40                  45

Asp Tyr Thr Ser Ser Pro Arg His Val Arg Leu Ala Glu Met Gln Arg
 50                  55                  60

Asn Ile Asp Arg Glu Ala Arg Arg Ala Pro Thr Gly Leu Tyr Glu Gly
 65                  70                  75                  80

Pro Thr Ile Thr Thr Lys Asp Gly Ala Arg Pro Leu Phe Pro Pro Glu
                 85                  90                  95

Lys Ala Arg His Pro Asn Arg Gly Pro Pro Arg Gly Ala Thr Pro
            100                 105                 110

Pro Thr Tyr Ala Pro Gln Phe Val Ala Pro Ala Ala Thr Arg Glu Asp
        115                 120                 125

Met Met Pro Pro Gln Ser Asp Ser Tyr Gln Arg Asp Leu Arg Ser Asp
130                 135                 140

Pro Ala Tyr Ala Asp Asp Pro Glu His Ile Val Ala Ala Arg Gln Arg
145                 150                 155                 160
```

```
Ile Met Thr Met Gln Ser Asp Ser Tyr Gly Glu Ala Met Arg Gly Met
            165                 170                 175

Val Ala Pro Pro Pro Leu Asp Pro Asp Ala Pro Gln Ala Tyr Arg
        180                 185                 190

Gln Pro Arg Val Gln Leu Asp Asp Asn Trp Trp Ile Leu Met Trp Ser
        195                 200                 205

Phe Ala Ala Leu Phe Val Val Met Ala Met Tyr Gly Lys
210                 215                 220

<210> SEQ ID NO 5
<211> LENGTH: 483
<212> TYPE: DNA
<213> ORGANISM: Leishmania infantum
<220> FEATURE:
<221> NAME/KEY: CDS
<222> LOCATION: (1)..(483)

<400> SEQUENCE: 5
```

| | | | | | | | | | | | | | | | | |
|---|---|---|---|---|---|---|---|---|---|---|---|---|---|---|---|---|
| atg | cag | cgc | aat | atc | gac | agg | gag | gcg | aga | agg | gcg | ccg | acc | gga | ctc | 48 |
| Met | Gln | Arg | Asn | Ile | Asp | Arg | Glu | Ala | Arg | Arg | Ala | Pro | Thr | Gly | Leu | |
| 1 | | | | 5 | | | | | 10 | | | | | 15 | | |
| tac | gaa | ggc | ccg | acc | atc | acc | acc | aag | gac | ggt | gcg | agg | cca | ctc | ttt | 96 |
| Tyr | Glu | Gly | Pro | Thr | Ile | Thr | Thr | Lys | Asp | Gly | Ala | Arg | Pro | Leu | Phe | |
| | | | 20 | | | | | 25 | | | | | 30 | | | |
| ccg | ccc | gaa | aaa | gca | cgc | cac | cca | aac | cgc | ggc | ccg | gcc | cca | cgt | gga | 144 |
| Pro | Pro | Glu | Lys | Ala | Arg | His | Pro | Asn | Arg | Gly | Pro | Ala | Pro | Arg | Gly | |
| | | 35 | | | | | 40 | | | | | 45 | | | | |
| gcg | cca | ccg | ccg | acg | tat | gcc | ccg | cag | ttt | gtc | gca | ccg | gct | gcg | acg | 192 |
| Ala | Pro | Pro | Pro | Thr | Tyr | Ala | Pro | Gln | Phe | Val | Ala | Pro | Ala | Ala | Thr | |
| 50 | | | | | 55 | | | | | 60 | | | | | | |
| cgc | gag | gac | atg | atg | ccg | ccg | cag | ccc | gat | tcc | tac | cag | cgc | gac | ctc | 240 |
| Arg | Glu | Asp | Met | Met | Pro | Pro | Gln | Pro | Asp | Ser | Tyr | Gln | Arg | Asp | Leu | |
| 65 | | | | | 70 | | | | | 75 | | | | | 80 | |
| cgc | agc | gac | ccc | gcg | tac | gca | gat | gat | cca | gag | cat | att | gtg | gcg | gca | 288 |
| Arg | Ser | Asp | Pro | Ala | Tyr | Ala | Asp | Asp | Pro | Glu | His | Ile | Val | Ala | Ala | |
| | | | | 85 | | | | | 90 | | | | | 95 | | |
| cgt | cag | cgg | att | atg | act | atg | cag | agc | gac | tct | tac | ggc | gaa | gcg | atg | 336 |
| Arg | Gln | Arg | Ile | Met | Thr | Met | Gln | Ser | Asp | Ser | Tyr | Gly | Glu | Ala | Met | |
| | | | | 100 | | | | | 105 | | | | | 110 | | |
| cgc | gga | atg | gtg | gct | ccg | ccg | ccg | ctg | gat | cct | gac | gcg | ccg | cag | | 384 |
| Arg | Gly | Met | Val | Ala | Pro | Pro | Pro | Leu | Asp | Pro | Asp | Ala | Pro | Gln | | |
| | | 115 | | | | | 120 | | | | | 125 | | | | |
| gcg | tac | cgg | cag | cct | cgg | gtg | cag | ctg | gat | gac | agc | tgg | tgg | atc | ctg | 432 |
| Ala | Tyr | Arg | Gln | Pro | Arg | Val | Gln | Leu | Asp | Asp | Ser | Trp | Trp | Ile | Leu | |
| | | 130 | | | | | 135 | | | | | 140 | | | | |
| atg | tgg | tcc | ttt | gca | gcc | ctg | ttc | gtg | gtg | atg | gcc | atg | tat | gga | aag | 480 |
| Met | Trp | Ser | Phe | Ala | Ala | Leu | Phe | Val | Val | Met | Ala | Met | Tyr | Gly | Lys | |
| 145 | | | | | 150 | | | | | 155 | | | | | 160 | |
| tag | | | | | | | | | | | | | | | | 483 |

```
<210> SEQ ID NO 6
<211> LENGTH: 160
<212> TYPE: PRT
<213> ORGANISM: Leishmania infantum

<400> SEQUENCE: 6

Met Gln Arg Asn Ile Asp Arg Glu Ala Arg Arg Ala Pro Thr Gly Leu
1               5                   10                  15

Tyr Glu Gly Pro Thr Ile Thr Thr Lys Asp Gly Ala Arg Pro Leu Phe
            20                  25                  30
```

```
Pro Pro Glu Lys Ala Arg His Pro Asn Arg Gly Pro Ala Pro Arg Gly
            35                  40                  45

Ala Pro Pro Thr Tyr Ala Pro Gln Phe Val Ala Pro Ala Ala Thr
 50                  55                  60

Arg Glu Asp Met Met Pro Gln Pro Asp Ser Tyr Gln Arg Asp Leu
 65                  70                  75                  80

Arg Ser Asp Pro Ala Tyr Ala Asp Pro Glu His Ile Val Ala Ala
                 85                  90                  95

Arg Gln Arg Ile Met Thr Met Gln Ser Asp Ser Tyr Gly Glu Ala Met
                100                 105                 110

Arg Gly Met Val Ala Pro Pro Pro Leu Asp Pro Asp Ala Pro Gln
            115                 120                 125

Ala Tyr Arg Gln Pro Arg Val Gln Leu Asp Asp Ser Trp Trp Ile Leu
130                 135                 140

Met Trp Ser Phe Ala Ala Leu Phe Val Val Met Ala Met Tyr Gly Lys
145                 150                 155                 160

<210> SEQ ID NO 7
<211> LENGTH: 495
<212> TYPE: DNA
<213> ORGANISM: Trypanosoma brucei
<220> FEATURE:
<221> NAME/KEY: CDS
<222> LOCATION: (1)..(495)

<400> SEQUENCE: 7 atg cga cgc cgt ggg tcc aca ctt ttc tgt gag ggt gca gtt tta acg     48
Met Arg Arg Arg Gly Ser Thr Leu Phe Cys Glu Gly Ala Val Leu Thr
  1               5                  10                  15 tgg agg cgc tct ttt gct cgg ggc cgg ccg tac aca cca ctc ggt act     96
Trp Arg Arg Ser Phe Ala Arg Gly Arg Pro Tyr Thr Pro Leu Gly Thr
                 20                  25                  30 gta cag gac ttc aca tct tct cca cac cac gca caa ctc gcg gag aag    144
Val Gln Asp Phe Thr Ser Ser Pro His His Ala Gln Leu Ala Glu Lys
             35                  40                  45 cag cgc gag ttg gac cgg atg tgt ggc cgg ccg ccc tca cat ctt tac    192
Gln Arg Glu Leu Asp Arg Met Cys Gly Arg Pro Pro Ser His Leu Tyr
 50                  55                  60 gaa ggg ccc acc atc aca acc cct cac ggg gcc cgg cca ctc ttc gag    240
Glu Gly Pro Thr Ile Thr Thr Pro His Gly Ala Arg Pro Leu Phe Glu
 65                  70                  75                  80 cga gac atg cgc gac gac ccg cga aat gac gag ctg ccg gag cat tac    288
Arg Asp Met Arg Asp Asp Pro Arg Asn Asp Glu Leu Pro Glu His Tyr
                 85                  90                  95 gtg gcg gcg cag cag cgg atg gcg gtg tta caa agt gac agc tat gga    336
Val Ala Ala Gln Gln Arg Met Ala Val Leu Gln Ser Asp Ser Tyr Gly
            100                 105                 110 gaa tca ata cgt gga gtg gtg gca ccg ccg cct cct ctg ggg gag ttt    384
Glu Ser Ile Arg Gly Val Val Ala Pro Pro Pro Pro Leu Gly Glu Phe
            115                 120                 125 gat gcg gta agg gca tat caa acg ccg cgg gtg gaa ctt ggg acg gtt    432
Asp Ala Val Arg Ala Tyr Gln Thr Pro Arg Val Glu Leu Gly Thr Val
130                 135                 140 tgg tgg act gcc atg gcg acg att gta ttg ata ttt ttg ctg atg gtg    480
Trp Trp Thr Ala Met Ala Thr Ile Val Leu Ile Phe Leu Leu Met Val
145                 150                 155                 160 aga tat gga cat taa                                                495
Arg Tyr Gly His
```

```
<210> SEQ ID NO 8
<211> LENGTH: 164
<212> TYPE: PRT
<213> ORGANISM: Trypanosoma brucei

<400> SEQUENCE: 8

Met Arg Arg Arg Gly Ser Thr Leu Phe Cys Glu Gly Ala Val Leu Thr
1               5                   10                  15

Trp Arg Arg Ser Phe Ala Arg Gly Arg Pro Tyr Thr Pro Leu Gly Thr
            20                  25                  30

Val Gln Asp Phe Thr Ser Ser Pro His His Ala Gln Leu Ala Glu Lys
        35                  40                  45

Gln Arg Glu Leu Asp Arg Met Cys Gly Arg Pro Ser His Leu Tyr
    50                  55                  60

Glu Gly Pro Thr Ile Thr Thr Pro His Gly Ala Arg Pro Leu Phe Glu
65                  70                  75                  80

Arg Asp Met Arg Asp Asp Pro Arg Asn Asp Glu Leu Pro Glu His Tyr
                85                  90                  95

Val Ala Ala Gln Gln Arg Met Ala Val Leu Gln Ser Asp Ser Tyr Gly
            100                 105                 110

Glu Ser Ile Arg Gly Val Val Ala Pro Pro Pro Leu Gly Glu Phe
        115                 120                 125

Asp Ala Val Arg Ala Tyr Gln Thr Pro Arg Val Glu Leu Gly Thr Val
    130                 135                 140

Trp Trp Thr Ala Met Ala Thr Ile Val Leu Ile Phe Leu Leu Met Val
145                 150                 155                 160

Arg Tyr Gly His

<210> SEQ ID NO 9
<211> LENGTH: 1065
<212> TYPE: DNA
<213> ORGANISM: Trypanosoma cruzi
<220> FEATURE:
<221> NAME/KEY: CDS
<222> LOCATION: (1)..(1065)

<400> SEQUENCE: 9 atg att gta ttg aat gga att tct gag gag caa aaa aaa ctt gcg gtg    48
Met Ile Val Leu Asn Gly Ile Ser Glu Glu Gln Lys Lys Leu Ala Val
1               5                   10                  15 gtt ggg gct gct gca gcc ttt ttt tcc tct gca gtt acc gcg gcg gtg    96
Val Gly Ala Ala Ala Ala Phe Phe Ser Ser Ala Val Thr Ala Ala Val
            20                  25                  30 gtg cgt gtg ctt tcg agg cag ccc ttg aag gct gtg gag gaa ccc cca   144
Val Arg Val Leu Ser Arg Gln Pro Leu Lys Ala Val Glu Glu Pro Pro
        35                  40                  45 cct gtc gta aaa gtg gcg acg gag aag aat aaa tgt gcc agc gag gcc   192
Pro Val Val Lys Val Ala Thr Glu Lys Asn Lys Cys Ala Ser Glu Ala
    50                  55                  60 aga gag gaa aag aag gaa ggt agt gaa atg tat aaa agc gag ttg tgc   240
Arg Glu Glu Lys Lys Glu Gly Ser Glu Met Tyr Lys Ser Glu Leu Cys
65                  70                  75                  80 gct cgt cag tac atg gaa ttc cat tac acc ccc tct cgt acc agc tat   288
Ala Arg Gln Tyr Met Glu Phe His Tyr Thr Pro Ser Arg Thr Ser Tyr
                85                  90                  95 gcg caa cga ctt cgg act att agc gag agt ttt gac ttc cca cag agg   336
Ala Gln Arg Leu Arg Thr Ile Ser Glu Ser Phe Asp Phe Pro Gln Arg
            100                 105                 110 atg gcg cag aaa ttt aag gag ttt ttt cca gag gcg aag aat gag cag   384
Met Ala Gln Lys Phe Lys Glu Phe Phe Pro Glu Ala Lys Asn Glu Gln
```

```
                                                                              -continued Met Ala Gln Lys Phe Lys Glu Phe Pro Glu Ala Lys Asn Glu Gln
    115                 120                 125 aca cgt gcg ttg gaa att ggg tgt gct aca ggt gcc tct gta ttg gag    432
Thr Arg Ala Leu Glu Ile Gly Cys Ala Thr Gly Ala Ser Val Leu Glu
130                 135                 140 atg agc aaa tat ttt gac agc gtt atc ggt gtt gac tac tcg gag att    480
Met Ser Lys Tyr Phe Asp Ser Val Ile Gly Val Asp Tyr Ser Glu Ile
145                 150                 155                 160 ttt att cat ttt gcg cag gaa gtt ttg agg gag aat tct gtg cct cat    528
Phe Ile His Phe Ala Gln Glu Val Leu Arg Glu Asn Ser Val Pro His
                165                 170                 175 gtt tct cgg gta tca ttt ggg gcg gtg gat cag ggc gac atc gag gtc    576
Val Ser Arg Val Ser Phe Gly Ala Val Asp Gln Gly Asp Ile Glu Val
            180                 185                 190 acg cgt cat gtg cgt ctt tca cac gga ctt ttt ccg aaa cga tgt cag    624
Thr Arg His Val Arg Leu Ser His Gly Leu Phe Pro Lys Arg Cys Gln
        195                 200                 205 ttt ttt tgg ggt gat gcg atg aat ctt ttg gga gga gga gga ggc gcg    672
Phe Phe Trp Gly Asp Ala Met Asn Leu Leu Gly Gly Gly Gly Gly Ala
    210                 215                 220 aag aca aat ttg gtg ggg aga cat tcc agt cgt tat gac gat gtt tca    720
Lys Thr Asn Leu Val Gly Arg His Ser Ser Arg Tyr Asp Asp Val Ser
225                 230                 235                 240 tgg tat cag gtg cct gcg gga gag ctc ttt gat ggg gtg ctt gtg tcc    768
Trp Tyr Gln Val Pro Ala Gly Glu Leu Phe Asp Gly Val Leu Val Ser
                245                 250                 255 aac atc ctc tgc cgt gtg tcg gac cca cgc aag ctg ctg gac aca ctc    816
Asn Ile Leu Cys Arg Val Ser Asp Pro Arg Lys Leu Leu Asp Thr Leu
            260                 265                 270 ccc cgg ctg ctc cgc aaa ggc ggc atc ctt gtg ctc gcc tcc ccg tac    864
Pro Arg Leu Leu Arg Lys Gly Gly Ile Leu Val Leu Ala Ser Pro Tyr
        275                 280                 285 tcg tgg agt gat ggg ata aca ccg aag agc aaa tgg atc ggt ggg ttg    912
Ser Trp Ser Asp Gly Ile Thr Pro Lys Ser Lys Trp Ile Gly Gly Leu
    290                 295                 300 cct gac ggg ccg cgg tcg gag gat gtt gtg aag gag ata ctt atg aaa    960
Pro Asp Gly Pro Arg Ser Glu Asp Val Val Lys Glu Ile Leu Met Lys
305                 310                 315                 320 aat ttt gaa ctt cta aat gag aca gat gag gcg ttt ttg att cgt gac   1008
Asn Phe Glu Leu Leu Asn Glu Thr Asp Glu Ala Phe Leu Ile Arg Asp
                325                 330                 335 cac gta cgt cgt tat cag ttg ggg ttt tcg cac tgc acg gtg tgg agg   1056
His Val Arg Arg Tyr Gln Leu Gly Phe Ser His Cys Thr Val Trp Arg
            340                 345                 350 cgc agc tga                                                        1065
Arg Ser

<210> SEQ ID NO 10
<211> LENGTH: 354
<212> TYPE: PRT
<213> ORGANISM: Trypanosoma cruzi

<400> SEQUENCE: 10

Met Ile Val Leu Asn Gly Ile Ser Glu Glu Gln Lys Lys Leu Ala Val
1               5                   10                  15

Val Gly Ala Ala Ala Ala Phe Phe Ser Ser Ala Val Thr Ala Ala Val
                20                  25                  30

Val Arg Val Leu Ser Arg Gln Pro Leu Lys Ala Val Glu Glu Pro Pro
            35                  40                  45
```

```
Pro Val Val Lys Val Ala Thr Glu Lys Asn Lys Cys Ala Ser Glu Ala
    50                  55                  60

Arg Glu Glu Lys Lys Glu Gly Ser Glu Met Tyr Lys Ser Glu Leu Cys
65                  70                  75                  80

Ala Arg Gln Tyr Met Glu Phe His Tyr Thr Pro Ser Arg Thr Ser Tyr
                85                  90                  95

Ala Gln Arg Leu Arg Thr Ile Ser Glu Ser Phe Asp Phe Pro Gln Arg
            100                 105                 110

Met Ala Gln Lys Phe Lys Glu Phe Phe Pro Glu Ala Lys Asn Glu Gln
        115                 120                 125

Thr Arg Ala Leu Glu Ile Gly Cys Ala Thr Gly Ala Ser Val Leu Glu
    130                 135                 140

Met Ser Lys Tyr Phe Asp Ser Val Ile Gly Val Asp Tyr Ser Glu Ile
145                 150                 155                 160

Phe Ile His Phe Ala Gln Glu Val Leu Arg Glu Asn Ser Val Pro His
                165                 170                 175

Val Ser Arg Val Ser Phe Gly Ala Val Asp Gln Gly Asp Ile Glu Val
            180                 185                 190

Thr Arg His Val Arg Leu Ser His Gly Leu Phe Pro Lys Arg Cys Gln
        195                 200                 205

Phe Phe Trp Gly Asp Ala Met Asn Leu Leu Gly Gly Gly Gly Gly Ala
    210                 215                 220

Lys Thr Asn Leu Val Gly Arg His Ser Ser Arg Tyr Asp Asp Val Ser
225                 230                 235                 240

Trp Tyr Gln Val Pro Ala Gly Glu Leu Phe Asp Gly Val Leu Val Ser
                245                 250                 255

Asn Ile Leu Cys Arg Val Ser Asp Pro Arg Lys Leu Leu Asp Thr Leu
            260                 265                 270

Pro Arg Leu Leu Arg Lys Gly Gly Ile Leu Val Leu Ala Ser Pro Tyr
        275                 280                 285

Ser Trp Ser Asp Gly Ile Thr Pro Lys Ser Lys Trp Ile Gly Gly Leu
    290                 295                 300

Pro Asp Gly Pro Arg Ser Glu Asp Val Val Lys Glu Ile Leu Met Lys
305                 310                 315                 320

Asn Phe Glu Leu Leu Asn Glu Thr Asp Glu Ala Phe Leu Ile Arg Asp
                325                 330                 335

His Val Arg Arg Tyr Gln Leu Gly Phe Ser His Cys Thr Val Trp Arg
            340                 345                 350

Arg Ser

<210> SEQ ID NO 11
<211> LENGTH: 1038
<212> TYPE: DNA
<213> ORGANISM: Leishmania major
<220> FEATURE:
<221> NAME/KEY: CDS
<222> LOCATION: (1)..(1038)

<400> SEQUENCE: 11 atg cag caa ctt caa gca cga ctc tct gac aag ctc aat gag ctg acg    48
Met Gln Gln Leu Gln Ala Arg Leu Ser Asp Lys Leu Asn Glu Leu Thr
1               5                   10                  15 aaa gac tgg aca gcc gag cag cgg aag ctc tac ggt gcg gtc gcc ttg    96
Lys Asp Trp Thr Ala Glu Gln Arg Lys Leu Tyr Gly Ala Val Ala Leu
            20                  25                  30 acg gct gtc gtt gcc tct ggc gcc acg ttg att gtt gtc aag gtg atg    144
```

```
            Thr Ala Val Val Ala Ser Gly Ala Thr Leu Ile Val Lys Val Met
                     35                  40                  45 cga cgg tgc tgc ggg gcc ggc aac gac gcc acc cgc tcg gaa agt cat        192
Arg Arg Cys Cys Gly Ala Gly Asn Asp Ala Thr Arg Ser Glu Ser His
         50                  55                  60 tcg aag agc tct gac atc tac gag agt gag acg gcg gcg cgc cag tac        240
Ser Lys Ser Ser Asp Ile Tyr Glu Ser Glu Thr Ala Ala Arg Gln Tyr
 65                  70                  75                  80 atg gag ttc cac tac acg ccg tcg tgc gag agc tac acg cag cgg ctg        288
Met Glu Phe His Tyr Thr Pro Ser Cys Glu Ser Tyr Thr Gln Arg Leu
                     85                  90                  95 cgc tca gtg agc gag gcc tac gac ttc ccg acg cgc gtt gct cac aag        336
Arg Ser Val Ser Glu Ala Tyr Asp Phe Pro Thr Arg Val Ala His Lys
                 100                 105                 110 ttc cgc acc tac atg cag cca ggc aag cgc aag ctg cgc ggg ctc gac        384
Phe Arg Thr Tyr Met Gln Pro Gly Lys Arg Lys Leu Arg Gly Leu Asp
             115                 120                 125 atc ggc tgc gca aca ggg gcc tcg gtg ctg gag atg tcc aag gtg ttc        432
Ile Gly Cys Ala Thr Gly Ala Ser Val Leu Glu Met Ser Lys Val Phe
         130                 135                 140 gac ggc ggc gtc atc ggc ata gat ttt tcg gag gtc ttc att cac ctc        480
Asp Gly Gly Val Ile Gly Ile Asp Phe Ser Glu Val Phe Ile His Leu
145                 150                 155                 160 gcc aag gag gtg gtg agt cag ccg acc tca ggc aag aag gtc acc tac        528
Ala Lys Glu Val Val Ser Gln Pro Thr Ser Gly Lys Lys Val Thr Tyr
                 165                 170                 175 acc gcc cct gtg caa ggc gag atc acg gag aag cgc gag ctg gag ctg        576
Thr Ala Pro Val Gln Gly Glu Ile Thr Glu Lys Arg Glu Leu Glu Leu
             180                 185                 190 cct cgc gcg gtg cgg cca gag cgc tgc gag ttt tac gcc ggt gac gcc        624
Pro Arg Ala Val Arg Pro Glu Arg Cys Glu Phe Tyr Ala Gly Asp Ala
         195                 200                 205 atg aac atg ttc gag gag gac ggc aag atc gca act acg acg tcg cgc        672
Met Asn Met Phe Glu Glu Asp Gly Lys Ile Ala Thr Thr Thr Ser Arg
210                 215                 220 ctg tac ccc gac gtc aag tac tgg cag gca aag aag ggc gag acc ttt        720
Leu Tyr Pro Asp Val Lys Tyr Trp Gln Ala Lys Lys Gly Glu Thr Phe
225                 230                 235                 240 gac ggc gtg ctc tgc ctt aac ctg att gat cgc gtg cca gac ccg cag        768
Asp Gly Val Leu Cys Leu Asn Leu Ile Asp Arg Val Pro Asp Pro Gln
                 245                 250                 255 cgc ctg ctc aac agc gtt gta cgt ctc ctg gct aag gat gga att ctc        816
Arg Leu Leu Asn Ser Val Val Arg Leu Leu Ala Lys Asp Gly Ile Leu
             260                 265                 270 att ctc gca gac ccg tac tcg tgg tgg gag gat gcg acg gag aag tca        864
Ile Leu Ala Asp Pro Tyr Ser Trp Trp Glu Asp Ala Thr Glu Lys Ser
         275                 280                 285 cgc tgg ctg ggc ggc cgc aac gac gac ggc gtg cgc agc gag gat gca        912
Arg Trp Leu Gly Gly Arg Asn Asp Asp Gly Val Arg Ser Glu Asp Ala
290                 295                 300 gtg aag gcg gcg ttg ggg ggc aag ttg gag ctc ctg agc gag tcg gac        960
Val Lys Ala Ala Leu Gly Gly Lys Leu Glu Leu Leu Ser Glu Ser Asp
305                 310                 315                 320 gag gcc ttc ctc atc cgc gat cac att cgc cac tat cag ctg ggg ttc        1008
Glu Ala Phe Leu Ile Arg Asp His Ile Arg His Tyr Gln Leu Gly Phe
                 325                 330                 335 tcc cac tgt act gtg tgg cgc agg aag tag                                1038
Ser His Cys Thr Val Trp Arg Arg Lys
             340                 345
```

<210> SEQ ID NO 12
<211> LENGTH: 345
<212> TYPE: PRT
<213> ORGANISM: Leishmania major

<400> SEQUENCE: 12

```
Met Gln Gln Leu Gln Ala Arg Leu Ser Asp Lys Leu Asn Glu Leu Thr
 1               5                  10                  15

Lys Asp Trp Thr Ala Glu Gln Arg Lys Leu Tyr Gly Ala Val Ala Leu
            20                  25                  30

Thr Ala Val Val Ala Ser Gly Ala Thr Leu Ile Val Val Lys Val Met
        35                  40                  45

Arg Arg Cys Cys Gly Ala Gly Asn Asp Ala Thr Arg Ser Glu Ser His
 50                  55                  60

Ser Lys Ser Ser Asp Ile Tyr Glu Ser Glu Thr Ala Ala Arg Gln Tyr
 65                  70                  75                  80

Met Glu Phe His Tyr Thr Pro Ser Cys Glu Ser Tyr Thr Gln Arg Leu
                85                  90                  95

Arg Ser Val Ser Glu Ala Tyr Asp Phe Pro Thr Arg Val Ala His Lys
            100                 105                 110

Phe Arg Thr Tyr Met Gln Pro Gly Lys Arg Lys Leu Arg Gly Leu Asp
        115                 120                 125

Ile Gly Cys Ala Thr Gly Ala Ser Val Leu Glu Met Ser Lys Val Phe
130                 135                 140

Asp Gly Gly Val Ile Gly Ile Asp Phe Ser Glu Val Phe Ile His Leu
145                 150                 155                 160

Ala Lys Glu Val Val Ser Gln Pro Thr Ser Gly Lys Lys Val Thr Tyr
                165                 170                 175

Thr Ala Pro Val Gln Gly Glu Ile Thr Glu Lys Arg Glu Leu Glu Leu
            180                 185                 190

Pro Arg Ala Val Arg Pro Glu Arg Cys Glu Phe Tyr Ala Gly Asp Ala
        195                 200                 205

Met Asn Met Phe Glu Glu Asp Gly Lys Ile Ala Thr Thr Thr Ser Arg
210                 215                 220

Leu Tyr Pro Asp Val Lys Tyr Trp Gln Ala Lys Lys Gly Glu Thr Phe
225                 230                 235                 240

Asp Gly Val Leu Cys Leu Asn Leu Ile Asp Arg Val Pro Asp Pro Gln
                245                 250                 255

Arg Leu Leu Asn Ser Val Val Arg Leu Leu Ala Lys Asp Gly Ile Leu
            260                 265                 270

Ile Leu Ala Asp Pro Tyr Ser Trp Trp Glu Asp Ala Thr Glu Lys Ser
        275                 280                 285

Arg Trp Leu Gly Gly Arg Asn Asp Gly Val Arg Ser Glu Asp Ala
290                 295                 300

Val Lys Ala Ala Leu Gly Gly Lys Leu Glu Leu Leu Ser Glu Ser Asp
305                 310                 315                 320

Glu Ala Phe Leu Ile Arg Asp His Ile Arg His Tyr Gln Leu Gly Phe
                325                 330                 335

Ser His Cys Thr Val Trp Arg Arg Lys
            340                 345
```

<210> SEQ ID NO 13
<211> LENGTH: 1050
<212> TYPE: DNA
<213> ORGANISM: Leishmania infantum

```
<220> FEATURE:
<221> NAME/KEY: CDS
<222> LOCATION: (1)..(1050)

<400> SEQUENCE: 13 atg cag caa ctt caa gcg cgg ctc tcc gac aag ctc gat gag ctg acg      48
Met Gln Gln Leu Gln Ala Arg Leu Ser Asp Lys Leu Asp Glu Leu Thr
1               5                   10                  15 aag gac tgg aca gcc gag cag cgg aag ctg tac ggc gct gtc gcc ctg      96
Lys Asp Trp Thr Ala Glu Gln Arg Lys Leu Tyr Gly Ala Val Ala Leu
            20                  25                  30 acg gct gtc gtc gcc tct ggc gcg ttg atc ggt gcc aac gtg atg          144
Thr Ala Val Val Ala Ser Gly Ala Ala Leu Ile Gly Ala Asn Val Met
        35                  40                  45 caa cgc tgc tgc ggc ggg cgc ggc agg gca ggc aac gac gcc acc cgc      192
Gln Arg Cys Cys Gly Gly Arg Gly Arg Ala Gly Asn Asp Ala Thr Arg
50                  55                  60 tca gaa agt cac tcg aag agc tcc gac atc tat gag agt gag gcg gcg     240
Ser Glu Ser His Ser Lys Ser Ser Asp Ile Tyr Glu Ser Glu Ala Ala
65                  70                  75                  80 gcg cgc cag tac atg gag ttc cac tac acg ccg tcg cgc gag agc tac     288
Ala Arg Gln Tyr Met Glu Phe His Tyr Thr Pro Ser Arg Glu Ser Tyr
                85                  90                  95 acg cag cgg ctg cgc tcc gtg agc gag gcc tac gac ttt ccg acg cgc     336
Thr Gln Arg Leu Arg Ser Val Ser Glu Ala Tyr Asp Phe Pro Thr Arg
            100                 105                 110 gtc gct cac aag ttc cgc acc tac gtg cag cca ggc aag cgc aag ctg     384
Val Ala His Lys Phe Arg Thr Tyr Val Gln Pro Gly Lys Arg Lys Leu
        115                 120                 125 cgc ggg ctc gac atc ggc tgc gca act ggg gcc tcg gtg ctg gag atg     432
Arg Gly Leu Asp Ile Gly Cys Ala Thr Gly Ala Ser Val Leu Glu Met
130                 135                 140 tcc aag gtg ttc gac ggc ggt gtc atc ggc ata gac ttt tcg gag gtc     480
Ser Lys Val Phe Asp Gly Gly Val Ile Gly Ile Asp Phe Ser Glu Val
145                 150                 155                 160 ttc att cac ctc gcc aag gag gtg gtg aac cag ccg acg tca ggc aag     528
Phe Ile His Leu Ala Lys Glu Val Val Asn Gln Pro Thr Ser Gly Lys
                165                 170                 175 aag gtc acc tac acc gcc cct gtg cag ggc gag atc acg gag aag cgc     576
Lys Val Thr Tyr Thr Ala Pro Val Gln Gly Glu Ile Thr Glu Lys Arg
            180                 185                 190 gag cta gag ctg cct cgc gcg gtg cgg ccg gag cgc tgc gag ttt tac     624
Glu Leu Glu Leu Pro Arg Ala Val Arg Pro Glu Arg Cys Glu Phe Tyr
        195                 200                 205 gcc ggt gac gcc atg aac atg ttc gag gag gac agc aag atc aca act     672
Ala Gly Asp Ala Met Asn Met Phe Glu Glu Asp Ser Lys Ile Thr Thr
210                 215                 220 acg acg tcg cgc ctg tac ccc gac gtc aag tac tgg cag gca aag aag     720
Thr Thr Ser Arg Leu Tyr Pro Asp Val Lys Tyr Trp Gln Ala Lys Lys
225                 230                 235                 240 ggc gag acc ttt gac ggc gta ctc tgc ctt aat ctg atc gat cgc gtg     768
Gly Glu Thr Phe Asp Gly Val Leu Cys Leu Asn Leu Ile Asp Arg Val
                245                 250                 255 cca gac ccg cag cgc ctg ctc aac agc gtt gta cgg ctc ctg gct aag     816
Pro Asp Pro Gln Arg Leu Leu Asn Ser Val Val Arg Leu Leu Ala Lys
            260                 265                 270 gat ggc att ctc att ctc gca gac ccg tac tcg tgg tgg gag gat gcg     864
Asp Gly Ile Leu Ile Leu Ala Asp Pro Tyr Ser Trp Trp Glu Asp Ala
        275                 280                 285 aca gag aag tca cgc tgg ctg ggc ggc cgc aaa gac gac ggc gtg cgc     912
```

```
Thr Glu Lys Ser Arg Trp Leu Gly Gly Arg Lys Asp Asp Gly Val Arg
    290             295                 300
agc gag gat gcg gtg aag gcg gct ctg gag ggc aag ttg gag ctc ctg       960
Ser Glu Asp Ala Val Lys Ala Ala Leu Glu Gly Lys Leu Glu Leu Leu
305             310                 315                 320
aac gag tcg gac gag gcc ttc ctt atc cgc gat cac att cgc cac tat      1008
Asn Glu Ser Asp Glu Ala Phe Leu Ile Arg Asp His Ile Arg His Tyr
                325                 330                 335
cag ctg gga ttc tcc cac tgc act gtg tgg cgc agg aag tag              1050
Gln Leu Gly Phe Ser His Cys Thr Val Trp Arg Arg Lys
                340                 345

<210> SEQ ID NO 14
<211> LENGTH: 349
<212> TYPE: PRT
<213> ORGANISM: Leishmania infantum

<400> SEQUENCE: 14

Met Gln Gln Leu Gln Ala Arg Leu Ser Asp Lys Leu Asp Glu Leu Thr
1               5                   10                  15
Lys Asp Trp Thr Ala Glu Gln Arg Lys Leu Tyr Gly Ala Val Ala Leu
                20                  25                  30
Thr Ala Val Val Ala Ser Gly Ala Ala Leu Ile Gly Ala Asn Val Met
                35                  40                  45
Gln Arg Cys Cys Gly Gly Arg Gly Arg Ala Gly Asn Asp Ala Thr Arg
50                  55                  60
Ser Glu Ser His Ser Lys Ser Ser Asp Ile Tyr Glu Ser Glu Ala Ala
65                  70                  75                  80
Ala Arg Gln Tyr Met Glu Phe His Tyr Thr Pro Ser Arg Glu Ser Tyr
                85                  90                  95
Thr Gln Arg Leu Arg Ser Val Ser Glu Ala Tyr Asp Phe Pro Thr Arg
                100                 105                 110
Val Ala His Lys Phe Arg Thr Tyr Val Gln Pro Gly Lys Arg Lys Leu
                115                 120                 125
Arg Gly Leu Asp Ile Gly Cys Ala Thr Gly Ala Ser Val Leu Glu Met
130                 135                 140
Ser Lys Val Phe Asp Gly Gly Val Ile Gly Ile Asp Phe Ser Glu Val
145                 150                 155                 160
Phe Ile His Leu Ala Lys Glu Val Val Asn Gln Pro Thr Ser Gly Lys
                165                 170                 175
Lys Val Thr Tyr Thr Ala Pro Val Gln Gly Glu Ile Thr Glu Lys Arg
                180                 185                 190
Glu Leu Glu Leu Pro Arg Ala Val Arg Pro Glu Arg Cys Glu Phe Tyr
                195                 200                 205
Ala Gly Asp Ala Met Asn Met Phe Glu Glu Asp Ser Lys Ile Thr Thr
210                 215                 220
Thr Thr Ser Arg Leu Tyr Pro Asp Val Lys Tyr Trp Gln Ala Lys Lys
225                 230                 235                 240
Gly Glu Thr Phe Asp Gly Val Leu Cys Leu Asn Leu Ile Asp Arg Val
                245                 250                 255
Pro Asp Pro Gln Arg Leu Leu Asn Ser Val Val Arg Leu Leu Ala Lys
                260                 265                 270
Asp Gly Ile Leu Ile Leu Ala Asp Pro Tyr Ser Trp Trp Glu Asp Ala
                275                 280                 285
Thr Glu Lys Ser Arg Trp Leu Gly Gly Arg Lys Asp Asp Gly Val Arg
                290                 295                 300
```

```
Ser Glu Asp Ala Val Lys Ala Ala Leu Glu Gly Lys Leu Glu Leu Leu
305                 310                 315                 320

Asn Glu Ser Asp Glu Ala Phe Leu Ile Arg Asp His Ile Arg His Tyr
            325                 330                 335

Gln Leu Gly Phe Ser His Cys Thr Val Trp Arg Arg Lys
        340                 345

<210> SEQ ID NO 15
<211> LENGTH: 1104
<212> TYPE: DNA
<213> ORGANISM: Trypanosoma brucei
<220> FEATURE:
<221> NAME/KEY: CDS
<222> LOCATION: (1)..(1104)

<400> SEQUENCE: 15
```

| | | | | | | | | | | | | | | | | |
|---|---|---|---|---|---|---|---|---|---|---|---|---|---|---|---|---|
| atg | ctg | gcg | ttg | tgc | aaa | tgt | acc | gct | ccc | gag | acg | aga | tgt | tta | gtg | 48 |
| Met | Leu | Ala | Leu | Cys | Lys | Cys | Thr | Ala | Pro | Glu | Thr | Arg | Cys | Leu | Val | |
| 1 | | | | 5 | | | | | 10 | | | | | 15 | | |
| ggt | agt | gtc | att | ttt | acg | gct | gtc | gtt | tcc | tcc | gca | gcg | aca | tat | gcc | 96 |
| Gly | Ser | Val | Ile | Phe | Thr | Ala | Val | Val | Ser | Ser | Ala | Ala | Thr | Tyr | Ala | |
| | | | 20 | | | | | 25 | | | | | 30 | | | |
| ttt | cgt | gac | gtt | ttt | gat | cac | ttc | ctg | cgc | tgt | cgc | tac | aag | ttc | cta | 144 |
| Phe | Arg | Asp | Val | Phe | Asp | His | Phe | Leu | Arg | Cys | Arg | Tyr | Lys | Phe | Leu | |
| | | 35 | | | | | 40 | | | | | 45 | | | | |
| tct | tgg | acg | gat | ggg | gtt | tgg | gtg | ctt | cgt | aaa | ctg | ttt | ggg | ttt | ttt | 192 |
| Ser | Trp | Thr | Asp | Gly | Val | Trp | Val | Leu | Arg | Lys | Leu | Phe | Gly | Phe | Phe | |
| | 50 | | | | | 55 | | | | | 60 | | | | | |
| gga | aag | tgg | ttt | ccc | cat | tgg | gcg | ctc | tgt | cgt | ccc | tca | gaa | ccg | gcg | 240 |
| Gly | Lys | Trp | Phe | Pro | His | Trp | Ala | Leu | Cys | Arg | Pro | Ser | Glu | Pro | Ala | |
| 65 | | | | | 70 | | | | | 75 | | | | | 80 | |
| aac | gtt | tac | gaa | agt | gat | gca | agt | gtg | cgg | caa | tac | atg | gag | ttt | cac | 288 |
| Asn | Val | Tyr | Glu | Ser | Asp | Ala | Ser | Val | Arg | Gln | Tyr | Met | Glu | Phe | His | |
| | | | | 85 | | | | | 90 | | | | | 95 | | |
| tac | acc | ctc | tcg | tcg | gaa | agc | ttt | gcg | caa | aac | ctt | cgt | atg | ata | tct | 336 |
| Tyr | Thr | Leu | Ser | Ser | Glu | Ser | Phe | Ala | Gln | Asn | Leu | Arg | Met | Ile | Ser | |
| | | | 100 | | | | | 105 | | | | | 110 | | | |
| gag | agc | ttt | gat | tat | ccc | atc | cga | gtc | gct | cgc | aag | ttt | cat | gaa | ttt | 384 |
| Glu | Ser | Phe | Asp | Tyr | Pro | Ile | Arg | Val | Ala | Arg | Lys | Phe | His | Glu | Phe | |
| | | | 115 | | | | | 120 | | | | | 125 | | | |
| gtg | cct | gct | aat | gat | gga | aag | gaa | aga | cgt | gct | ctt | gat | ttg | ggg | tgt | 432 |
| Val | Pro | Ala | Asn | Asp | Gly | Lys | Glu | Arg | Arg | Ala | Leu | Asp | Leu | Gly | Cys | |
| | 130 | | | | | 135 | | | | | 140 | | | | | |
| gcg | gtt | ggt | gct | tcc | tct | ctg | gag | atg | agt | aaa | tat | ttc | agc | cgg | gtt | 480 |
| Ala | Val | Gly | Ala | Ser | Ser | Leu | Glu | Met | Ser | Lys | Tyr | Phe | Ser | Arg | Val | |
| 145 | | | | | 150 | | | | | 155 | | | | | 160 | |
| gtc | ggg | att | gat | tac | tct | gtg | gca | ttc | atc | aaa | atg | gcg | aga | aat | gtc | 528 |
| Val | Gly | Ile | Asp | Tyr | Ser | Val | Ala | Phe | Ile | Lys | Met | Ala | Arg | Asn | Val | |
| | | | | 165 | | | | | 170 | | | | | 175 | | |
| gtg | caa | agc | gcg | ctg | aac | cca | aac | ata | cag | cca | atc | aaa | tat | gag | gcc | 576 |
| Val | Gln | Ser | Ala | Leu | Asn | Pro | Asn | Ile | Gln | Pro | Ile | Lys | Tyr | Glu | Ala | |
| | | | 180 | | | | | 185 | | | | | 190 | | | |
| cct | ttg | cag | ggt | gat | att | aca | gtg | gag | cgc | act | gca | tgt | cta | ccg | gat | 624 |
| Pro | Leu | Gln | Gly | Asp | Ile | Thr | Val | Glu | Arg | Thr | Ala | Cys | Leu | Pro | Asp | |
| | | | 195 | | | | | 200 | | | | | 205 | | | |
| ggg | gcg | gtt | cct | caa | cgg | tgc | cgt | ttc | tat | cgg | ggc | gac | gca | atg | aat | 672 |
| Gly | Ala | Val | Pro | Gln | Arg | Cys | Arg | Phe | Tyr | Arg | Gly | Asp | Ala | Met | Asn | |
| | | 210 | | | | | 215 | | | | | 220 | | | | |
| ctt | ctt | gat | tcg | gat | ggc | gat | gat | ggc | aga | ggt | cat | att | gtg | cct | ccc | 720 |
| Leu | Leu | Asp | Ser | Asp | Gly | Asp | Asp | Gly | Arg | Gly | His | Ile | Val | Pro | Pro | |

```
                    225                 230                 235                 240
gtc cac cat ggt gat aca aat gat gaa gat ata act tca tgg tac cgt        768
Val His His Gly Asp Thr Asn Asp Glu Asp Ile Thr Ser Trp Tyr Arg
                    245                 250                 255 gtt cct tca gga gag cgc ttt gac gct gtg ctt gtt gcg aat ctg ctc        816
Val Pro Ser Gly Glu Arg Phe Asp Ala Val Leu Val Ala Asn Leu Leu
                    260                 265                 270 tgt cgc gtt ccc aac cct cgc aag ctg ttg gat atg ctg ccg ctg ctg        864
Cys Arg Val Pro Asn Pro Arg Lys Leu Leu Asp Met Leu Pro Leu Leu
                275                 280                 285 ctc gtt tct ggt ggc atc ctc gtg atc tcc tca cca tat tca tgg gag        912
Leu Val Ser Gly Gly Ile Leu Val Ile Ser Ser Pro Tyr Ser Trp Glu
                290                 295                 300 ggt tcg gta gag gag cgg gat acg tgg gtt ggt gga agg gca gaa ggg        960
Gly Ser Val Glu Glu Arg Asp Thr Trp Val Gly Gly Arg Ala Glu Gly
305                 310                 315                 320 tca acg agt gaa ata ttg gtg aag gaa ata ttg gga gcg aac ttt gat       1008
Ser Thr Ser Glu Ile Leu Val Lys Glu Ile Leu Gly Ala Asn Phe Asp
                325                 330                 335 ctt ctc agt gaa aca gat gag gca ttt ctt att cgt gat cat gtt cgt       1056
Leu Leu Ser Glu Thr Asp Glu Ala Phe Leu Ile Arg Asp His Val Arg
                340                 345                 350 cgc tac cag ttg ggg gtt gct cat tgc acc gtg tgg cgg cgc cgc tga       1104
Arg Tyr Gln Leu Gly Val Ala His Cys Thr Val Trp Arg Arg Arg
                355                 360                 365

<210> SEQ ID NO 16
<211> LENGTH: 367
<212> TYPE: PRT
<213> ORGANISM: Trypanosoma brucei

<400> SEQUENCE: 16

Met Leu Ala Leu Cys Lys Cys Thr Ala Pro Glu Thr Arg Cys Leu Val
1               5                   10                  15

Gly Ser Val Ile Phe Thr Ala Val Ser Ser Ala Ala Thr Tyr Ala
                20                  25                  30

Phe Arg Asp Val Phe Asp His Phe Leu Arg Cys Arg Tyr Lys Phe Leu
            35                  40                  45

Ser Trp Thr Asp Gly Val Trp Val Leu Arg Lys Leu Phe Gly Phe Phe
        50                  55                  60

Gly Lys Trp Phe Pro His Trp Ala Leu Cys Arg Pro Ser Glu Pro Ala
65                  70                  75                  80

Asn Val Tyr Glu Ser Asp Ala Ser Val Arg Gln Tyr Met Glu Phe His
                85                  90                  95

Tyr Thr Leu Ser Ser Glu Ser Phe Ala Gln Asn Leu Arg Met Ile Ser
            100                 105                 110

Glu Ser Phe Asp Tyr Pro Ile Arg Val Ala Arg Lys Phe His Glu Phe
        115                 120                 125

Val Pro Ala Asn Asp Gly Lys Glu Arg Arg Ala Leu Asp Leu Gly Cys
    130                 135                 140

Ala Val Gly Ala Ser Ser Leu Glu Met Ser Lys Tyr Phe Ser Arg Val
145                 150                 155                 160

Val Gly Ile Asp Tyr Ser Val Ala Phe Ile Lys Met Ala Arg Asn Val
                165                 170                 175

Val Gln Ser Ala Leu Asn Pro Asn Ile Gln Pro Ile Lys Tyr Glu Ala
            180                 185                 190

Pro Leu Gln Gly Asp Ile Thr Val Glu Arg Thr Ala Cys Leu Pro Asp
```

```
                195                 200                 205
Gly Ala Val Pro Gln Arg Cys Arg Phe Tyr Arg Gly Asp Ala Met Asn
210                 215                 220

Leu Leu Asp Ser Asp Gly Asp Gly Arg Gly His Ile Val Pro Pro
225                 230                 235                 240

Val His His Gly Asp Thr Asn Asp Glu Asp Ile Thr Ser Trp Tyr Arg
                245                 250                 255

Val Pro Ser Gly Glu Arg Phe Asp Ala Val Leu Val Ala Asn Leu Leu
                260                 265                 270

Cys Arg Val Pro Asn Pro Arg Lys Leu Leu Asp Met Leu Pro Leu Leu
                275                 280                 285

Leu Val Ser Gly Gly Ile Leu Val Ile Ser Ser Pro Tyr Ser Trp Glu
                290                 295                 300

Gly Ser Val Glu Glu Arg Asp Thr Trp Val Gly Gly Arg Ala Glu Gly
305                 310                 315                 320

Ser Thr Ser Glu Ile Leu Val Lys Glu Ile Leu Gly Ala Asn Phe Asp
                325                 330                 335

Leu Leu Ser Glu Thr Asp Glu Ala Phe Leu Ile Arg Asp His Val Arg
                340                 345                 350

Arg Tyr Gln Leu Gly Val Ala His Cys Thr Val Trp Arg Arg Arg
                355                 360                 365

<210> SEQ ID NO 17
<211> LENGTH: 1041
<212> TYPE: DNA
<213> ORGANISM: Trypanosoma cruzi
<220> FEATURE:
<221> NAME/KEY: CDS
<222> LOCATION: (1)..(1041)

<400> SEQUENCE: 17 atg ttt ccg gcg cag gaa ttc ctc aga tat tca atg aaa agt ctt tta      48
Met Phe Pro Ala Gln Glu Phe Leu Arg Tyr Ser Met Lys Ser Leu Leu
1               5                   10                  15 cta gcg tcc agc ttg gcg gtg gca gct ggt tgg gcg tac gtg cgg cac      96
Leu Ala Ser Ser Leu Ala Val Ala Ala Gly Trp Ala Tyr Val Arg His
                20                  25                  30 att cag ctt cct gct ggg cca tcg cgc ctc gat tgg ggg gca tgt gtc     144
Ile Gln Leu Pro Ala Gly Pro Ser Arg Leu Asp Trp Gly Ala Cys Val
            35                  40                  45 ttt gga cat cgc ggc tgc aga ggt gtg ccg gga gtg cca gag aac aca     192
Phe Gly His Arg Gly Cys Arg Gly Val Pro Gly Val Pro Glu Asn Thr
    50                  55                  60 ctg gat gct ttt aag tac gcc ctt tcg cgc ggt gcg gcc ggc ata gag     240
Leu Asp Ala Phe Lys Tyr Ala Leu Ser Arg Gly Ala Ala Gly Ile Glu
65                  70                  75                  80 gtc gac gtg cgg ttg acg aaa gac aac gaa ctc gcc ata ttt cat gac     288
Val Asp Val Arg Leu Thr Lys Asp Asn Glu Leu Ala Ile Phe His Asp
                85                  90                  95 ttc tct tgt aat ggt cac ctg aaa ggg gtg gag aca aca aag cgc ata     336
Phe Ser Cys Asn Gly His Leu Lys Gly Val Glu Thr Thr Lys Arg Ile
                100                 105                 110 gat gag ctc aca ctt cac gag ctg aag agt ctt ccg ttt caa gcc gat     384
Asp Glu Leu Thr Leu His Glu Leu Lys Ser Leu Pro Phe Gln Ala Asp
            115                 120                 125 cca aca gga caa ata cgc ctg cca aca tta gag gaa tcg ctc ctg ttt     432
Pro Thr Gly Gln Ile Arg Leu Pro Thr Leu Glu Glu Ser Leu Leu Phe
        130                 135                 140
```

| | | |
|---|---|---|
| tgt cgg gaa aac aaa ctc aag atg ctc att gaa atc aag gaa atg cgg<br>Cys Arg Glu Asn Lys Leu Lys Met Leu Ile Glu Ile Lys Glu Met Arg<br>145                   150               155               160 | | 480 |
| aga gcg cgg ctt tgc gca gac aaa gtt ttg gat ttg tac cgc cgt tat<br>Arg Ala Arg Leu Cys Ala Asp Lys Val Leu Asp Leu Tyr Arg Arg Tyr<br>                  165               170               175 | | 528 |
| cca gat tat atg tat gag cat aca gtc att att gcg ttc aac ccg gcg<br>Pro Asp Tyr Met Tyr Glu His Thr Val Ile Ile Ala Phe Asn Pro Ala<br>                180               185               190 | | 576 |
| gta ctt tat tat gtg cgg gaa cgg gac cgt aac gtg gcg gtg gga caa<br>Val Leu Tyr Tyr Val Arg Glu Arg Asp Arg Asn Val Ala Val Gly Gln<br>           195               200               205 | | 624 |
| ctc cac tct gga cga gtt ttg cgc tca tgg att agt tcg gga agc gta<br>Leu His Ser Gly Arg Val Leu Arg Ser Trp Ile Ser Ser Gly Ser Val<br>           210               215               220 | | 672 |
| gag gtg ccg tgg tac gca cgt ctc tgc cca act gtt ctg gac tgg ttg<br>Glu Val Pro Trp Tyr Ala Arg Leu Cys Pro Thr Val Leu Asp Trp Leu<br>225                   230               235               240 | | 720 |
| ctg aat tat gta cag gaa agt att aac ccg tgg ctg tcg ggc gtt tca<br>Leu Asn Tyr Val Gln Glu Ser Ile Asn Pro Trp Leu Ser Gly Val Ser<br>                  245               250               255 | | 768 |
| tta atg tgc cca cac tat gat ctc ttt tcc gag acc tac aag cgc cgt<br>Leu Met Cys Pro His Tyr Asp Leu Phe Ser Glu Thr Tyr Lys Arg Arg<br>                260               265               270 | | 816 |
| tgg cac acg cgc aag att ggt gtc ctt ttg tgg ggt ttc tct tcc cca<br>Trp His Thr Arg Lys Ile Gly Val Leu Leu Trp Gly Phe Ser Ser Pro<br>           275               280               285 | | 864 |
| gcg cag tgc acc cgc gag atg cgg acg ccg ggc gtg att gtt gaa agc<br>Ala Gln Cys Thr Arg Glu Met Arg Thr Pro Gly Val Ile Val Glu Ser<br>290                   295               300 | | 912 |
| gac gat cag cac gaa gaa ttt gcc tcg cca aag cca ccg gcg aac ttt<br>Asp Asp Gln His Glu Glu Phe Ala Ser Pro Lys Pro Pro Ala Asn Phe<br>305                   310               315               320 | | 960 |
| gat ata ttt ggt gac cag gcc cgt gaa cgg gag cgt gag gaa gaa gag<br>Asp Ile Phe Gly Asp Gln Ala Arg Glu Arg Glu Arg Glu Glu Glu Glu<br>                  325               330               335 | | 1008 |
| cag cgg cgt cgt ttg aag ttg gga gcg gag taa<br>Gln Arg Arg Arg Leu Lys Leu Gly Ala Glu<br>           340               345 | | 1041 |

<210> SEQ ID NO 18
<211> LENGTH: 346
<212> TYPE: PRT
<213> ORGANISM: Trypanosoma cruzi

<400> SEQUENCE: 18

Met Phe Pro Ala Gln Glu Phe Leu Arg Tyr Ser Met Lys Ser Leu Leu
1                 5                    10                 15

Leu Ala Ser Ser Leu Ala Val Ala Ala Gly Trp Ala Tyr Val Arg His
                  20                  25                 30

Ile Gln Leu Pro Ala Gly Pro Ser Arg Leu Asp Trp Gly Ala Cys Val
           35                  40                 45

Phe Gly His Arg Gly Cys Arg Gly Val Pro Gly Val Pro Glu Asn Thr
     50                  55                  60

Leu Asp Ala Phe Lys Tyr Ala Leu Ser Arg Gly Ala Ala Gly Ile Glu
65                  70                 75               80

Val Asp Val Arg Leu Thr Lys Asp Asn Glu Leu Ala Ile Phe His Asp
                  85                  90                 95

Phe Ser Cys Asn Gly His Leu Lys Gly Val Glu Thr Thr Lys Arg Ile

```
            100                 105                 110
Asp Glu Leu Thr Leu His Glu Leu Lys Ser Leu Pro Phe Gln Ala Asp
        115                 120                 125

Pro Thr Gly Gln Ile Arg Leu Pro Thr Leu Glu Glu Ser Leu Leu Phe
    130                 135                 140

Cys Arg Glu Asn Lys Leu Lys Met Leu Ile Glu Ile Lys Glu Met Arg
145                 150                 155                 160

Arg Ala Arg Leu Cys Ala Asp Lys Val Leu Asp Leu Tyr Arg Arg Tyr
                165                 170                 175

Pro Asp Tyr Met Tyr Glu His Thr Val Ile Ile Ala Phe Asn Pro Ala
            180                 185                 190

Val Leu Tyr Tyr Val Arg Glu Arg Asp Arg Asn Val Ala Val Gly Gln
        195                 200                 205

Leu His Ser Gly Arg Val Leu Arg Ser Trp Ile Ser Ser Gly Ser Val
    210                 215                 220

Glu Val Pro Trp Tyr Ala Arg Leu Cys Pro Thr Val Leu Asp Trp Leu
225                 230                 235                 240

Leu Asn Tyr Val Gln Glu Ser Ile Asn Pro Trp Leu Ser Gly Val Ser
                245                 250                 255

Leu Met Cys Pro His Tyr Asp Leu Phe Ser Glu Thr Tyr Lys Arg Arg
            260                 265                 270

Trp His Thr Arg Lys Ile Gly Val Leu Leu Trp Gly Phe Ser Ser Pro
        275                 280                 285

Ala Gln Cys Thr Arg Glu Met Arg Thr Pro Gly Val Ile Val Glu Ser
    290                 295                 300

Asp Asp Gln His Glu Glu Phe Ala Ser Pro Lys Pro Pro Ala Asn Phe
305                 310                 315                 320

Asp Ile Phe Gly Asp Gln Ala Arg Glu Arg Glu Arg Glu Glu Glu Glu
                325                 330                 335

Gln Arg Arg Arg Leu Lys Leu Gly Ala Glu
            340                 345
```

<210> SEQ ID NO 19
<211> LENGTH: 1002
<212> TYPE: DNA
<213> ORGANISM: Leishmania major
<220> FEATURE:
<221> NAME/KEY: CDS
<222> LOCATION: (1)..(1002)

<400> SEQUENCE: 19

```
atg aag cta gta ctt ttc ctc ggc agc gtt ggg gct gcg ttg ggg tgg      48
Met Lys Leu Val Leu Phe Leu Gly Ser Val Gly Ala Ala Leu Gly Trp
1               5                   10                  15 tcg tac ttg aga cac att cag ctg ccc gtg ggc ccg tcg cgg ctc ctg      96
Ser Tyr Leu Arg His Ile Gln Leu Pro Val Gly Pro Ser Arg Leu Leu
                20                  25                  30 tgg ggc ggc gtc gtg ttc ggg cac cgt ggg tgc cgt ggt gtg gcg ggg     144
Trp Gly Gly Val Val Phe Gly His Arg Gly Cys Arg Gly Val Ala Gly
            35                  40                  45 acg ccg gag aac acg ctg gag gca ttc cgg cac gcg gcc gca tcc gga     192
Thr Pro Glu Asn Thr Leu Glu Ala Phe Arg His Ala Ala Ala Ser Gly
        50                  55                  60 tgt ggc ggt gtc gaa tgt gat gcc cgt ctc acc aaa gac aac gaa gtc     240
Cys Gly Gly Val Glu Cys Asp Ala Arg Leu Thr Lys Asp Asn Glu Val
65                  70                  75                  80 gtc atc ttt cac gac gcc ttc gtc aac ggc cac ctc cga gac gtc ccg     288
```

```
Val Ile Phe His Asp Ala Phe Val Asn Gly His Leu Arg Asp Val Pro
             85                  90                  95 ccg acg cgc cgc atc gat gag ctg acg ctg ttt gag ctg cgc cag tgc      336
Pro Thr Arg Arg Ile Asp Glu Leu Thr Leu Phe Glu Leu Arg Gln Cys
        100                 105                 110 acc ttc acg gcc gac ccc acg gga aag gtt cgc gtt cct acg ctg gag      384
Thr Phe Thr Ala Asp Pro Thr Gly Lys Val Arg Val Pro Thr Leu Glu
        115                 120                 125 gaa gcc atc ttg ttc tgc cgt gat aac aac atg cgc atg ctg atc gag      432
Glu Ala Ile Leu Phe Cys Arg Asp Asn Asn Met Arg Met Leu Ile Glu
    130                 135                 140 gtg aaa gat ctg aag cga acg tac cta tgc acg gac aag gtg ctc gac      480
Val Lys Asp Leu Lys Arg Thr Tyr Leu Cys Thr Asp Lys Val Leu Asp
145                 150                 155                 160 ctc tac cgc cgc tat ccg gac tac atg tac gat cat acc acc ctc atc      528
Leu Tyr Arg Arg Tyr Pro Asp Tyr Met Tyr Asp His Thr Thr Leu Ile
                165                 170                 175 tcc ttt cac agc ggc tcc ctc tac cat gcc agg aag gtg gac aag cga      576
Ser Phe His Ser Gly Ser Leu Tyr His Ala Arg Lys Val Asp Lys Arg
            180                 185                 190 gtt gca gtg tgc cag ctg tac gcc gca aac atg gtg agc tcg tat att      624
Val Ala Val Cys Gln Leu Tyr Ala Ala Asn Met Val Ser Ser Tyr Ile
        195                 200                 205 gcg ctg aaa gtc gac acg ctg ccg tgg gtg ctg cgc ctc tgt ccg gcg      672
Ala Leu Lys Val Asp Thr Leu Pro Trp Val Leu Arg Leu Cys Pro Ala
    210                 215                 220 ttg tgg gat tgc gtg ctg ctc ttt gtg cat gag agg gtg ata ccg tgg      720
Leu Trp Asp Cys Val Leu Leu Phe Val His Glu Arg Val Ile Pro Trp
225                 230                 235                 240 ctg acg ggg tgc tcc atg gtg ggg ccg cgc aat gac ctg ttc acc gag      768
Leu Thr Gly Cys Ser Met Val Gly Pro Arg Asn Asp Leu Phe Thr Glu
                245                 250                 255 gcg agc cgc aag cgg tgg gtt acg cgg aac atc tgc atg tac ctg tgg      816
Ala Ser Arg Lys Arg Trp Val Thr Arg Asn Ile Cys Met Tyr Leu Trp
            260                 265                 270 ggg ttc gag cgc gcc gag cag tac acg cca gcg atg cgg cag cct ggt      864
Gly Phe Glu Arg Ala Glu Gln Tyr Thr Pro Ala Met Arg Gln Pro Gly
        275                 280                 285 gtg tgt atc tcg agc gac aaa tat caa ggc ttt gga aca ccg aag cca      912
Val Cys Ile Ser Ser Asp Lys Tyr Gln Gly Phe Gly Thr Pro Lys Pro
    290                 295                 300 ccg cca aac tac gac ata ttc gat gat agg cag cgg aag ttg gag gga      960
Pro Pro Asn Tyr Asp Ile Phe Asp Asp Arg Gln Arg Lys Leu Glu Gly
305                 310                 315                 320 cag cag gat gcg acg tgt aag cag ctg cgc att gcc aag tag             1002
Gln Gln Asp Ala Thr Cys Lys Gln Leu Arg Ile Ala Lys
                325                 330

<210> SEQ ID NO 20
<211> LENGTH: 333
<212> TYPE: PRT
<213> ORGANISM: Leishmania major

<400> SEQUENCE: 20

Met Lys Leu Val Leu Phe Leu Gly Ser Val Gly Ala Ala Leu Gly Trp
1               5                   10                  15

Ser Tyr Leu Arg His Ile Gln Leu Pro Val Gly Pro Ser Arg Leu Leu
            20                  25                  30

Trp Gly Gly Val Val Phe Gly His Arg Gly Cys Arg Gly Val Ala Gly
        35                  40                  45
```

```
Thr Pro Glu Asn Thr Leu Glu Ala Phe Arg His Ala Ala Ser Gly
    50                  55                  60

Cys Gly Gly Val Glu Cys Asp Ala Arg Leu Thr Lys Asp Asn Glu Val
65                  70                  75                  80

Val Ile Phe His Asp Ala Phe Val Asn Gly His Leu Arg Asp Val Pro
                85                  90                  95

Pro Thr Arg Arg Ile Asp Glu Leu Thr Leu Phe Glu Leu Arg Gln Cys
            100                 105                 110

Thr Phe Thr Ala Asp Pro Thr Gly Lys Val Arg Val Pro Thr Leu Glu
        115                 120                 125

Glu Ala Ile Leu Phe Cys Arg Asp Asn Asn Met Arg Met Leu Ile Glu
    130                 135                 140

Val Lys Asp Leu Lys Arg Thr Tyr Leu Cys Thr Asp Lys Val Leu Asp
145                 150                 155                 160

Leu Tyr Arg Arg Tyr Pro Asp Tyr Met Tyr Asp His Thr Thr Leu Ile
                165                 170                 175

Ser Phe His Ser Gly Ser Leu Tyr His Ala Arg Lys Val Asp Lys Arg
            180                 185                 190

Val Ala Val Cys Gln Leu Tyr Ala Ala Asn Met Val Ser Ser Tyr Ile
        195                 200                 205

Ala Leu Lys Val Asp Thr Leu Pro Trp Val Leu Arg Leu Cys Pro Ala
    210                 215                 220

Leu Trp Asp Cys Val Leu Leu Phe Val His Glu Arg Val Ile Pro Trp
225                 230                 235                 240

Leu Thr Gly Cys Ser Met Val Gly Pro Arg Asn Asp Leu Phe Thr Glu
                245                 250                 255

Ala Ser Arg Lys Arg Trp Val Thr Arg Asn Ile Cys Met Tyr Leu Trp
            260                 265                 270

Gly Phe Glu Arg Ala Glu Gln Tyr Thr Pro Ala Met Arg Gln Pro Gly
        275                 280                 285

Val Cys Ile Ser Ser Asp Lys Tyr Gln Gly Phe Gly Thr Pro Lys Pro
    290                 295                 300

Pro Pro Asn Tyr Asp Ile Phe Asp Asp Arg Gln Arg Lys Leu Glu Gly
305                 310                 315                 320

Gln Gln Asp Ala Thr Cys Lys Gln Leu Arg Ile Ala Lys
                325                 330
```

<210> SEQ ID NO 21
<211> LENGTH: 1005
<212> TYPE: DNA
<213> ORGANISM: Leishmania infantum
<220> FEATURE:
<221> NAME/KEY: CDS
<222> LOCATION: (1)..(1005)

<400> SEQUENCE: 21

```
atg aag cta gta ctt ttc ctc ggc agc gtc ggg gct gcg ttg ggg tgg      48
Met Lys Leu Val Leu Phe Leu Gly Ser Val Gly Ala Ala Leu Gly Trp
1               5                   10                  15 tcg tac ttg agg cac att cag ctg ccc gtg ggc ccg tcg cgg ctc ctg      96
Ser Tyr Leu Arg His Ile Gln Leu Pro Val Gly Pro Ser Arg Leu Leu
                20                  25                  30 tgg ggc ggc gtc gtg ttc ggg cac cgt ggg tgc cgt ggt gtg gcg ggg     144
Trp Gly Gly Val Val Phe Gly His Arg Gly Cys Arg Gly Val Ala Gly
            35                  40                  45 acg ccg gag aac acg ctg gag gca ttc cgg cac gca gcc gca tcc ggg     192
```

```
Thr Pro Glu Asn Thr Leu Glu Ala Phe Arg His Ala Ala Ser Gly
    50              55                  60 tgt ggc ggt atc gaa tgc gat gct cgc ctc acc aaa gac aac gaa gtc       240
Cys Gly Gly Ile Glu Cys Asp Ala Arg Leu Thr Lys Asp Asn Glu Val
 65              70                  75                  80 gtc atc ttt cac gac gcc ttc gtc aac ggc cac ctc cgc gac gtc ccg       288
Val Ile Phe His Asp Ala Phe Val Asn Gly His Leu Arg Asp Val Pro
                 85                  90                  95 ccg acg cgc cgc atc gat gag ctg acg ctg ttt gag ctg cgc cag tgc       336
Pro Thr Arg Arg Ile Asp Glu Leu Thr Leu Phe Glu Leu Arg Gln Cys
            100                 105                 110 acc ttc acg gcc gac ccc acg gga aag gtc cgc gtt cct aca ctg gag       384
Thr Phe Thr Ala Asp Pro Thr Gly Lys Val Arg Val Pro Thr Leu Glu
        115                 120                 125 gaa gcc atc ttg ttc tgc cgt gat aat aac atg cgc atg ttg atc gag       432
Glu Ala Ile Leu Phe Cys Arg Asp Asn Asn Met Arg Met Leu Ile Glu
    130                 135                 140 gtg aaa gat ctg aag cga acg tat cta tgc acg gac aag gtc ctc gaa       480
Val Lys Asp Leu Lys Arg Thr Tyr Leu Cys Thr Asp Lys Val Leu Glu
145                 150                 155                 160 ctc tac cgc cgc tat ccg gac tac atg tac gat cag acc acc ctc att       528
Leu Tyr Arg Arg Tyr Pro Asp Tyr Met Tyr Asp Gln Thr Thr Leu Ile
                165                 170                 175 tcc ttt cac agc ggt gcc ctc tac cat gcc agg aaa gtg gac aag cga       576
Ser Phe His Ser Gly Ala Leu Tyr His Ala Arg Lys Val Asp Lys Arg
            180                 185                 190 gtt gca gtg tgc cag ctg tac gct gcg agc atg gtg cgc tcg tgg att       624
Val Ala Val Cys Gln Leu Tyr Ala Ala Ser Met Val Arg Ser Trp Ile
        195                 200                 205 gcg ctg aaa gtc gac acg ctg ccg tgg gtg ctg cgc ctt tgc ccg gcg       672
Ala Leu Lys Val Asp Thr Leu Pro Trp Val Leu Arg Leu Cys Pro Ala
    210                 215                 220 ttt tgg gat tgc gta ctg ctc ttt gtg tat gag agg gtg ata ccg tgg       720
Phe Trp Asp Cys Val Leu Leu Phe Val Tyr Glu Arg Val Ile Pro Trp
225                 230                 235                 240 ctg acg ggc tgc tcc atg gtg ggg ccg cgc cat gac ctg ttc acc gag       768
Leu Thr Gly Cys Ser Met Val Gly Pro Arg His Asp Leu Phe Thr Glu
                245                 250                 255 gcg agc cgc agg cgc tgg gtt acg cgg aac atc tgc atg tac ctg tgg       816
Ala Ser Arg Arg Arg Trp Val Thr Arg Asn Ile Cys Met Tyr Leu Trp
            260                 265                 270 ggg ttc gag tgc gcc gag cag tac acg cca gcg atg cgg caa ccg ggt       864
Gly Phe Glu Cys Ala Glu Gln Tyr Thr Pro Ala Met Arg Gln Pro Gly
        275                 280                 285 gtg tgc atc tcg agt gac gaa tac aaa gaa ggc ttt gga aca ccg aag       912
Val Cys Ile Ser Ser Asp Glu Tyr Lys Glu Gly Phe Gly Thr Pro Lys
    290                 295                 300 cca ccg cca aac tac gac ata ttc ggt gat cgg cag cgg gag ttg gag       960
Pro Pro Pro Asn Tyr Asp Ile Phe Gly Asp Arg Gln Arg Glu Leu Glu
305                 310                 315                 320 aga cag cag gat gcg acg tgt aag cgg ctg cgc att ggc aag tag          1005
Arg Gln Gln Asp Ala Thr Cys Lys Arg Leu Arg Ile Gly Lys
                325                 330

<210> SEQ ID NO 22
<211> LENGTH: 334
<212> TYPE: PRT
<213> ORGANISM: Leishmania infantum

<400> SEQUENCE: 22
```

| | | | | | | | | | | | | | | |
|---|---|---|---|---|---|---|---|---|---|---|---|---|---|---|
| Met | Lys | Leu | Val | Leu | Phe | Leu | Gly | Ser | Val | Gly | Ala | Ala | Leu | Gly | Trp |
| 1 | | | | 5 | | | | | 10 | | | | | 15 | |

| Ser | Tyr | Leu | Arg | His | Ile | Gln | Leu | Pro | Val | Gly | Pro | Ser | Arg | Leu | Leu |
|---|---|---|---|---|---|---|---|---|---|---|---|---|---|---|---|
| | | | 20 | | | | | 25 | | | | | 30 | | |

| Trp | Gly | Gly | Val | Val | Phe | Gly | His | Arg | Gly | Cys | Arg | Gly | Val | Ala | Gly |
|---|---|---|---|---|---|---|---|---|---|---|---|---|---|---|---|
| | | | 35 | | | | | 40 | | | | | 45 | | |

| Thr | Pro | Glu | Asn | Thr | Leu | Glu | Ala | Phe | Arg | His | Ala | Ala | Ser | Gly |
|---|---|---|---|---|---|---|---|---|---|---|---|---|---|---|
| | 50 | | | | | 55 | | | | | 60 | | | |

| Cys | Gly | Gly | Ile | Glu | Cys | Asp | Ala | Arg | Leu | Thr | Lys | Asp | Asn | Glu | Val |
|---|---|---|---|---|---|---|---|---|---|---|---|---|---|---|---|
| 65 | | | | | 70 | | | | | 75 | | | | | 80 |

| Val | Ile | Phe | His | Asp | Ala | Phe | Val | Asn | Gly | His | Leu | Arg | Asp | Val | Pro |
|---|---|---|---|---|---|---|---|---|---|---|---|---|---|---|---|
| | | | | 85 | | | | | 90 | | | | | 95 | |

| Pro | Thr | Arg | Arg | Ile | Asp | Glu | Leu | Thr | Leu | Phe | Glu | Leu | Arg | Gln | Cys |
|---|---|---|---|---|---|---|---|---|---|---|---|---|---|---|---|
| | | | | 100 | | | | | 105 | | | | | 110 | |

| Thr | Phe | Thr | Ala | Asp | Pro | Thr | Gly | Lys | Val | Arg | Val | Pro | Thr | Leu | Glu |
|---|---|---|---|---|---|---|---|---|---|---|---|---|---|---|---|
| | | | 115 | | | | | 120 | | | | | 125 | | |

| Glu | Ala | Ile | Leu | Phe | Cys | Arg | Asp | Asn | Met | Arg | Met | Leu | Ile | Glu |
|---|---|---|---|---|---|---|---|---|---|---|---|---|---|---|
| | 130 | | | | | 135 | | | | | 140 | | | |

| Val | Lys | Asp | Leu | Lys | Arg | Thr | Tyr | Leu | Cys | Thr | Asp | Lys | Val | Leu | Glu |
|---|---|---|---|---|---|---|---|---|---|---|---|---|---|---|---|
| 145 | | | | | 150 | | | | | 155 | | | | | 160 |

| Leu | Tyr | Arg | Arg | Tyr | Pro | Asp | Tyr | Met | Tyr | Asp | Gln | Thr | Thr | Leu | Ile |
|---|---|---|---|---|---|---|---|---|---|---|---|---|---|---|---|
| | | | | 165 | | | | | 170 | | | | | 175 | |

| Ser | Phe | His | Ser | Gly | Ala | Leu | Tyr | His | Ala | Arg | Lys | Val | Asp | Lys | Arg |
|---|---|---|---|---|---|---|---|---|---|---|---|---|---|---|---|
| | | | | 180 | | | | | 185 | | | | | 190 | |

| Val | Ala | Val | Cys | Gln | Leu | Tyr | Ala | Ala | Ser | Met | Val | Arg | Ser | Trp | Ile |
|---|---|---|---|---|---|---|---|---|---|---|---|---|---|---|---|
| | | | 195 | | | | | 200 | | | | | 205 | | |

| Ala | Leu | Lys | Val | Asp | Thr | Leu | Pro | Trp | Val | Leu | Arg | Leu | Cys | Pro | Ala |
|---|---|---|---|---|---|---|---|---|---|---|---|---|---|---|---|
| | 210 | | | | | 215 | | | | | 220 | | | | |

| Phe | Trp | Asp | Cys | Val | Leu | Leu | Phe | Val | Tyr | Glu | Arg | Val | Ile | Pro | Trp |
|---|---|---|---|---|---|---|---|---|---|---|---|---|---|---|---|
| 225 | | | | | 230 | | | | | 235 | | | | | 240 |

| Leu | Thr | Gly | Cys | Ser | Met | Val | Gly | Pro | Arg | His | Asp | Leu | Phe | Thr | Glu |
|---|---|---|---|---|---|---|---|---|---|---|---|---|---|---|---|
| | | | | 245 | | | | | 250 | | | | | 255 | |

| Ala | Ser | Arg | Arg | Arg | Trp | Val | Thr | Arg | Asn | Ile | Cys | Met | Tyr | Leu | Trp |
|---|---|---|---|---|---|---|---|---|---|---|---|---|---|---|---|
| | | | 260 | | | | | 265 | | | | | 270 | | |

| Gly | Phe | Glu | Cys | Ala | Glu | Gln | Tyr | Thr | Pro | Ala | Met | Arg | Gln | Pro | Gly |
|---|---|---|---|---|---|---|---|---|---|---|---|---|---|---|---|
| | | | 275 | | | | | 280 | | | | | 285 | | |

| Val | Cys | Ile | Ser | Ser | Asp | Glu | Tyr | Lys | Glu | Gly | Phe | Gly | Thr | Pro | Lys |
|---|---|---|---|---|---|---|---|---|---|---|---|---|---|---|---|
| | 290 | | | | | 295 | | | | | 300 | | | | |

| Pro | Pro | Pro | Asn | Tyr | Asp | Ile | Phe | Gly | Asp | Arg | Gln | Arg | Glu | Leu | Glu |
|---|---|---|---|---|---|---|---|---|---|---|---|---|---|---|---|
| 305 | | | | | 310 | | | | | 315 | | | | | 320 |

| Arg | Gln | Gln | Asp | Ala | Thr | Cys | Lys | Arg | Leu | Arg | Ile | Gly | Lys |
|---|---|---|---|---|---|---|---|---|---|---|---|---|---|
| | | | | 325 | | | | | 330 | | | | |

<210> SEQ ID NO 23
<211> LENGTH: 1002
<212> TYPE: DNA
<213> ORGANISM: Trypanosoma brucei
<220> FEATURE:
<221> NAME/KEY: CDS
<222> LOCATION: (1)..(1002)

<400> SEQUENCE: 23

| atg | aag | agt | gta | ttt | gta | gca | tct | agt | atg | gct | gtg | gct | gca | ggt | tgg | 48 |
|---|---|---|---|---|---|---|---|---|---|---|---|---|---|---|---|---|
| Met | Lys | Ser | Val | Phe | Val | Ala | Ser | Ser | Met | Ala | Val | Ala | Ala | Gly | Trp | |
| 1 | | | | 5 | | | | | 10 | | | | | 15 | | |

| gct | tac | gta | cgt | cac | ctg | caa | ctt | cca | gca | ggt | ccc | aca | cgt | tta | agt | 96 |
|---|---|---|---|---|---|---|---|---|---|---|---|---|---|---|---|---|

```
Ala Tyr Val Arg His Leu Gln Leu Pro Ala Gly Pro Thr Arg Leu Ser
             20                  25                  30 tgg gga agt tta gtg ttt ggc cac cgc ggc tgc aga gga gta ctt ggc      144
Trp Gly Ser Leu Val Phe Gly His Arg Gly Cys Arg Gly Val Leu Gly
         35                  40                  45 gtt cct gag aat act ctt gac gcc ttt aaa tat gca ctt tcc cga ggt      192
Val Pro Glu Asn Thr Leu Asp Ala Phe Lys Tyr Ala Leu Ser Arg Gly
 50                  55                  60 gct gct ggt atc gag gtg gat gta cga cta acg aaa gat aac gaa ctt      240
Ala Ala Gly Ile Glu Val Asp Val Arg Leu Thr Lys Asp Asn Glu Leu
 65                  70                  75                  80 gtt gtg ttc cat gat gcc gtg gct aat gga cag ttg aag ggt gtt ccg      288
Val Val Phe His Asp Ala Val Ala Asn Gly Gln Leu Lys Gly Val Pro
                 85                  90                  95 gcg acg aaa cgg att gat gaa ctc acg ctc ctt caa cta aag gag ctt      336
Ala Thr Lys Arg Ile Asp Glu Leu Thr Leu Leu Gln Leu Lys Glu Leu
                100                 105                 110 cct ttt atc act gat ccc acg ggg cag att cgc gtc cca aca cta gaa      384
Pro Phe Ile Thr Asp Pro Thr Gly Gln Ile Arg Val Pro Thr Leu Glu
            115                 120                 125 gat tct gtg ctg ttc tgt cgt gag aac aac ctt aaa atg ctt att gaa      432
Asp Ser Val Leu Phe Cys Arg Glu Asn Asn Leu Lys Met Leu Ile Glu
130                 135                 140 gtg aag gaa aga aat cga tcg cgg tta tgt gtt gat agg tta ctt gac      480
Val Lys Glu Arg Asn Arg Ser Arg Leu Cys Val Asp Arg Leu Leu Asp
145                 150                 155                 160 ctc tac aag cgg tac cca gat tac atg tat gag caa acg aca gtt att      528
Leu Tyr Lys Arg Tyr Pro Asp Tyr Met Tyr Glu Gln Thr Thr Val Ile
                165                 170                 175 tca ttt gac cca cga gtg ctg tat tat gtc cgt cag cgg gac cgc aac      576
Ser Phe Asp Pro Arg Val Leu Tyr Tyr Val Arg Gln Arg Asp Arg Asn
            180                 185                 190 gtc gct gta gga caa att cat tcg ggt cag gtt tta cgg acg tgg att      624
Val Ala Val Gly Gln Ile His Ser Gly Gln Val Leu Arg Thr Trp Ile
        195                 200                 205 caa acc ggt ggt gaa agc gta tca tgg gcg gta cgt gtt tgc cct ggt      672
Gln Thr Gly Gly Glu Ser Val Ser Trp Ala Val Arg Val Cys Pro Gly
    210                 215                 220 att cta gac aga ata ctt cat tgg gtg cag caa agc atc agt ccg tgg      720
Ile Leu Asp Arg Ile Leu His Trp Val Gln Gln Ser Ile Ser Pro Trp
225                 230                 235                 240 gtg gcc ggt gtt tca atg gta tgc cca tat tac aaa ctt tat tcg gaa      768
Val Ala Gly Val Ser Met Val Cys Pro Tyr Tyr Lys Leu Tyr Ser Glu
                245                 250                 255 aaa tac aag cgc cgc tgg cat acg cgt aag att gga att gca gtt tgg      816
Lys Tyr Lys Arg Arg Trp His Thr Arg Lys Ile Gly Ile Ala Val Trp
            260                 265                 270 ggt ttt aca aat cca aca gaa tgc act tgg gag atg cgg gtg ccg gga      864
Gly Phe Thr Asn Pro Thr Glu Cys Thr Trp Glu Met Arg Val Pro Gly
        275                 280                 285 gtt gtt gtt gag tgc gat gac aat cac gaa gag ttt gca gct ccg aag      912
Val Val Val Glu Cys Asp Asp Asn His Glu Glu Phe Ala Ala Pro Lys
    290                 295                 300 cag ccg cca gat ttt gac ata ttt ggt gat agg gct cga gag cga gag      960
Gln Pro Pro Asp Phe Asp Ile Phe Gly Asp Arg Ala Arg Glu Arg Glu
305                 310                 315                 320 gag gaa cag cag agg aga gca gca aaa ctt ccc agc aaa tga             1002
Glu Glu Gln Gln Arg Arg Ala Ala Lys Leu Pro Ser Lys
                325                 330
```

<210> SEQ ID NO 24
<211> LENGTH: 333
<212> TYPE: PRT
<213> ORGANISM: Trypanosoma brucei

<400> SEQUENCE: 24

Met Lys Ser Val Phe Val Ala Ser Ser Met Ala Val Ala Ala Gly Trp
1               5                   10                  15

Ala Tyr Val Arg His Leu Gln Leu Pro Ala Gly Pro Thr Arg Leu Ser
            20                  25                  30

Trp Gly Ser Leu Val Phe Gly His Arg Gly Cys Arg Gly Val Leu Gly
        35                  40                  45

Val Pro Glu Asn Thr Leu Asp Ala Phe Lys Tyr Ala Leu Ser Arg Gly
    50                  55                  60

Ala Ala Gly Ile Glu Val Asp Val Arg Leu Thr Lys Asp Asn Glu Leu
65                  70                  75                  80

Val Val Phe His Asp Ala Val Ala Asn Gly Gln Leu Lys Gly Val Pro
                85                  90                  95

Ala Thr Lys Arg Ile Asp Glu Leu Thr Leu Leu Gln Leu Lys Glu Leu
            100                 105                 110

Pro Phe Ile Thr Asp Pro Thr Gly Gln Ile Arg Val Pro Thr Leu Glu
        115                 120                 125

Asp Ser Val Leu Phe Cys Arg Glu Asn Asn Leu Lys Met Leu Ile Glu
    130                 135                 140

Val Lys Glu Arg Asn Arg Ser Arg Leu Cys Val Asp Arg Leu Leu Asp
145                 150                 155                 160

Leu Tyr Lys Arg Tyr Pro Asp Tyr Met Tyr Glu Gln Thr Thr Val Ile
                165                 170                 175

Ser Phe Asp Pro Arg Val Leu Tyr Tyr Val Arg Gln Arg Asp Arg Asn
            180                 185                 190

Val Ala Val Gly Gln Ile His Ser Gly Gln Val Leu Arg Thr Trp Ile
        195                 200                 205

Gln Thr Gly Gly Glu Ser Val Ser Trp Ala Val Arg Val Cys Pro Gly
    210                 215                 220

Ile Leu Asp Arg Ile Leu His Trp Val Gln Gln Ser Ile Ser Pro Trp
225                 230                 235                 240

Val Ala Gly Val Ser Met Val Cys Pro Tyr Tyr Lys Leu Tyr Ser Glu
                245                 250                 255

Lys Tyr Lys Arg Arg Trp His Thr Arg Lys Ile Gly Ile Ala Val Trp
            260                 265                 270

Gly Phe Thr Asn Pro Thr Glu Cys Thr Trp Glu Met Arg Val Pro Gly
        275                 280                 285

Val Val Val Glu Cys Asp Asp Asn His Glu Glu Phe Ala Ala Pro Lys
    290                 295                 300

Gln Pro Pro Asp Phe Asp Ile Phe Gly Asp Arg Ala Arg Glu Arg Glu
305                 310                 315                 320

Glu Glu Gln Gln Arg Arg Ala Ala Lys Leu Pro Ser Lys
                325                 330

<210> SEQ ID NO 25
<211> LENGTH: 1269
<212> TYPE: DNA
<213> ORGANISM: Trypanosoma cruzi
<220> FEATURE:
<221> NAME/KEY: CDS
<222> LOCATION: (1)..(1269)

<400> SEQUENCE: 25

```
atg cgt cgc act tta ttt tgt ctg tca acg ctt gtc aaa ata ggt cga    48
Met Arg Arg Thr Leu Phe Cys Leu Ser Thr Leu Val Lys Ile Gly Arg
1               5                   10                  15 ggt gca gag aat gtg acg gag gca gct agc aat gcc ctt ctg gaa tcc    96
Gly Ala Glu Asn Val Thr Glu Ala Ala Ser Asn Ala Leu Leu Glu Ser
            20                  25                  30 ctc cag atg cat ggc tat tgc tac gtg cag cat cca ttt att cag aag    144
Leu Gln Met His Gly Tyr Cys Tyr Val Gln His Pro Phe Ile Gln Lys
        35                  40                  45 gag att ttg gat cag ctt cac cgt gac agc cgc atc ttt ttt gag cgc    192
Glu Ile Leu Asp Gln Leu His Arg Asp Ser Arg Ile Phe Phe Glu Arg
    50                  55                  60 tac gtc aca gac acc gcc gcc gct gcg aga cca gcg acg atg acg        240
Tyr Val Thr Asp Thr Ala Ala Ala Ala Arg Pro Ala Thr Met Thr
65                  70                  75                  80 acg cga ttt aag caa gac acg cac cag cag cct gtt ctg ccc ctt tcg    288
Thr Arg Phe Lys Gln Asp Thr His Gln Gln Pro Val Leu Pro Leu Ser
                85                  90                  95 ccg tac gag ttg gag agt atc aag tcg ccc tct gga ttc cgt ggg tac    336
Pro Tyr Glu Leu Glu Ser Ile Lys Ser Pro Ser Gly Phe Arg Gly Tyr
            100                 105                 110 cac cgt tat gtc ggt gcc agt ggg ctg gat gat gcc att gag tgt ttc    384
His Arg Tyr Val Gly Ala Ser Gly Leu Asp Asp Ala Ile Glu Cys Phe
        115                 120                 125 tcc gtc ggt cgt gag gtg gag cag ccg gca cac ctg cgg gag gcg tat    432
Ser Val Gly Arg Glu Val Glu Gln Pro Ala His Leu Arg Glu Ala Tyr
    130                 135                 140 tac aaa ctg agt ggg tgg aat gaa gag gag tac aaa ccg ctg att agc    480
Tyr Lys Leu Ser Gly Trp Asn Glu Glu Glu Tyr Lys Pro Leu Ile Ser
145                 150                 155                 160 cga cag acg ccc tgg cag gtg ctg ctt aac cac ccc agt ggc aat gta    528
Arg Gln Thr Pro Trp Gln Val Leu Leu Asn His Pro Ser Gly Asn Val
                165                 170                 175 agc agc ccc ggc acg gac acc ttc atg gcc gac tac cgt gag atg atg    576
Ser Ser Pro Gly Thr Asp Thr Phe Met Ala Asp Tyr Arg Glu Met Met
            180                 185                 190 ttg gca tac ttt gac ctc tgc gcg gag gtg tca att gat gtg ctg cga    624
Leu Ala Tyr Phe Asp Leu Cys Ala Glu Val Ser Ile Asp Val Leu Arg
        195                 200                 205 cat atc agc tgt gga tta ggc gtc cgc cct acg att cca cag ggt ggc    672
His Ile Ser Cys Gly Leu Gly Val Arg Pro Thr Ile Pro Gln Gly Gly
    210                 215                 220 cca gac ccg gcg agc ggt tac gat ctt gac ttc ttc acc ccc ttc cac    720
Pro Asp Pro Ala Ser Gly Tyr Asp Leu Asp Phe Phe Thr Pro Phe His
225                 230                 235                 240 aac aaa ctt gac ttt gac ctg cag gca aag tac tac cca cag ttg gga    768
Asn Lys Leu Asp Phe Asp Leu Gln Ala Lys Tyr Tyr Pro Gln Leu Gly
                245                 250                 255 cag gta acg cgc atg aat aat ggt gtg gag atc aaa aac gcg cgc tct    816
Gln Val Thr Arg Met Asn Asn Gly Val Glu Ile Lys Asn Ala Arg Ser
            260                 265                 270 gcc tca aat ccg tat gga gca aaa gta ctg cga cgc aaa ggt gcc ctc    864
Ala Ser Asn Pro Tyr Gly Ala Lys Val Leu Arg Arg Lys Gly Ala Leu
        275                 280                 285 gcg cag cca tta ctg aag gaa ggc aca gac gag gca aaa ggg gat gta    912
Ala Gln Pro Leu Leu Lys Glu Gly Thr Asp Glu Ala Lys Gly Asp Val
    290                 295                 300
```

```
acc att cgc ctt gac aca cac aaa gac ctg agc acc atc acc cta cta       960
Thr Ile Arg Leu Asp Thr His Lys Asp Leu Ser Thr Ile Thr Leu Leu
305                 310                 315                 320 gcg cag gac gcc ctc ggt ggt ctg gag gtc tgg gac gac gag gat gaa      1008
Ala Gln Asp Ala Leu Gly Gly Leu Glu Val Trp Asp Asp Glu Asp Glu
            325                 330                 335 aag tac gtt gcc gtg cct gtt ctc aat gac gcg ctg ctt gtt aac gcg      1056
Lys Tyr Val Ala Val Pro Val Leu Asn Asp Ala Leu Leu Val Asn Ala
                340                 345                 350 ggt cta ttc ctg gaa aag tgg acc ggt gga ctg ctg gag gca aca ccg      1104
Gly Leu Phe Leu Glu Lys Trp Thr Gly Gly Leu Leu Glu Ala Thr Pro
355                 360                 365 cac cgc gtg cga aat gtg aag gat gga agc agt cgt tgc agc gtt gtc      1152
His Arg Val Arg Asn Val Lys Asp Gly Ser Ser Arg Cys Ser Val Val
            370                 375                 380 ttt ttt tgt ctt cca aac cac gac gcg aag gtg gag ccg ctg ctg cag      1200
Phe Phe Cys Leu Pro Asn His Asp Ala Lys Val Glu Pro Leu Leu Gln
385                 390                 395                 400 cag gat gag aac ccc tcg ctt gac gcc cag gaa gga ttc tac gcc ggg      1248
Gln Asp Glu Asn Pro Ser Leu Asp Ala Gln Glu Gly Phe Tyr Ala Gly
                405                 410                 415 gac ttg atg ccg gta tca taa                                          1269
Asp Leu Met Pro Val Ser
            420

<210> SEQ ID NO 26
<211> LENGTH: 422
<212> TYPE: PRT
<213> ORGANISM: Trypanosoma cruzi

<400> SEQUENCE: 26

Met Arg Arg Thr Leu Phe Cys Leu Ser Thr Leu Val Lys Ile Gly Arg
1               5                   10                  15

Gly Ala Glu Asn Val Thr Glu Ala Ala Ser Asn Ala Leu Leu Glu Ser
            20                  25                  30

Leu Gln Met His Gly Tyr Cys Tyr Val Gln His Pro Phe Ile Gln Lys
        35                  40                  45

Glu Ile Leu Asp Gln Leu His Arg Asp Ser Arg Ile Phe Phe Glu Arg
    50                  55                  60

Tyr Val Thr Asp Thr Ala Ala Ala Ala Arg Pro Ala Thr Met Thr
65                  70                  75                  80

Thr Arg Phe Lys Gln Asp Thr His Gln Gln Pro Val Leu Pro Leu Ser
                85                  90                  95

Pro Tyr Glu Leu Glu Ser Ile Lys Ser Pro Ser Gly Phe Arg Gly Tyr
            100                 105                 110

His Arg Tyr Val Gly Ala Ser Gly Leu Asp Asp Ala Ile Glu Cys Phe
        115                 120                 125

Ser Val Gly Arg Glu Val Glu Gln Pro Ala His Leu Arg Glu Ala Tyr
    130                 135                 140

Tyr Lys Leu Ser Gly Trp Asn Glu Glu Tyr Lys Pro Leu Ile Ser
145                 150                 155                 160

Arg Gln Thr Pro Trp Gln Val Leu Leu Asn His Pro Ser Gly Asn Val
                165                 170                 175

Ser Ser Pro Gly Thr Asp Thr Phe Met Ala Asp Tyr Arg Glu Met Met
            180                 185                 190

Leu Ala Tyr Phe Asp Leu Cys Ala Glu Val Ser Ile Asp Val Leu Arg
        195                 200                 205
```

```
His Ile Ser Cys Gly Leu Gly Val Arg Pro Thr Ile Pro Gln Gly Gly
    210                 215                 220

Pro Asp Pro Ala Ser Gly Tyr Asp Leu Asp Phe Phe Thr Pro Phe His
225                 230                 235                 240

Asn Lys Leu Asp Phe Asp Leu Gln Ala Lys Tyr Tyr Pro Gln Leu Gly
                245                 250                 255

Gln Val Thr Arg Met Asn Asn Gly Val Glu Ile Lys Asn Ala Arg Ser
            260                 265                 270

Ala Ser Asn Pro Tyr Gly Ala Lys Val Leu Arg Arg Lys Gly Ala Leu
        275                 280                 285

Ala Gln Pro Leu Leu Lys Glu Gly Thr Asp Glu Ala Lys Gly Asp Val
    290                 295                 300

Thr Ile Arg Leu Asp Thr His Lys Asp Leu Ser Thr Ile Thr Leu Leu
305                 310                 315                 320

Ala Gln Asp Ala Leu Gly Gly Leu Glu Val Trp Asp Asp Glu Asp Glu
                325                 330                 335

Lys Tyr Val Ala Val Pro Val Leu Asn Asp Ala Leu Leu Val Asn Ala
            340                 345                 350

Gly Leu Phe Leu Glu Lys Trp Thr Gly Gly Leu Leu Glu Ala Thr Pro
        355                 360                 365

His Arg Val Arg Asn Val Lys Asp Gly Ser Ser Arg Cys Ser Val Val
    370                 375                 380

Phe Phe Cys Leu Pro Asn His Asp Ala Lys Val Glu Pro Leu Leu Gln
385                 390                 395                 400

Gln Asp Glu Asn Pro Ser Leu Asp Ala Gln Glu Gly Phe Tyr Ala Gly
                405                 410                 415

Asp Leu Met Pro Val Ser
            420

<210> SEQ ID NO 27
<211> LENGTH: 1296
<212> TYPE: DNA
<213> ORGANISM: Leishmania major
<220> FEATURE:
<221> NAME/KEY: CDS
<222> LOCATION: (1)..(1296)

<400> SEQUENCE: 27 atg ctt cgc gct aca att ctt gct cgc ggc acg ctt gta aag atc ggc      48
Met Leu Arg Ala Thr Ile Leu Ala Arg Gly Thr Leu Val Lys Ile Gly
1               5                   10                  15 cgc ggc ccg aac aac gta acg gag tcg gcc agc aat gcc ctt ctc gaa      96
Arg Gly Pro Asn Asn Val Thr Glu Ser Ala Ser Asn Ala Leu Leu Glu
            20                  25                  30 tcc cta caa gat cat ggt tat tgc tat atc cag cac ccc ttc att cag     144
Ser Leu Gln Asp His Gly Tyr Cys Tyr Ile Gln His Pro Phe Ile Gln
        35                  40                  45 aag acc ata ctc gat cag ctt cac cgc gat tgc cgc atc ttc ttc gag     192
Lys Thr Ile Leu Asp Gln Leu His Arg Asp Cys Arg Ile Phe Phe Glu
    50                  55                  60 cag tat gtc ctg cac ctg cac gac gct gct gcg cag ggc agc ctg aag     240
Gln Tyr Val Leu His Leu His Asp Ala Ala Ala Gln Gly Ser Leu Lys
65                  70                  75                  80 cgc aac aac ctg cac aac tac aac tgc acc caa ctc tcc ccg tac gaa     288
Arg Asn Asn Leu His Asn Tyr Asn Cys Thr Gln Leu Ser Pro Tyr Glu
                85                  90                  95 ctg gag agc atc aag tcc ccg agt ggg ttc cgc ggc tac tac cgc tac     336
Leu Glu Ser Ile Lys Ser Pro Ser Gly Phe Arg Gly Tyr Tyr Arg Tyr
```

-continued

```
                100                 105                 110
gtc ggc gcg agc ggc atc gat gac gct atc gaa tgc ttc tcc gtt ggc     384
Val Gly Ala Ser Gly Ile Asp Asp Ala Ile Glu Cys Phe Ser Val Gly
        115                 120                 125 cgc gac gac gtg gct gac ccg gca gtg ctg cgg cgc gac tac tac aag     432
Arg Asp Asp Val Ala Asp Pro Ala Val Leu Arg Arg Asp Tyr Tyr Lys
    130                 135                 140 caa gcc ggt tgg gag gag agc gag tac ctg agc atg att agc cgc cgc     480
Gln Ala Gly Trp Glu Glu Ser Glu Tyr Leu Ser Met Ile Ser Arg Arg
145                 150                 155                 160 aac ccg tgg gac atc ttg ctg aac cac gtc aac tca atc ccc gca tcc     528
Asn Pro Trp Asp Ile Leu Leu Asn His Val Asn Ser Ile Pro Ala Ser
                165                 170                 175 ggc agc ggc atc gtc ccg ggc atg gac cgc aac gac aac ttc atg tcc     576
Gly Ser Gly Ile Val Pro Gly Met Asp Arg Asn Asp Asn Phe Met Ser
            180                 185                 190 gac ttc aag gac atg atg atg gcc tac tac gac ctc tgc tac acg gtg     624
Asp Phe Lys Asp Met Met Met Ala Tyr Tyr Asp Leu Cys Tyr Thr Val
        195                 200                 205 agc atg gac gtg atg cgg cac atc agc tgc ggc ctc ggc atc cgc ccc     672
Ser Met Asp Val Met Arg His Ile Ser Cys Gly Leu Gly Ile Arg Pro
    210                 215                 220 tcc atc ccg caa ggc ggg tcg gac ccg acg atg gac ttc gag ctc gag     720
Ser Ile Pro Gln Gly Gly Ser Asp Pro Thr Met Asp Phe Glu Leu Glu
225                 230                 235                 240 tac ttc acg tcg ttc cac cag aag cgc gac tgc gac ttg caa gcc aag     768
Tyr Phe Thr Ser Phe His Gln Lys Arg Asp Cys Asp Leu Gln Ala Lys
                245                 250                 255 tac tac ccg cag ctc ggg gca ggg gca cga ctc aag aac ggc gtc gac     816
Tyr Tyr Pro Gln Leu Gly Ala Gly Ala Arg Leu Lys Asn Gly Val Asp
            260                 265                 270 atc caa aat cag cgg tcg gcg cac aac ccg gac ggc gtg aaa gtg ctg     864
Ile Gln Asn Gln Arg Ser Ala His Asn Pro Asp Gly Val Lys Val Leu
        275                 280                 285 cgg cgc aag gga gcc aag acg cag cct ctg gtg agg acg gcg agc acc     912
Arg Arg Lys Gly Ala Lys Thr Gln Pro Leu Val Arg Thr Ala Ser Thr
    290                 295                 300 gag gac ggc gat ggt gag aag gac gtg aca gtg cgc ctc gac acg cac     960
Glu Asp Gly Asp Gly Glu Lys Asp Val Thr Val Arg Leu Asp Thr His
305                 310                 315                 320 aaa gac ctc agc acc atc act ctg ctc tcc cag gac tct ctt ggg ggg    1008
Lys Asp Leu Ser Thr Ile Thr Leu Leu Ser Gln Asp Ser Leu Gly Gly
                325                 330                 335 ctg gag gtg tgg gac gag gag aag gcc tcc tat atg gcc gtt ccg gtg    1056
Leu Glu Val Trp Asp Glu Glu Lys Ala Ser Tyr Met Ala Val Pro Val
            340                 345                 350 ctc gag gac gcg ctt ctc gtg aac gcc ggc ttg ttc ctg gag aag tgg    1104
Leu Glu Asp Ala Leu Leu Val Asn Ala Gly Leu Phe Leu Glu Lys Trp
        355                 360                 365 acg ggc ggc ctc atc gag gca aca ccc cac cgc gtg cgc aac gcc aag    1152
Thr Gly Gly Leu Ile Glu Ala Thr Pro His Arg Val Arg Asn Ala Lys
    370                 375                 380 ggc ggc agc agc cgc tgc agc att gtc ttc ttt gcc ctg ccc gac cac    1200
Gly Gly Ser Ser Arg Cys Ser Ile Val Phe Phe Ala Leu Pro Asp His
385                 390                 395                 400 gat gcc cgc atc gag ccg ctc ctg cag caa gaa gac aac ccg gca gtg    1248
Asp Ala Arg Ile Glu Pro Leu Leu Gln Gln Glu Asp Asn Pro Ala Val
                405                 410                 415 gat gcg cag gac agc ttc ctt gca ggt gac atg atg ccc gcc ccg taa    1296
Asp Ala Gln Asp Ser Phe Leu Ala Gly Asp Met Met Pro Ala Pro
```

Asp Ala Gln Asp Ser Phe Leu Ala Gly Asp Met Met Pro Ala Pro
            420                 425                 430

<210> SEQ ID NO 28
<211> LENGTH: 431
<212> TYPE: PRT
<213> ORGANISM: Leishmania major

<400> SEQUENCE: 28

Met Leu Arg Ala Thr Ile Leu Ala Arg Gly Thr Leu Val Lys Ile Gly
1               5                   10                  15

Arg Gly Pro Asn Asn Val Thr Glu Ser Ala Ser Asn Ala Leu Leu Glu
            20                  25                  30

Ser Leu Gln Asp His Gly Tyr Cys Tyr Ile Gln His Pro Phe Ile Gln
        35                  40                  45

Lys Thr Ile Leu Asp Gln Leu His Arg Asp Cys Arg Ile Phe Phe Glu
    50                  55                  60

Gln Tyr Val Leu His Leu His Asp Ala Ala Gln Gly Ser Leu Lys
65                  70                  75                  80

Arg Asn Asn Leu His Asn Tyr Asn Cys Thr Gln Leu Ser Pro Tyr Glu
                85                  90                  95

Leu Glu Ser Ile Lys Ser Pro Ser Gly Phe Arg Gly Tyr Tyr Arg Tyr
            100                 105                 110

Val Gly Ala Ser Gly Ile Asp Asp Ala Ile Glu Cys Phe Ser Val Gly
        115                 120                 125

Arg Asp Asp Val Ala Asp Pro Ala Val Leu Arg Arg Asp Tyr Tyr Lys
    130                 135                 140

Gln Ala Gly Trp Glu Glu Ser Glu Tyr Leu Ser Met Ile Ser Arg Arg
145                 150                 155                 160

Asn Pro Trp Asp Ile Leu Leu Asn His Val Asn Ser Ile Pro Ala Ser
                165                 170                 175

Gly Ser Gly Ile Val Pro Gly Met Asp Arg Asn Asp Asn Phe Met Ser
            180                 185                 190

Asp Phe Lys Asp Met Met Met Ala Tyr Tyr Asp Leu Cys Tyr Thr Val
        195                 200                 205

Ser Met Asp Val Met Arg His Ile Ser Cys Gly Leu Gly Ile Arg Pro
    210                 215                 220

Ser Ile Pro Gln Gly Gly Ser Asp Pro Thr Met Asp Phe Glu Leu Glu
225                 230                 235                 240

Tyr Phe Thr Ser Phe His Gln Lys Arg Asp Cys Asp Leu Gln Ala Lys
                245                 250                 255

Tyr Tyr Pro Gln Leu Gly Ala Gly Ala Arg Leu Lys Asn Gly Val Asp
            260                 265                 270

Ile Gln Asn Gln Arg Ser Ala His Asn Pro Asp Gly Val Lys Val Leu
        275                 280                 285

Arg Arg Lys Gly Ala Lys Thr Gln Pro Leu Val Arg Thr Ala Ser Thr
    290                 295                 300

Glu Asp Gly Asp Gly Glu Lys Asp Val Thr Val Arg Leu Asp Thr His
305                 310                 315                 320

Lys Asp Leu Ser Thr Ile Thr Leu Leu Ser Gln Asp Ser Leu Gly Gly
                325                 330                 335

Leu Glu Val Trp Asp Glu Glu Lys Ala Ser Tyr Met Ala Val Pro Val
            340                 345                 350

Leu Glu Asp Ala Leu Leu Val Asn Ala Gly Leu Phe Leu Glu Lys Trp
        355                 360                 365

-continued

```
Thr Gly Gly Leu Ile Glu Ala Thr Pro His Arg Val Arg Asn Ala Lys
    370                 375                 380

Gly Gly Ser Ser Arg Cys Ser Ile Val Phe Phe Ala Leu Pro Asp His
385                 390                 395                 400

Asp Ala Arg Ile Glu Pro Leu Leu Gln Gln Glu Asp Asn Pro Ala Val
            405                 410                 415

Asp Ala Gln Asp Ser Phe Leu Ala Gly Asp Met Met Pro Ala Pro
        420                 425                 430

<210> SEQ ID NO 29
<211> LENGTH: 1296
<212> TYPE: DNA
<213> ORGANISM: Leishmania infantum
<220> FEATURE:
<221> NAME/KEY: CDS
<222> LOCATION: (1)..(1296)
<220> FEATURE:
<221> NAME/KEY: misc_feature
<222> LOCATION: (74)..(74)
<223> OTHER INFORMATION: n is a, c, g, or t

<400> SEQUENCE: 29 atg ctt cgc gct act act ctt gct cgc ggc acg ctt gta aag atc ggc        48
Met Leu Arg Ala Thr Thr Leu Ala Arg Gly Thr Leu Val Lys Ile Gly
1               5                   10                  15 cgc ggc ccg aac aac gta acg gaa tnt gcc aga aac gcc ctt ctc gaa        96
Arg Gly Pro Asn Asn Val Thr Glu Xaa Ala Arg Asn Ala Leu Leu Glu
            20                  25                  30 tcc cta caa gac cac ggc tac tgc tat atc cag cac ccc ttc att cag       144
Ser Leu Gln Asp His Gly Tyr Cys Tyr Ile Gln His Pro Phe Ile Gln
        35                  40                  45 aag acc atc ctc gat cag ctt cac cgc gat tgc cgc atc ttc ttt gag       192
Lys Thr Ile Leu Asp Gln Leu His Arg Asp Cys Arg Ile Phe Phe Glu
    50                  55                  60 cag tat gtc ctg cac ctg cac gac gct gct gcg cag ggc agc ctg aag       240
Gln Tyr Val Leu His Leu His Asp Ala Ala Ala Gln Gly Ser Leu Lys
65                  70                  75                  80 cgc aac aac ctg cac aac tac aac tgc aca caa ctc tcc ccg tac gaa       288
Arg Asn Asn Leu His Asn Tyr Asn Cys Thr Gln Leu Ser Pro Tyr Glu
                85                  90                  95 ctg gag agc ata aag tcc ccg agt ggg ttc cgc ggc tac tac cgc tac       336
Leu Glu Ser Ile Lys Ser Pro Ser Gly Phe Arg Gly Tyr Tyr Arg Tyr
            100                 105                 110 gtc ggc gcg agc ggc atc gat gac gct atc gag tgc ttc tcc gtt ggc       384
Val Gly Ala Ser Gly Ile Asp Asp Ala Ile Glu Cys Phe Ser Val Gly
        115                 120                 125 cgc gac gac gtg gct gac ccg gca gtg ctg cgg cgc gac tac tac aag       432
Arg Asp Asp Val Ala Asp Pro Ala Val Leu Arg Arg Asp Tyr Tyr Lys
    130                 135                 140 caa gcc ggt tgg gag gag agc gag tac ctg agc atg att agc cgt cgc       480
Gln Ala Gly Trp Glu Glu Ser Glu Tyr Leu Ser Met Ile Ser Arg Arg
145                 150                 155                 160 aac ccg tgg gac atc ttg ctg aac cac gtc aac tca atc ccc gca tcc       528
Asn Pro Trp Asp Ile Leu Leu Asn His Val Asn Ser Ile Pro Ala Ser
                165                 170                 175 ggc agc ggc ctc ggc ccg ggc atg gac cgc aac gac aac ttc atg tcc       576
Gly Ser Gly Leu Gly Pro Gly Met Asp Arg Asn Asp Asn Phe Met Ser
            180                 185                 190 gac ttc aag gac atg atg atg gcc tac tac gac ctc tgc tac acg gtg       624
Asp Phe Lys Asp Met Met Met Ala Tyr Tyr Asp Leu Cys Tyr Thr Val
        195                 200                 205
```

```
agc atg gac gtg atg cgg cac atc agc tgc ggc ctc ggt atc cgc ccc      672
Ser Met Asp Val Met Arg His Ile Ser Cys Gly Leu Gly Ile Arg Pro
    210                 215                 220 tcc atc ccg caa ggc ggg ccg gac ccg acg atg gac ttc gag ctt gag      720
Ser Ile Pro Gln Gly Gly Pro Asp Pro Thr Met Asp Phe Glu Leu Glu
225                 230                 235                 240 tac ttc acg tcg ttc cac cag aag cgc gac tgc gac ttg caa gcc aag      768
Tyr Phe Thr Ser Phe His Gln Lys Arg Asp Cys Asp Leu Gln Ala Lys
                245                 250                 255 tac tac ccg cag ctc ggg gaa ggg gcg cga ctc aag aac ggc gtc gac      816
Tyr Tyr Pro Gln Leu Gly Glu Gly Ala Arg Leu Lys Asn Gly Val Asp
            260                 265                 270 atc caa aat caa cgg tcg gcg cac aac ccg gac ggc gtg aaa gtg ctc      864
Ile Gln Asn Gln Arg Ser Ala His Asn Pro Asp Gly Val Lys Val Leu
        275                 280                 285 cgg cgc aag gga gcc aag atg cag cct ctg gtg agg acg gcg agc gcc      912
Arg Arg Lys Gly Ala Lys Met Gln Pro Leu Val Arg Thr Ala Ser Ala
    290                 295                 300 gag gac ggc gat gat gac aag gac gtg acg gtg cgc ctc gac acg cac      960
Glu Asp Gly Asp Asp Asp Lys Asp Val Thr Val Arg Leu Asp Thr His
305                 310                 315                 320 aaa gac ctc agc acc atc acc ctg ctc tcc cag gac tcg ctt ggg ggg     1008
Lys Asp Leu Ser Thr Ile Thr Leu Leu Ser Gln Asp Ser Leu Gly Gly
                325                 330                 335 ctg gag gtg tgg gac gac gag aag ggc tcc tac atg gcc gtc ccg gtg     1056
Leu Glu Val Trp Asp Asp Glu Lys Gly Ser Tyr Met Ala Val Pro Val
            340                 345                 350 ctc gag gac gcg ctt ctc gtg aac gcc ggc ttg ttc ctg gag aag tgg     1104
Leu Glu Asp Ala Leu Leu Val Asn Ala Gly Leu Phe Leu Glu Lys Trp
        355                 360                 365 acg ggt ggc ctc atc gag gca aca ccc cac cgc gtg cgc aac gcc aag     1152
Thr Gly Gly Leu Ile Glu Ala Thr Pro His Arg Val Arg Asn Ala Lys
    370                 375                 380 ggc ggc agc agc cgc tgc agc att gtc ttc ttt gcc ctg ccc gac cac     1200
Gly Gly Ser Ser Arg Cys Ser Ile Val Phe Phe Ala Leu Pro Asp His
385                 390                 395                 400 gat gcc cgc atc gag ccg ctc ctg cag cag gag gac aat ccg gca gtg     1248
Asp Ala Arg Ile Glu Pro Leu Leu Gln Gln Glu Asp Asn Pro Ala Val
                405                 410                 415 gat gcg cag gac agc ttc ctt gca ggt gac atg atg ccc gcc ccg taa     1296
Asp Ala Gln Asp Ser Phe Leu Ala Gly Asp Met Met Pro Ala Pro
            420                 425                 430

<210> SEQ ID NO 30
<211> LENGTH: 431
<212> TYPE: PRT
<213> ORGANISM: Leishmania infantum
<220> FEATURE:
<221> NAME/KEY: misc_feature
<222> LOCATION: (25)..(25)
<223> OTHER INFORMATION: The 'Xaa' at location 25 stands for Tyr, Cys,
      Ser, or Phe.

<400> SEQUENCE: 30

Met Leu Arg Ala Thr Thr Leu Ala Arg Gly Thr Leu Val Lys Ile Gly
1               5                   10                  15

Arg Gly Pro Asn Asn Val Thr Glu Xaa Ala Arg Asn Ala Leu Leu Glu
            20                  25                  30

Ser Leu Gln Asp His Gly Tyr Cys Tyr Ile Gln His Pro Phe Ile Gln
        35                  40                  45
```

```
Lys Thr Ile Leu Asp Gln Leu His Arg Asp Cys Arg Ile Phe Phe Glu
     50                  55                  60

Gln Tyr Val Leu His Leu His Asp Ala Ala Gln Gly Ser Leu Lys
 65                  70                  75                  80

Arg Asn Asn Leu His Asn Tyr Asn Cys Thr Gln Leu Ser Pro Tyr Glu
                 85                  90                  95

Leu Glu Ser Ile Lys Ser Pro Ser Gly Phe Arg Gly Tyr Tyr Arg Tyr
            100                 105                 110

Val Gly Ala Ser Gly Ile Asp Asp Ala Ile Glu Cys Phe Ser Val Gly
            115                 120                 125

Arg Asp Asp Val Ala Asp Pro Ala Val Leu Arg Arg Asp Tyr Tyr Lys
130                 135                 140

Gln Ala Gly Trp Glu Ser Glu Tyr Leu Ser Met Ile Ser Arg Arg
145                 150                 155                 160

Asn Pro Trp Asp Ile Leu Leu Asn His Val Asn Ser Ile Pro Ala Ser
                165                 170                 175

Gly Ser Gly Leu Gly Pro Gly Met Asp Arg Asn Asp Asn Phe Met Ser
            180                 185                 190

Asp Phe Lys Asp Met Met Met Ala Tyr Tyr Asp Leu Cys Tyr Thr Val
            195                 200                 205

Ser Met Asp Val Met Arg His Ile Ser Cys Gly Leu Gly Ile Arg Pro
210                 215                 220

Ser Ile Pro Gln Gly Gly Pro Asp Pro Thr Met Asp Phe Glu Leu Glu
225                 230                 235                 240

Tyr Phe Thr Ser Phe His Gln Lys Arg Asp Cys Asp Leu Gln Ala Lys
                245                 250                 255

Tyr Tyr Pro Gln Leu Gly Glu Gly Ala Arg Leu Lys Asn Gly Val Asp
            260                 265                 270

Ile Gln Asn Gln Arg Ser Ala His Asn Pro Asp Gly Val Lys Val Leu
            275                 280                 285

Arg Arg Lys Gly Ala Lys Met Gln Pro Leu Val Arg Thr Ala Ser Ala
290                 295                 300

Glu Asp Gly Asp Asp Lys Asp Val Thr Val Arg Leu Asp Thr His
305                 310                 315                 320

Lys Asp Leu Ser Thr Ile Thr Leu Leu Ser Gln Asp Ser Leu Gly Gly
                325                 330                 335

Leu Glu Val Trp Asp Asp Glu Lys Gly Ser Tyr Met Ala Val Pro Val
            340                 345                 350

Leu Glu Asp Ala Leu Leu Val Asn Ala Gly Leu Phe Leu Glu Lys Trp
            355                 360                 365

Thr Gly Gly Leu Ile Glu Ala Thr Pro His Arg Val Arg Asn Ala Lys
370                 375                 380

Gly Gly Ser Ser Arg Cys Ser Ile Val Phe Phe Ala Leu Pro Asp His
385                 390                 395                 400

Asp Ala Arg Ile Glu Pro Leu Leu Gln Gln Glu Asp Asn Pro Ala Val
                405                 410                 415

Asp Ala Gln Asp Ser Phe Leu Ala Gly Asp Met Met Pro Ala Pro
            420                 425                 430

<210> SEQ ID NO 31
<211> LENGTH: 1263
<212> TYPE: DNA
<213> ORGANISM: Trypanosoma brucei
<220> FEATURE:
<221> NAME/KEY: CDS
```

<222> LOCATION: (1)..(1263)

<400> SEQUENCE: 31

| | | | | | | | | | | | | | | | | |
|---|---|---|---|---|---|---|---|---|---|---|---|---|---|---|---|---|
| atg | cgt | cgt | act | ttt | tcg | ctt | ttc | aca | act | ctc | gtt | aga | cta | ggt | cgc | 48 |
| Met | Arg | Arg | Thr | Phe | Ser | Leu | Phe | Thr | Thr | Leu | Val | Arg | Leu | Gly | Arg | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ggg | ccg | gag | aat | gtg | acg | gag | gag | gca | agc | aac | tcg | ctc | ttg | gaa | gcc | 96 |
| Gly | Pro | Glu | Asn | Val | Thr | Glu | Glu | Ala | Ser | Asn | Ser | Leu | Leu | Glu | Ala | |
| | | | 20 | | | | | 25 | | | | | 30 | | | |

| | | | | | | | | | | | | | | | | |
|---|---|---|---|---|---|---|---|---|---|---|---|---|---|---|---|---|
| ctg | caa | aag | cac | ggt | tac | tgc | tac | gtg | cag | cat | ccg | ttt | ata | cag | tgg | 144 |
| Leu | Gln | Lys | His | Gly | Tyr | Cys | Tyr | Val | Gln | His | Pro | Phe | Ile | Gln | Trp | |
| | | 35 | | | | | 40 | | | | | 45 | | | | |

| | | | | | | | | | | | | | | | | |
|---|---|---|---|---|---|---|---|---|---|---|---|---|---|---|---|---|
| gag | ata | tta | gat | caa | gtt | cac | cgc | gat | agt | cgc | atc | ttt | ttt | gag | cgt | 192 |
| Glu | Ile | Leu | Asp | Gln | Val | His | Arg | Asp | Ser | Arg | Ile | Phe | Phe | Glu | Arg | |
| | 50 | | | | | 55 | | | | | 60 | | | | | |

| | | | | | | | | | | | | | | | | |
|---|---|---|---|---|---|---|---|---|---|---|---|---|---|---|---|---|
| tat | ttg | ttg | gac | ctc | ccg | gag | gaa | aag | cag | aga | acg | agg | aaa | gag | aag | 240 |
| Tyr | Leu | Leu | Asp | Leu | Pro | Glu | Glu | Lys | Gln | Arg | Thr | Arg | Lys | Glu | Lys | |
| 65 | | | | | 70 | | | | | 75 | | | | | 80 | |

| | | | | | | | | | | | | | | | | |
|---|---|---|---|---|---|---|---|---|---|---|---|---|---|---|---|---|
| ttc | tcc | aag | aaa | cta | ata | gcc | ccc | cgt | aag | cca | atc | agg | gca | atg | acc | 288 |
| Phe | Ser | Lys | Lys | Leu | Ile | Ala | Pro | Arg | Lys | Pro | Ile | Arg | Ala | Met | Thr | |
| | | | | 85 | | | | | 90 | | | | | 95 | | |

| | | | | | | | | | | | | | | | | |
|---|---|---|---|---|---|---|---|---|---|---|---|---|---|---|---|---|
| cca | tac | gaa | tta | gaa | agc | att | aaa | aca | tcc | tcg | ggt | ttc | cgg | ggg | tat | 336 |
| Pro | Tyr | Glu | Leu | Glu | Ser | Ile | Lys | Thr | Ser | Ser | Gly | Phe | Arg | Gly | Tyr | |
| | | | 100 | | | | | 105 | | | | | 110 | | | |

| | | | | | | | | | | | | | | | | |
|---|---|---|---|---|---|---|---|---|---|---|---|---|---|---|---|---|
| tac | cgt | tac | att | ggc | gca | ggc | ggc | gtg | gat | gat | gcg | atc | gag | tgc | ttt | 384 |
| Tyr | Arg | Tyr | Ile | Gly | Ala | Gly | Gly | Val | Asp | Asp | Ala | Ile | Glu | Cys | Phe | |
| | | 115 | | | | | 120 | | | | | 125 | | | | |

| | | | | | | | | | | | | | | | | |
|---|---|---|---|---|---|---|---|---|---|---|---|---|---|---|---|---|
| tcc | gtt | ggc | cgc | gag | gtg | cag | agc | ccc | gtg | gaa | tta | cgg | gaa | ccg | tac | 432 |
| Ser | Val | Gly | Arg | Glu | Val | Gln | Ser | Pro | Val | Glu | Leu | Arg | Glu | Pro | Tyr | |
| | 130 | | | | | 135 | | | | | 140 | | | | | |

| | | | | | | | | | | | | | | | | |
|---|---|---|---|---|---|---|---|---|---|---|---|---|---|---|---|---|
| tac | aga | ttg | agc | ggt | tgg | caa | cgc | gat | gag | tat | ttg | cca | ctg | att | agc | 480 |
| Tyr | Arg | Leu | Ser | Gly | Trp | Gln | Arg | Asp | Glu | Tyr | Leu | Pro | Leu | Ile | Ser | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| cgg | aga | aat | gcg | tgg | gat | tca | ctt | cta | act | cac | cct | aag | gat | ggt | agt | 528 |
| Arg | Arg | Asn | Ala | Trp | Asp | Ser | Leu | Leu | Thr | His | Pro | Lys | Asp | Gly | Ser | |
| | | | | 165 | | | | | 170 | | | | | 175 | | |

| | | | | | | | | | | | | | | | | |
|---|---|---|---|---|---|---|---|---|---|---|---|---|---|---|---|---|
| gga | gac | ccc | aat | ggt | gtg | cac | gcc | ttc | atg | gca | gat | tat | cgt | gag | atg | 576 |
| Gly | Asp | Pro | Asn | Gly | Val | His | Ala | Phe | Met | Ala | Asp | Tyr | Arg | Glu | Met | |
| | | | 180 | | | | | 185 | | | | | 190 | | | |

| | | | | | | | | | | | | | | | | |
|---|---|---|---|---|---|---|---|---|---|---|---|---|---|---|---|---|
| ata | ctg | gcg | tat | tat | gac | ctt | tgc | agc | gag | gtc | gcc | ctc | gat | gtg | ctg | 624 |
| Ile | Leu | Ala | Tyr | Tyr | Asp | Leu | Cys | Ser | Glu | Val | Ala | Leu | Asp | Val | Leu | |
| | | 195 | | | | | 200 | | | | | 205 | | | | |

| | | | | | | | | | | | | | | | | |
|---|---|---|---|---|---|---|---|---|---|---|---|---|---|---|---|---|
| cgg | cat | ata | agt | tgt | ggt | ttg | ggc | gtc | aga | ccc | agc | att | cca | cag | ggt | 672 |
| Arg | His | Ile | Ser | Cys | Gly | Leu | Gly | Val | Arg | Pro | Ser | Ile | Pro | Gln | Gly | |
| | 210 | | | | | 215 | | | | | 220 | | | | | |

| | | | | | | | | | | | | | | | | |
|---|---|---|---|---|---|---|---|---|---|---|---|---|---|---|---|---|
| ggt | cct | gat | cct | gat | agc | gga | tac | gat | ctc | gaa | tac | ttc | aca | cag | ttc | 720 |
| Gly | Pro | Asp | Pro | Asp | Ser | Gly | Tyr | Asp | Leu | Glu | Tyr | Phe | Thr | Gln | Phe | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| cac | aac | aaa | ctt | gac | ttc | gac | tta | caa | gca | aag | tat | tat | ccg | agg | ttc | 768 |
| His | Asn | Lys | Leu | Asp | Phe | Asp | Leu | Gln | Ala | Lys | Tyr | Tyr | Pro | Arg | Phe | |
| | | | | 245 | | | | | 250 | | | | | 255 | | |

| | | | | | | | | | | | | | | | | |
|---|---|---|---|---|---|---|---|---|---|---|---|---|---|---|---|---|
| gga | caa | ggg | gct | cgg | aca | cgt | ggt | ggt | gta | gag | gtt | aag | gga | gtg | cag | 816 |
| Gly | Gln | Gly | Ala | Arg | Thr | Arg | Gly | Gly | Val | Glu | Val | Lys | Gly | Val | Gln | |
| | | | 260 | | | | | 265 | | | | | 270 | | | |

| | | | | | | | | | | | | | | | | |
|---|---|---|---|---|---|---|---|---|---|---|---|---|---|---|---|---|
| agc | gcc | tcg | aac | ccc | aag | ggt | gta | aaa | gtt | cta | cgt | cgc | aag | aca | gct | 864 |
| Ser | Ala | Ser | Asn | Pro | Lys | Gly | Val | Lys | Val | Leu | Arg | Arg | Lys | Thr | Ala | |
| | | 275 | | | | | 280 | | | | | 285 | | | | |

| | | | | | | | | | | | | | | | | |
|---|---|---|---|---|---|---|---|---|---|---|---|---|---|---|---|---|
| cga | gga | caa | ccg | ttg | gtt | aat | gaa | gat | gaa | gaa | aac | gcc | gtg | ttg | cgg | 912 |
| Arg | Gly | Gln | Pro | Leu | Val | Asn | Glu | Asp | Glu | Glu | Asn | Ala | Val | Leu | Arg | |
| | 290 | | | | | 295 | | | | | 300 | | | | | |

```
ctg gat tcg cac aag gac ctc agt act gtc aca ctc ctc gca cag gac    960
Leu Asp Ser His Lys Asp Leu Ser Thr Val Thr Leu Leu Ala Gln Asp
305                 310                 315                 320 gct ctc ggt gga ttg gag gtt tgg gac aat gag tcg gaa cag ttc aat   1008
Ala Leu Gly Gly Leu Glu Val Trp Asp Asn Glu Ser Glu Gln Phe Asn
                325                 330                 335 ccg gtc cct gtg ctg aat gat gca ttg ctt gta aac gcg ggg ttg ttc   1056
Pro Val Pro Val Leu Asn Asp Ala Leu Leu Val Asn Ala Gly Leu Phe
        340                 345                 350 ctt gag aag tgg act ggc ggg ttg tta gag gcg aca ccg cat cga gtg   1104
Leu Glu Lys Trp Thr Gly Gly Leu Leu Glu Ala Thr Pro His Arg Val
355                 360                 365 cgg aac gtg aga ggc gga agt agt cga tgt agt gtt gtc ttc ttc tgc   1152
Arg Asn Val Arg Gly Gly Ser Ser Arg Cys Ser Val Val Phe Phe Cys
    370                 375                 380 tta cct aac cat gac gcc cgg ata gag ccc cta ctg cag cga gat gaa   1200
Leu Pro Asn His Asp Ala Arg Ile Glu Pro Leu Leu Gln Arg Asp Glu
385                 390                 395                 400 aat cct tct ctt gac gcg gaa gaa ggt ttc tac gcg ggt gat cta atg   1248
Asn Pro Ser Leu Asp Ala Glu Glu Gly Phe Tyr Ala Gly Asp Leu Met
                405                 410                 415 cca gca gca cct taa                                                1263
Pro Ala Ala Pro
        420

<210> SEQ ID NO 32
<211> LENGTH: 420
<212> TYPE: PRT
<213> ORGANISM: Trypanosoma brucei

<400> SEQUENCE: 32

Met Arg Arg Thr Phe Ser Leu Phe Thr Thr Leu Val Arg Leu Gly Arg
1               5                   10                  15

Gly Pro Glu Asn Val Thr Glu Glu Ala Ser Asn Ser Leu Leu Glu Ala
            20                  25                  30

Leu Gln Lys His Gly Tyr Cys Tyr Val Gln His Pro Phe Ile Gln Trp
        35                  40                  45

Glu Ile Leu Asp Gln Val His Arg Asp Ser Arg Ile Phe Phe Glu Arg
    50                  55                  60

Tyr Leu Leu Asp Leu Pro Glu Glu Lys Gln Arg Thr Arg Lys Glu Lys
65                  70                  75                  80

Phe Ser Lys Lys Leu Ile Ala Pro Arg Lys Pro Ile Arg Ala Met Thr
                85                  90                  95

Pro Tyr Glu Leu Glu Ser Ile Lys Thr Ser Ser Gly Phe Arg Gly Tyr
            100                 105                 110

Tyr Arg Tyr Ile Gly Ala Gly Val Asp Asp Ala Ile Glu Cys Phe
        115                 120                 125

Ser Val Gly Arg Glu Val Gln Ser Pro Val Glu Leu Arg Glu Pro Tyr
    130                 135                 140

Tyr Arg Leu Ser Gly Trp Gln Arg Asp Glu Tyr Leu Pro Leu Ile Ser
145                 150                 155                 160

Arg Arg Asn Ala Trp Asp Ser Leu Leu Thr His Pro Lys Asp Gly Ser
                165                 170                 175

Gly Asp Pro Asn Gly Val His Ala Phe Met Ala Asp Tyr Arg Glu Met
            180                 185                 190

Ile Leu Ala Tyr Tyr Asp Leu Cys Ser Glu Val Ala Leu Asp Val Leu
        195                 200                 205
```

```
Arg His Ile Ser Cys Gly Leu Gly Val Arg Pro Ser Ile Pro Gln Gly
    210                 215                 220

Gly Pro Asp Pro Asp Ser Gly Tyr Asp Leu Glu Tyr Phe Thr Gln Phe
225                 230                 235                 240

His Asn Lys Leu Asp Phe Asp Leu Gln Ala Lys Tyr Tyr Pro Arg Phe
                245                 250                 255

Gly Gln Gly Ala Arg Thr Arg Gly Val Glu Val Lys Gly Val Gln
                260                 265                 270

Ser Ala Ser Asn Pro Lys Gly Val Lys Val Leu Arg Arg Lys Thr Ala
            275                 280                 285

Arg Gly Gln Pro Leu Val Asn Glu Asp Glu Asn Ala Val Leu Arg
        290                 295                 300

Leu Asp Ser His Lys Asp Leu Ser Thr Val Thr Leu Ala Gln Asp
305                 310                 315                 320

Ala Leu Gly Gly Leu Glu Val Trp Asp Asn Glu Ser Glu Gln Phe Asn
                325                 330                 335

Pro Val Pro Val Leu Asn Asp Ala Leu Leu Val Asn Ala Gly Leu Phe
                340                 345                 350

Leu Glu Lys Trp Thr Gly Gly Leu Leu Glu Ala Thr Pro His Arg Val
            355                 360                 365

Arg Asn Val Arg Gly Gly Ser Ser Arg Cys Ser Val Val Phe Phe Cys
370                 375                 380

Leu Pro Asn His Asp Ala Arg Ile Glu Pro Leu Leu Gln Arg Asp Glu
385                 390                 395                 400

Asn Pro Ser Leu Asp Ala Glu Glu Gly Phe Tyr Ala Gly Asp Leu Met
                405                 410                 415

Pro Ala Ala Pro
            420

<210> SEQ ID NO 33
<211> LENGTH: 1944
<212> TYPE: DNA
<213> ORGANISM: Trypanosoma cruzi
<220> FEATURE:
<221> NAME/KEY: CDS
<222> LOCATION: (1)..(1944)

<400> SEQUENCE: 33 atg cgc act tct tct gcc gtg tct ttt ttt ctt ctt gct gtg gcc gcc      48
Met Arg Thr Ser Ser Ala Val Ser Phe Phe Leu Leu Ala Val Ala Ala
1               5                   10                  15 gtg tta ttc tcg ccg ttt gtt gcg gat gcc ttt tac att ccg ggc atg      96
Val Leu Phe Ser Pro Phe Val Ala Asp Ala Phe Tyr Ile Pro Gly Met
            20                  25                  30 cag ccc aag tac tac agc gag ggc gag act gtg cca ttt atg gtg aat    144
Gln Pro Lys Tyr Tyr Ser Glu Gly Glu Thr Val Pro Phe Met Val Asn
        35                  40                  45 tcc ctc cgc tcc ttg aag gag ttg ttt cca cag ggc tac tac aat ctg    192
Ser Leu Arg Ser Leu Lys Glu Leu Phe Pro Gln Gly Tyr Tyr Asn Leu
    50                  55                  60 ccc ttt tgt gcg ccc gag ttc atc aag acg aag cca gag gcc ctt ggg    240
Pro Phe Cys Ala Pro Glu Phe Ile Lys Thr Lys Pro Glu Ala Leu Gly
65                  70                  75                  80 gag gtc ata tgg gga gac cgc ata cag aac tct ctt tac tcg gtg aac    288
Glu Val Ile Trp Gly Asp Arg Ile Gln Asn Ser Leu Tyr Ser Val Asn
                85                  90                  95 atg aag aaa aac tca acc tgc aca aaa ctc ccc gat tgc gac gtg gtg    336
```

|     |     |     |     |     |     |     |     |     |     |     |     |     |
| --- | --- | --- | --- | --- | --- | --- | --- | --- | --- | --- | --- | --- |
| Met | Lys | Lys | Asn | Ser | Thr | Cys | Thr | Lys | Leu | Pro | Asp | Cys | Asp | Val | Val |
|     |     |     |     | 100 |     |     |     | 105 |     |     |     | 110 |

```
gct aac aat cgc aac atc agg aat aat att gat aag ctg gag aag tac      384
Ala Asn Asn Arg Asn Ile Arg Asn Asn Ile Asp Lys Leu Glu Lys Tyr
            115                 120                 125 att gaa aaa ggc tac cga ggc ttt atg aac gtt gat aat ctt ccc gtc      432
Ile Glu Lys Gly Tyr Arg Gly Phe Met Asn Val Asp Asn Leu Pro Val
130                 135                 140 ttt ggg gat ggg ctg ccc gag tat ctt gct tcc tgt aag ttt caa tca      480
Phe Gly Asp Gly Leu Pro Glu Tyr Leu Ala Ser Cys Lys Phe Gln Ser
145                 150                 155                 160 aaa gac atg cag tac aac tac tat cgc ggc tac ccc atc ggt gtc cca      528
Lys Asp Met Gln Tyr Asn Tyr Tyr Arg Gly Tyr Pro Ile Gly Val Pro
            165                 170                 175 cgt cag tgc gcg ggc aag aca ctt atc aac aat cac ctg gat ttt gtc      576
Arg Gln Cys Ala Gly Lys Thr Leu Ile Asn Asn His Leu Asp Phe Val
            180                 185                 190 att gac tac aac acc gct cca agg gac agc gaa aag ttc atg gtt gtc      624
Ile Asp Tyr Asn Thr Ala Pro Arg Asp Ser Glu Lys Phe Met Val Val
            195                 200                 205 ggt cta agg gtt act ccc cac agc att aag cac gat ata ggt gga aat      672
Gly Leu Arg Val Thr Pro His Ser Ile Lys His Asp Ile Gly Gly Asn
210                 215                 220 agc tgt agt gag gct ctg gta ttc cgg cgg ggt gag atg aac ttt ctc      720
Ser Cys Ser Glu Ala Leu Val Phe Arg Arg Gly Glu Met Asn Phe Leu
225                 230                 235                 240 agc aca gat gat gtg cgt gag ggc gca acg gtg tat tgg acg tac agt      768
Ser Thr Asp Asp Val Arg Glu Gly Ala Thr Val Tyr Trp Thr Tyr Ser
                    245                 250                 255 gtc aca tgg cag cct tcc aat gtt att tgg gca aca cgt tgg gac gcc      816
Val Thr Trp Gln Pro Ser Asn Val Ile Trp Ala Thr Arg Trp Asp Ala
            260                 265                 270 tat ctt cat agc tca att gcg gat act agt gct agt ttt cat tgg ctt      864
Tyr Leu His Ser Ser Ile Ala Asp Thr Ser Ala Ser Phe His Trp Leu
            275                 280                 285 tac gtt tgc ggt agc tta ctg ata gtt atc ttg tgc gcc acc tcc gtc      912
Tyr Val Cys Gly Ser Leu Leu Ile Val Ile Leu Cys Ala Thr Ser Val
290                 295                 300 gcc acg gta ttg atg cgt gcc tta cac aaa gat ttt aac cgt tac aat      960
Ala Thr Val Leu Met Arg Ala Leu His Lys Asp Phe Asn Arg Tyr Asn
305                 310                 315                 320 tcc ctt gat cct gag gat aat cag gag gag acc ggt tgg aaa ctc gta     1008
Ser Leu Asp Pro Glu Asp Asn Gln Glu Glu Thr Gly Trp Lys Leu Val
                325                 330                 335 cat gcc gac gtg ttc cgt ccc cca gat cga gca cca ctg ctg gcc tca     1056
His Ala Asp Val Phe Arg Pro Pro Asp Arg Ala Pro Leu Leu Ala Ser
            340                 345                 350 ctc acg ggt act ggt ttc cag gtg tta tcc atg ttc acc ggt gtg ttg     1104
Leu Thr Gly Thr Gly Phe Gln Val Leu Ser Met Phe Thr Gly Val Leu
            355                 360                 365 ctc ttt gcg ctg ttg ggt ttt ctt tcc cct gca cga cgt ggt gct ctt     1152
Leu Phe Ala Leu Leu Gly Phe Leu Ser Pro Ala Arg Arg Gly Ala Leu
370                 375                 380 ttg act gcc atc atc att ctc ttt gtg ttt atg tcc act gtg gct gga     1200
Leu Thr Ala Ile Ile Ile Leu Phe Val Phe Met Ser Thr Val Ala Gly
385                 390                 395                 400 tac gta tgt ggg ttc ctg ctt aaa tat ttt aat cgt cgt gaa tgg aag     1248
Tyr Val Cys Gly Phe Leu Leu Lys Tyr Phe Asn Arg Arg Glu Trp Lys
                405                 410                 415
```

| | | | | | | | | | | | | | | | | |
|---|---|---|---|---|---|---|---|---|---|---|---|---|---|---|---|---|
| cac | gtg | ttc | ttc | tgc | ggt | tgt | gca | ttc | cct | ggg | act | gtt | ttt | ggt | gtc | 1296 |
| His | Val | Phe | Phe | Cys | Gly | Cys | Ala | Phe | Pro | Gly | Thr | Val | Phe | Gly | Val | |
| | | | | 420 | | | | 425 | | | | | 430 | | | |
| tac | gcc | ttt | gcg | aac | atg | atc | aat | tgg | gct | cac | ggc | tcc | aca | gac | acc | 1344 |
| Tyr | Ala | Phe | Ala | Asn | Met | Ile | Asn | Trp | Ala | His | Gly | Ser | Thr | Asp | Thr | |
| | | 435 | | | | 440 | | | | | 445 | | | | | |
| gta | tcc | ttc | tcc | gtc | ctt | ttc | acc | att | ttc | ttg | ctg | tgg | atg | ctg | atc | 1392 |
| Val | Ser | Phe | Ser | Val | Leu | Phe | Thr | Ile | Phe | Leu | Leu | Trp | Met | Leu | Ile | |
| | 450 | | | | | 455 | | | | | 460 | | | | | |
| agt | ctg | cca | ctg | acc | ttt | ttg | ggc | gcc | tcc | ttc | tcg | ttt | agg | cag | gac | 1440 |
| Ser | Leu | Pro | Leu | Thr | Phe | Leu | Gly | Ala | Ser | Phe | Ser | Phe | Arg | Gln | Asp | |
| 465 | | | | | 470 | | | | | 475 | | | | | 480 | |
| cca | cct | gca | aac | cct | gtg | aga | gta | ggc | cgt | ctg | gcg | cgt | gag | atc | cca | 1488 |
| Pro | Pro | Ala | Asn | Pro | Val | Arg | Val | Gly | Arg | Leu | Ala | Arg | Glu | Ile | Pro | |
| | | | | 485 | | | | | 490 | | | | | 495 | | |
| cca | cag | atg | tgg | gca | aac | agt | ccc | tcg | ttt | ctg | tac | gtc | att | cct | ccc | 1536 |
| Pro | Gln | Met | Trp | Ala | Asn | Ser | Pro | Ser | Phe | Leu | Tyr | Val | Ile | Pro | Pro | |
| | | | 500 | | | | | 505 | | | | | 510 | | | |
| ata | ttt | cct | ctt | tcc | aca | atc | atc | ttg | gag | ttg | aat | ttc | gta | ctg | cag | 1584 |
| Ile | Phe | Pro | Leu | Ser | Thr | Ile | Ile | Leu | Glu | Leu | Asn | Phe | Val | Leu | Gln | |
| | | 515 | | | | | 520 | | | | | 525 | | | | |
| gcg | ctg | tgg | gcc | ggc | cag | gtg | tat | tac | gtg | ttc | ggt | ttt | ctt | gcg | ctg | 1632 |
| Ala | Leu | Trp | Ala | Gly | Gln | Val | Tyr | Tyr | Val | Phe | Gly | Phe | Leu | Ala | Leu | |
| | 530 | | | | | 535 | | | | | 540 | | | | | |
| gtt | ttt | ctt | ctt | tgg | atc | gcc | att | aca | gcc | ctc | atg | acg | gtt | ttc | cac | 1680 |
| Val | Phe | Leu | Leu | Trp | Ile | Ala | Ile | Thr | Ala | Leu | Met | Thr | Val | Phe | His | |
| 545 | | | | | 550 | | | | | 555 | | | | | 560 | |
| ctt | tac | tac | gtc | ttg | tgt | tac | gag | aac | cat | cag | tgg | tgg | tgg | atc | agt | 1728 |
| Leu | Tyr | Tyr | Val | Leu | Cys | Tyr | Glu | Asn | His | Gln | Trp | Trp | Trp | Ile | Ser | |
| | | | | 565 | | | | | 570 | | | | | 575 | | |
| ttt | att | ctc | tcg | gga | gga | cta | gga | ata | cat | gtt | ttt | att | tac | tcg | atc | 1776 |
| Phe | Ile | Leu | Ser | Gly | Gly | Leu | Gly | Ile | His | Val | Phe | Ile | Tyr | Ser | Ile | |
| | | | 580 | | | | | 585 | | | | | 590 | | | |
| tac | ttc | tac | tgc | acg | cag | ctc | gca | atc | agc | tcg | ttt | gcc | tca | tcg | cta | 1824 |
| Tyr | Phe | Tyr | Cys | Thr | Gln | Leu | Ala | Ile | Ser | Ser | Phe | Ala | Ser | Ser | Leu | |
| | | 595 | | | | | 600 | | | | | 605 | | | | |
| ctg | tac | ttt | atg | tac | atg | ggg | ctg | ctt | tca | tgt | gca | tac | ggc | ctt | gca | 1872 |
| Leu | Tyr | Phe | Met | Tyr | Met | Gly | Leu | Leu | Ser | Cys | Ala | Tyr | Gly | Leu | Ala | |
| | 610 | | | | | 615 | | | | | 620 | | | | | |
| gca | ggg | gcg | att | gga | ctc | act | tct | ggc | ata | tgt | ttt | gta | cgc | aca | ata | 1920 |
| Ala | Gly | Ala | Ile | Gly | Leu | Thr | Ser | Gly | Ile | Cys | Phe | Val | Arg | Thr | Ile | |
| 625 | | | | | 630 | | | | | 635 | | | | | 640 | |
| tac | gcg | agc | att | aaa | gtc | gac | tga | | | | | | | | | 1944 |
| Tyr | Ala | Ser | Ile | Lys | Val | Asp | | | | | | | | | | |
| | | | | 645 | | | | | | | | | | | | |

<210> SEQ ID NO 34
<211> LENGTH: 647
<212> TYPE: PRT
<213> ORGANISM: Trypanosoma cruzi

<400> SEQUENCE: 34

Met Arg Thr Ser Ser Ala Val Ser Phe Phe Leu Leu Ala Val Ala Ala
1               5                   10                  15

Val Leu Phe Ser Pro Phe Val Ala Asp Ala Phe Tyr Ile Pro Gly Met
                20                  25                  30

Gln Pro Lys Tyr Tyr Ser Glu Gly Glu Thr Val Pro Phe Met Val Asn
            35                  40                  45

Ser Leu Arg Ser Leu Lys Glu Leu Phe Pro Gln Gly Tyr Tyr Asn Leu
        50                  55                  60

```
Pro Phe Cys Ala Pro Glu Phe Ile Lys Thr Lys Pro Glu Ala Leu Gly
 65                  70                  75                  80

Glu Val Ile Trp Gly Asp Arg Ile Gln Asn Ser Leu Tyr Ser Val Asn
                 85                  90                  95

Met Lys Lys Asn Ser Thr Cys Thr Lys Leu Pro Asp Cys Asp Val Val
                100                 105                 110

Ala Asn Asn Arg Asn Ile Arg Asn Asn Ile Asp Lys Leu Glu Lys Tyr
                115                 120                 125

Ile Glu Lys Gly Tyr Arg Gly Phe Met Asn Val Asp Asn Leu Pro Val
        130                 135                 140

Phe Gly Asp Gly Leu Pro Glu Tyr Leu Ala Ser Cys Lys Phe Gln Ser
145                 150                 155                 160

Lys Asp Met Gln Tyr Asn Tyr Tyr Arg Gly Tyr Pro Ile Gly Val Pro
                165                 170                 175

Arg Gln Cys Ala Gly Lys Thr Leu Ile Asn Asn His Leu Asp Phe Val
                180                 185                 190

Ile Asp Tyr Asn Thr Ala Pro Arg Asp Ser Glu Lys Phe Met Val Val
        195                 200                 205

Gly Leu Arg Val Thr Pro His Ser Ile Lys His Asp Ile Gly Gly Asn
210                 215                 220

Ser Cys Ser Glu Ala Leu Val Phe Arg Arg Gly Glu Met Asn Phe Leu
225                 230                 235                 240

Ser Thr Asp Asp Val Arg Glu Gly Ala Thr Val Tyr Trp Thr Tyr Ser
                245                 250                 255

Val Thr Trp Gln Pro Ser Asn Val Ile Trp Ala Thr Arg Trp Asp Ala
                260                 265                 270

Tyr Leu His Ser Ser Ile Ala Asp Thr Ser Ala Ser Phe His Trp Leu
        275                 280                 285

Tyr Val Cys Gly Ser Leu Leu Ile Val Ile Leu Cys Ala Thr Ser Val
290                 295                 300

Ala Thr Val Leu Met Arg Ala Leu His Lys Asp Phe Asn Arg Tyr Asn
305                 310                 315                 320

Ser Leu Asp Pro Glu Asp Asn Gln Glu Glu Thr Gly Trp Lys Leu Val
                325                 330                 335

His Ala Asp Val Phe Arg Pro Pro Asp Arg Ala Pro Leu Leu Ala Ser
                340                 345                 350

Leu Thr Gly Thr Gly Phe Gln Val Leu Ser Met Phe Thr Gly Val Leu
        355                 360                 365

Leu Phe Ala Leu Leu Gly Phe Leu Ser Pro Ala Arg Arg Gly Ala Leu
370                 375                 380

Leu Thr Ala Ile Ile Ile Leu Phe Val Phe Met Ser Thr Val Ala Gly
385                 390                 395                 400

Tyr Val Cys Gly Phe Leu Leu Lys Tyr Phe Asn Arg Arg Glu Trp Lys
                405                 410                 415

His Val Phe Phe Cys Gly Cys Ala Phe Pro Gly Thr Val Phe Gly Val
                420                 425                 430

Tyr Ala Phe Ala Asn Met Ile Asn Trp Ala His Gly Ser Thr Asp Thr
        435                 440                 445

Val Ser Phe Ser Val Leu Phe Thr Ile Phe Leu Leu Trp Met Leu Ile
        450                 455                 460

Ser Leu Pro Leu Thr Phe Leu Gly Ala Ser Phe Ser Phe Arg Gln Asp
465                 470                 475                 480
```

```
Pro Pro Ala Asn Pro Val Arg Val Gly Arg Leu Ala Arg Glu Ile Pro
                485                 490                 495

Pro Gln Met Trp Ala Asn Ser Pro Ser Phe Leu Tyr Val Ile Pro Pro
        500                 505                 510

Ile Phe Pro Leu Ser Thr Ile Ile Leu Glu Leu Asn Phe Val Leu Gln
            515                 520                 525

Ala Leu Trp Ala Gly Gln Val Tyr Tyr Val Phe Gly Phe Leu Ala Leu
        530                 535                 540

Val Phe Leu Leu Trp Ile Ala Ile Thr Ala Leu Met Thr Val Phe His
545                 550                 555                 560

Leu Tyr Tyr Val Leu Cys Tyr Glu Asn His Gln Trp Trp Trp Ile Ser
                565                 570                 575

Phe Ile Leu Ser Gly Gly Leu Gly Ile His Val Phe Ile Tyr Ser Ile
            580                 585                 590

Tyr Phe Tyr Cys Thr Gln Leu Ala Ile Ser Ser Phe Ala Ser Ser Leu
        595                 600                 605

Leu Tyr Phe Met Tyr Met Gly Leu Leu Ser Cys Ala Tyr Gly Leu Ala
    610                 615                 620

Ala Gly Ala Ile Gly Leu Thr Ser Gly Ile Cys Phe Val Arg Thr Ile
625                 630                 635                 640

Tyr Ala Ser Ile Lys Val Asp
                645

<210> SEQ ID NO 35
<211> LENGTH: 2043
<212> TYPE: DNA
<213> ORGANISM: Leishmania major
<220> FEATURE:
<221> NAME/KEY: CDS
<222> LOCATION: (1)..(2043)

<400> SEQUENCE: 35 atg tcg gct tcc acc caa cat gcg cac tcc cac tgc agc agc aac ggt      48
Met Ser Ala Ser Thr Gln His Ala His Ser His Cys Ser Ser Asn Gly
1               5                   10                  15 ggt gcg agg cct cca ctg ctg ctg ctg ctc acc ctg ctg gtg gcg cta      96
Gly Ala Arg Pro Pro Leu Leu Leu Leu Leu Thr Leu Leu Val Ala Leu
            20                  25                  30 cag ctg ctg gcc gcg ggc gcg acc cct gca agc gcc ttc tat gtg ccg     144
Gln Leu Leu Ala Ala Gly Ala Thr Pro Ala Ser Ala Phe Tyr Val Pro
        35                  40                  45 ggc gcc gca gag aaa tcg tac aag aaa ggc gaa gcc gtg aaa ttc atg     192
Gly Ala Ala Glu Lys Ser Tyr Lys Lys Gly Glu Ala Val Lys Phe Met
    50                  55                  60 gtg aat tcg ctg cga tcc tcg tcg gag atg ttt ccc atc gac tac tca     240
Val Asn Ser Leu Arg Ser Ser Ser Glu Met Phe Pro Ile Asp Tyr Ser
65                  70                  75                  80 aag atg ccg ttt tgt cag ccg gca agg cag gag ttc aag gag gag tcc     288
Lys Met Pro Phe Cys Gln Pro Ala Arg Gln Glu Phe Lys Glu Glu Ser
                85                  90                  95 att ggc gag atc atc tgg ggt gac cgc gtg ctc aac tcc ctg tac acc     336
Ile Gly Glu Ile Ile Trp Gly Asp Arg Val Leu Asn Ser Leu Tyr Thr
            100                 105                 110 gtc aag atg aag gaa gat ggg aag tgt atg act ctc ccc gat tgc gac     384
Val Lys Met Lys Glu Asp Gly Lys Cys Met Thr Leu Pro Asp Cys Asp
        115                 120                 125 ttc atc gcc aac acc gag acg att cgc cgc aag gag tcg aag aac ctc     432
Phe Ile Ala Asn Thr Glu Thr Ile Arg Arg Lys Glu Ser Lys Asn Leu
    130                 135                 140
```

```
aca aag atg atc aat aaa tgg tac cgt gtg tac atg aac att gac aac    480
Thr Lys Met Ile Asn Lys Trp Tyr Arg Val Tyr Met Asn Ile Asp Asn
145                 150                 155                 160 ttg ccc gtc ttc tcc acc aac ccg gag agc aca cag atg agc gag tgc    528
Leu Pro Val Phe Ser Thr Asn Pro Glu Ser Thr Gln Met Ser Glu Cys
                165                 170                 175 gcg aag aag ctc ggc aag gac atc aag atc tac gca cag cga ggg ttc    576
Ala Lys Lys Leu Gly Lys Asp Ile Lys Ile Tyr Ala Gln Arg Gly Phe
            180                 185                 190 ccg ctc ggt ctc ccg gcc aaa tgc acg agt gac agg gcg gcg ctg cta    624
Pro Leu Gly Leu Pro Ala Lys Cys Thr Ser Asp Arg Ala Ala Leu Leu
        195                 200                 205 aac aat cac ctt gat ttc acg att cac tac aac cgc gac agc aag acg    672
Asn Asn His Leu Asp Phe Thr Ile His Tyr Asn Arg Asp Ser Lys Thr
    210                 215                 220 acc agc acg acg gcg gaa gag gaa agg aag tat atc gtt gtt ttt atc    720
Thr Ser Thr Thr Ala Glu Glu Glu Arg Lys Tyr Ile Val Val Phe Ile
225                 230                 235                 240 gac gtc aag gcc aga agc atc gct tgg agc gac ccc cta gag tgc aac    768
Asp Val Lys Ala Arg Ser Ile Ala Trp Ser Asp Pro Leu Glu Cys Asn
                245                 250                 255 agc gag atg aaa gtc gcg ccg gag gtt ctc gcg cca atg cgc ggc ctc    816
Ser Glu Met Lys Val Ala Pro Glu Val Leu Ala Pro Met Arg Gly Leu
            260                 265                 270 aag atg aag gac gtg atg cag aac aag acg acg gtg tac tgg acg tac    864
Lys Met Lys Asp Val Met Gln Asn Lys Thr Thr Val Tyr Trp Thr Tyr
        275                 280                 285 agc gtc cag tgg aag gag agc ccg aac gtt aag tgg gcg acg cgc tgg    912
Ser Val Gln Trp Lys Glu Ser Pro Asn Val Lys Trp Ala Thr Arg Trp
    290                 295                 300 gac ttc tac ctc aca gcc gcc gcc gct gcc gca ccc gct ggc cac att    960
Asp Phe Tyr Leu Thr Ala Ala Ala Ala Ala Ala Pro Ala Gly His Ile
305                 310                 315                 320 ctc ttt atc atc ctc tcg ctc atg gtg gtg ctg ttt att ggc agt gcg    1008
Leu Phe Ile Ile Leu Ser Leu Met Val Val Leu Phe Ile Gly Ser Ala
                325                 330                 335 gtg atg ggg gtt ctg cta agg gcg ctg cac aaa gac ttt aac cgc tac    1056
Val Met Gly Val Leu Leu Arg Ala Leu His Lys Asp Phe Asn Arg Tyr
            340                 345                 350 aac tcc gaa gac cca gag gac ttg cag gag gag gtg gga tgg aag ctg    1104
Asn Ser Glu Asp Pro Glu Asp Leu Gln Glu Glu Val Gly Trp Lys Leu
        355                 360                 365 gtt cac gcc gac gtg ttc cgc ccg cca ctt tat gca aac tgg ctt gcc    1152
Val His Ala Asp Val Phe Arg Pro Pro Leu Tyr Ala Asn Trp Leu Ala
    370                 375                 380 atc ttc gtc gcc aac ggt gtc caa atc ctc acg act gtt ggg gtg gtg    1200
Ile Phe Val Ala Asn Gly Val Gln Ile Leu Thr Thr Val Gly Val Val
385                 390                 395                 400 ctc atc ata gcg ctc atg ggc ttc ctc tct ccc tct cgg cgc ggc gcg    1248
Leu Ile Ile Ala Leu Met Gly Phe Leu Ser Pro Ser Arg Arg Gly Ala
                405                 410                 415 ctc ctc acg aca ctg ctg ctg acc gcc gtc ttc acg tcg ctc att agc    1296
Leu Leu Thr Thr Leu Leu Leu Thr Ala Val Phe Thr Ser Leu Ile Ser
            420                 425                 430 ggc tat gtc tgc ggt gtg ctg ctg cag tac ctc aac tgc cgt gcg tgg    1344
Gly Tyr Val Cys Gly Val Leu Leu Gln Tyr Leu Asn Cys Arg Ala Trp
        435                 440                 445 aaa cac att ttc atg tgc agc ttc aca ctg ccc ggt gcg atg ctg ctc    1392
Lys His Ile Phe Met Cys Ser Phe Thr Leu Pro Gly Ala Met Leu Leu
```

```
                 450                 455                 460
atc tac atc ttc atc ctc atc atc aac aag gcg cac ggc gcc act act   1440
Ile Tyr Ile Phe Ile Leu Ile Ile Asn Lys Ala His Gly Ala Thr Thr
465                 470                 475                 480 gcc atc ccg ttc atg acg ctg ttg gag gtg ctg acg ctt ttt gtg gcg   1488
Ala Ile Pro Phe Met Thr Leu Leu Glu Val Leu Thr Leu Phe Val Ala
                485                 490                 495 gtg agc ctg ccg ctg acg gtg ctg ggc ggc tcc ata gcc ttc cgc caa   1536
Val Ser Leu Pro Leu Thr Val Leu Gly Gly Ser Ile Ala Phe Arg Gln
            500                 505                 510 caa ccg atc acg aac ccg acg cgg gtc ggt cgt ctc gct cgc gag atc   1584
Gln Pro Ile Thr Asn Pro Thr Arg Val Gly Arg Leu Ala Arg Glu Ile
            515                 520                 525 ccg aca caa agc tgg ctc aac aag ccc atg ttc atc tgc gtc ttc tgg   1632
Pro Thr Gln Ser Trp Leu Asn Lys Pro Met Phe Ile Cys Val Phe Trp
        530                 535                 540 ccc tct gtt ccg ctt gtc gtc atc gtg atc gag ctc tac tac atc atg   1680
Pro Ser Val Pro Leu Val Val Ile Val Ile Glu Leu Tyr Tyr Ile Met
545                 550                 555                 560 caa gac cta tgg gag gga cag atc tat tac tcc ttc ggc ttc ctc acc   1728
Gln Asp Leu Trp Glu Gly Gln Ile Tyr Tyr Ser Phe Gly Phe Leu Thr
                565                 570                 575 gtg acg gcg tgc att tgg gtt ctc atc tgc gct ctt gtc acg gtg tcg   1776
Val Thr Ala Cys Ile Trp Val Leu Ile Cys Ala Leu Val Thr Val Ser
            580                 585                 590 tgc ctg tac tac gtt ctt tgc tac gag aat cat cgc tgg tgg tgg att   1824
Cys Leu Tyr Tyr Val Leu Cys Tyr Glu Asn His Arg Trp Trp Trp Ile
            595                 600                 605 gcg tac ctc gta ccc ggc ggt gct ggt gtc cac atg ctc tgc atg tcc   1872
Ala Tyr Leu Val Pro Gly Gly Ala Gly Val His Met Leu Cys Met Ser
        610                 615                 620 ctc att ttt ttc atg tct cac att tcc gtg agc agc ttc gcc tct gcg   1920
Leu Ile Phe Phe Met Ser His Ile Ser Val Ser Ser Phe Ala Ser Ala
625                 630                 635                 640 gtg ctt ttc ttt ttc tac atg ggg atg gtg tcg tac atg tac gga atg   1968
Val Leu Phe Phe Phe Tyr Met Gly Met Val Ser Tyr Met Tyr Gly Met
                645                 650                 655 gcg gct ggt gcc gtc ggc gtg att gtc tcc atc gcg ttc gtg cgc agg   2016
Ala Ala Gly Ala Val Gly Val Ile Val Ser Ile Ala Phe Val Arg Arg
            660                 665                 670 atc tac ggc agc atc aag att gac tag                               2043
Ile Tyr Gly Ser Ile Lys Ile Asp
        675                 680

<210> SEQ ID NO 36
<211> LENGTH: 680
<212> TYPE: PRT
<213> ORGANISM: Leishmania major

<400> SEQUENCE: 36

Met Ser Ala Ser Thr Gln His Ala His Ser His Cys Ser Ser Asn Gly
1               5                   10                  15

Gly Ala Arg Pro Pro Leu Leu Leu Leu Thr Leu Leu Val Ala Leu
            20                  25                  30

Gln Leu Leu Ala Ala Gly Ala Thr Pro Ala Ser Ala Phe Tyr Val Pro
        35                  40                  45

Gly Ala Ala Glu Lys Ser Tyr Lys Lys Gly Glu Ala Val Lys Phe Met
    50                  55                  60

Val Asn Ser Leu Arg Ser Ser Ser Glu Met Phe Pro Ile Asp Tyr Ser
```

```
              65                  70                  75                  80
Lys Met Pro Phe Cys Gln Pro Ala Arg Gln Glu Phe Lys Glu Glu Ser
                     85                  90                  95

Ile Gly Glu Ile Ile Trp Gly Asp Arg Val Leu Asn Ser Leu Tyr Thr
                    100                 105                 110

Val Lys Met Lys Glu Asp Gly Lys Cys Met Thr Leu Pro Asp Cys Asp
                    115                 120                 125

Phe Ile Ala Asn Thr Glu Thr Ile Arg Arg Lys Glu Ser Lys Asn Leu
        130                 135                 140

Thr Lys Met Ile Asn Lys Trp Tyr Arg Val Tyr Met Asn Ile Asp Asn
145                 150                 155                 160

Leu Pro Val Phe Ser Thr Asn Pro Glu Ser Thr Gln Met Ser Glu Cys
                    165                 170                 175

Ala Lys Lys Leu Gly Lys Asp Ile Lys Ile Tyr Ala Gln Arg Gly Phe
                    180                 185                 190

Pro Leu Gly Leu Pro Ala Lys Cys Thr Ser Asp Arg Ala Ala Leu Leu
                    195                 200                 205

Asn Asn His Leu Asp Phe Thr Ile His Tyr Asn Arg Asp Ser Lys Thr
        210                 215                 220

Thr Ser Thr Thr Ala Glu Glu Arg Lys Tyr Ile Val Val Phe Ile
225                 230                 235                 240

Asp Val Lys Ala Arg Ser Ile Ala Trp Ser Asp Pro Leu Glu Cys Asn
                    245                 250                 255

Ser Glu Met Lys Val Ala Pro Glu Val Leu Ala Pro Met Arg Gly Leu
                    260                 265                 270

Lys Met Lys Asp Val Met Gln Asn Lys Thr Thr Val Tyr Trp Thr Tyr
                    275                 280                 285

Ser Val Gln Trp Lys Glu Ser Pro Asn Val Lys Trp Ala Thr Arg Trp
                    290                 295                 300

Asp Phe Tyr Leu Thr Ala Ala Ala Ala Ala Pro Ala Gly His Ile
305                 310                 315                 320

Leu Phe Ile Ile Leu Ser Leu Met Val Val Leu Phe Ile Gly Ser Ala
                    325                 330                 335

Val Met Gly Val Leu Leu Arg Ala Leu His Lys Asp Phe Asn Arg Tyr
                    340                 345                 350

Asn Ser Glu Asp Pro Glu Asp Leu Gln Glu Glu Val Gly Trp Lys Leu
                    355                 360                 365

Val His Ala Asp Val Phe Arg Pro Pro Leu Tyr Ala Asn Trp Leu Ala
        370                 375                 380

Ile Phe Val Ala Asn Gly Val Gln Ile Leu Thr Thr Val Gly Val Val
385                 390                 395                 400

Leu Ile Ile Ala Leu Met Gly Phe Leu Ser Pro Ser Arg Arg Gly Ala
                    405                 410                 415

Leu Leu Thr Thr Leu Leu Leu Thr Ala Val Phe Thr Ser Leu Ile Ser
                    420                 425                 430

Gly Tyr Val Cys Gly Val Leu Leu Gln Tyr Leu Asn Cys Arg Ala Trp
                    435                 440                 445

Lys His Ile Phe Met Cys Ser Phe Thr Leu Pro Gly Ala Met Leu Leu
        450                 455                 460

Ile Tyr Ile Phe Ile Leu Ile Ile Asn Lys Ala His Gly Ala Thr Thr
465                 470                 475                 480

Ala Ile Pro Phe Met Thr Leu Leu Glu Val Leu Thr Leu Phe Val Ala
                    485                 490                 495
```

```
Val Ser Leu Pro Leu Thr Val Leu Gly Gly Ser Ile Ala Phe Arg Gln
        500                 505                 510

Gln Pro Ile Thr Asn Pro Thr Arg Val Gly Arg Leu Ala Arg Glu Ile
        515                 520                 525

Pro Thr Gln Ser Trp Leu Asn Lys Pro Met Phe Ile Cys Val Phe Trp
        530                 535                 540

Pro Ser Val Pro Leu Val Val Ile Val Ile Glu Leu Tyr Tyr Ile Met
545                 550                 555                 560

Gln Asp Leu Trp Glu Gly Gln Ile Tyr Tyr Ser Phe Gly Phe Leu Thr
                565                 570                 575

Val Thr Ala Cys Ile Trp Val Leu Ile Cys Ala Leu Val Thr Val Ser
                580                 585                 590

Cys Leu Tyr Tyr Val Leu Cys Tyr Glu Asn His Arg Trp Trp Trp Ile
                595                 600                 605

Ala Tyr Leu Val Pro Gly Gly Ala Gly Val His Met Leu Cys Met Ser
        610                 615                 620

Leu Ile Phe Phe Met Ser His Ile Ser Val Ser Ser Phe Ala Ser Ala
625                 630                 635                 640

Val Leu Phe Phe Tyr Met Gly Met Val Ser Tyr Met Tyr Gly Met
                645                 650                 655

Ala Ala Gly Ala Val Gly Val Ile Val Ser Ile Ala Phe Val Arg Arg
        660                 665                 670

Ile Tyr Gly Ser Ile Lys Ile Asp
        675                 680

<210> SEQ ID NO 37
<211> LENGTH: 2043
<212> TYPE: DNA
<213> ORGANISM: Leishmania infantum
<220> FEATURE:
<221> NAME/KEY: CDS
<222> LOCATION: (1)..(2043)

<400> SEQUENCE: 37 atg tcg gtt tcc acc cag cat gcg cgc tcc cac tgc agc agc aac gca      48
Met Ser Val Ser Thr Gln His Ala Arg Ser His Cys Ser Ser Asn Ala
1               5                   10                  15 ggt gcg agg cct cca ctg ctg ctg ctc acc ctg ctg gtg gtg cta           96
Gly Ala Arg Pro Pro Leu Leu Leu Leu Thr Leu Leu Val Val Leu
            20                  25                  30 cag ctg ctg gcc gcg ggc gcg acc cct gca agc gcc ttt tat gtg cct     144
Gln Leu Leu Ala Ala Gly Ala Thr Pro Ala Ser Ala Phe Tyr Val Pro
        35                  40                  45 ggc gca gca gag aaa gcg tac aag aaa ggc gaa aag gtg aaa ttc atg     192
Gly Ala Ala Glu Lys Ala Tyr Lys Lys Gly Glu Lys Val Lys Phe Met
    50                  55                  60 gtg aac tcg ttg cga tcc tcg tcg gag atg ttt ccc atc gac tac tca     240
Val Asn Ser Leu Arg Ser Ser Ser Glu Met Phe Pro Ile Asp Tyr Ser
65                  70                  75                  80 aag atg ccg ttc tgt cag ccg gcg agg cag gag ttc aag gag gag tcc     288
Lys Met Pro Phe Cys Gln Pro Ala Arg Gln Glu Phe Lys Glu Glu Ser
                85                  90                  95 att ggc gag atc ata tgg ggt gac cgc atg ctc aac tcc ctg tac acc     336
Ile Gly Glu Ile Ile Trp Gly Asp Arg Met Leu Asn Ser Leu Tyr Thr
            100                 105                 110 gtc agg atg aag gaa gat gtg aag tgc atg gct ctc ccc gat tgc gac     384
Val Arg Met Lys Glu Asp Val Lys Cys Met Ala Leu Pro Asp Cys Asp
        115                 120                 125
```

```
ttc atc gcc aac acc gag aca att cgc cgc aag gag tcg aag aac ctc      432
Phe Ile Ala Asn Thr Glu Thr Ile Arg Arg Lys Glu Ser Lys Asn Leu
    130                 135                 140 aca aag atg atc aat aaa tgg tac cgt gtg tac atg aac atc gac aac      480
Thr Lys Met Ile Asn Lys Trp Tyr Arg Val Tyr Met Asn Ile Asp Asn
145                 150                 155                 160 ttg ccc gtc ttc tcc acc aac ccg gaa agc aca cag atg agc gag tgc      528
Leu Pro Val Phe Ser Thr Asn Pro Glu Ser Thr Gln Met Ser Glu Cys
                165                 170                 175 gcc aag aaa ctc ggc aag gac gtc aag atc tac gca cag cga ggg ttc      576
Ala Lys Lys Leu Gly Lys Asp Val Lys Ile Tyr Ala Gln Arg Gly Phe
            180                 185                 190 ccg ctc ggt gtc ccg gcc aaa tgc acg agc gac cgg gcg gcg ctg cta      624
Pro Leu Gly Val Pro Ala Lys Cys Thr Ser Asp Arg Ala Ala Leu Leu
        195                 200                 205 aac aat cac ctt gat ttc acg att cac tac aac cac gac agc cag acg      672
Asn Asn His Leu Asp Phe Thr Ile His Tyr Asn His Asp Ser Gln Thr
    210                 215                 220 acc agc acg aca gca gag gag gaa agg agg tat atc gtg gtc ttt atc      720
Thr Ser Thr Thr Ala Glu Glu Glu Arg Arg Tyr Ile Val Val Phe Ile
225                 230                 235                 240 gac gtc aag gcc aga agc atc gct tgg agc gac tcc cta gag tgc aac      768
Asp Val Lys Ala Arg Ser Ile Ala Trp Ser Asp Ser Leu Glu Cys Asn
                245                 250                 255 agc cag atg aaa gtc gcg ccg gag gtt ctc gcg cca atg cgc ggc ctc      816
Ser Gln Met Lys Val Ala Pro Glu Val Leu Ala Pro Met Arg Gly Leu
            260                 265                 270 aag atg aag aat gtt acg cag aac aag gcg acg gtg tac tgg acg tac      864
Lys Met Lys Asn Val Thr Gln Asn Lys Ala Thr Val Tyr Trp Thr Tyr
        275                 280                 285 agc gtc aag tgg aag gag aac ccg aac gtt aag tgg gcg acg cgc tgg      912
Ser Val Lys Trp Lys Glu Asn Pro Asn Val Lys Trp Ala Thr Arg Trp
    290                 295                 300 gac ttc tac ctc act gcc gcc gcc gct gcc gca ccc gct ggc cac atc      960
Asp Phe Tyr Leu Thr Ala Ala Ala Ala Ala Ala Pro Ala Gly His Ile
305                 310                 315                 320 ctc ttt atc atc ctc tcg ctc gtg gtg gtg ctg ttc att ggc agc gcg     1008
Leu Phe Ile Ile Leu Ser Leu Val Val Val Leu Phe Ile Gly Ser Ala
                325                 330                 335 gtg atg ggg gtt ctg cta agg gcg ctg cac aag gac ttt aac cgc tac     1056
Val Met Gly Val Leu Leu Arg Ala Leu His Lys Asp Phe Asn Arg Tyr
            340                 345                 350 aac tcc gaa gac cca gag gac ttg caa gag gag gtg gga tgg aag ctg     1104
Asn Ser Glu Asp Pro Glu Asp Leu Gln Glu Glu Val Gly Trp Lys Leu
        355                 360                 365 gtt cac gcc gac gtg ttc cgc ccg cca ctt tac gca aac tgg ctt gcc     1152
Val His Ala Asp Val Phe Arg Pro Pro Leu Tyr Ala Asn Trp Leu Ala
    370                 375                 380 atc ttc gtc gcc aac ggt gtc caa atc ctc acg act gtt ggg gtg gtg     1200
Ile Phe Val Ala Asn Gly Val Gln Ile Leu Thr Thr Val Gly Val Val
385                 390                 395                 400 cta atc ata gcg ctt atg ggc ttc ctc tcc ccc tct cgg cgc ggt gct     1248
Leu Ile Ile Ala Leu Met Gly Phe Leu Ser Pro Ser Arg Arg Gly Ala
                405                 410                 415 ctc ctc acg aca atg ctg ctg acc gcc gtc ttc acg tcg ctc att agc     1296
Leu Leu Thr Thr Met Leu Leu Thr Ala Val Phe Thr Ser Leu Ile Ser
            420                 425                 430 ggc tat gtc tgc ggt gtg ctg ctg cag tac ctc aac tgc cgt gca tgg     1344
Gly Tyr Val Cys Gly Val Leu Leu Gln Tyr Leu Asn Cys Arg Ala Trp
```

```
                 435                 440                 445
aaa aac att ttc acg tgc agc ttc aca ctg ccg ggt gca atg ctg ctc    1392
Lys Asn Ile Phe Thr Cys Ser Phe Thr Leu Pro Gly Ala Met Leu Leu
450                 455                 460 atc tac att ttc atc ctc atc atc aac aag gcg cac ggc gcc act act    1440
Ile Tyr Ile Phe Ile Leu Ile Ile Asn Lys Ala His Gly Ala Thr Thr
465                 470                 475                 480 gcc atc ccg ttc atg acg ctg ttg gag atg ctg acg ctc ttc gtg gcg    1488
Ala Ile Pro Phe Met Thr Leu Leu Glu Met Leu Thr Leu Phe Val Ala
                485                 490                 495 gtg agc ctg ccg ctg acg gtg ttg gga ggc tcc gtg gcc ttc cgc cag    1536
Val Ser Leu Pro Leu Thr Val Leu Gly Gly Ser Val Ala Phe Arg Gln
            500                 505                 510 cag ccc atc acg aac ccg acg cgg gtc ggt cgc ctc gct cgc gag atc    1584
Gln Pro Ile Thr Asn Pro Thr Arg Val Gly Arg Leu Ala Arg Glu Ile
        515                 520                 525 ccg aca caa agc tgg atc aat cag ccc att ttc atc tgc gtc ttc tgg    1632
Pro Thr Gln Ser Trp Ile Asn Gln Pro Ile Phe Ile Cys Val Phe Trp
    530                 535                 540 cca tct gtt ccg ctt gtc gtc gtc gtg atc gag ctc tac tac atc atg    1680
Pro Ser Val Pro Leu Val Val Val Val Ile Glu Leu Tyr Tyr Ile Met
545                 550                 555                 560 caa gat ctg tgg gag gga cag atc tat tac tcc ttc ggc ttc ctc acc    1728
Gln Asp Leu Trp Glu Gly Gln Ile Tyr Tyr Ser Phe Gly Phe Leu Thr
                565                 570                 575 gtg acg gcg tgc att tgg gta ctc gtc tgc gct ctc gtc acg ata tcg    1776
Val Thr Ala Cys Ile Trp Val Leu Val Cys Ala Leu Val Thr Ile Ser
            580                 585                 590 tgc ctg tac tac gtt ctt tgc tac gag aat cat cgc tgg tgg tgg att    1824
Cys Leu Tyr Tyr Val Leu Cys Tyr Glu Asn His Arg Trp Trp Trp Ile
        595                 600                 605 gcg tac ctc gtg ccc ggc ggt gcc ggt gtt cac atg ttc tgc atg tcg    1872
Ala Tyr Leu Val Pro Gly Gly Ala Gly Val His Met Phe Cys Met Ser
    610                 615                 620 ctc att ttt ttc atg tct cac gtc tcc gtg agc agc ttc gcc tct gcg    1920
Leu Ile Phe Phe Met Ser His Val Ser Val Ser Ser Phe Ala Ser Ala
625                 630                 635                 640 gtg ctt ttc ttt tcc tac atg ggg atg gtg tcg tat atg tac gga atg    1968
Val Leu Phe Phe Ser Tyr Met Gly Met Val Ser Tyr Met Tyr Gly Met
                645                 650                 655 gcg gct ggt gcc gtc ggc gtg atc gtc tcc atc gtg ttc gtg cgc agg    2016
Ala Ala Gly Ala Val Gly Val Ile Val Ser Ile Val Phe Val Arg Arg
            660                 665                 670 atc tac ggc agc atc aag att gac tag                                2043
Ile Tyr Gly Ser Ile Lys Ile Asp
        675                 680

<210> SEQ ID NO 38
<211> LENGTH: 680
<212> TYPE: PRT
<213> ORGANISM: Leishmania infantum

<400> SEQUENCE: 38

Met Ser Val Ser Thr Gln His Ala Arg Ser His Cys Ser Ser Asn Ala
1               5                   10                  15

Gly Ala Arg Pro Pro Leu Leu Leu Leu Thr Leu Leu Val Val Leu
            20                  25                  30

Gln Leu Leu Ala Ala Gly Ala Thr Pro Ala Ser Ala Phe Tyr Val Pro
        35                  40                  45
```

-continued

```
Gly Ala Ala Glu Lys Ala Tyr Lys Lys Gly Glu Lys Val Lys Phe Met
     50                  55                  60

Val Asn Ser Leu Arg Ser Ser Glu Met Phe Pro Ile Asp Tyr Ser
 65                  70                  75                  80

Lys Met Pro Phe Cys Gln Pro Ala Arg Gln Glu Phe Lys Glu Ser
                 85                  90                  95

Ile Gly Glu Ile Ile Trp Gly Asp Arg Met Leu Asn Ser Leu Tyr Thr
                100                 105                 110

Val Arg Met Lys Glu Asp Val Lys Cys Met Ala Leu Pro Asp Cys Asp
             115                 120                 125

Phe Ile Ala Asn Thr Glu Thr Ile Arg Arg Lys Glu Ser Lys Asn Leu
130                 135                 140

Thr Lys Met Ile Asn Lys Trp Tyr Arg Val Tyr Met Asn Ile Asp Asn
145                 150                 155                 160

Leu Pro Val Phe Ser Thr Asn Pro Glu Ser Thr Gln Met Ser Glu Cys
                165                 170                 175

Ala Lys Lys Leu Gly Lys Asp Val Lys Ile Tyr Ala Gln Arg Gly Phe
                180                 185                 190

Pro Leu Gly Val Pro Ala Lys Cys Thr Ser Asp Arg Ala Ala Leu Leu
            195                 200                 205

Asn Asn His Leu Asp Phe Thr Ile His Tyr Asn His Asp Ser Gln Thr
210                 215                 220

Thr Ser Thr Thr Ala Glu Glu Arg Arg Tyr Ile Val Val Phe Ile
225                 230                 235                 240

Asp Val Lys Ala Arg Ser Ile Ala Trp Ser Asp Ser Leu Glu Cys Asn
                245                 250                 255

Ser Gln Met Lys Val Ala Pro Glu Val Leu Ala Pro Met Arg Gly Leu
            260                 265                 270

Lys Met Lys Asn Val Thr Gln Asn Lys Ala Thr Val Tyr Trp Thr Tyr
        275                 280                 285

Ser Val Lys Trp Lys Glu Asn Pro Asn Val Lys Trp Ala Thr Arg Trp
    290                 295                 300

Asp Phe Tyr Leu Thr Ala Ala Ala Ala Ala Pro Ala Gly His Ile
305                 310                 315                 320

Leu Phe Ile Ile Leu Ser Leu Val Val Leu Phe Ile Gly Ser Ala
                325                 330                 335

Val Met Gly Val Leu Leu Arg Ala Leu His Lys Asp Phe Asn Arg Tyr
            340                 345                 350

Asn Ser Glu Asp Pro Glu Asp Leu Gln Glu Glu Val Gly Trp Lys Leu
        355                 360                 365

Val His Ala Asp Val Phe Arg Pro Pro Leu Tyr Ala Asn Trp Leu Ala
    370                 375                 380

Ile Phe Val Ala Asn Gly Val Gln Ile Leu Thr Thr Val Gly Val Val
385                 390                 395                 400

Leu Ile Ile Ala Leu Met Gly Phe Leu Ser Pro Ser Arg Arg Gly Ala
                405                 410                 415

Leu Leu Thr Thr Met Leu Leu Thr Ala Val Phe Thr Ser Leu Ile Ser
            420                 425                 430

Gly Tyr Val Cys Gly Val Leu Leu Gln Tyr Leu Asn Cys Arg Ala Trp
        435                 440                 445

Lys Asn Ile Phe Thr Cys Ser Phe Thr Leu Pro Gly Ala Met Leu Leu
    450                 455                 460

Ile Tyr Ile Phe Ile Leu Ile Ile Asn Lys Ala His Gly Ala Thr Thr
```

```
                465                 470                 475                 480
Ala Ile Pro Phe Met Thr Leu Leu Glu Met Leu Thr Leu Phe Val Ala
                    485                 490                 495

Val Ser Leu Pro Leu Thr Val Leu Gly Gly Ser Val Ala Phe Arg Gln
                500                 505                 510

Gln Pro Ile Thr Asn Pro Thr Arg Val Gly Arg Leu Ala Arg Glu Ile
            515                 520                 525

Pro Thr Gln Ser Trp Ile Asn Gln Pro Ile Phe Ile Cys Val Phe Trp
        530                 535                 540

Pro Ser Val Pro Leu Val Val Val Ile Glu Leu Tyr Tyr Ile Met
545                 550                 555                 560

Gln Asp Leu Trp Glu Gly Gln Ile Tyr Tyr Ser Phe Gly Phe Leu Thr
                565                 570                 575

Val Thr Ala Cys Ile Trp Val Leu Val Cys Ala Leu Val Thr Ile Ser
                580                 585                 590

Cys Leu Tyr Tyr Val Leu Cys Tyr Glu Asn His Arg Trp Trp Trp Ile
            595                 600                 605

Ala Tyr Leu Val Pro Gly Gly Ala Gly Val His Met Phe Cys Met Ser
        610                 615                 620

Leu Ile Phe Phe Met Ser His Val Ser Val Ser Ser Phe Ala Ser Ala
625                 630                 635                 640

Val Leu Phe Phe Ser Tyr Met Gly Met Val Ser Tyr Met Tyr Gly Met
                645                 650                 655

Ala Ala Gly Ala Val Gly Val Ile Val Ser Ile Val Phe Val Arg Arg
            660                 665                 670

Ile Tyr Gly Ser Ile Lys Ile Asp
        675                 680

<210> SEQ ID NO 39
<211> LENGTH: 2190
<212> TYPE: DNA
<213> ORGANISM: Trypanosoma brucei
<220> FEATURE:
<221> NAME/KEY: CDS
<222> LOCATION: (1)..(2190)

<400> SEQUENCE: 39 atg ctt cgc ggt gcg tgg ctc tat ttg gtg cat tct att ttt tct ctg     48
Met Leu Arg Gly Ala Trp Leu Tyr Leu Val His Ser Ile Phe Ser Leu
1               5                   10                  15 act tcc att gaa tcc agt ttt tcg ttc ttg agc tct ttt act aac cgc     96
Thr Ser Ile Glu Ser Ser Phe Ser Phe Leu Ser Ser Phe Thr Asn Arg
            20                  25                  30 ttt cac ctc tca cct tct ctg ttg acc cac atc ttt gtt tcc ctc act    144
Phe His Leu Ser Pro Ser Leu Leu Thr His Ile Phe Val Ser Leu Thr
        35                  40                  45 tac acc caa aac aac aac att aaa gaa acc ttc tct tca ctt att ttg    192
Tyr Thr Gln Asn Asn Asn Ile Lys Glu Thr Phe Ser Ser Leu Ile Leu
    50                  55                  60 agc gta tcg cca ttt ttt ttt tta cat att tac cca cgt gcg cac gcg    240
Ser Val Ser Pro Phe Phe Phe Leu His Ile Tyr Pro Arg Ala His Ala
65                  70                  75                  80 gag gcg gtc gga atg act cgc ttc tcg tgt gtt gcg ctt ggc gtc ttt    288
Glu Ala Val Gly Met Thr Arg Phe Ser Cys Val Ala Leu Gly Val Phe
                85                  90                  95 gcc ttc ctc atc tct gca ttg gct gtg act gac gcc ttt tac att cca    336
Ala Phe Leu Ile Ser Ala Leu Ala Val Thr Asp Ala Phe Tyr Ile Pro
            100                 105                 110
```

```
ggt gtt caa ccc agg tac tat gct gaa ggt gac gag gtt cat ttt tgg      384
Gly Val Gln Pro Arg Tyr Tyr Ala Glu Gly Asp Glu Val His Phe Trp
        115                 120                 125 gtg aac tca ctt cgc tca ctt cag gtg ttg ttc cca aag gag tac tac      432
Val Asn Ser Leu Arg Ser Leu Gln Val Leu Phe Pro Lys Glu Tyr Tyr
    130                 135                 140 acg ctt ccc ttc tgt agg ccg agt gaa atc att aca aag gac gag tcc      480
Thr Leu Pro Phe Cys Arg Pro Ser Glu Ile Ile Thr Lys Asp Glu Ser
145                 150                 155                 160 atc ggt gaa atc ata tgg gga gat cgt ata cag aat tcc ttg tac gtc      528
Ile Gly Glu Ile Ile Trp Gly Asp Arg Ile Gln Asn Ser Leu Tyr Val
                165                 170                 175 aca aac atg aag aaa aac acg aac tgt acc gtg ctt cca aac tgt gac      576
Thr Asn Met Lys Lys Asn Thr Asn Cys Thr Val Leu Pro Asn Cys Asp
            180                 185                 190 gca gtt gcc aac act aag acc att ttg agt aat ata gat gac ttg gag      624
Ala Val Ala Asn Thr Lys Thr Ile Leu Ser Asn Ile Asp Asp Leu Glu
        195                 200                 205 ggc tcc att gaa aag ggg tat cgc ggt ttc atg aac atc gac aac ctt      672
Gly Ser Ile Glu Lys Gly Tyr Arg Gly Phe Met Asn Ile Asp Asn Leu
    210                 215                 220 ccc gtt ttc gga gag gtg cca ccg gac ttg ctt gct cat tgt gcc tcc      720
Pro Val Phe Gly Glu Val Pro Pro Asp Leu Leu Ala His Cys Ala Ser
225                 230                 235                 240 gtc cca aag gac atg cgt cac act ttc tac cgc ggc tat tgg att ggc      768
Val Pro Lys Asp Met Arg His Thr Phe Tyr Arg Gly Tyr Trp Ile Gly
                245                 250                 255 acg ccc agt gcc tgc acc ggt aaa aca ctc att aac aat cac ctt gaa      816
Thr Pro Ser Ala Cys Thr Gly Lys Thr Leu Ile Asn Asn His Leu Glu
            260                 265                 270 ttt gtg atc aag tac aat cat gcc cct cat gac cct aac aaa ttc atg      864
Phe Val Ile Lys Tyr Asn His Ala Pro His Asp Pro Asn Lys Phe Met
        275                 280                 285 gta gtt gga ctt aag gcc acg cct tat agc atc aaa cac agt gat gac      912
Val Val Gly Leu Lys Ala Thr Pro Tyr Ser Ile Lys His Ser Asp Asp
    290                 295                 300 ggg ctg agt tgt aat gcg gat atg tcc gcc act ggg agc gcg tta gac      960
Gly Leu Ser Cys Asn Ala Asp Met Ser Ala Thr Gly Ser Ala Leu Asp
305                 310                 315                 320 tat ctt acc acc gat gat gtg cgt ggg gga gcc gtt gtg cac tgg tcg     1008
Tyr Leu Thr Thr Asp Asp Val Arg Gly Gly Ala Val Val His Trp Ser
                325                 330                 335 tat ggc gtc aaa tgg gag aaa tct gat gtt att tgg gcc acc cgg tgg     1056
Tyr Gly Val Lys Trp Glu Lys Ser Asp Val Ile Trp Ala Thr Arg Trp
            340                 345                 350 gat gaa tac ctc cac agc tcg gtt gca gat tcc agt cct gca ttt cac     1104
Asp Glu Tyr Leu His Ser Ser Val Ala Asp Ser Ser Pro Ala Phe His
        355                 360                 365 tgg ctt tat gtc tgc agc agt tta gtt gtc gtg ctc atg tgt gcc gcc     1152
Trp Leu Tyr Val Cys Ser Ser Leu Val Val Val Leu Met Cys Ala Ala
    370                 375                 380 tct gtc gca acc att ctc atg cgt act ctc cac aag gac ttc agc cgc     1200
Ser Val Ala Thr Ile Leu Met Arg Thr Leu His Lys Asp Phe Ser Arg
385                 390                 395                 400 tac aac tcc ccc gtt ctg gaa gat ggt gag gag gaa agc ggt tgg aag     1248
Tyr Asn Ser Pro Val Leu Glu Asp Gly Glu Glu Glu Ser Gly Trp Lys
                405                 410                 415 ctt gtt cat gct gat gtg ttt cgg ccg cca gac cgc gcc cca ctg ctt     1296
Leu Val His Ala Asp Val Phe Arg Pro Pro Asp Arg Ala Pro Leu Leu
```

-continued

```
              420                 425                 430
gcc gcc cta act gga aat ggg tac cag gtg ttg ggc atg agc gcc gga    1344
Ala Ala Leu Thr Gly Asn Gly Tyr Gln Val Leu Gly Met Ser Ala Gly
            435                 440                 445 aca atg tta ttt gct ttg ctt ggt ttc ctt tct ccc gcc cgc cgc ggt    1392
Thr Met Leu Phe Ala Leu Leu Gly Phe Leu Ser Pro Ala Arg Arg Gly
450                 455                 460 gct ctt ttg agt gct gtt ata ttt ctg ttc gtg ttt atg tca gtt gtg    1440
Ala Leu Leu Ser Ala Val Ile Phe Leu Phe Val Phe Met Ser Val Val
465                 470                 475                 480 tct ggg tac gtg tgc ggc ttc ttg ctc aag tac ttt gga cga tgt gag    1488
Ser Gly Tyr Val Cys Gly Phe Leu Leu Lys Tyr Phe Gly Arg Cys Glu
            485                 490                 495 tgg aag cac atc ttt ttc tgc ggc tgc gcc ttc cct ggc gcc atc gtt    1536
Trp Lys His Ile Phe Phe Cys Gly Cys Ala Phe Pro Gly Ala Ile Val
            500                 505                 510 ggc gtc tac acc ttc gcc aat atc atc aat tat tcc cat ggc tct tcg    1584
Gly Val Tyr Thr Phe Ala Asn Ile Ile Asn Tyr Ser His Gly Ser Ser
            515                 520                 525 gga acg att cca ttt tcg ctc ttg ttt att cta ctg tcg ctg tgg att    1632
Gly Thr Ile Pro Phe Ser Leu Leu Phe Ile Leu Leu Ser Leu Trp Ile
530                 535                 540 ctt atc agt gtt cca ctt acc gtc ctc ggc gcc tcg ttc tca ttc cgc    1680
Leu Ile Ser Val Pro Leu Thr Val Leu Gly Ala Ser Phe Ser Phe Arg
545                 550                 555                 560 cag gag tcc ctc gct aat cct gtc gct gtt ggc cgt tta gcg cgc gag    1728
Gln Glu Ser Leu Ala Asn Pro Val Ala Val Gly Arg Leu Ala Arg Glu
            565                 570                 575 att cca cca cag acg tat atg aat cgg act ctg ttt tta ctg gtg gtt    1776
Ile Pro Pro Gln Thr Tyr Met Asn Arg Thr Leu Phe Leu Leu Val Val
            580                 585                 590 cct ccc atc ttt ccg cta tgt aca atc ata tta gag ctc aac ttt gtc    1824
Pro Pro Ile Phe Pro Leu Cys Thr Ile Ile Leu Glu Leu Asn Phe Val
            595                 600                 605 ctg cag gcg ctg tgg tct ggg cag gtg tat tat gtg ttt ggg ttt ctg    1872
Leu Gln Ala Leu Trp Ser Gly Gln Val Tyr Tyr Val Phe Gly Phe Leu
610                 615                 620 gcg ttg gtg agc ttt att tgg gtc atc ata aca gct ctt gtc aca gtg    1920
Ala Leu Val Ser Phe Ile Trp Val Ile Ile Thr Ala Leu Val Thr Val
625                 630                 635                 640 ttc cat cta tat tac gtt ctg tgc cgt gag aat cac cag tgg tgg tgg    1968
Phe His Leu Tyr Tyr Val Leu Cys Arg Glu Asn His Gln Trp Trp Trp
            645                 650                 655 ccc gca ttc ttc atc cct ggt ggg ttc ggt gtg ccg ctc ttc gtt tac    2016
Pro Ala Phe Phe Ile Pro Gly Gly Phe Gly Val Pro Leu Phe Val Tyr
            660                 665                 670 tcg att ttc ttc tac atg acg caa ttg gca att cac act ttt gct tcc    2064
Ser Ile Phe Phe Tyr Met Thr Gln Leu Ala Ile His Thr Phe Ala Ser
            675                 680                 685 tct tta ctg tat ttc ttg tac atg gga ttg ata tcg tat gcc tat ggg    2112
Ser Leu Leu Tyr Phe Leu Tyr Met Gly Leu Ile Ser Tyr Ala Tyr Gly
            690                 695                 700 ctg gca gcg gga gca gtg ggg ctc aca tcg gga att atg ttt gtt cgc    2160
Leu Ala Ala Gly Ala Val Gly Leu Thr Ser Gly Ile Met Phe Val Arg
705                 710                 715                 720 aaa ata tat gga agc atc aag gtg gac tga                            2190
Lys Ile Tyr Gly Ser Ile Lys Val Asp
            725
```

```
<210> SEQ ID NO 40
<211> LENGTH: 729
<212> TYPE: PRT
<213> ORGANISM: Trypanosoma brucei

<400> SEQUENCE: 40

Met Leu Arg Gly Ala Trp Leu Tyr Leu Val His Ser Ile Phe Ser Leu
1               5                   10                  15

Thr Ser Ile Glu Ser Ser Phe Ser Phe Leu Ser Ser Phe Thr Asn Arg
            20                  25                  30

Phe His Leu Ser Pro Ser Leu Leu Thr His Ile Phe Val Ser Leu Thr
        35                  40                  45

Tyr Thr Gln Asn Asn Ile Lys Glu Thr Phe Ser Ser Leu Ile Leu
    50                  55                  60

Ser Val Ser Pro Phe Phe Phe Leu His Ile Tyr Pro Arg Ala His Ala
65                  70                  75                  80

Glu Ala Val Gly Met Thr Arg Phe Ser Cys Val Ala Leu Gly Val Phe
                85                  90                  95

Ala Phe Leu Ile Ser Ala Leu Ala Val Thr Asp Ala Phe Tyr Ile Pro
            100                 105                 110

Gly Val Gln Pro Arg Tyr Tyr Ala Glu Gly Asp Glu Val His Phe Trp
        115                 120                 125

Val Asn Ser Leu Arg Ser Leu Gln Val Leu Phe Pro Lys Glu Tyr Tyr
    130                 135                 140

Thr Leu Pro Phe Cys Arg Pro Ser Glu Ile Ile Thr Lys Asp Glu Ser
145                 150                 155                 160

Ile Gly Glu Ile Ile Trp Gly Asp Arg Ile Gln Asn Ser Leu Tyr Val
                165                 170                 175

Thr Asn Met Lys Lys Asn Thr Asn Cys Thr Val Leu Pro Asn Cys Asp
            180                 185                 190

Ala Val Ala Asn Thr Lys Thr Ile Leu Ser Asn Ile Asp Asp Leu Glu
        195                 200                 205

Gly Ser Ile Glu Lys Gly Tyr Arg Gly Phe Met Asn Ile Asp Asn Leu
    210                 215                 220

Pro Val Phe Gly Glu Val Pro Asp Leu Leu Ala His Cys Ala Ser
225                 230                 235                 240

Val Pro Lys Asp Met Arg His Thr Phe Tyr Arg Gly Tyr Trp Ile Gly
                245                 250                 255

Thr Pro Ser Ala Cys Thr Gly Lys Thr Leu Ile Asn Asn His Leu Glu
            260                 265                 270

Phe Val Ile Lys Tyr Asn His Ala Pro His Asp Pro Asn Lys Phe Met
        275                 280                 285

Val Val Gly Leu Lys Ala Thr Pro Tyr Ser Ile Lys His Ser Asp Asp
    290                 295                 300

Gly Leu Ser Cys Asn Ala Asp Met Ser Ala Thr Gly Ser Ala Leu Asp
305                 310                 315                 320

Tyr Leu Thr Thr Asp Asp Val Arg Gly Gly Ala Val His Trp Ser
                325                 330                 335

Tyr Gly Val Lys Trp Glu Lys Ser Asp Val Ile Trp Ala Thr Arg Trp
            340                 345                 350

Asp Glu Tyr Leu His Ser Ser Val Ala Asp Ser Ser Pro Ala Phe His
        355                 360                 365

Trp Leu Tyr Val Cys Ser Ser Leu Val Val Val Leu Met Cys Ala Ala
    370                 375                 380
```

```
Ser Val Ala Thr Ile Leu Met Arg Thr Leu His Lys Asp Phe Ser Arg
385                 390                 395                 400

Tyr Asn Ser Pro Val Leu Glu Asp Gly Glu Glu Ser Gly Trp Lys
            405                 410                 415

Leu Val His Ala Asp Val Phe Arg Pro Pro Asp Arg Ala Pro Leu Leu
            420                 425                 430

Ala Ala Leu Thr Gly Asn Gly Tyr Gln Val Leu Gly Met Ser Ala Gly
            435                 440                 445

Thr Met Leu Phe Ala Leu Leu Gly Phe Leu Ser Pro Ala Arg Arg Gly
    450                 455                 460

Ala Leu Leu Ser Ala Val Ile Phe Leu Phe Val Phe Met Ser Val Val
465                 470                 475                 480

Ser Gly Tyr Val Cys Gly Phe Leu Leu Lys Tyr Phe Gly Arg Cys Glu
            485                 490                 495

Trp Lys His Ile Phe Phe Cys Gly Cys Ala Phe Pro Gly Ala Ile Val
            500                 505                 510

Gly Val Tyr Thr Phe Ala Asn Ile Ile Asn Tyr Ser His Gly Ser Ser
            515                 520                 525

Gly Thr Ile Pro Phe Ser Leu Leu Phe Ile Leu Leu Ser Leu Trp Ile
    530                 535                 540

Leu Ile Ser Val Pro Leu Thr Val Leu Gly Ala Ser Phe Ser Phe Arg
545                 550                 555                 560

Gln Glu Ser Leu Ala Asn Pro Val Ala Val Gly Arg Leu Ala Arg Glu
            565                 570                 575

Ile Pro Pro Gln Thr Tyr Met Asn Arg Thr Leu Phe Leu Leu Val Val
            580                 585                 590

Pro Pro Ile Phe Pro Leu Cys Thr Ile Ile Leu Glu Leu Asn Phe Val
            595                 600                 605

Leu Gln Ala Leu Trp Ser Gly Gln Val Tyr Tyr Val Phe Gly Phe Leu
    610                 615                 620

Ala Leu Val Ser Phe Ile Trp Val Ile Thr Ala Leu Val Thr Val
625                 630                 635                 640

Phe His Leu Tyr Tyr Val Leu Cys Arg Glu Asn His Gln Trp Trp Trp
            645                 650                 655

Pro Ala Phe Phe Ile Pro Gly Gly Phe Gly Val Pro Leu Phe Val Tyr
            660                 665                 670

Ser Ile Phe Phe Tyr Met Thr Gln Leu Ala Ile His Thr Phe Ala Ser
            675                 680                 685

Ser Leu Leu Tyr Phe Leu Tyr Met Gly Leu Ile Ser Tyr Ala Tyr Gly
    690                 695                 700

Leu Ala Ala Gly Ala Val Gly Leu Thr Ser Gly Ile Met Phe Val Arg
705                 710                 715                 720

Lys Ile Tyr Gly Ser Ile Lys Val Asp
            725
```

<210> SEQ ID NO 41
<211> LENGTH: 1521
<212> TYPE: DNA
<213> ORGANISM: Trypanosoma cruzi
<220> FEATURE:
<221> NAME/KEY: CDS
<222> LOCATION: (1)..(1521)

<400> SEQUENCE: 41

```
atg tct gct aaa gcc tca cgg cga tgc aat cga ctg att gtc ctt ttt      48
Met Ser Ala Lys Ala Ser Arg Arg Cys Asn Arg Leu Ile Val Leu Phe
```

```
          1               5                  10                   15
agt tct atc aac ggc gtg acg gca tgg cca ttt tgg aag ttt ctg cag        96
Ser Ser Ile Asn Gly Val Thr Ala Trp Pro Phe Trp Lys Phe Leu Gln
            20                  25                  30 atg aag aaa gta aag ggt gta acg gat ctt tcc atc ctt gcc ttt aac       144
Met Lys Lys Val Lys Gly Val Thr Asp Leu Ser Ile Leu Ala Phe Asn
                35                  40                  45 agc cag ggt ggc agc ttt gag gcc cgc att gac gga cag gag tac atg       192
Ser Gln Gly Gly Ser Phe Glu Ala Arg Ile Asp Gly Gln Glu Tyr Met
    50                  55                  60 ttg aag aac tac gaa aac gtt gta ggc tac tcg cag gac atg ttg gag       240
Leu Lys Asn Tyr Glu Asn Val Val Gly Tyr Ser Gln Asp Met Leu Glu
65                  70                  75                  80 cgt ttt ctg cac cgt tgg tac gac cct ggg cgc agt tat ttt gtc tac       288
Arg Phe Leu His Arg Trp Tyr Asp Pro Gly Arg Ser Tyr Phe Val Tyr
                    85                  90                  95 ggc ggt cac gga atg ggt gac tac ctg gag ctg gag gaa aac aag gtg       336
Gly Gly His Gly Met Gly Asp Tyr Leu Glu Leu Glu Glu Asn Lys Val
                100                 105                 110 ggg tta caa tgc cac gaa ctg gca gcg ata ttt gga gac aaa aag ttt       384
Gly Leu Gln Cys His Glu Leu Ala Ala Ile Phe Gly Asp Lys Lys Phe
        115                 120                 125 gag gcg atc acc ttt gac gca tgc tta atg gca agc ctg gac tgc gct       432
Glu Ala Ile Thr Phe Asp Ala Cys Leu Met Ala Ser Leu Asp Cys Ala
    130                 135                 140 tat cat ctg cgg aat aac acg cgt tac att ggc gcc tgt gag gga tac       480
Tyr His Leu Arg Asn Asn Thr Arg Tyr Ile Gly Ala Cys Glu Gly Tyr
145                 150                 155                 160 ttg tgg gag ccc gac aca agc ctc gac cat cat gtc ttc aac acg tac       528
Leu Trp Glu Pro Asp Thr Ser Leu Asp His His Val Phe Asn Thr Tyr
                    165                 170                 175 acc gcc tcc gcg atg agc cgc ttt cgc gat ccg aag cac att ctt tta       576
Thr Ala Ser Ala Met Ser Arg Phe Arg Asp Pro Lys His Ile Leu Leu
                180                 185                 190 gcc gtg cag cgt gac tac tgc agc aaa tct tca ctt gct gac ttt gcc       624
Ala Val Gln Arg Asp Tyr Cys Ser Lys Ser Ser Leu Ala Asp Phe Ala
        195                 200                 205 gtg ctg gac acc acg cat gta gag gct ttg cgg aac tat gtg gaa gag       672
Val Leu Asp Thr Thr His Val Glu Ala Leu Arg Asn Tyr Val Glu Glu
    210                 215                 220 cac gtg atg caa cgt gtc tac gac cgt gcc act ttt tat aat gtc cag       720
His Val Met Gln Arg Val Tyr Asp Arg Ala Thr Phe Tyr Asn Val Gln
225                 230                 235                 240 cag cag cag aaa tta agc tgc atg gcg gag gag gca ttg caa ctt agc       768
Gln Gln Gln Lys Leu Ser Cys Met Ala Glu Glu Ala Leu Gln Leu Ser
                    245                 250                 255 cgg aaa aat tcg aat gct gac atc aag atg cca gct tca tca tca tca       816
Arg Lys Asn Ser Asn Ala Asp Ile Lys Met Pro Ala Ser Ser Ser Ser
                260                 265                 270 cca tcg tca tct cct gac acg gta gcc atg cga gcg atg gcg act aag       864
Pro Ser Ser Ser Pro Asp Thr Val Ala Met Arg Ala Met Ala Thr Lys
        275                 280                 285 ttg cag aac aaa cgg ttg gca aga cgt tcc aag ctg cag cat gcg gtt       912
Leu Gln Asn Lys Arg Leu Ala Arg Arg Ser Lys Leu Gln His Ala Val
    290                 295                 300 cag ttt gag cac gcc ttg tat cca tct gag ccg ggc gac aag tac atc       960
Gln Phe Glu His Ala Leu Tyr Pro Ser Glu Pro Gly Asp Lys Tyr Ile
305                 310                 315                 320 ctt gac ctt cgt tcc tac ctg atc gat atg gcg cgt gag gag gag gaa      1008
```

```
Leu Asp Leu Arg Ser Tyr Leu Ile Asp Met Ala Arg Glu Glu Glu
                325                 330                 335 tta gct atc gcc tct ccg tca ccg cga act gcc gtt gtg gag gca cat      1056
Leu Ala Ile Ala Ser Pro Ser Pro Arg Thr Ala Val Val Glu Ala His
            340                 345                 350 ggg agt ttg cca aat gaa aaa aag cat ctc cac ccg cgg ttt gcc aaa      1104
Gly Ser Leu Pro Asn Glu Lys Lys His Leu His Pro Arg Phe Ala Lys
                355                 360                 365 ggc agc gca cac gag gga ctg gac ttg ttt cat cgc gtc gtc gtc aat      1152
Gly Ser Ala His Glu Gly Leu Asp Leu Phe His Arg Val Val Val Asn
            370                 375                 380 cac ata ccc cct gag gaa aag cat ata tac gcg tca cac ctg ggg ggc      1200
His Ile Pro Pro Glu Glu Lys His Ile Tyr Ala Ser His Leu Gly Gly
385                 390                 395                 400 ctg tct att cca gta tat gag ttt agt tcc atg tca aag ccg ctg atg      1248
Leu Ser Ile Pro Val Tyr Glu Phe Ser Ser Met Ser Lys Pro Leu Met
                405                 410                 415 ccg tgg aat cgt gta aac cga caa ata ttc aaa caa agg gca aac gaa      1296
Pro Trp Asn Arg Val Asn Arg Gln Ile Phe Lys Gln Arg Ala Asn Glu
            420                 425                 430 ttt ttg cgt cgt ggt gtc atg cag gaa gtg aag atg aac cag cgc acc      1344
Phe Leu Arg Arg Gly Val Met Gln Glu Val Lys Met Asn Gln Arg Thr
                435                 440                 445 caa agc ggt ttg cac gaa acg gaa ggt cgc agc tcg tca tca tcg cca      1392
Gln Ser Gly Leu His Glu Thr Glu Gly Arg Ser Ser Ser Ser Ser Pro
            450                 455                 460 tcg acg ggt tca cca ggt cca acc ata tat ctc cca att tca ggg tac      1440
Ser Thr Gly Ser Pro Gly Pro Thr Ile Tyr Leu Pro Ile Ser Gly Tyr
465                 470                 475                 480 tcc ggc aac acc aac ggc aat cga aac aaa ccc ggt agc gga aac ttg      1488
Ser Gly Asn Thr Asn Gly Asn Arg Asn Lys Pro Gly Ser Gly Asn Leu
                485                 490                 495 tcg ggg cct cag cac tgt gag gcg aga cga tga                         1521
Ser Gly Pro Gln His Cys Glu Ala Arg Arg
            500                 505

<210> SEQ ID NO 42
<211> LENGTH: 506
<212> TYPE: PRT
<213> ORGANISM: Trypanosoma cruzi

<400> SEQUENCE: 42

Met Ser Ala Lys Ala Ser Arg Arg Cys Asn Arg Leu Ile Val Leu Phe
1               5                   10                  15

Ser Ser Ile Asn Gly Val Thr Ala Trp Pro Phe Trp Lys Phe Leu Gln
                20                  25                  30

Met Lys Lys Val Lys Gly Val Thr Asp Leu Ser Ile Leu Ala Phe Asn
            35                  40                  45

Ser Gln Gly Gly Ser Phe Glu Ala Arg Ile Asp Gly Gln Glu Tyr Met
        50                  55                  60

Leu Lys Asn Tyr Glu Asn Val Val Gly Tyr Ser Gln Asp Met Leu Glu
65                  70                  75                  80

Arg Phe Leu His Arg Trp Tyr Asp Pro Gly Arg Ser Tyr Phe Val Tyr
                85                  90                  95

Gly Gly His Gly Met Gly Asp Tyr Leu Glu Leu Glu Glu Asn Lys Val
            100                 105                 110

Gly Leu Gln Cys His Glu Leu Ala Ala Ile Phe Gly Asp Lys Lys Phe
        115                 120                 125
```

```
Glu Ala Ile Thr Phe Asp Ala Cys Leu Met Ala Ser Leu Asp Cys Ala
            130                 135                 140

Tyr His Leu Arg Asn Asn Thr Arg Tyr Ile Gly Ala Cys Glu Gly Tyr
145                 150                 155                 160

Leu Trp Glu Pro Asp Thr Ser Leu Asp His His Val Phe Asn Thr Tyr
                165                 170                 175

Thr Ala Ser Ala Met Ser Arg Phe Arg Asp Pro Lys His Ile Leu Leu
            180                 185                 190

Ala Val Gln Arg Asp Tyr Cys Ser Lys Ser Leu Ala Asp Phe Ala
        195                 200                 205

Val Leu Asp Thr Thr His Val Glu Ala Leu Arg Asn Tyr Val Glu Glu
210                 215                 220

His Val Met Gln Arg Val Tyr Asp Arg Ala Thr Phe Tyr Asn Val Gln
225                 230                 235                 240

Gln Gln Gln Lys Leu Ser Cys Met Ala Glu Glu Ala Leu Gln Leu Ser
            245                 250                 255

Arg Lys Asn Ser Asn Ala Asp Ile Lys Met Pro Ala Ser Ser Ser Ser
                260                 265                 270

Pro Ser Ser Ser Pro Asp Thr Val Ala Met Arg Ala Met Ala Thr Lys
            275                 280                 285

Leu Gln Asn Lys Arg Leu Ala Arg Arg Ser Lys Leu Gln His Ala Val
290                 295                 300

Gln Phe Glu His Ala Leu Tyr Pro Ser Glu Pro Gly Asp Lys Tyr Ile
305                 310                 315                 320

Leu Asp Leu Arg Ser Tyr Leu Ile Asp Met Ala Arg Glu Glu Glu
            325                 330                 335

Leu Ala Ile Ala Ser Pro Ser Pro Arg Thr Ala Val Val Glu Ala His
            340                 345                 350

Gly Ser Leu Pro Asn Glu Lys Lys His Leu His Pro Arg Phe Ala Lys
            355                 360                 365

Gly Ser Ala His Glu Gly Leu Asp Leu Phe His Arg Val Val Val Asn
            370                 375                 380

His Ile Pro Pro Glu Glu Lys His Ile Tyr Ala Ser His Leu Gly Gly
385                 390                 395                 400

Leu Ser Ile Pro Val Tyr Glu Phe Ser Ser Met Ser Lys Pro Leu Met
                405                 410                 415

Pro Trp Asn Arg Val Asn Arg Gln Ile Phe Lys Gln Arg Ala Asn Glu
                420                 425                 430

Phe Leu Arg Arg Gly Val Met Gln Glu Val Lys Met Asn Gln Arg Thr
            435                 440                 445

Gln Ser Gly Leu His Glu Thr Glu Gly Arg Ser Ser Ser Ser Ser Pro
450                 455                 460

Ser Thr Gly Ser Pro Gly Pro Thr Ile Tyr Leu Pro Ile Ser Gly Tyr
465                 470                 475                 480

Ser Gly Asn Thr Asn Gly Asn Arg Asn Lys Pro Gly Ser Gly Asn Leu
            485                 490                 495

Ser Gly Pro Gln His Cys Glu Ala Arg Arg
            500                 505

<210> SEQ ID NO 43
<211> LENGTH: 1962
<212> TYPE: DNA
<213> ORGANISM: Leishmania major
<220> FEATURE:
<221> NAME/KEY: CDS
```

<222> LOCATION: (1)..(1962)

<400> SEQUENCE: 43

| | | | | | | | | | | | | | | | | |
|---|---|---|---|---|---|---|---|---|---|---|---|---|---|---|---|---|
| atg | ccc | cca | aag | cgc | tac | ccc | aac | cgc | ctc | ttg | gtg | ctg | tgc | gcc | tcc | 48 |
| Met | Pro | Pro | Lys | Arg | Tyr | Pro | Asn | Arg | Leu | Leu | Val | Leu | Cys | Ala | Ser | |
| 1 | | | | 5 | | | | | 10 | | | | | 15 | | |

| atc | aac | gat | gtc | aca | gca | tgg | ccg | ttt | tgg | aag | ttc | ttg | cag | atg | aag | 96 |
|---|---|---|---|---|---|---|---|---|---|---|---|---|---|---|---|---|
| Ile | Asn | Asp | Val | Thr | Ala | Trp | Pro | Phe | Trp | Lys | Phe | Leu | Gln | Met | Lys | |
| | | | 20 | | | | | 25 | | | | | 30 | | | |

| aag | att | cgc | ggc | gtg | acg | gac | atg | gcg | ctg | ctc | gcc | ttc | aac | agc | gac | 144 |
|---|---|---|---|---|---|---|---|---|---|---|---|---|---|---|---|---|
| Lys | Ile | Arg | Gly | Val | Thr | Asp | Met | Ala | Leu | Leu | Ala | Phe | Asn | Ser | Asp | |
| | | 35 | | | | | 40 | | | | | 45 | | | | |

| ggc | ggc | agc | ttc | gag | gct | cgc | att | gac | ggc | gac | aaa | tac | cag | ctc | aag | 192 |
|---|---|---|---|---|---|---|---|---|---|---|---|---|---|---|---|---|
| Gly | Gly | Ser | Phe | Glu | Ala | Arg | Ile | Asp | Gly | Asp | Lys | Tyr | Gln | Leu | Lys | |
| | 50 | | | | | 55 | | | | | 60 | | | | | |

| aac | tat | gcc | aag | gtt | cgc | ggc | tac | cag | cat | gac | atg | ttt | gag | agc | ttc | 240 |
|---|---|---|---|---|---|---|---|---|---|---|---|---|---|---|---|---|
| Asn | Tyr | Ala | Lys | Val | Arg | Gly | Tyr | Gln | His | Asp | Met | Phe | Glu | Ser | Phe | |
| 65 | | | | 70 | | | | | 75 | | | | | 80 | | |

| gtg | cat | cgc | tgg | cac | gat | ccg | ggc | cga | agc | tat | ttt | gtg | tat | ggc | ggg | 288 |
|---|---|---|---|---|---|---|---|---|---|---|---|---|---|---|---|---|
| Val | His | Arg | Trp | His | Asp | Pro | Gly | Arg | Ser | Tyr | Phe | Val | Tyr | Gly | Gly | |
| | | | | 85 | | | | | 90 | | | | | 95 | | |

| cat | ggc | atg | ggt | gac | tat | gtg | gag | cta | gaa | cag | aac | cgt | gtc | tcg | ctg | 336 |
|---|---|---|---|---|---|---|---|---|---|---|---|---|---|---|---|---|
| His | Gly | Met | Gly | Asp | Tyr | Val | Glu | Leu | Glu | Gln | Asn | Arg | Val | Ser | Leu | |
| | | | 100 | | | | | 105 | | | | | 110 | | | |

| cag | gtg | cac | gag | ctc | gcc | gac | gtc | ttc | ggc | acg | cgt | gtc | ttc | gaa | gca | 384 |
|---|---|---|---|---|---|---|---|---|---|---|---|---|---|---|---|---|
| Gln | Val | His | Glu | Leu | Ala | Asp | Val | Phe | Gly | Thr | Arg | Val | Phe | Glu | Ala | |
| | | 115 | | | | | 120 | | | | | 125 | | | | |

| gtg | ctc | ttt | gac | gcc | tgc | ttc | atg | gcg | aac | atc | gac | tgc | gcc | tat | cat | 432 |
|---|---|---|---|---|---|---|---|---|---|---|---|---|---|---|---|---|
| Val | Leu | Phe | Asp | Ala | Cys | Phe | Met | Ala | Asn | Ile | Asp | Cys | Ala | Tyr | His | |
| | 130 | | | | | 135 | | | | | 140 | | | | | |

| ctg | cgc | cac | aac | acg | cgg | tac | atc | ggt | gcc | tgc | gag | ggg | tac | atg | tgg | 480 |
|---|---|---|---|---|---|---|---|---|---|---|---|---|---|---|---|---|
| Leu | Arg | His | Asn | Thr | Arg | Tyr | Ile | Gly | Ala | Cys | Glu | Gly | Tyr | Met | Trp | |
| 145 | | | | 150 | | | | | 155 | | | | | 160 | | |

| gag | cct | gac | acg | gcc | ctc | gac | tac | cat | gtc | ttc | aac | acc | cac | aac | gcg | 528 |
|---|---|---|---|---|---|---|---|---|---|---|---|---|---|---|---|---|
| Glu | Pro | Asp | Thr | Ala | Leu | Asp | Tyr | His | Val | Phe | Asn | Thr | His | Asn | Ala | |
| | | | | 165 | | | | | 170 | | | | | 175 | | |

| agc | gcc | atg | agc | cgc | ttc | aaa | gac | ccg | ctg | cac | atc | ctc | cgt | gtt | att | 576 |
|---|---|---|---|---|---|---|---|---|---|---|---|---|---|---|---|---|
| Ser | Ala | Met | Ser | Arg | Phe | Lys | Asp | Pro | Leu | His | Ile | Leu | Arg | Val | Ile | |
| | | | 180 | | | | | 185 | | | | | 190 | | | |

| cag | acg | gac | tac | tgc | agc | aag | gcg | cca | cgt | ggc | gac | ttc | acc | atc | atc | 624 |
|---|---|---|---|---|---|---|---|---|---|---|---|---|---|---|---|---|
| Gln | Thr | Asp | Tyr | Cys | Ser | Lys | Ala | Pro | Arg | Gly | Asp | Phe | Thr | Ile | Ile | |
| | | 195 | | | | | 200 | | | | | 205 | | | | |

| gac | acc | acg | cac | atc | gcg | gcg | ctg | cgg | cag | tac | gtg | cag | gag | cac | gtc | 672 |
|---|---|---|---|---|---|---|---|---|---|---|---|---|---|---|---|---|
| Asp | Thr | Thr | His | Ile | Ala | Ala | Leu | Arg | Gln | Tyr | Val | Gln | Glu | His | Val | |
| | 210 | | | | | 215 | | | | | 220 | | | | | |

| atg | cag | cgt | gtt | tat | gac | cgg | gcg | acc | ttc | tac | agc | tta | ccg | cag | cga | 720 |
|---|---|---|---|---|---|---|---|---|---|---|---|---|---|---|---|---|
| Met | Gln | Arg | Val | Tyr | Asp | Arg | Ala | Thr | Phe | Tyr | Ser | Leu | Pro | Gln | Arg | |
| 225 | | | | 230 | | | | | 235 | | | | | 240 | | |

| gag | cga | ctg | cag | caa | atc | gcc | gag | gcg | tcg | att | cag | gcg | tcg | ata | tct | 768 |
|---|---|---|---|---|---|---|---|---|---|---|---|---|---|---|---|---|
| Glu | Arg | Leu | Gln | Gln | Ile | Ala | Glu | Ala | Ser | Ile | Gln | Ala | Ser | Ile | Ser | |
| | | | | 245 | | | | | 250 | | | | | 255 | | |

| cag | ttt | ggc | cac | ccc | ggc | ggt | gac | acc | aac | gtg | att | aat | ggc | gtt | ggc | 816 |
|---|---|---|---|---|---|---|---|---|---|---|---|---|---|---|---|---|
| Gln | Phe | Gly | His | Pro | Gly | Gly | Asp | Thr | Asn | Val | Ile | Asn | Gly | Val | Gly | |
| | | | 260 | | | | | 265 | | | | | 270 | | | |

| agt | ggc | act | gac | cgc | ccg | cgc | acc | gcc | cca | tcg | tca | ccc | gag | gtg | ctt | 864 |
|---|---|---|---|---|---|---|---|---|---|---|---|---|---|---|---|---|
| Ser | Gly | Thr | Asp | Arg | Pro | Arg | Thr | Ala | Pro | Ser | Ser | Pro | Glu | Val | Leu | |
| | | 275 | | | | | 280 | | | | | 285 | | | | |

| gca | ctt | tcc | gcc | gcc | ggc | aga | ccg | acg | cgg | cgg | cag | cga | atg | ctg | cag | 912 |
|---|---|---|---|---|---|---|---|---|---|---|---|---|---|---|---|---|
| Ala | Leu | Ser | Ala | Ala | Gly | Arg | Pro | Thr | Arg | Arg | Gln | Arg | Met | Leu | Gln | |
| | 290 | | | | | 295 | | | | | 300 | | | | | |

```
gcg att cag ttt gag cac tcg ctg tac ccg tcg gag gtc gac gac aag      960
Ala Ile Gln Phe Glu His Ser Leu Tyr Pro Ser Glu Val Asp Asp Lys
305                 310                 315                 320 cag ctg ctc gac ctc aag tcg tat ctc act gac atg ctg cac gag gag     1008
Gln Leu Leu Asp Leu Lys Ser Tyr Leu Thr Asp Met Leu His Glu Glu
                325                 330                 335 cag cag cta aag gcg tgg gag gca gcg ctg ggg ccg cag cgc cgc         1056
Gln Gln Leu Lys Ala Trp Glu Ala Ala Leu Gly Pro Gln Arg Arg
        340                 345                 350 att gcg gcg ggt cgc cgc cgc gtg cga agt gat gca ctg cag cat ggt     1104
Ile Ala Ala Gly Arg Arg Arg Val Arg Ser Asp Ala Leu Gln His Gly
            355                 360                 365 ggc agc tcc ggc atc gcc gcc ccc tcc acc gcc tcg tcc tcc ttc gcc     1152
Gly Ser Ser Gly Ile Ala Ala Pro Ser Thr Ala Ser Ser Ser Phe Ala
370                 375                 380 gtc tgg aag gcg ccg ccg tcg cgg gcg ctg ttt gct gat cgg cac ggg     1200
Val Trp Lys Ala Pro Pro Ser Arg Ala Leu Phe Ala Asp Arg His Gly
385                 390                 395                 400 cgg ccg cct gct gcc agt tct gca gag tgc tcg ccg tcc atc aac ggt     1248
Arg Pro Pro Ala Ala Ser Ser Ala Glu Cys Ser Pro Ser Ile Asn Gly
                405                 410                 415 ggc cca gcc gca gca cac gac acg cag aag ggg gcg acg gcg ctc tct     1296
Gly Pro Ala Ala Ala His Asp Thr Gln Lys Gly Ala Thr Ala Leu Ser
            420                 425                 430 cct cca gtc ctt gcg acc act cca acg aag gca gca ccg ccg cct ccg     1344
Pro Pro Val Leu Ala Thr Thr Pro Thr Lys Ala Ala Pro Pro Pro Pro
        435                 440                 445 tct ctc tcc acc tct tac aag ggc agc gcg cag gag ggg cta gat ctt     1392
Ser Leu Ser Thr Ser Tyr Lys Gly Ser Ala Gln Glu Gly Leu Asp Leu
450                 455                 460 ttc tac cag gtt gtc gtg agc cac atc cca ccg aag gcc gct tcc atc     1440
Phe Tyr Gln Val Val Val Ser His Ile Pro Pro Lys Ala Ala Ser Ile
465                 470                 475                 480 tac gcg acc cag ctc ggg ggg tta tcc ttt acg gtg cac gag tac agt     1488
Tyr Ala Thr Gln Leu Gly Gly Leu Ser Phe Thr Val His Glu Tyr Ser
                485                 490                 495 gcc atg tcg cgg ccg gca gag ccg tgg ttg gtg ggc tcg aag agg ttg     1536
Ala Met Ser Arg Pro Ala Glu Pro Trp Leu Val Gly Ser Lys Arg Leu
            500                 505                 510 ctg aag cgc cgg gca aag caa ttc ctg aag aac ggc gaa ctc tcg gag     1584
Leu Lys Arg Arg Ala Lys Gln Phe Leu Lys Asn Gly Glu Leu Ser Glu
        515                 520                 525 gtg gtg atg gag tcc ccg aag gcg agc gcg tcc gtc acc agc gct gcc     1632
Val Val Met Glu Ser Pro Lys Ala Ser Ala Ser Val Thr Ser Ala Ala
530                 535                 540 ctc gtg gca gcc gtc gac aag gtg aca gca acg gcg gcg gtg acg         1680
Leu Val Ala Ala Val Asp Lys Val Thr Ala Thr Ala Ala Val Thr
545                 550                 555                 560 ggt gct tct gca gga aaa ccc gag cct gcg act tcc gcc gcc gcg ctg     1728
Gly Ala Ser Ala Gly Lys Pro Glu Pro Ala Thr Ser Ala Ala Ala Leu
                565                 570                 575 ccg ctg tca ccc aga gca cac atg ccc tcc acg gat cag cgt ctg cgt     1776
Pro Leu Ser Pro Arg Ala His Met Pro Ser Thr Asp Gln Arg Leu Arg
            580                 585                 590 ttc acg agc agc ggt aat ggc aca gac agc gac agc tcc ttg tca ctg     1824
Phe Thr Ser Ser Gly Asn Gly Thr Asp Ser Asp Ser Ser Leu Ser Leu
        595                 600                 605 agc ttg tcc gta ccg ctc tcc act tcc tcc acg gat gca tac aac aac     1872
Ser Leu Ser Val Pro Leu Ser Thr Ser Ser Thr Asp Ala Tyr Asn Asn
```

```
                  610              615              620
agc atg aaa acg gta att ctc gac tcg cca cag cgg gct gcc tcc tat         1920
Ser Met Lys Thr Val Ile Leu Asp Ser Pro Gln Arg Ala Ala Ser Tyr
625                 630                 635                 640 aca tcg tta ccc aac tcc aaa gaa cgt aca agc gcc tgc tga                 1962
Thr Ser Leu Pro Asn Ser Lys Glu Arg Thr Ser Ala Cys
                645                 650

<210> SEQ ID NO 44
<211> LENGTH: 653
<212> TYPE: PRT
<213> ORGANISM: Leishmania major

<400> SEQUENCE: 44

Met Pro Pro Lys Arg Tyr Pro Asn Arg Leu Leu Val Leu Cys Ala Ser
1               5                   10                  15

Ile Asn Asp Val Thr Ala Trp Pro Phe Trp Lys Phe Leu Gln Met Lys
            20                  25                  30

Lys Ile Arg Gly Val Thr Asp Met Ala Leu Leu Ala Phe Asn Ser Asp
        35                  40                  45

Gly Gly Ser Phe Glu Ala Arg Ile Asp Gly Asp Lys Tyr Gln Leu Lys
    50                  55                  60

Asn Tyr Ala Lys Val Arg Gly Tyr Gln His Asp Met Phe Glu Ser Phe
65                  70                  75                  80

Val His Arg Trp His Asp Pro Gly Arg Ser Tyr Phe Val Tyr Gly Gly
                85                  90                  95

His Gly Met Gly Asp Tyr Val Glu Leu Glu Gln Asn Arg Val Ser Leu
            100                 105                 110

Gln Val His Glu Leu Ala Asp Val Phe Gly Thr Arg Val Phe Glu Ala
        115                 120                 125

Val Leu Phe Asp Ala Cys Phe Met Ala Asn Ile Asp Cys Ala Tyr His
    130                 135                 140

Leu Arg His Asn Thr Arg Tyr Ile Gly Ala Cys Glu Gly Tyr Met Trp
145                 150                 155                 160

Glu Pro Asp Thr Ala Leu Asp Tyr His Val Phe Asn Thr His Asn Ala
                165                 170                 175

Ser Ala Met Ser Arg Phe Lys Asp Pro Leu His Ile Leu Arg Val Ile
            180                 185                 190

Gln Thr Asp Tyr Cys Ser Lys Ala Pro Arg Gly Asp Phe Thr Ile Ile
        195                 200                 205

Asp Thr Thr His Ile Ala Ala Leu Arg Gln Tyr Val Gln Glu His Val
    210                 215                 220

Met Gln Arg Val Tyr Asp Arg Ala Thr Phe Tyr Ser Leu Pro Gln Arg
225                 230                 235                 240

Glu Arg Leu Gln Gln Ile Ala Glu Ala Ser Ile Gln Ala Ser Ile Ser
                245                 250                 255

Gln Phe Gly His Pro Gly Gly Asp Thr Asn Val Ile Asn Gly Val Gly
            260                 265                 270

Ser Gly Thr Asp Arg Pro Arg Thr Ala Pro Ser Ser Pro Glu Val Leu
        275                 280                 285

Ala Leu Ser Ala Ala Gly Arg Pro Thr Arg Gln Arg Met Leu Gln
    290                 295                 300

Ala Ile Gln Phe Glu His Ser Leu Tyr Pro Ser Glu Val Asp Asp Lys
305                 310                 315                 320

Gln Leu Leu Asp Leu Lys Ser Tyr Leu Thr Asp Met Leu His Glu Glu
```

```
                    325                 330                 335
Gln Gln Leu Lys Ala Trp Glu Ala Ala Ala Leu Gly Pro Gln Arg Arg
            340                 345                 350

Ile Ala Ala Gly Arg Arg Val Arg Ser Asp Ala Leu Gln His Gly
            355                 360                 365

Gly Ser Ser Gly Ile Ala Ala Pro Ser Thr Ala Ser Ser Phe Ala
        370                 375                 380

Val Trp Lys Ala Pro Pro Ser Arg Ala Leu Phe Ala Asp Arg His Gly
385                 390                 395                 400

Arg Pro Pro Ala Ala Ser Ser Ala Glu Cys Ser Pro Ser Ile Asn Gly
                405                 410                 415

Gly Pro Ala Ala Ala His Asp Thr Gln Lys Gly Ala Thr Ala Leu Ser
            420                 425                 430

Pro Pro Val Leu Ala Thr Thr Pro Thr Lys Ala Ala Pro Pro Pro
        435                 440                 445

Ser Leu Ser Thr Ser Tyr Lys Gly Ser Ala Gln Glu Gly Leu Asp Leu
        450                 455                 460

Phe Tyr Gln Val Val Ser His Ile Pro Pro Lys Ala Ala Ser Ile
465                 470                 475                 480

Tyr Ala Thr Gln Leu Gly Gly Leu Ser Phe Thr Val His Glu Tyr Ser
                485                 490                 495

Ala Met Ser Arg Pro Ala Glu Pro Trp Leu Val Gly Ser Lys Arg Leu
            500                 505                 510

Leu Lys Arg Arg Ala Lys Gln Phe Leu Lys Asn Gly Glu Leu Ser Glu
        515                 520                 525

Val Val Met Glu Ser Pro Lys Ala Ser Ala Ser Val Thr Ser Ala Ala
        530                 535                 540

Leu Val Ala Ala Val Asp Lys Val Thr Ala Thr Ala Ala Val Thr
545                 550                 555                 560

Gly Ala Ser Ala Gly Lys Pro Glu Pro Ala Thr Ser Ala Ala Ala Leu
                565                 570                 575

Pro Leu Ser Pro Arg Ala His Met Pro Ser Thr Asp Gln Arg Leu Arg
            580                 585                 590

Phe Thr Ser Ser Gly Asn Gly Thr Asp Ser Asp Ser Ser Leu Ser Leu
        595                 600                 605

Ser Leu Ser Val Pro Leu Ser Thr Ser Ser Thr Asp Ala Tyr Asn Asn
        610                 615                 620

Ser Met Lys Thr Val Ile Leu Asp Ser Pro Gln Arg Ala Ala Ser Tyr
625                 630                 635                 640

Thr Ser Leu Pro Asn Ser Lys Glu Arg Thr Ser Ala Cys
                645                 650

<210> SEQ ID NO 45
<211> LENGTH: 1962
<212> TYPE: DNA
<213> ORGANISM: Leishmania infantum
<220> FEATURE:
<221> NAME/KEY: CDS
<222> LOCATION: (1)..(1962)

<400> SEQUENCE: 45 atg ccg ccg agg cgc tgc cca aac cgc ctc ctg gtg ctg tgc gcc tcc      48
Met Pro Pro Arg Arg Cys Pro Asn Arg Leu Leu Val Leu Cys Ala Ser
1               5                   10                  15 atc aat gat gtc aca gca tgg ccg ttt tgg aag ttc ttg cag atg aag      96
Ile Asn Asp Val Thr Ala Trp Pro Phe Trp Lys Phe Leu Gln Met Lys
```

```
                  20                  25                  30
aag att cgc ggc gtg acg gac atg gcg ctg ctc gcc ttc aac agc gac    144
Lys Ile Arg Gly Val Thr Asp Met Ala Leu Leu Ala Phe Asn Ser Asp
         35                  40                  45 ggc agc ttt gag gct cgc atc gat ggc gac agg tac cag ctc aag        192
Gly Ser Phe Glu Ala Arg Ile Asp Gly Asp Arg Tyr Gln Leu Lys
 50                  55                  60 aac tac gcc aag gtg cgc ggc tac cag cac gac atg ttt gag agc ttc    240
Asn Tyr Ala Lys Val Arg Gly Tyr Gln His Asp Met Phe Glu Ser Phe
 65                  70                  75                  80 gtg cat cgc tgg cac gat ccg ggc cga agc tat ttc gtg tat ggc ggg    288
Val His Arg Trp His Asp Pro Gly Arg Ser Tyr Phe Val Tyr Gly Gly
                     85                  90                  95 cat ggt atg ggc gac tat gtg gag cta gag cag aac cgt gtt tcg ctg    336
His Gly Met Gly Asp Tyr Val Glu Leu Glu Gln Asn Arg Val Ser Leu
            100                 105                 110 cag gcg cac gag ctc gcc gac gtc ttc ggc acg cgt gtc ttc gaa gcc    384
Gln Ala His Glu Leu Ala Asp Val Phe Gly Thr Arg Val Phe Glu Ala
        115                 120                 125 gtg ctc ttt gac gcc tgc ttc atg gcg aac ctt gac tgc gcc tat cat    432
Val Leu Phe Asp Ala Cys Phe Met Ala Asn Leu Asp Cys Ala Tyr His
130                 135                 140 ctg cgc cac aac acg cgg tac atc ggt gcc tgt gag ggg tac atg tgg    480
Leu Arg His Asn Thr Arg Tyr Ile Gly Ala Cys Glu Gly Tyr Met Trp
145                 150                 155                 160 gag cct gac acg gcc ctc gac tac cat gtc ttc aac acc cac aac gcg    528
Glu Pro Asp Thr Ala Leu Asp Tyr His Val Phe Asn Thr His Asn Ala
                165                 170                 175 agc gcc atg agc cgc ttc aaa gac ccg ctg cac atc ctc cgc gtt att    576
Ser Ala Met Ser Arg Phe Lys Asp Pro Leu His Ile Leu Arg Val Ile
            180                 185                 190 cag gcg gac tac tgc agc aag gcg ccg cgt ggc gac ttc acc atc atc    624
Gln Ala Asp Tyr Cys Ser Lys Ala Pro Arg Gly Asp Phe Thr Ile Ile
        195                 200                 205 gac acc acg cac att gcg gcg ctg cgg cag tac gtg cag gag cat gtc    672
Asp Thr Thr His Ile Ala Ala Leu Arg Gln Tyr Val Gln Glu His Val
210                 215                 220 atg cag cgc gtt tat gac cgg gcg acc ttc tac agc cta ccg cag cga    720
Met Gln Arg Val Tyr Asp Arg Ala Thr Phe Tyr Ser Leu Pro Gln Arg
225                 230                 235                 240 gag cga ctg cag caa atc gcc gag gcg tcg att cag gcg tcc ata tcc    768
Glu Arg Leu Gln Gln Ile Ala Glu Ala Ser Ile Gln Ala Ser Ile Ser
                245                 250                 255 cag ttt ggc cac ccc ggc ggt gac acc aac gtg atg aat ggc gtt ggc    816
Gln Phe Gly His Pro Gly Gly Asp Thr Asn Val Met Asn Gly Val Gly
            260                 265                 270 agt ggt act ggc cgc ccg cgc acc gcc cca tcg tca ccc gag gtg ctt    864
Ser Gly Thr Gly Arg Pro Arg Thr Ala Pro Ser Ser Pro Glu Val Leu
        275                 280                 285 gcg ctt tcc gcc gcc ggt aga ccg acg cgg cag cga atg ctg cag        912
Ala Leu Ser Ala Ala Gly Arg Pro Thr Arg Arg Gln Arg Met Leu Gln
290                 295                 300 gcg att cag ttt gag cac tcg ctg tac ccg tcg gag gta gac gac aaa    960
Ala Ile Gln Phe Glu His Ser Leu Tyr Pro Ser Glu Val Asp Asp Lys
305                 310                 315                 320 cag ctg ctc gac ctc aag tcg tat ctc acg gac atg ctg cgg gag gag   1008
Gln Leu Leu Asp Leu Lys Ser Tyr Leu Thr Asp Met Leu Arg Glu Glu
                325                 330                 335 cag cag cta aag gcg tgg gag gca gcg gcg ctg ggg ccg cag cgc cgc   1056
```

```
                        -continued

Gln Gln Leu Lys Ala Trp Glu Ala Ala Leu Gly Pro Gln Arg Arg
            340                 345                 350 att gcg gct ggc cgc cgc cgc ttg cga agt gat gca ctg cag cat ggt      1104
Ile Ala Ala Gly Arg Arg Arg Leu Arg Ser Asp Ala Leu Gln His Gly
            355                 360                 365 ggc agc tcc gga atc gcc gcc ccc tcc tcc gcc tcg tcc tcc ttc gcc      1152
Gly Ser Ser Gly Ile Ala Ala Pro Ser Ser Ala Ser Ser Ser Phe Ala
370                 375                 380 gtc tgg aag gcg ccg ccg tcg cgg gcg ctg ttt gtt gat cgg cac gga      1200
Val Trp Lys Ala Pro Pro Ser Arg Ala Leu Phe Val Asp Arg His Gly
385                 390                 395                 400 cgg ctg cct gct gcc agc tct aca ggg tgc tcg ccg tcc atc aac ggt      1248
Arg Leu Pro Ala Ala Ser Ser Thr Gly Cys Ser Pro Ser Ile Asn Gly
                405                 410                 415 ggc cca gcc gca gca aac gac aag caa aaa gag gcg acg gcg ctc tct      1296
Gly Pro Ala Ala Ala Asn Asp Lys Gln Lys Glu Ala Thr Ala Leu Ser
            420                 425                 430 cct cca gcc ctt gca gcc act cta acg atg gca aca gcg ccg cct ccg      1344
Pro Pro Ala Leu Ala Ala Thr Leu Thr Met Ala Thr Ala Pro Pro Pro
            435                 440                 445 tct ctc tcc acc tct tac aag ggc agc gcg cag gag ggg cta gat ctt      1392
Ser Leu Ser Thr Ser Tyr Lys Gly Ser Ala Gln Glu Gly Leu Asp Leu
        450                 455                 460 ttt cac cag gtt gtc gtg agc cac atc cca ccc aag gcc gct tcc atc      1440
Phe His Gln Val Val Val Ser His Ile Pro Pro Lys Ala Ala Ser Ile
465                 470                 475                 480 tac gca acc cag ctc ggg ggg cta tcc tta acg gtg cac gag tac agt      1488
Tyr Ala Thr Gln Leu Gly Gly Leu Ser Leu Thr Val His Glu Tyr Ser
                485                 490                 495 gcc atg tcg cgg ccg gca gag ccg tgg tcg gtg ggc tcg aag agg ttg      1536
Ala Met Ser Arg Pro Ala Glu Pro Trp Ser Val Gly Ser Lys Arg Leu
            500                 505                 510 ctg aag cgc cgg gca aag caa ttc ctg aag aac ggc gaa ctc tcg gag      1584
Leu Lys Arg Arg Ala Lys Gln Phe Leu Lys Asn Gly Glu Leu Ser Glu
            515                 520                 525 gtg gtg atg gag tcc ccg aag gcg agc cca tcc gtc acc agc gct gcc      1632
Val Val Met Glu Ser Pro Lys Ala Ser Pro Ser Val Thr Ser Ala Ala
530                 535                 540 ctc gcg gca acc gtg aac aag gcg aca gcg acg gcc gcg gca gtg aag      1680
Leu Ala Ala Thr Val Asn Lys Ala Thr Ala Thr Ala Ala Ala Val Lys
545                 550                 555                 560 ggt gct tct gca gga aaa ccc cag cat gcg act tcc gcc gcc gcg ctg      1728
Gly Ala Ser Ala Gly Lys Pro Gln His Ala Thr Ser Ala Ala Ala Leu
                565                 570                 575 ccg cta tca ccc aga aca cga atg ctc ttc ccg gac cag cgt ctg agt      1776
Pro Leu Ser Pro Arg Thr Arg Met Leu Phe Pro Asp Gln Arg Leu Ser
            580                 585                 590 ttc acg agc agc agt aat ggc aca gac agc gac agc tcc ttg ccg ctc      1824
Phe Thr Ser Ser Ser Asn Gly Thr Asp Ser Asp Ser Ser Leu Pro Leu
            595                 600                 605 agc ttg tcc gca ccg ctt tcc acc tca tcc acg gat gca tgc aac agc      1872
Ser Leu Ser Ala Pro Leu Ser Thr Ser Ser Thr Asp Ala Cys Asn Ser
        610                 615                 620 agc atg aaa aca gta att ctc gac ccg cca cag cgg gct gcc tcc tgt      1920
Ser Met Lys Thr Val Ile Leu Asp Pro Pro Gln Arg Ala Ala Ser Cys
625                 630                 635                 640 acg tcg tta ccc aac tcc aaa caa cgt aca agc gcc tgc tga              1962
Thr Ser Leu Pro Asn Ser Lys Gln Arg Thr Ser Ala Cys
                645                 650
```

-continued

```
<210> SEQ ID NO 46
<211> LENGTH: 653
<212> TYPE: PRT
<213> ORGANISM: Leishmania infantum

<400> SEQUENCE: 46

Met Pro Pro Arg Arg Cys Pro Asn Arg Leu Leu Val Leu Cys Ala Ser
1               5                   10                  15

Ile Asn Asp Val Thr Ala Trp Pro Phe Trp Lys Phe Leu Gln Met Lys
            20                  25                  30

Lys Ile Arg Gly Val Thr Asp Met Ala Leu Leu Ala Phe Asn Ser Asp
        35                  40                  45

Gly Gly Ser Phe Glu Ala Arg Ile Asp Gly Asp Arg Tyr Gln Leu Lys
    50                  55                  60

Asn Tyr Ala Lys Val Arg Gly Tyr Gln His Asp Met Phe Glu Ser Phe
65                  70                  75                  80

Val His Arg Trp His Asp Pro Gly Arg Ser Tyr Phe Val Tyr Gly Gly
                85                  90                  95

His Gly Met Gly Asp Tyr Val Glu Leu Glu Gln Asn Arg Val Ser Leu
            100                 105                 110

Gln Ala His Glu Leu Ala Asp Val Phe Gly Thr Arg Val Phe Glu Ala
        115                 120                 125

Val Leu Phe Asp Ala Cys Phe Met Ala Asn Leu Asp Cys Ala Tyr His
    130                 135                 140

Leu Arg His Asn Thr Arg Tyr Ile Gly Ala Cys Glu Gly Tyr Met Trp
145                 150                 155                 160

Glu Pro Asp Thr Ala Leu Asp Tyr His Val Phe Asn Thr His Asn Ala
                165                 170                 175

Ser Ala Met Ser Arg Phe Lys Asp Pro Leu His Ile Leu Arg Val Ile
            180                 185                 190

Gln Ala Asp Tyr Cys Ser Lys Ala Pro Arg Gly Asp Phe Thr Ile Ile
        195                 200                 205

Asp Thr Thr His Ile Ala Ala Leu Arg Gln Tyr Val Gln Glu His Val
    210                 215                 220

Met Gln Arg Val Tyr Asp Arg Ala Thr Phe Tyr Ser Leu Pro Gln Arg
225                 230                 235                 240

Glu Arg Leu Gln Gln Ile Ala Glu Ala Ser Ile Gln Ala Ser Ile Ser
                245                 250                 255

Gln Phe Gly His Pro Gly Gly Asp Thr Asn Val Met Asn Gly Val Gly
            260                 265                 270

Ser Gly Thr Gly Arg Pro Arg Thr Ala Pro Ser Ser Pro Glu Val Leu
        275                 280                 285

Ala Leu Ser Ala Ala Gly Arg Pro Thr Arg Arg Gln Arg Met Leu Gln
    290                 295                 300

Ala Ile Gln Phe Glu His Ser Leu Tyr Pro Ser Glu Val Asp Lys
305                 310                 315                 320

Gln Leu Leu Asp Leu Lys Ser Tyr Leu Thr Asp Met Leu Arg Glu Glu
                325                 330                 335

Gln Gln Leu Lys Ala Trp Glu Ala Ala Leu Gly Pro Gln Arg Arg
            340                 345                 350

Ile Ala Ala Gly Arg Arg Leu Arg Ser Asp Ala Leu Gln His Gly
        355                 360                 365

Gly Ser Ser Gly Ile Ala Ala Pro Ser Ser Ala Ser Ser Phe Ala
    370                 375                 380
```

```
Val Trp Lys Ala Pro Pro Ser Arg Ala Leu Phe Val Asp Arg His Gly
385                 390                 395                 400

Arg Leu Pro Ala Ala Ser Ser Thr Gly Cys Ser Pro Ser Ile Asn Gly
            405                 410                 415

Gly Pro Ala Ala Ala Asn Asp Lys Gln Lys Glu Ala Thr Ala Leu Ser
            420                 425                 430

Pro Pro Ala Leu Ala Ala Thr Leu Thr Met Ala Thr Ala Pro Pro Pro
            435                 440                 445

Ser Leu Ser Thr Ser Tyr Lys Gly Ser Ala Gln Glu Gly Leu Asp Leu
    450                 455                 460

Phe His Gln Val Val Ser His Ile Pro Pro Lys Ala Ala Ser Ile
465                 470                 475                 480

Tyr Ala Thr Gln Leu Gly Gly Leu Ser Leu Thr Val His Glu Tyr Ser
                485                 490                 495

Ala Met Ser Arg Pro Ala Glu Pro Trp Ser Val Gly Ser Lys Arg Leu
            500                 505                 510

Leu Lys Arg Arg Ala Lys Gln Phe Leu Lys Asn Gly Glu Leu Ser Glu
        515                 520                 525

Val Val Met Glu Ser Pro Lys Ala Ser Pro Ser Val Thr Ser Ala Ala
530                 535                 540

Leu Ala Ala Thr Val Asn Lys Ala Thr Ala Thr Ala Ala Ala Val Lys
545                 550                 555                 560

Gly Ala Ser Ala Gly Lys Pro Gln His Ala Thr Ser Ala Ala Ala Leu
                565                 570                 575

Pro Leu Ser Pro Arg Thr Arg Met Leu Phe Pro Asp Gln Arg Leu Ser
            580                 585                 590

Phe Thr Ser Ser Ser Asn Gly Thr Asp Ser Asp Ser Ser Leu Pro Leu
        595                 600                 605

Ser Leu Ser Ala Pro Leu Ser Thr Ser Ser Thr Asp Ala Cys Asn Ser
    610                 615                 620

Ser Met Lys Thr Val Ile Leu Asp Pro Pro Gln Arg Ala Ala Ser Cys
625                 630                 635                 640

Thr Ser Leu Pro Asn Ser Lys Gln Arg Thr Ser Ala Cys
                645                 650

<210> SEQ ID NO 47
<211> LENGTH: 1593
<212> TYPE: DNA
<213> ORGANISM: Trypanosoma brucei
<220> FEATURE:
<221> NAME/KEY: CDS
<222> LOCATION: (1)..(1593)

<400> SEQUENCE: 47 atg ttg tcc cga gcc cca cga cca aat aac cgc ctc atc gtg gtc tgc      48
Met Leu Ser Arg Ala Pro Arg Pro Asn Asn Arg Leu Ile Val Val Cys
1               5                   10                  15 agt tgc att aaa aat gtg tcg ggg tgg cca ttc tgg aag ttt cag caa      96
Ser Cys Ile Lys Asn Val Ser Gly Trp Pro Phe Trp Lys Phe Gln Gln
            20                  25                  30 atg agg aag gta aag ggc gtt acc gat ctt tgc atg ctt gcc ttt aac     144
Met Arg Lys Val Lys Gly Val Thr Asp Leu Cys Met Leu Ala Phe Asn
        35                  40                  45 tcc agt ggt ggg agc ttt gaa gca agt atc act ggg agc gac tac aca     192
Ser Ser Gly Gly Ser Phe Glu Ala Ser Ile Thr Gly Ser Asp Tyr Thr
    50                  55                  60
```

| | | |
|---|---|---|
| ttg aag aac tac gaa aat gtt gtt ggc tat cgt cag gac atg ctt gaa<br>Leu Lys Asn Tyr Glu Asn Val Val Gly Tyr Arg Gln Asp Met Leu Glu<br>65                      70                      75                      80 | 240 |
| gac ttt cta cag cgt tgc cac gac ccc ggt cgg agt tat ttt gtg tac<br>Asp Phe Leu Gln Arg Cys His Asp Pro Gly Arg Ser Tyr Phe Val Tyr<br>                    85                      90                      95 | 288 |
| ggt ggt cat ggg atg gga gat tac ctg gaa tta gag gag aac aaa ctg<br>Gly Gly His Gly Met Gly Asp Tyr Leu Glu Leu Glu Glu Asn Lys Leu<br>                100                      105                      110 | 336 |
| gcg ttg caa tgc cat gag ctc gcc tcc att ctc ggc aag cga aaa ttt<br>Ala Leu Gln Cys His Glu Leu Ala Ser Ile Leu Gly Lys Arg Lys Phe<br>115                      120                      125 | 384 |
| gag gcg atg gtc ttt gat tcg tgt ttt atg gcc agt ctc gaa tgc gct<br>Glu Ala Met Val Phe Asp Ser Cys Phe Met Ala Ser Leu Glu Cys Ala<br>130                      135                      140 | 432 |
| tat caa cta cgc cat aac aca cgt tac att ggg gcc tgt gag ggt tat<br>Tyr Gln Leu Arg His Asn Thr Arg Tyr Ile Gly Ala Cys Glu Gly Tyr<br>145                      150                      155                      160 | 480 |
| gtg tgg gca cct gac ccc aac ctt gac caa cac gtc ttt aac cag tac<br>Val Trp Ala Pro Asp Pro Asn Leu Asp Gln His Val Phe Asn Gln Tyr<br>                    165                      170                      175 | 528 |
| tct gcc tct gct atg agt cgc ttt aaa cat cca aaa aac atc cta ctt<br>Ser Ala Ser Ala Met Ser Arg Phe Lys His Pro Lys Asn Ile Leu Leu<br>                  180                      185                      190 | 576 |
| gcc atc cag aga gac tac tgc aac aag tct cct ctc gcc gac ttc gct<br>Ala Ile Gln Arg Asp Tyr Cys Asn Lys Ser Pro Leu Ala Asp Phe Ala<br>                    195                      200                      205 | 624 |
| gtg ttg gat acc act cat gtg gag tcg ctc aag aag tat gtt gaa gaa<br>Val Leu Asp Thr Thr His Val Glu Ser Leu Lys Lys Tyr Val Glu Glu<br>210                      215                      220 | 672 |
| cat gtg atg cag cga gta tac gat cga gca acg ttt tac aac agt gag<br>His Val Met Gln Arg Val Tyr Asp Arg Ala Thr Phe Tyr Asn Ser Glu<br>225                      230                      235                      240 | 720 |
| cag cag cag agg ttg agt agt atc gca cag aaa gaa ttg caa aac gcc<br>Gln Gln Gln Arg Leu Ser Ser Ile Ala Gln Lys Glu Leu Gln Asn Ala<br>                    245                      250                      255 | 768 |
| tat gag gat atc aaa tgt gga gcc aag atg cta gct gcc gcg ccg tta<br>Tyr Glu Asp Ile Lys Cys Gly Ala Lys Met Leu Ala Ala Ala Pro Leu<br>                    260                      265                      270 | 816 |
| aca gca cag gcg ccc tta tgc acg gcg ctg cgg aga gat tcg ggg gac<br>Thr Ala Gln Ala Pro Leu Cys Thr Ala Leu Arg Arg Asp Ser Gly Asp<br>275                      280                      285 | 864 |
| cta att cca aag aag aag aag agg gag ccg gct cgc tta gct ctt ttg<br>Leu Ile Pro Lys Lys Lys Lys Arg Glu Pro Ala Arg Leu Ala Leu Leu<br>290                      295                      300 | 912 |
| cgg gct gcg cat ttt gaa cat gct tta tac cct tcg gag gtg gat gac<br>Arg Ala Ala His Phe Glu His Ala Leu Tyr Pro Ser Glu Val Asp Asp<br>305                      310                      315                      320 | 960 |
| aag cac ata ctc gac cta aaa tcc tat ctt att gac atg gcg cgt gag<br>Lys His Ile Leu Asp Leu Lys Ser Tyr Leu Ile Asp Met Ala Arg Glu<br>                    325                      330                      335 | 1008 |
| gag gag gag gga gcc ctt gtt ctg cca aaa ggg agt gag tta ata tca<br>Glu Glu Glu Gly Ala Leu Val Leu Pro Lys Gly Ser Glu Leu Ile Ser<br>                    340                      345                      350 | 1056 |
| aca tca ggt gcc tgt ggt gcc ctt aag gga ccg cca cca cgt acc ggt<br>Thr Ser Gly Ala Cys Gly Ala Leu Lys Gly Pro Pro Pro Arg Thr Gly<br>                    355                      360                      365 | 1104 |
| gtt gtg gag gtt cat ggt agc ctt cca ccg cgg gaa aca cat aat agc<br>Val Val Glu Val His Gly Ser Leu Pro Pro Arg Glu Thr His Asn Ser<br>370                      375                      380 | 1152 |

```
gca cga tac ggg cga gac agc cgc cat aaa ggc ctc gac cta ttc cac    1200
Ala Arg Tyr Gly Arg Asp Ser Arg His Lys Gly Leu Asp Leu Phe His
385                 390                 395                 400 cgt gtc gtt att agt cat aga caa ccc cgt aga aag agc ata tac gct    1248
Arg Val Val Ile Ser His Arg Gln Pro Arg Arg Lys Ser Ile Tyr Ala
            405                 410                 415 tcg cac ttg ggt ggg ctc tct ttc ccc gtg ttg gaa tac agc cca ttg    1296
Ser His Leu Gly Gly Leu Ser Phe Pro Val Leu Glu Tyr Ser Pro Leu
        420                 425                 430 tcg aag ccg ctg cgg gat tgg gag ggt atg gac aag aag gag ttg ttg    1344
Ser Lys Pro Leu Arg Asp Trp Glu Gly Met Asp Lys Lys Glu Leu Leu
    435                 440                 445 cga aaa gca agg gag ttc cta cga aag ggt gtt gtg gag ggt gtt cag    1392
Arg Lys Ala Arg Glu Phe Leu Arg Lys Gly Val Val Glu Gly Val Gln
450                 455                 460 atg agt gag agt gga gcc agc gaa tgt ggt gtt agg ggt ggc agt agc    1440
Met Ser Glu Ser Gly Ala Ser Glu Cys Gly Val Arg Gly Gly Ser Ser
465                 470                 475                 480 agc atc acc gaa aat agt gat agc gtg gcg tca tcc atg gtt tct cca    1488
Ser Ile Thr Glu Asn Ser Asp Ser Val Ala Ser Ser Met Val Ser Pro
            485                 490                 495 cag aat gtg aag ttg gga att gca ccg tca gca tta atg cgc gca tca    1536
Gln Asn Val Lys Leu Gly Ile Ala Pro Ser Ala Leu Met Arg Ala Ser
        500                 505                 510 ttg acg aca cca tcg tcg gga gct cca gga caa acc gtg agc agt gag    1584
Leu Thr Thr Pro Ser Ser Gly Ala Pro Gly Gln Thr Val Ser Ser Glu
    515                 520                 525 aac ggc taa                                                        1593
Asn Gly
    530

<210> SEQ ID NO 48
<211> LENGTH: 530
<212> TYPE: PRT
<213> ORGANISM: Trypanosoma brucei

<400> SEQUENCE: 48

Met Leu Ser Arg Ala Pro Arg Pro Asn Asn Arg Leu Ile Val Val Cys
1               5                   10                  15

Ser Cys Ile Lys Asn Val Ser Gly Trp Pro Phe Trp Lys Phe Gln Gln
            20                  25                  30

Met Arg Lys Val Lys Gly Val Thr Asp Leu Cys Met Leu Ala Phe Asn
        35                  40                  45

Ser Ser Gly Gly Ser Phe Glu Ala Ser Ile Thr Gly Ser Asp Tyr Thr
    50                  55                  60

Leu Lys Asn Tyr Glu Asn Val Val Gly Tyr Arg Gln Asp Met Leu Glu
65                  70                  75                  80

Asp Phe Leu Gln Arg Cys His Asp Pro Gly Arg Ser Tyr Phe Val Tyr
                85                  90                  95

Gly Gly His Gly Met Gly Asp Tyr Leu Glu Leu Glu Glu Asn Lys Leu
            100                 105                 110

Ala Leu Gln Cys His Glu Leu Ala Ser Ile Leu Gly Lys Arg Lys Phe
        115                 120                 125

Glu Ala Met Val Phe Asp Ser Cys Phe Met Ala Ser Leu Glu Cys Ala
    130                 135                 140

Tyr Gln Leu Arg His Asn Thr Arg Tyr Ile Gly Ala Cys Glu Gly Tyr
145                 150                 155                 160
```

```
Val Trp Ala Pro Asp Pro Asn Leu Asp Gln His Val Phe Asn Gln Tyr
            165                 170                 175

Ser Ala Ser Ala Met Ser Arg Phe Lys His Pro Lys Asn Ile Leu Leu
        180                 185                 190

Ala Ile Gln Arg Asp Tyr Cys Asn Lys Ser Pro Leu Ala Asp Phe Ala
    195                 200                 205

Val Leu Asp Thr Thr His Val Glu Ser Leu Lys Lys Tyr Val Glu Glu
210                 215                 220

His Val Met Gln Arg Val Tyr Asp Arg Ala Thr Phe Tyr Asn Ser Glu
225                 230                 235                 240

Gln Gln Gln Arg Leu Ser Ser Ile Ala Gln Lys Glu Leu Gln Asn Ala
                245                 250                 255

Tyr Glu Asp Ile Lys Cys Gly Ala Lys Met Leu Ala Ala Ala Pro Leu
            260                 265                 270

Thr Ala Gln Ala Pro Leu Cys Thr Ala Leu Arg Arg Asp Ser Gly Asp
        275                 280                 285

Leu Ile Pro Lys Lys Lys Arg Glu Pro Ala Arg Leu Ala Leu Leu
    290                 295                 300

Arg Ala Ala His Phe Glu His Ala Leu Tyr Pro Ser Glu Val Asp Asp
305                 310                 315                 320

Lys His Ile Leu Asp Leu Lys Ser Tyr Leu Ile Asp Met Ala Arg Glu
                325                 330                 335

Glu Glu Glu Gly Ala Leu Val Leu Pro Lys Gly Ser Glu Leu Ile Ser
            340                 345                 350

Thr Ser Gly Ala Cys Gly Ala Leu Lys Gly Pro Pro Arg Thr Gly
        355                 360                 365

Val Val Glu Val His Gly Ser Leu Pro Pro Arg Glu Thr His Asn Ser
370                 375                 380

Ala Arg Tyr Gly Arg Asp Ser Arg His Lys Gly Leu Asp Leu Phe His
385                 390                 395                 400

Arg Val Val Ile Ser His Arg Gln Pro Arg Lys Ser Ile Tyr Ala
                405                 410                 415

Ser His Leu Gly Gly Leu Ser Phe Pro Val Leu Glu Tyr Ser Pro Leu
            420                 425                 430

Ser Lys Pro Leu Arg Asp Trp Glu Gly Met Asp Lys Lys Glu Leu Leu
        435                 440                 445

Arg Lys Ala Arg Glu Phe Leu Arg Lys Gly Val Val Glu Gly Val Gln
    450                 455                 460

Met Ser Glu Ser Gly Ala Ser Glu Cys Gly Val Arg Gly Gly Ser Ser
465                 470                 475                 480

Ser Ile Thr Glu Asn Ser Asp Ser Val Ala Ser Ser Met Val Ser Pro
                485                 490                 495

Gln Asn Val Lys Leu Gly Ile Ala Pro Ser Ala Leu Met Arg Ala Ser
            500                 505                 510

Leu Thr Thr Pro Ser Ser Gly Ala Pro Gly Gln Thr Val Ser Ser Glu
        515                 520                 525

Asn Gly
    530

<210> SEQ ID NO 49
<211> LENGTH: 1518
<212> TYPE: DNA
<213> ORGANISM: Trypanosoma cruzi
<220> FEATURE:
<221> NAME/KEY: CDS
```

<222> LOCATION: (1)..(1518)

<400> SEQUENCE: 49

```
atg tct gtt aaa gcc tca cgg cga tgc aat cga ctg att gtc ctt ttt      48
Met Ser Val Lys Ala Ser Arg Arg Cys Asn Arg Leu Ile Val Leu Phe
1               5                  10                  15 agt tct atc aac gac gtg acg gca tgg cca ttt tgg aag ttt ctg cag      96
Ser Ser Ile Asn Asp Val Thr Ala Trp Pro Phe Trp Lys Phe Leu Gln
            20                  25                  30 atg aag aaa gta aag ggt gta acg gat ctt tcc ata ctt gcc ttt aac     144
Met Lys Lys Val Lys Gly Val Thr Asp Leu Ser Ile Leu Ala Phe Asn
        35                  40                  45 agc cag ggt ggc agc ttt gag gcc cgc att gac gga cag gag tac atg     192
Ser Gln Gly Gly Ser Phe Glu Ala Arg Ile Asp Gly Gln Glu Tyr Met
    50                  55                  60 ttg aag aac tac gaa aac gtt gta ggc tac tcg cag gac atg ttg gag     240
Leu Lys Asn Tyr Glu Asn Val Val Gly Tyr Ser Gln Asp Met Leu Glu
65                  70                  75                  80 cgt ttt ctg cac cgt tgg tac gac cct ggg cgc agt tat ttt gtc tac     288
Arg Phe Leu His Arg Trp Tyr Asp Pro Gly Arg Ser Tyr Phe Val Tyr
                85                  90                  95 ggc ggt cac gga atg ggt gac tac ctg gag ctg gag gaa aac aag gtg     336
Gly Gly His Gly Met Gly Asp Tyr Leu Glu Leu Glu Glu Asn Lys Val
            100                 105                 110 gga tta caa tgc cac gaa ctg gca gcg ata ttt gga gac aaa aag ttt     384
Gly Leu Gln Cys His Glu Leu Ala Ala Ile Phe Gly Asp Lys Lys Phe
        115                 120                 125 gag gcg atc acc ttt gac gca tgc tta atg gca agc ctg gac tgc gct     432
Glu Ala Ile Thr Phe Asp Ala Cys Leu Met Ala Ser Leu Asp Cys Ala
    130                 135                 140 tat cat ctg cgg aat aac acg cgt tac att ggc gcc tgt gag gga tac     480
Tyr His Leu Arg Asn Asn Thr Arg Tyr Ile Gly Ala Cys Glu Gly Tyr
145                 150                 155                 160 ttg tgg gag ccc gac aca agc ctc gac cat cat gtc ttc aac acg tac     528
Leu Trp Glu Pro Asp Thr Ser Leu Asp His His Val Phe Asn Thr Tyr
                165                 170                 175 acc gcc tcc gcg atg agc cgc ttt cgt gat ccg aag cac att ctt tta     576
Thr Ala Ser Ala Met Ser Arg Phe Arg Asp Pro Lys His Ile Leu Leu
            180                 185                 190 gcc gtg cag cgt gac tac tgc agc aaa tct tca ctt gct gac ttt gcc     624
Ala Val Gln Arg Asp Tyr Cys Ser Lys Ser Ser Leu Ala Asp Phe Ala
        195                 200                 205 gtg ctg gac acc acg cat gta gag gct ttg cgg agt tat gtg gaa gag     672
Val Leu Asp Thr Thr His Val Glu Ala Leu Arg Ser Tyr Val Glu Glu
    210                 215                 220 cac gtg atg caa cgt gtt tac gac cgt gcc act ttt tat aat gtc cag     720
His Val Met Gln Arg Val Tyr Asp Arg Ala Thr Phe Tyr Asn Val Gln
225                 230                 235                 240 cag cag cag aaa tta agc tac atg gcg gag gaa gca ttg caa ctc agc     768
Gln Gln Gln Lys Leu Ser Tyr Met Ala Glu Glu Ala Leu Gln Leu Ser
                245                 250                 255 cgg caa aat tcg aat act gac atc aag atg cca gct tca tca tca tca     816
Arg Gln Asn Ser Asn Thr Asp Ile Lys Met Pro Ala Ser Ser Ser Ser
            260                 265                 270 tcg tca tct cct gac acg gta gcc atg cga gcg atg gcg act aag ttg     864
Ser Ser Ser Pro Asp Thr Val Ala Met Arg Ala Met Ala Thr Lys Leu
        275                 280                 285 cag aac aaa cgg ttg gca aga cgt tcc aag ctg cag cat gcg gtt cag     912
Gln Asn Lys Arg Leu Ala Arg Arg Ser Lys Leu Gln His Ala Val Gln
    290                 295                 300
```

| | | | | | | | | | | | | | | | | |
|---|---|---|---|---|---|---|---|---|---|---|---|---|---|---|---|---|
| ttt | gag | cac | gcc | ttg | tat | cca | tct | gag | ccg | ggc | gac | aag | tac | atc | ctt | 960 |
| Phe | Glu | His | Ala | Leu | Tyr | Pro | Ser | Glu | Pro | Gly | Asp | Lys | Tyr | Ile | Leu | |
| 305 | | | | 310 | | | | | 315 | | | | | 320 | | |
| gac | ctt | cgt | tcc | tac | ctg | atc | gat | atg | gcg | cgt | gag | gag | gag | gaa | tta | 1008 |
| Asp | Leu | Arg | Ser | Tyr | Leu | Ile | Asp | Met | Ala | Arg | Glu | Glu | Glu | Glu | Leu | |
| | | | | 325 | | | | | 330 | | | | | 335 | | |
| gct | atc | gcc | tcc | ccg | tca | ccg | cga | act | gcc | gtt | gtg | gag | gca | cat | ggg | 1056 |
| Ala | Ile | Ala | Ser | Pro | Ser | Pro | Arg | Thr | Ala | Val | Val | Glu | Ala | His | Gly | |
| | | | 340 | | | | | 345 | | | | | 350 | | | |
| agt | ttg | cca | aat | gaa | aaa | aag | cat | ctc | cac | ccg | cgg | ttt | gcc | aaa | ggc | 1104 |
| Ser | Leu | Pro | Asn | Glu | Lys | Lys | His | Leu | His | Pro | Arg | Phe | Ala | Lys | Gly | |
| | | | | 355 | | | | | 360 | | | | | 365 | | |
| agc | gca | cac | gag | gga | ctg | gac | ttg | ttt | cat | cgc | gta | gtc | gtc | aat | cac | 1152 |
| Ser | Ala | His | Glu | Gly | Leu | Asp | Leu | Phe | His | Arg | Val | Val | Val | Asn | His | |
| | | 370 | | | | | 375 | | | | | 380 | | | | |
| ata | ccc | cct | gag | gaa | aag | cat | ata | tac | gcg | tca | cac | ctg | ggg | ggc | ctg | 1200 |
| Ile | Pro | Pro | Glu | Glu | Lys | His | Ile | Tyr | Ala | Ser | His | Leu | Gly | Gly | Leu | |
| 385 | | | | | 390 | | | | | 395 | | | | | 400 | |
| tct | att | cca | gta | tat | gag | ttt | agt | tcc | atg | tca | aag | ccg | ctg | atg | ccg | 1248 |
| Ser | Ile | Pro | Val | Tyr | Glu | Phe | Ser | Ser | Met | Ser | Lys | Pro | Leu | Met | Pro | |
| | | | | 405 | | | | | 410 | | | | | 415 | | |
| tgg | aat | cgt | gta | aac | cga | caa | ata | ttc | aaa | caa | aag | gca | aac | gaa | ttt | 1296 |
| Trp | Asn | Arg | Val | Asn | Arg | Gln | Ile | Phe | Lys | Gln | Lys | Ala | Asn | Glu | Phe | |
| | | | | 420 | | | | | 425 | | | | | 430 | | |
| ttg | cgt | cgt | ggt | gtc | atg | cag | gaa | gtg | aag | atg | aac | cag | cgc | acc | cac | 1344 |
| Leu | Arg | Arg | Gly | Val | Met | Gln | Glu | Val | Lys | Met | Asn | Gln | Arg | Thr | His | |
| | | | 435 | | | | | 440 | | | | | 445 | | | |
| agc | ggt | ttg | cgc | gaa | acg | gaa | agt | cgc | aac | tcg | tca | tca | tcg | cca | tcg | 1392 |
| Ser | Gly | Leu | Arg | Glu | Thr | Glu | Ser | Arg | Asn | Ser | Ser | Ser | Ser | Pro | Ser | |
| | 450 | | | | | 455 | | | | | 460 | | | | | |
| acg | ggc | tca | cca | ggt | cca | acc | ata | tat | ctc | cca | att | tca | ggg | tac | tcc | 1440 |
| Thr | Gly | Ser | Pro | Gly | Pro | Thr | Ile | Tyr | Leu | Pro | Ile | Ser | Gly | Tyr | Ser | |
| 465 | | | | | 470 | | | | | 475 | | | | | 480 | |
| ggc | aac | agc | aac | agc | aat | cga | aac | aaa | ccc | ggt | agc | gga | aac | ttg | ccg | 1488 |
| Gly | Asn | Ser | Asn | Ser | Asn | Arg | Asn | Lys | Pro | Gly | Ser | Gly | Asn | Leu | Pro | |
| | | | | 485 | | | | | 490 | | | | | 495 | | |
| ggg | tcg | cag | cac | tgt | gag | gcg | aga | cga | tga | | | | | | | 1518 |
| Gly | Ser | Gln | His | Cys | Glu | Ala | Arg | Arg | | | | | | | | |
| | | | 500 | | | | 505 | | | | | | | | | |

<210> SEQ ID NO 50
<211> LENGTH: 505
<212> TYPE: PRT
<213> ORGANISM: Trypanosoma cruzi

<400> SEQUENCE: 50

Met Ser Val Lys Ala Ser Arg Arg Cys Asn Arg Leu Ile Val Leu Phe
1               5                   10                  15

Ser Ser Ile Asn Asp Val Thr Ala Trp Pro Phe Trp Lys Phe Leu Gln
                20                  25                  30

Met Lys Lys Val Lys Gly Val Thr Asp Leu Ser Ile Leu Ala Phe Asn
            35                  40                  45

Ser Gln Gly Gly Ser Phe Glu Ala Arg Ile Asp Gly Gln Glu Tyr Met
        50                  55                  60

Leu Lys Asn Tyr Glu Asn Val Val Gly Tyr Ser Gln Asp Met Leu Glu
65                  70                  75                  80

Arg Phe Leu His Arg Trp Tyr Asp Pro Gly Arg Ser Tyr Phe Val Tyr
                85                  90                  95

```
Gly Gly His Gly Met Gly Asp Tyr Leu Glu Leu Glu Glu Asn Lys Val
            100                 105                 110

Gly Leu Gln Cys His Glu Leu Ala Ala Ile Phe Gly Asp Lys Lys Phe
        115                 120                 125

Glu Ala Ile Thr Phe Asp Ala Cys Leu Met Ala Ser Leu Asp Cys Ala
    130                 135                 140

Tyr His Leu Arg Asn Asn Thr Arg Tyr Ile Gly Ala Cys Glu Gly Tyr
145                 150                 155                 160

Leu Trp Glu Pro Asp Thr Ser Leu Asp His His Val Phe Asn Thr Tyr
                165                 170                 175

Thr Ala Ser Ala Met Ser Arg Phe Arg Asp Pro Lys His Ile Leu Leu
            180                 185                 190

Ala Val Gln Arg Asp Tyr Cys Ser Lys Ser Leu Ala Asp Phe Ala
        195                 200                 205

Val Leu Asp Thr Thr His Val Glu Ala Leu Arg Ser Tyr Val Glu Glu
    210                 215                 220

His Val Met Gln Arg Val Tyr Asp Arg Ala Thr Phe Tyr Asn Val Gln
225                 230                 235                 240

Gln Gln Gln Lys Leu Ser Tyr Met Ala Glu Glu Ala Leu Gln Leu Ser
                245                 250                 255

Arg Gln Asn Ser Asn Thr Asp Ile Lys Met Pro Ala Ser Ser Ser Ser
            260                 265                 270

Ser Ser Ser Pro Asp Thr Val Ala Met Arg Ala Met Ala Thr Lys Leu
        275                 280                 285

Gln Asn Lys Arg Leu Ala Arg Arg Ser Lys Leu Gln His Ala Val Gln
290                 295                 300

Phe Glu His Ala Leu Tyr Pro Ser Glu Pro Gly Asp Lys Tyr Ile Leu
305                 310                 315                 320

Asp Leu Arg Ser Tyr Leu Ile Asp Met Ala Arg Glu Glu Glu Leu
                325                 330                 335

Ala Ile Ala Ser Pro Ser Pro Arg Thr Ala Val Val Glu Ala His Gly
        340                 345                 350

Ser Leu Pro Asn Glu Lys Lys His Leu His Pro Arg Phe Ala Lys Gly
            355                 360                 365

Ser Ala His Glu Gly Leu Asp Leu Phe His Arg Val Val Asn His
    370                 375                 380

Ile Pro Pro Glu Glu Lys His Ile Tyr Ala Ser His Leu Gly Gly Leu
385                 390                 395                 400

Ser Ile Pro Val Tyr Glu Phe Ser Ser Met Ser Lys Pro Leu Met Pro
                405                 410                 415

Trp Asn Arg Val Asn Arg Gln Ile Phe Lys Gln Lys Ala Asn Glu Phe
            420                 425                 430

Leu Arg Arg Gly Val Met Gln Glu Val Lys Met Asn Gln Arg Thr His
        435                 440                 445

Ser Gly Leu Arg Glu Thr Glu Ser Arg Asn Ser Ser Ser Pro Ser
    450                 455                 460

Thr Gly Ser Pro Gly Pro Thr Ile Tyr Leu Pro Ile Ser Gly Tyr Ser
465                 470                 475                 480

Gly Asn Ser Asn Ser Asn Arg Asn Lys Pro Gly Ser Gly Asn Leu Pro
                485                 490                 495

Gly Ser Gln His Cys Glu Ala Arg Arg
            500                 505
```

-continued

```
<210> SEQ ID NO 51
<211> LENGTH: 1962
<212> TYPE: DNA
<213> ORGANISM: Leishmania major
<220> FEATURE:
<221> NAME/KEY: CDS
<222> LOCATION: (1)..(1962)

<400> SEQUENCE: 51 atg ccc cca aag cgc tac ccc aac cgc ctc ttg gtg ctg tgc gcc tcc        48
Met Pro Pro Lys Arg Tyr Pro Asn Arg Leu Leu Val Leu Cys Ala Ser
1               5                  10                  15 atc aac gat gtc aca gca tgg ccg ttt tgg aag ttc ttg cag atg aag        96
Ile Asn Asp Val Thr Ala Trp Pro Phe Trp Lys Phe Leu Gln Met Lys
            20                  25                  30 aag att cgc ggc gtg acg gac atg gcg ctg ctc gcc ttc aac agc gac       144
Lys Ile Arg Gly Val Thr Asp Met Ala Leu Leu Ala Phe Asn Ser Asp
        35                  40                  45 ggc ggc agc ttc gag gct cgc att gac ggc gac aaa tac cag ctc aag       192
Gly Gly Ser Phe Glu Ala Arg Ile Asp Gly Asp Lys Tyr Gln Leu Lys
    50                  55                  60 aac tat gcc aag gtt cgc ggc tac cag cat gac atg ttt gag agc ttc       240
Asn Tyr Ala Lys Val Arg Gly Tyr Gln His Asp Met Phe Glu Ser Phe
65                  70                  75                  80 gtg cat cgc tgg cac gat ccg ggc cga agc tat ttt gtg tat ggc ggg       288
Val His Arg Trp His Asp Pro Gly Arg Ser Tyr Phe Val Tyr Gly Gly
                85                  90                  95 cat ggc atg ggt gac tat gtg gag cta gaa cag aac cgt gtc tcg ctg       336
His Gly Met Gly Asp Tyr Val Glu Leu Glu Gln Asn Arg Val Ser Leu
            100                 105                 110 cag gtg cac gag ctc gcc gac gtc ttc ggc acg cgt gtc ttc gaa gca       384
Gln Val His Glu Leu Ala Asp Val Phe Gly Thr Arg Val Phe Glu Ala
        115                 120                 125 gtg ctc ttt gac gcc tgc ttc atg gcg aac atc gac tgc gcc tat cat       432
Val Leu Phe Asp Ala Cys Phe Met Ala Asn Ile Asp Cys Ala Tyr His
    130                 135                 140 ctg cgc cac aac acg cgg tac atc ggt gcc tgc gag ggg tac atg tgg       480
Leu Arg His Asn Thr Arg Tyr Ile Gly Ala Cys Glu Gly Tyr Met Trp
145                 150                 155                 160 gag cct gac acg gcc ctc gac tac cat gtc ttc aac acc cac aac gcg       528
Glu Pro Asp Thr Ala Leu Asp Tyr His Val Phe Asn Thr His Asn Ala
                165                 170                 175 agc gcc atg agc cgc ttc aaa gac ccg ctg cac atc ctc cgt gtt att       576
Ser Ala Met Ser Arg Phe Lys Asp Pro Leu His Ile Leu Arg Val Ile
            180                 185                 190 cag acg gac tac tgc agc aag gcg cca cgt ggc gac ttc acc atc atc       624
Gln Thr Asp Tyr Cys Ser Lys Ala Pro Arg Gly Asp Phe Thr Ile Ile
        195                 200                 205 gac acc acg cac atc gcg gcg ctg cgg cag tac gtg cag gag cac gtc       672
Asp Thr Thr His Ile Ala Ala Leu Arg Gln Tyr Val Gln Glu His Val
    210                 215                 220 atg cag cgt gtt tat gac cgg gcg acc ttc tac agc tta ccg cag cga       720
Met Gln Arg Val Tyr Asp Arg Ala Thr Phe Tyr Ser Leu Pro Gln Arg
225                 230                 235                 240 gag cga ctg cag caa atc gcc gag gcg tcg att cag gcg tcg ata tct       768
Glu Arg Leu Gln Gln Ile Ala Glu Ala Ser Ile Gln Ala Ser Ile Ser
                245                 250                 255 cag ttt ggc cac ccc ggc ggt gac acc aac gtg att aat ggc gtt ggc       816
Gln Phe Gly His Pro Gly Gly Asp Thr Asn Val Ile Asn Gly Val Gly
            260                 265                 270 agt ggc act gac cgc ccg cgc acc gcc cca tcg tca ccc gag gtg ctt       864
```

```
                Ser Gly Thr Asp Arg Pro Arg Thr Ala Pro Ser Ser Pro Glu Val Leu
                            275                 280                 285 gca ctt tcc gcc gcc ggc aga ccg acg cgg cgg cag cga atg ctg cag            912
Ala Leu Ser Ala Ala Gly Arg Pro Thr Arg Arg Gln Arg Met Leu Gln
290                 295                 300 gcg att cag ttt gag cac tcg ctg tac ccg tcg gag gtc gac gac aag            960
Ala Ile Gln Phe Glu His Ser Leu Tyr Pro Ser Glu Val Asp Asp Lys
305                 310                 315                 320 cag ctg ctc gac ctc aag tcg tat ctc act gac atg ctg cac gag gag           1008
Gln Leu Leu Asp Leu Lys Ser Tyr Leu Thr Asp Met Leu His Glu Glu
                325                 330                 335 cag cag cta aag gcg tgg gag gca gcg gcg ctg ggc ccg cag cgc cgc           1056
Gln Gln Leu Lys Ala Trp Glu Ala Ala Ala Leu Gly Pro Gln Arg Arg
            340                 345                 350 att gcg gcg ggt cgc cgc cgc gtg cga agt gat gca ctg cag cat ggt           1104
Ile Ala Ala Gly Arg Arg Arg Val Arg Ser Asp Ala Leu Gln His Gly
                    355                 360                 365 ggc agc tcc ggc atc gcc gcc ccc tcc acc gcc tcg tcc tcc ttc gcc           1152
Gly Ser Ser Gly Ile Ala Ala Pro Ser Thr Ala Ser Ser Ser Phe Ala
370                 375                 380 gtc tgg aag gcg ccg ccg tcg cgg gcg ctg ttt gct gat cgg cac ggg           1200
Val Trp Lys Ala Pro Pro Ser Arg Ala Leu Phe Ala Asp Arg His Gly
385                 390                 395                 400 cgg ccg cct gct gcc agt tct gca gag tgc tcg ccg tcc atc aac ggt           1248
Arg Pro Pro Ala Ala Ser Ser Ala Glu Cys Ser Pro Ser Ile Asn Gly
                405                 410                 415 ggc cca gcc gca gca cac gac acg cag aag ggg gcg acg gcg ctc tct           1296
Gly Pro Ala Ala Ala His Asp Thr Gln Lys Gly Ala Thr Ala Leu Ser
            420                 425                 430 cct cca gtc ctt gcg acc act cca acg aag gca gca ccg ccg cct ccg           1344
Pro Pro Val Leu Ala Thr Thr Pro Thr Lys Ala Ala Pro Pro Pro Pro
                435                 440                 445 tct ctc tcc acc tct tac aag ggc agc gcg cag gag ggg cta gat ctt           1392
Ser Leu Ser Thr Ser Tyr Lys Gly Ser Ala Gln Glu Gly Leu Asp Leu
450                 455                 460 ttc tac cag gtt gtc gtg agc cac atc cca ccg aag gcc gct tcc atc           1440
Phe Tyr Gln Val Val Val Ser His Ile Pro Pro Lys Ala Ala Ser Ile
465                 470                 475                 480 tac gcg acc cag ctc ggg gga tta tcc ttt acg gtg cac gag tac agt           1488
Tyr Ala Thr Gln Leu Gly Gly Leu Ser Phe Thr Val His Glu Tyr Ser
                485                 490                 495 gcc atg tcg cgg ccg gca gag ccg tgg ttg gtg ggc tcg aag agg ttg           1536
Ala Met Ser Arg Pro Ala Glu Pro Trp Leu Val Gly Ser Lys Arg Leu
            500                 505                 510 ctg aag cgc cgg gca aag caa ttc ctg aag aac ggc gaa ctc tcg gag           1584
Leu Lys Arg Arg Ala Lys Gln Phe Leu Lys Asn Gly Glu Leu Ser Glu
                515                 520                 525 gtg gtg atg gag tcc ccg aag gcg agc gcg tcc gtc acc agc gct gcc           1632
Val Val Met Glu Ser Pro Lys Ala Ser Ala Ser Val Thr Ser Ala Ala
530                 535                 540 ctc gtg gca gcc gtc gac aag gtg aca gca acg gcg gcg gcg gtg acg           1680
Leu Val Ala Ala Val Asp Lys Val Thr Ala Thr Ala Ala Ala Val Thr
545                 550                 555                 560 ggt gct tct gca gga aaa ccc gag cct gcg act tcc gcc gcc gcg ctg           1728
Gly Ala Ser Ala Gly Lys Pro Glu Pro Ala Thr Ser Ala Ala Ala Leu
                565                 570                 575 ccg ctg tca ccc aga gca cac atg ccc tcc acg gat cag cgt ctg cgt           1776
Pro Leu Ser Pro Arg Ala His Met Pro Ser Thr Asp Gln Arg Leu Arg
            580                 585                 590
```

| | | | | | | | | | | | | | | | |
|---|---|---|---|---|---|---|---|---|---|---|---|---|---|---|---|
| ttc | acg | agc | agc | ggt | aat | ggc | aca | gac | agc | gac | agc | tcc | ttg | tca | ctg | 1824 |
| Phe | Thr | Ser | Ser | Gly | Asn | Gly | Thr | Asp | Ser | Asp | Ser | Ser | Leu | Ser | Leu | |
| | | 595 | | | | 600 | | | | | 605 | | | | | |
| agc | ttg | tcc | gta | ccg | ctc | tcc | act | tcc | tcc | acg | gat | gca | tac | aac | aac | 1872 |
| Ser | Leu | Ser | Val | Pro | Leu | Ser | Thr | Ser | Ser | Thr | Asp | Ala | Tyr | Asn | Asn | |
| | 610 | | | | | 615 | | | | | 620 | | | | | |
| agc | atg | aaa | acg | gta | att | ctc | gac | tcg | cca | cag | cgg | gct | gcc | tcc | tat | 1920 |
| Ser | Met | Lys | Thr | Val | Ile | Leu | Asp | Ser | Pro | Gln | Arg | Ala | Ala | Ser | Tyr | |
| 625 | | | | 630 | | | | | 635 | | | | | 640 | | |
| aca | tcg | tta | ccc | aac | tcc | aaa | gaa | cgt | aca | agc | gcc | tgc | tga | | | 1962 |
| Thr | Ser | Leu | Pro | Asn | Ser | Lys | Glu | Arg | Thr | Ser | Ala | Cys | | | | |
| | | | | 645 | | | | | 650 | | | | | | | |

<210> SEQ ID NO 52
<211> LENGTH: 653
<212> TYPE: PRT
<213> ORGANISM: Leishmania major

<400> SEQUENCE: 52

Met Pro Pro Lys Arg Tyr Pro Asn Arg Leu Leu Val Leu Cys Ala Ser
1               5                   10                  15

Ile Asn Asp Val Thr Ala Trp Pro Phe Trp Lys Phe Leu Gln Met Lys
            20                  25                  30

Lys Ile Arg Gly Val Thr Asp Met Ala Leu Leu Ala Phe Asn Ser Asp
        35                  40                  45

Gly Gly Ser Phe Glu Ala Arg Ile Asp Gly Asp Lys Tyr Gln Leu Lys
    50                  55                  60

Asn Tyr Ala Lys Val Arg Gly Tyr Gln His Asp Met Phe Glu Ser Phe
65                  70                  75                  80

Val His Arg Trp His Asp Pro Gly Arg Ser Tyr Phe Val Tyr Gly Gly
                85                  90                  95

His Gly Met Gly Asp Tyr Val Glu Leu Glu Gln Asn Arg Val Ser Leu
            100                 105                 110

Gln Val His Glu Leu Ala Asp Val Phe Gly Thr Arg Val Phe Glu Ala
        115                 120                 125

Val Leu Phe Asp Ala Cys Phe Met Ala Asn Ile Asp Cys Ala Tyr His
    130                 135                 140

Leu Arg His Asn Thr Arg Tyr Ile Gly Ala Cys Glu Gly Tyr Met Trp
145                 150                 155                 160

Glu Pro Asp Thr Ala Leu Asp Tyr His Val Phe Asn Thr His Asn Ala
                165                 170                 175

Ser Ala Met Ser Arg Phe Lys Asp Pro Leu His Ile Leu Arg Val Ile
            180                 185                 190

Gln Thr Asp Tyr Cys Ser Lys Ala Pro Arg Gly Asp Phe Thr Ile Ile
        195                 200                 205

Asp Thr Thr His Ile Ala Ala Leu Arg Gln Tyr Val Gln Glu His Val
    210                 215                 220

Met Gln Arg Val Tyr Asp Arg Ala Thr Phe Tyr Ser Leu Pro Gln Arg
225                 230                 235                 240

Glu Arg Leu Gln Gln Ile Ala Glu Ala Ser Ile Gln Ala Ser Ile Ser
                245                 250                 255

Gln Phe Gly His Pro Gly Gly Asp Thr Asn Val Ile Asn Gly Val Gly
            260                 265                 270

Ser Gly Thr Asp Arg Pro Arg Thr Ala Pro Ser Ser Pro Glu Val Leu
        275                 280                 285

Ala Leu Ser Ala Ala Gly Arg Pro Thr Arg Arg Gln Arg Met Leu Gln

```
                    290                 295                 300
Ala Ile Gln Phe Glu His Ser Leu Tyr Pro Ser Glu Val Asp Asp Lys
305                 310                 315                 320

Gln Leu Leu Asp Leu Lys Ser Tyr Leu Thr Asp Met Leu His Glu Glu
                325                 330                 335

Gln Gln Leu Lys Ala Trp Glu Ala Ala Leu Gly Pro Gln Arg Arg
            340                 345                 350

Ile Ala Ala Gly Arg Arg Val Arg Ser Asp Ala Leu Gln His Gly
        355                 360                 365

Gly Ser Ser Gly Ile Ala Ala Pro Ser Thr Ala Ser Ser Phe Ala
    370                 375                 380

Val Trp Lys Ala Pro Pro Ser Arg Ala Leu Phe Ala Asp Arg His Gly
385                 390                 395                 400

Arg Pro Pro Ala Ala Ser Ser Ala Glu Cys Ser Pro Ser Ile Asn Gly
                405                 410                 415

Gly Pro Ala Ala Ala His Asp Thr Gln Lys Gly Ala Thr Ala Leu Ser
                420                 425                 430

Pro Pro Val Leu Ala Thr Thr Pro Thr Lys Ala Ala Pro Pro Pro
            435                 440                 445

Ser Leu Ser Thr Ser Tyr Lys Gly Ser Ala Gln Glu Gly Leu Asp Leu
                450                 455                 460

Phe Tyr Gln Val Val Ser His Ile Pro Pro Lys Ala Ala Ser Ile
465                 470                 475                 480

Tyr Ala Thr Gln Leu Gly Gly Leu Ser Phe Thr Val His Glu Tyr Ser
                485                 490                 495

Ala Met Ser Arg Pro Ala Glu Pro Trp Leu Val Gly Ser Lys Arg Leu
                500                 505                 510

Leu Lys Arg Arg Ala Lys Gln Phe Leu Lys Asn Gly Glu Leu Ser Glu
                515                 520                 525

Val Val Met Glu Ser Pro Lys Ala Ser Ala Ser Val Thr Ser Ala Ala
                530                 535                 540

Leu Val Ala Ala Val Asp Lys Val Thr Ala Thr Ala Ala Ala Val Thr
545                 550                 555                 560

Gly Ala Ser Ala Gly Lys Pro Glu Pro Ala Thr Ser Ala Ala Ala Leu
                565                 570                 575

Pro Leu Ser Pro Arg Ala His Met Pro Ser Thr Asp Gln Arg Leu Arg
                580                 585                 590

Phe Thr Ser Ser Gly Asn Gly Thr Asp Ser Asp Ser Ser Leu Ser Leu
                595                 600                 605

Ser Leu Ser Val Pro Leu Ser Thr Ser Thr Asp Ala Tyr Asn Asn
            610                 615                 620

Ser Met Lys Thr Val Ile Leu Asp Ser Pro Gln Arg Ala Ala Ser Tyr
625                 630                 635                 640

Thr Ser Leu Pro Asn Ser Lys Glu Arg Thr Ser Ala Cys
                645                 650
```

<210> SEQ ID NO 53
<211> LENGTH: 1962
<212> TYPE: DNA
<213> ORGANISM: Leishmania infantum
<220> FEATURE:
<221> NAME/KEY: CDS
<222> LOCATION: (1)..(1962)

<400> SEQUENCE: 53

-continued

| | |
|---|---|
| atg ccg ccg agg cgc tgc cca aac cgc ctc ctg gtg ctg tgc gcc tcc<br>Met Pro Pro Arg Arg Cys Pro Asn Arg Leu Leu Val Leu Cys Ala Ser<br>1                      5                      10                   15 | 48 |
| atc aat gat gtc aca gca tgg ccg ttt tgg aag ttc ttg cag atg aag<br>Ile Asn Asp Val Thr Ala Trp Pro Phe Trp Lys Phe Leu Gln Met Lys<br>                20                      25                      30 | 96 |
| aag att cgc ggc gtg acg gac atg gcg ctg ctc gcc ttc aac agc gac<br>Lys Ile Arg Gly Val Thr Asp Met Ala Leu Leu Ala Phe Asn Ser Asp<br>        35                      40                      45 | 144 |
| ggc ggc agc ttt gag gct cgc atc gat ggc gac agg tac cag ctc aag<br>Gly Gly Ser Phe Glu Ala Arg Ile Asp Gly Asp Arg Tyr Gln Leu Lys<br>50                     55                      60 | 192 |
| aac tac gcc aag gtg cgc ggc tac cag cac gac atg ttt gag agc ttc<br>Asn Tyr Ala Lys Val Arg Gly Tyr Gln His Asp Met Phe Glu Ser Phe<br>65                      70                      75                   80 | 240 |
| gtg cat cgc tgg cac gat ccg ggc cga agc tat ttc gtg tat ggc ggg<br>Val His Arg Trp His Asp Pro Gly Arg Ser Tyr Phe Val Tyr Gly Gly<br>                      85                      90                   95 | 288 |
| cat ggt atg ggc gac tat gtg gag cta gag cag aac cgt gtt tcg ctg<br>His Gly Met Gly Asp Tyr Val Glu Leu Glu Gln Asn Arg Val Ser Leu<br>                100                     105                   110 | 336 |
| cag gcg cac gag ctc gcc gac gtc ttc ggc acg cgt gtc ttc gaa gcc<br>Gln Ala His Glu Leu Ala Asp Val Phe Gly Thr Arg Val Phe Glu Ala<br>        115                     120                     125 | 384 |
| gtg ctc ttt gac gcc tgc ttc atg gcg aac ctt gac tgc gcc tat cat<br>Val Leu Phe Asp Ala Cys Phe Met Ala Asn Leu Asp Cys Ala Tyr His<br>130                      135                     140 | 432 |
| ctg cgc cac aac acg cgg tac atc ggt gcc tgt gag ggg tac atg tgg<br>Leu Arg His Asn Thr Arg Tyr Ile Gly Ala Cys Glu Gly Tyr Met Trp<br>145                     150                     155                  160 | 480 |
| gag cct gac acg gcc ctc gac tac cat gtc ttc aac acc cac aac gcg<br>Glu Pro Asp Thr Ala Leu Asp Tyr His Val Phe Asn Thr His Asn Ala<br>                     165                     170                     175 | 528 |
| agc gcc atg agc cgc ttc aaa gac ccg ctg cac atc ctc cgc gtt att<br>Ser Ala Met Ser Arg Phe Lys Asp Pro Leu His Ile Leu Arg Val Ile<br>        180                     185                     190 | 576 |
| cag gcg gac tac tgc agc aag gcg ccg cgt ggc gac ttc acc atc atc<br>Gln Ala Asp Tyr Cys Ser Lys Ala Pro Arg Gly Asp Phe Thr Ile Ile<br>195                     200                     205 | 624 |
| gac acc acg cac att gcg gcg ctg cgg cag tac gtg cag gag cat gtc<br>Asp Thr Thr His Ile Ala Ala Leu Arg Gln Tyr Val Gln Glu His Val<br>210                     215                     220 | 672 |
| atg cag cgc gtt tat gac cgg gcg acc ttc tac agc cta ccg cag cga<br>Met Gln Arg Val Tyr Asp Arg Ala Thr Phe Tyr Ser Leu Pro Gln Arg<br>225                     230                     235                  240 | 720 |
| gag cga ctg cag caa atc gcc gag gcg tcg att cag gcg tcc ata tcc<br>Glu Arg Leu Gln Gln Ile Ala Glu Ala Ser Ile Gln Ala Ser Ile Ser<br>                   245                     250                     255 | 768 |
| cag ttt ggc cac ccc ggc ggt gac acc aac gtg atg aat ggc gtt ggc<br>Gln Phe Gly His Pro Gly Gly Asp Thr Asn Val Met Asn Gly Val Gly<br>        260                     265                     270 | 816 |
| agt ggt act ggc cgc ccg cgc acc gcc cca tcg tca ccc gag gtg ctt<br>Ser Gly Thr Gly Arg Pro Arg Thr Ala Pro Ser Ser Pro Glu Val Leu<br>275                     280                     285 | 864 |
| gcg ctt tcc gcc gcc ggt aga ccg acg cgg cgg cag cga atg ctg cag<br>Ala Leu Ser Ala Ala Gly Arg Pro Thr Arg Arg Gln Arg Met Leu Gln<br>290                      295                     300 | 912 |
| gcg att cag ttt gag cac tcg ctg tac ccg tcg gag gta gac gac aaa<br>Ala Ile Gln Phe Glu His Ser Leu Tyr Pro Ser Glu Val Asp Asp Lys<br>305                     310                     315                  320 | 960 |

```
cag ctg ctc gac ctc aag tcg tat ctc acg gac atg ctg cgg gag gag    1008
Gln Leu Leu Asp Leu Lys Ser Tyr Leu Thr Asp Met Leu Arg Glu Glu
            325                 330                 335 cag cag cta aag gcg tgg gag gca gcg gcg ctg ggg ccg cag cgc cgc    1056
Gln Gln Leu Lys Ala Trp Glu Ala Ala Ala Leu Gly Pro Gln Arg Arg
        340                 345                 350 att gcg gct ggc cgc cgc cgc ttg cga agt gat gca ctg cag cat ggt    1104
Ile Ala Ala Gly Arg Arg Arg Leu Arg Ser Asp Ala Leu Gln His Gly
    355                 360                 365 ggc agc tcc gga atc gcc gcc ccc tcc tcc gcc tcg tcc tcc ttc gcc    1152
Gly Ser Ser Gly Ile Ala Ala Pro Ser Ser Ala Ser Ser Ser Phe Ala
370                 375                 380 gtc tgg aag gcg ccg ccg tcg cgg gcg ctg ttt gtt gat cgg cac gga    1200
Val Trp Lys Ala Pro Pro Ser Arg Ala Leu Phe Val Asp Arg His Gly
385                 390                 395                 400 cgg ctg cct gct gcc agc tct aca ggg tgc tcg ccg tcc atc aac ggt    1248
Arg Leu Pro Ala Ala Ser Ser Thr Gly Cys Ser Pro Ser Ile Asn Gly
                405                 410                 415 ggc cca gcc gca gca aac gac aag caa aaa gag gcg acg gcg ctc tct    1296
Gly Pro Ala Ala Ala Asn Asp Lys Gln Lys Glu Ala Thr Ala Leu Ser
            420                 425                 430 cct cca gcc ctt gca gcc act cta acg atg gca aca gcg ccg cct ccg    1344
Pro Pro Ala Leu Ala Ala Thr Leu Thr Met Ala Thr Ala Pro Pro Pro
        435                 440                 445 tct ctc tcc acc tct tac aag ggc agc gcg cag gag ggg cta gat ctt    1392
Ser Leu Ser Thr Ser Tyr Lys Gly Ser Ala Gln Glu Gly Leu Asp Leu
    450                 455                 460 ttt cac cag gtt gtc gtg agc cac atc cca ccc aag gcc gct tcc atc    1440
Phe His Gln Val Val Val Ser His Ile Pro Pro Lys Ala Ala Ser Ile
465                 470                 475                 480 tac gca acc cag ctc ggg ggg cta tcc tta acg gtg cac gag tac agt    1488
Tyr Ala Thr Gln Leu Gly Gly Leu Ser Leu Thr Val His Glu Tyr Ser
                485                 490                 495 gcc atg tcg cgg ccg gca gag ccg tgg tcg gtg ggc tcg aag agg ttg    1536
Ala Met Ser Arg Pro Ala Glu Pro Trp Ser Val Gly Ser Lys Arg Leu
            500                 505                 510 ctg aag cgc cgg gca aag caa ttc ctg aag aac ggc gaa ctc tcg gag    1584
Leu Lys Arg Arg Ala Lys Gln Phe Leu Lys Asn Gly Glu Leu Ser Glu
        515                 520                 525 gtg gtg atg gag tcc ccg aag gcg agc cca tcc gtc acc agc gct gcc    1632
Val Val Met Glu Ser Pro Lys Ala Ser Pro Ser Val Thr Ser Ala Ala
    530                 535                 540 ctc gcg gca acc gtg aac aag gcg aca gcg acg gcc gcg gca gtg aag    1680
Leu Ala Ala Thr Val Asn Lys Ala Thr Ala Thr Ala Ala Val Lys
545                 550                 555                 560 ggt gct tct gca gga aaa ccc cag cat gcg act tcc gcc gcc gcg ctg    1728
Gly Ala Ser Ala Gly Lys Pro Gln His Ala Thr Ser Ala Ala Ala Leu
                565                 570                 575 ccg cta tca ccc aga aca cga atg ctc ttc ccg gac cag cgt ctg agt    1776
Pro Leu Ser Pro Arg Thr Arg Met Leu Phe Pro Asp Gln Arg Leu Ser
            580                 585                 590 ttc acg agc agc agt aat ggc aca gac agc gac agc tcc ttg ccg ctc    1824
Phe Thr Ser Ser Ser Asn Gly Thr Asp Ser Asp Ser Ser Leu Pro Leu
        595                 600                 605 agc ttg tcc gca ccg ctt tcc acc tca tcc acg gat gca tgc aac agc    1872
Ser Leu Ser Ala Pro Leu Ser Thr Ser Ser Thr Asp Ala Cys Asn Ser
    610                 615                 620 agc atg aaa aca gta att ctc gac ccg cca cag cgg gct gcc tcc tgt    1920
Ser Met Lys Thr Val Ile Leu Asp Pro Pro Gln Arg Ala Ala Ser Cys
```

```
                     625                 630                 635                 640
acg tcg tta ccc aac tcc aaa caa cgt aca agc gcc tgc tga                                    1962
Thr Ser Leu Pro Asn Ser Lys Gln Arg Thr Ser Ala Cys
                645                 650

<210> SEQ ID NO 54
<211> LENGTH: 653
<212> TYPE: PRT
<213> ORGANISM: Leishmania infantum

<400> SEQUENCE: 54

Met Pro Pro Arg Arg Cys Pro Asn Arg Leu Leu Val Leu Cys Ala Ser
1               5                   10                  15

Ile Asn Asp Val Thr Ala Trp Pro Phe Trp Lys Phe Leu Gln Met Lys
            20                  25                  30

Lys Ile Arg Gly Val Thr Asp Met Ala Leu Leu Ala Phe Asn Ser Asp
        35                  40                  45

Gly Gly Ser Phe Glu Ala Arg Ile Asp Gly Asp Arg Tyr Gln Leu Lys
    50                  55                  60

Asn Tyr Ala Lys Val Arg Gly Tyr Gln His Asp Met Phe Glu Ser Phe
65                  70                  75                  80

Val His Arg Trp His Asp Pro Gly Arg Ser Tyr Phe Val Tyr Gly Gly
                85                  90                  95

His Gly Met Gly Asp Tyr Val Glu Leu Glu Gln Asn Arg Val Ser Leu
            100                 105                 110

Gln Ala His Glu Leu Ala Asp Val Phe Gly Thr Arg Val Phe Glu Ala
        115                 120                 125

Val Leu Phe Asp Ala Cys Phe Met Ala Asn Leu Asp Cys Ala Tyr His
    130                 135                 140

Leu Arg His Asn Thr Arg Tyr Ile Gly Ala Cys Glu Gly Tyr Met Trp
145                 150                 155                 160

Glu Pro Asp Thr Ala Leu Asp Tyr His Val Phe Asn Thr His Asn Ala
                165                 170                 175

Ser Ala Met Ser Arg Phe Lys Asp Pro Leu His Ile Leu Arg Val Ile
            180                 185                 190

Gln Ala Asp Tyr Cys Ser Lys Ala Pro Arg Gly Asp Phe Thr Ile Ile
        195                 200                 205

Asp Thr Thr His Ile Ala Ala Leu Arg Gln Tyr Val Gln Glu His Val
    210                 215                 220

Met Gln Arg Val Tyr Asp Arg Ala Thr Phe Tyr Ser Leu Pro Gln Arg
225                 230                 235                 240

Glu Arg Leu Gln Gln Ile Ala Glu Ala Ser Ile Gln Ala Ser Ile Ser
                245                 250                 255

Gln Phe Gly His Pro Gly Gly Asp Thr Asn Val Met Asn Gly Val Gly
            260                 265                 270

Ser Gly Thr Gly Arg Pro Arg Thr Ala Pro Ser Ser Pro Glu Val Leu
        275                 280                 285

Ala Leu Ser Ala Ala Gly Arg Pro Thr Arg Arg Gln Arg Met Leu Gln
    290                 295                 300

Ala Ile Gln Phe Glu His Ser Leu Tyr Pro Ser Glu Val Asp Asp Lys
305                 310                 315                 320

Gln Leu Leu Asp Leu Lys Ser Tyr Leu Thr Asp Met Leu Arg Glu Glu
                325                 330                 335

Gln Gln Leu Lys Ala Trp Glu Ala Ala Ala Leu Gly Pro Gln Arg Arg
            340                 345                 350
```

```
Ile Ala Ala Gly Arg Arg Leu Arg Ser Asp Ala Leu Gln His Gly
        355                 360                 365

Gly Ser Ser Gly Ile Ala Pro Ser Ala Ser Ser Phe Ala
    370                 375                 380

Val Trp Lys Ala Pro Ser Arg Ala Leu Phe Val Asp Arg His Gly
385                 390                 395                 400

Arg Leu Pro Ala Ala Ser Ser Thr Gly Cys Ser Pro Ser Ile Asn Gly
                405                 410                 415

Gly Pro Ala Ala Ala Asn Asp Lys Gln Lys Glu Ala Thr Ala Leu Ser
                420                 425                 430

Pro Pro Ala Leu Ala Ala Thr Leu Thr Met Ala Thr Ala Pro Pro Pro
            435                 440                 445

Ser Leu Ser Thr Ser Tyr Lys Gly Ser Ala Gln Glu Gly Leu Asp Leu
        450                 455                 460

Phe His Gln Val Val Ser His Ile Pro Pro Lys Ala Ala Ser Ile
465                 470                 475                 480

Tyr Ala Thr Gln Leu Gly Gly Leu Ser Leu Thr Val His Glu Tyr Ser
                485                 490                 495

Ala Met Ser Arg Pro Ala Glu Pro Trp Ser Val Gly Ser Lys Arg Leu
            500                 505                 510

Leu Lys Arg Arg Ala Lys Gln Phe Leu Lys Asn Gly Glu Leu Ser Glu
        515                 520                 525

Val Val Met Glu Ser Pro Lys Ala Ser Pro Ser Val Thr Ser Ala Ala
    530                 535                 540

Leu Ala Ala Thr Val Asn Lys Ala Thr Ala Ala Ala Val Lys
545                 550                 555                 560

Gly Ala Ser Ala Gly Lys Pro Gln His Ala Thr Ser Ala Ala Leu
                565                 570                 575

Pro Leu Ser Pro Arg Thr Arg Met Leu Phe Pro Asp Gln Arg Leu Ser
            580                 585                 590

Phe Thr Ser Ser Ser Asn Gly Thr Asp Ser Asp Ser Ser Leu Pro Leu
        595                 600                 605

Ser Leu Ser Ala Pro Leu Ser Thr Ser Ser Thr Asp Ala Cys Asn Ser
    610                 615                 620

Ser Met Lys Thr Val Ile Leu Asp Pro Pro Gln Arg Ala Ala Ser Cys
625                 630                 635                 640

Thr Ser Leu Pro Asn Ser Lys Gln Arg Thr Ser Ala Cys
                645                 650

<210> SEQ ID NO 55
<211> LENGTH: 1593
<212> TYPE: DNA
<213> ORGANISM: Trypanosoma brucei
<220> FEATURE:
<221> NAME/KEY: CDS
<222> LOCATION: (1)..(1593)

<400> SEQUENCE: 55 atg ttg tcc cga gcc cca cga cca aat aac cgc ctc atc gtg gtc tgc      48
Met Leu Ser Arg Ala Pro Arg Pro Asn Asn Arg Leu Ile Val Val Cys
1               5                   10                  15 agt tgc att aaa aat gtg tcg ggg tgg cca ttc tgg aag ttt cag caa      96
Ser Cys Ile Lys Asn Val Ser Gly Trp Pro Phe Trp Lys Phe Gln Gln
            20                  25                  30 atg agg aag gta aag ggc gtt acc gat ctt tgc atg ctt gcc ttt aac     144
Met Arg Lys Val Lys Gly Val Thr Asp Leu Cys Met Leu Ala Phe Asn
```

|    |    |    |    |    |    |    |    |    |    |    |    |    |    |    |    |     |
|----|----|----|----|----|----|----|----|----|----|----|----|----|----|----|----|-----|
|    | 35 |    |    |    | 40 |    |    |    |    | 45 |    |    |    |    |    |     |

```
tcc agt ggt ggg agc ttt gaa gca agt atc act ggg agc gac tac aca      192
Ser Ser Gly Gly Ser Phe Glu Ala Ser Ile Thr Gly Ser Asp Tyr Thr
 50              55                  60 ttg aag aac tac gaa aat gtt gtt ggc tat cgt cag gac atg ctt gaa      240
Leu Lys Asn Tyr Glu Asn Val Val Gly Tyr Arg Gln Asp Met Leu Glu
 65              70                  75                  80 gac ttt cta cag cgt tgc cac gac ccc ggt cgg agt tat ttt gtg tac      288
Asp Phe Leu Gln Arg Cys His Asp Pro Gly Arg Ser Tyr Phe Val Tyr
                 85                  90                  95 ggt ggt cat ggg atg gga gat tac ctg gaa tta gag gag aac aaa ctg      336
Gly Gly His Gly Met Gly Asp Tyr Leu Glu Leu Glu Glu Asn Lys Leu
            100                 105                 110 gcg ttg caa tgc cat gag ctc gcc tcc att ctc ggc aag cga aaa ttt      384
Ala Leu Gln Cys His Glu Leu Ala Ser Ile Leu Gly Lys Arg Lys Phe
        115                 120                 125 gag gcg atg gtc ttt gat tcg tgt ttt atg gcc agt ctc gaa tgc gct      432
Glu Ala Met Val Phe Asp Ser Cys Phe Met Ala Ser Leu Glu Cys Ala
130                 135                 140 tat caa cta cgc cat aac aca cgt tac att ggg gcc tgt gag ggt tat      480
Tyr Gln Leu Arg His Asn Thr Arg Tyr Ile Gly Ala Cys Glu Gly Tyr
145                 150                 155                 160 gtg tgg gca cct gac ccc aac ctt gac caa cac gtc ttt aac cag tac      528
Val Trp Ala Pro Asp Pro Asn Leu Asp Gln His Val Phe Asn Gln Tyr
                165                 170                 175 tct gcc tct gct atg agt cgc ttt aaa cat cca aaa aac atc cta ctt      576
Ser Ala Ser Ala Met Ser Arg Phe Lys His Pro Lys Asn Ile Leu Leu
            180                 185                 190 gcc atc cag aga gac tac tgc aac aag tct cct ctc gcc gac ttc gct      624
Ala Ile Gln Arg Asp Tyr Cys Asn Lys Ser Pro Leu Ala Asp Phe Ala
        195                 200                 205 gtg ttg gat acc act cat gtg gag tcg ctc aag aag tat gtt gaa gaa      672
Val Leu Asp Thr Thr His Val Glu Ser Leu Lys Lys Tyr Val Glu Glu
210                 215                 220 cat gtg atg cag cga gta tac gat cga gca acg ttt tac aac agt gag      720
His Val Met Gln Arg Val Tyr Asp Arg Ala Thr Phe Tyr Asn Ser Glu
225                 230                 235                 240 cag cag cag agg ttg agt agt atc gca cag aaa gaa ttg caa aac gcc      768
Gln Gln Gln Arg Leu Ser Ser Ile Ala Gln Lys Glu Leu Gln Asn Ala
                245                 250                 255 tat gag gat atc aaa tgt gga gcc aag atg cta gct gcc gcg ccg tta      816
Tyr Glu Asp Ile Lys Cys Gly Ala Lys Met Leu Ala Ala Ala Pro Leu
            260                 265                 270 aca gca cag gcg ccc tta tgc acg gcg ctg cgg aga gat tcg ggg gac      864
Thr Ala Gln Ala Pro Leu Cys Thr Ala Leu Arg Arg Asp Ser Gly Asp
        275                 280                 285 cta att cca aag aag aag aag agg gag ccg gct cgc tta gct ctt ttg      912
Leu Ile Pro Lys Lys Lys Lys Arg Glu Pro Ala Arg Leu Ala Leu Leu
290                 295                 300 cgg gct gcg cat ttt gaa cat gct tta tac cct tcg gag gtg gat gac      960
Arg Ala Ala His Phe Glu His Ala Leu Tyr Pro Ser Glu Val Asp Asp
305                 310                 315                 320 aag cac ata ctc gac cta aaa tcc tat ctt att gac atg gcg cgt gag     1008
Lys His Ile Leu Asp Leu Lys Ser Tyr Leu Ile Asp Met Ala Arg Glu
                325                 330                 335 gag gag gag gga gcc ctt gtt ctg cca aaa ggg agt gag tta ata tca     1056
Glu Glu Glu Gly Ala Leu Val Leu Pro Lys Gly Ser Glu Leu Ile Ser
            340                 345                 350 aca tca ggt gcc tgt ggt gcc ctt aag gga ccg cca cca cgt acc ggt     1104
```

```
                Thr Ser Gly Ala Cys Gly Ala Leu Lys Gly Pro Pro Arg Thr Gly
                    355                 360                 365 gtt gtg gag gtt cat ggt agc ctt cca ccg cgg gaa aca cat aat agc        1152
Val Val Glu Val His Gly Ser Leu Pro Pro Arg Glu Thr His Asn Ser
370                 375                 380 gca cga tac ggg cga gac agc cgc cat aaa ggc ctc gac cta ttc cac        1200
Ala Arg Tyr Gly Arg Asp Ser Arg His Lys Gly Leu Asp Leu Phe His
385                 390                 395                 400 cgt gtc gtt att agt cat aga caa ccc cgt aga aag agc ata tac gct        1248
Arg Val Val Ile Ser His Arg Gln Pro Arg Arg Lys Ser Ile Tyr Ala
                405                 410                 415 tcg cac ttg ggt ggg ctc tct ttc ccc gtg ttg gaa tac agc cca ttg        1296
Ser His Leu Gly Gly Leu Ser Phe Pro Val Leu Glu Tyr Ser Pro Leu
            420                 425                 430 tcg aag ccg ctg cgg gat tgg gag ggt atg gac aag aag gag ttg ttg        1344
Ser Lys Pro Leu Arg Asp Trp Glu Gly Met Asp Lys Lys Glu Leu Leu
        435                 440                 445 cga aaa gca agg gag ttc cta cga aag ggt gtt gtg gag ggt gtt cag        1392
Arg Lys Ala Arg Glu Phe Leu Arg Lys Gly Val Val Glu Gly Val Gln
    450                 455                 460 atg agt gag agt gga gcc agc gaa tgt ggt gtt agg ggt ggc agt agc        1440
Met Ser Glu Ser Gly Ala Ser Glu Cys Gly Val Arg Gly Gly Ser Ser
465                 470                 475                 480 agc atc acc gaa aat agt gat agc gtg gcg tca tcc atg gtt tct cca        1488
Ser Ile Thr Glu Asn Ser Asp Ser Val Ala Ser Ser Met Val Ser Pro
                485                 490                 495 cag aat gtg aag ttg gga att gca ccg tca gca tta atg cgc gca tca        1536
Gln Asn Val Lys Leu Gly Ile Ala Pro Ser Ala Leu Met Arg Ala Ser
            500                 505                 510 ttg acg aca cca tcg tcg gga gct cca gga caa acc gtg agc agt gag        1584
Leu Thr Thr Pro Ser Ser Gly Ala Pro Gly Gln Thr Val Ser Ser Glu
        515                 520                 525 aac ggc taa                                                            1593
Asn Gly
    530

<210> SEQ ID NO 56
<211> LENGTH: 530
<212> TYPE: PRT
<213> ORGANISM: Trypanosoma brucei

<400> SEQUENCE: 56

Met Leu Ser Arg Ala Pro Arg Pro Asn Asn Arg Leu Ile Val Val Cys
1               5                   10                  15

Ser Cys Ile Lys Asn Val Ser Gly Trp Pro Phe Trp Lys Phe Gln Gln
                20                  25                  30

Met Arg Lys Val Lys Gly Val Thr Asp Leu Cys Met Leu Ala Phe Asn
            35                  40                  45

Ser Ser Gly Gly Ser Phe Glu Ala Ser Ile Thr Gly Ser Asp Tyr Thr
        50                  55                  60

Leu Lys Asn Tyr Glu Asn Val Val Gly Tyr Arg Gln Asp Met Leu Glu
65                  70                  75                  80

Asp Phe Leu Gln Arg Cys His Asp Pro Gly Arg Ser Tyr Phe Val Tyr
                85                  90                  95

Gly Gly His Gly Met Gly Asp Tyr Leu Glu Leu Glu Glu Asn Lys Leu
            100                 105                 110

Ala Leu Gln Cys His Glu Leu Ala Ser Ile Leu Gly Lys Arg Lys Phe
        115                 120                 125
```

```
Glu Ala Met Val Phe Asp Ser Cys Phe Met Ala Ser Leu Glu Cys Ala
130                 135                 140

Tyr Gln Leu Arg His Asn Thr Arg Tyr Ile Gly Ala Cys Glu Gly Tyr
145                 150                 155                 160

Val Trp Ala Pro Asp Pro Asn Leu Asp Gln His Val Phe Asn Gln Tyr
                165                 170                 175

Ser Ala Ser Ala Met Ser Arg Phe Lys His Pro Lys Asn Ile Leu Leu
            180                 185                 190

Ala Ile Gln Arg Asp Tyr Cys Asn Lys Ser Pro Leu Ala Asp Phe Ala
        195                 200                 205

Val Leu Asp Thr Thr His Val Glu Ser Leu Lys Lys Tyr Val Glu Glu
210                 215                 220

His Val Met Gln Arg Val Tyr Asp Arg Ala Thr Phe Tyr Asn Ser Glu
225                 230                 235                 240

Gln Gln Gln Arg Leu Ser Ser Ile Ala Gln Lys Glu Leu Gln Asn Ala
                245                 250                 255

Tyr Glu Asp Ile Lys Cys Gly Ala Lys Met Leu Ala Ala Ala Pro Leu
            260                 265                 270

Thr Ala Gln Ala Pro Leu Cys Thr Ala Leu Arg Arg Asp Ser Gly Asp
        275                 280                 285

Leu Ile Pro Lys Lys Lys Arg Glu Pro Ala Arg Leu Ala Leu Leu
290                 295                 300

Arg Ala Ala His Phe Glu His Ala Leu Tyr Pro Ser Glu Val Asp Asp
305                 310                 315                 320

Lys His Ile Leu Asp Leu Lys Ser Tyr Leu Ile Asp Met Ala Arg Glu
                325                 330                 335

Glu Glu Glu Gly Ala Leu Val Leu Pro Lys Gly Ser Glu Leu Ile Ser
            340                 345                 350

Thr Ser Gly Ala Cys Gly Ala Leu Lys Gly Pro Pro Arg Thr Gly
        355                 360                 365

Val Val Glu Val His Gly Ser Leu Pro Pro Arg Glu Thr His Asn Ser
370                 375                 380

Ala Arg Tyr Gly Arg Asp Ser Arg His Lys Gly Leu Asp Leu Phe His
385                 390                 395                 400

Arg Val Val Ile Ser His Arg Gln Pro Arg Arg Lys Ser Ile Tyr Ala
                405                 410                 415

Ser His Leu Gly Gly Leu Ser Phe Pro Val Leu Glu Tyr Ser Pro Leu
            420                 425                 430

Ser Lys Pro Leu Arg Asp Trp Glu Gly Met Asp Lys Lys Glu Leu Leu
        435                 440                 445

Arg Lys Ala Arg Glu Phe Leu Arg Lys Gly Val Val Glu Gly Val Gln
450                 455                 460

Met Ser Glu Ser Gly Ala Ser Glu Cys Gly Val Arg Gly Gly Ser Ser
465                 470                 475                 480

Ser Ile Thr Glu Asn Ser Asp Ser Val Ala Ser Ser Met Val Ser Pro
                485                 490                 495

Gln Asn Val Lys Leu Gly Ile Ala Pro Ser Ala Leu Met Arg Ala Ser
            500                 505                 510

Leu Thr Thr Pro Ser Ser Gly Ala Pro Gly Gln Thr Val Ser Ser Glu
        515                 520                 525

Asn Gly
530
```

-continued

```
<210> SEQ ID NO 57
<211> LENGTH: 612
<212> TYPE: DNA
<213> ORGANISM: Trypanosoma cruzi
<220> FEATURE:
<221> NAME/KEY: CDS
<222> LOCATION: (1)..(612)

<400> SEQUENCE: 57 atg cgg tgg gtg ata gtt gta ttt gct tta ttt gcc ttc atg gct gtg        48
Met Arg Trp Val Ile Val Val Phe Ala Leu Phe Ala Phe Met Ala Val
1               5                   10                  15 gga tct ctg gcc cag ctc gat aca ctg ccg ttc cta ttt gtc tcc aag        96
Gly Ser Leu Ala Gln Leu Asp Thr Leu Pro Phe Leu Phe Val Ser Lys
            20                  25                  30 tcc gtc tca gac gac tac gtg gta gct ggt aac agc gtg gag ttc act       144
Ser Val Ser Asp Asp Tyr Val Val Ala Gly Asn Ser Val Glu Phe Thr
        35                  40                  45 gtc act gtt tac aac tac ggc cag agc cct gcg atg gat gtg aca gtc       192
Val Thr Val Tyr Asn Tyr Gly Gln Ser Pro Ala Met Asp Val Thr Val
    50                  55                  60 aca gac att ttg gtg gac ggc acg aca cgt aca aag cgt gta gaa atg       240
Thr Asp Ile Leu Val Asp Gly Thr Thr Arg Thr Lys Arg Val Glu Met
65                  70                  75                  80 ctt tcc ttt gga gag agt gcc gtg ctg aag tac acc gta ata ccg aaa       288
Leu Ser Phe Gly Glu Ser Ala Val Leu Lys Tyr Thr Val Ile Pro Lys
                85                  90                  95 gag ctt ggc aac tac gtt gtt ggc gtt gca gag gtg aca tat gcc ctg       336
Glu Leu Gly Asn Tyr Val Val Gly Val Ala Glu Val Thr Tyr Ala Leu
            100                 105                 110 gag aag ggg aag cca gct aca cac aga gcg tac agc aat gtc att cgc       384
Glu Lys Gly Lys Pro Ala Thr His Arg Ala Tyr Ser Asn Val Ile Arg
        115                 120                 125 gag agt aat gcg cac ttc ctg gga gaa aaa tac gac gac gag agt ttt       432
Glu Ser Asn Ala His Phe Leu Gly Glu Lys Tyr Asp Asp Glu Ser Phe
    130                 135                 140 cgt gga gtt gtg tcg gtt gta acg cgg gaa cgt tac gat cgt tta cac       480
Arg Gly Val Val Ser Val Val Thr Arg Glu Arg Tyr Asp Arg Leu His
145                 150                 155                 160 aag cgg tat gtt cgt gaa att gtg gcg tat agt ata ctt tgc gtc att       528
Lys Arg Tyr Val Arg Glu Ile Val Ala Tyr Ser Ile Leu Cys Val Ile
                165                 170                 175 ccc gcg ctt ttt cct ttt ttt gtt tac cgc gcg gag caa aat cag gtg       576
Pro Ala Leu Phe Pro Phe Phe Val Tyr Arg Ala Glu Gln Asn Gln Val
            180                 185                 190 gaa ctt ctg att cgc cgc tcc aaa ctc aac aag tag                        612
Glu Leu Leu Ile Arg Arg Ser Lys Leu Asn Lys
        195                 200

<210> SEQ ID NO 58
<211> LENGTH: 203
<212> TYPE: PRT
<213> ORGANISM: Trypanosoma cruzi

<400> SEQUENCE: 58

Met Arg Trp Val Ile Val Val Phe Ala Leu Phe Ala Phe Met Ala Val
1               5                   10                  15

Gly Ser Leu Ala Gln Leu Asp Thr Leu Pro Phe Leu Phe Val Ser Lys
            20                  25                  30

Ser Val Ser Asp Asp Tyr Val Val Ala Gly Asn Ser Val Glu Phe Thr
        35                  40                  45
```

```
Val Thr Val Tyr Asn Tyr Gly Gln Ser Pro Ala Met Asp Val Thr Val
 50                  55                  60

Thr Asp Ile Leu Val Asp Gly Thr Thr Arg Thr Lys Arg Val Glu Met
 65                  70                  75                  80

Leu Ser Phe Gly Glu Ser Ala Val Leu Lys Tyr Thr Val Ile Pro Lys
                 85                  90                  95

Glu Leu Gly Asn Tyr Val Val Gly Val Ala Glu Val Thr Tyr Ala Leu
                100                 105                 110

Glu Lys Gly Lys Pro Ala Thr His Arg Ala Tyr Ser Asn Val Ile Arg
                115                 120                 125

Glu Ser Asn Ala His Phe Leu Gly Glu Lys Tyr Asp Asp Glu Ser Phe
130                 135                 140

Arg Gly Val Val Ser Val Val Thr Arg Glu Arg Tyr Asp Arg Leu His
145                 150                 155                 160

Lys Arg Tyr Val Arg Glu Ile Val Ala Tyr Ser Ile Leu Cys Val Ile
                165                 170                 175

Pro Ala Leu Phe Pro Phe Phe Val Tyr Arg Ala Glu Gln Asn Gln Val
                180                 185                 190

Glu Leu Leu Ile Arg Arg Ser Lys Leu Asn Lys
                195                 200

<210> SEQ ID NO 59
<211> LENGTH: 639
<212> TYPE: DNA
<213> ORGANISM: Leishmania major
<220> FEATURE:
<221> NAME/KEY: CDS
<222> LOCATION: (1)..(639)

<400> SEQUENCE: 59 atg gcc gct ctc aag gtg ctg ctc tta ctg tgc ttg gcc acc ttg gtg      48
Met Ala Ala Leu Lys Val Leu Leu Leu Leu Cys Leu Ala Thr Leu Val
 1               5                  10                  15 gcg acg acg tgc ttc gcg cag gtg gcg cag gag gca gag ata aat cca      96
Ala Thr Thr Cys Phe Ala Gln Val Ala Gln Glu Ala Glu Ile Asn Pro
             20                  25                  30 cac ccg ctg ctg ttt gtg tcc aag acg aca tcg aac gac gac atc gtc     144
His Pro Leu Leu Phe Val Ser Lys Thr Thr Ser Asn Asp Asp Ile Val
         35                  40                  45 ctt ggc tcc tct gtg gag gtg gtg tcg acg gtg acg aac tac ggc cag     192
Leu Gly Ser Ser Val Glu Val Val Ser Thr Val Thr Asn Tyr Gly Gln
 50                  55                  60 agt ccc gcc ttt gac gtg cag ata tct gac ctg ctg gat gac ggc tcg     240
Ser Pro Ala Phe Asp Val Gln Ile Ser Asp Leu Leu Asp Asp Gly Ser
 65                  70                  75                  80 ctg cag agc aag tct atc gcc tac ctc ccc tac agc gct tcg gag acg     288
Leu Gln Ser Lys Ser Ile Ala Tyr Leu Pro Tyr Ser Ala Ser Glu Thr
                 85                  90                  95 ctg cgc tac acg gtg acc cct acc gca ctg ggc aac tac gcc gtc tcc     336
Leu Arg Tyr Thr Val Thr Pro Thr Ala Leu Gly Asn Tyr Ala Val Ser
                100                 105                 110 gtt gct gag gtg acg tac aat gtg gag cag ggc aat cct gcg acg tcc     384
Val Ala Glu Val Thr Tyr Asn Val Glu Gln Gly Asn Pro Ala Thr Ser
                115                 120                 125 cgc aag gct ctc agc aac ctg atc cgc gag ggt gag gcg tac tac tat     432
Arg Lys Ala Leu Ser Asn Leu Ile Arg Glu Gly Glu Ala Tyr Tyr Tyr
130                 135                 140 ggc gag ggt gtc gat gac gag agc ttt cgc ggc gtc atc tcc gtt ctc     480
Gly Glu Gly Val Asp Asp Glu Ser Phe Arg Gly Val Ile Ser Val Leu
```

```
                    145                 150                 155                 160
acc cgc gac cgc tac gac cgc ctg cac gcg cgc tac atc aag gag tcg         528
Thr Arg Asp Arg Tyr Asp Arg Leu His Ala Arg Tyr Ile Lys Glu Ser
                165                 170                 175 acg gcg tac atc ttc cta ggc gcc atc ccg gct ctg ttt ccc tac gtg         576
Thr Ala Tyr Ile Phe Leu Gly Ala Ile Pro Ala Leu Phe Pro Tyr Val
        180                 185                 190 cta tac cgc gtg aag cag agc gag gtg gat gcg ctg ctc cgc cag cgc         624
Leu Tyr Arg Val Lys Gln Ser Glu Val Asp Ala Leu Leu Arg Gln Arg
        195                 200                 205 aag gcc agc aag tag                                                     639
Lys Ala Ser Lys
    210

<210> SEQ ID NO 60
<211> LENGTH: 212
<212> TYPE: PRT
<213> ORGANISM: Leishmania major

<400> SEQUENCE: 60

Met Ala Ala Leu Lys Val Leu Leu Leu Cys Leu Ala Thr Leu Val
1               5                   10                  15

Ala Thr Thr Cys Phe Ala Gln Val Ala Gln Glu Ala Glu Ile Asn Pro
                20                  25                  30

His Pro Leu Leu Phe Val Ser Lys Thr Thr Ser Asn Asp Asp Ile Val
            35                  40                  45

Leu Gly Ser Ser Val Glu Val Val Thr Val Thr Asn Tyr Gly Gln
        50                  55                  60

Ser Pro Ala Phe Asp Val Gln Ile Ser Asp Leu Leu Asp Asp Gly Ser
65                  70                  75                  80

Leu Gln Ser Lys Ser Ile Ala Tyr Leu Pro Tyr Ser Ala Ser Glu Thr
                85                  90                  95

Leu Arg Tyr Thr Val Thr Pro Thr Ala Leu Gly Asn Tyr Ala Val Ser
            100                 105                 110

Val Ala Glu Val Thr Tyr Asn Val Glu Gln Gly Asn Pro Ala Thr Ser
        115                 120                 125

Arg Lys Ala Leu Ser Asn Leu Ile Arg Glu Gly Glu Ala Tyr Tyr Tyr
    130                 135                 140

Gly Glu Gly Val Asp Asp Glu Ser Phe Arg Gly Val Ile Ser Val Leu
145                 150                 155                 160

Thr Arg Asp Arg Tyr Asp Arg Leu His Ala Arg Tyr Ile Lys Glu Ser
                165                 170                 175

Thr Ala Tyr Ile Phe Leu Gly Ala Ile Pro Ala Leu Phe Pro Tyr Val
            180                 185                 190

Leu Tyr Arg Val Lys Gln Ser Glu Val Asp Ala Leu Leu Arg Gln Arg
        195                 200                 205

Lys Ala Ser Lys
    210

<210> SEQ ID NO 61
<211> LENGTH: 639
<212> TYPE: DNA
<213> ORGANISM: Leishmania infantum
<220> FEATURE:
<221> NAME/KEY: CDS
<222> LOCATION: (1)..(639)

<400> SEQUENCE: 61
```

| | | |
|---|---|---|
| atg gcc act ctc aag gtg ctg ctc tta ctg tgc ttg gcc acc ttg gtg<br>Met Ala Thr Leu Lys Val Leu Leu Leu Leu Cys Leu Ala Thr Leu Val<br>1                        5                       10                    15 | | 48 |
| gca acg acg tgt ttc gcg cag gtg gcg cag gag gca gag ata aat ccg<br>Ala Thr Thr Cys Phe Ala Gln Val Ala Gln Glu Ala Glu Ile Asn Pro<br>                    20                       25                      30 | | 96 |
| cat ccg ctg ctg ttt gtg tcc aag acg aca tcg agc gac gac atc gtt<br>His Pro Leu Leu Phe Val Ser Lys Thr Thr Ser Ser Asp Asp Ile Val<br>              35                       40                       45 | | 144 |
| ctc gga tcc tcc gtg gag gtg gtc acg gta acg aac tac ggc cag<br>Leu Gly Ser Ser Val Glu Val Val Thr Val Thr Asn Tyr Gly Gln<br>50                      55                      60 | | 192 |
| agt ccc gcc ttt gac gtg cag ata tct gac ctg ctg gag gac ggc tcg<br>Ser Pro Ala Phe Asp Val Gln Ile Ser Asp Leu Leu Glu Asp Gly Ser<br>65                      70                     75                    80 | | 240 |
| ctg cag agc aag tct atc gcc tac ctc ccc tac ggc gct tcg gag acg<br>Leu Gln Ser Lys Ser Ile Ala Tyr Leu Pro Tyr Gly Ala Ser Glu Thr<br>                      85                       90                      95 | | 288 |
| ctg cgc tac acg gtg acc cct acc gca ctg ggc aac tac gcc gtc tcc<br>Leu Arg Tyr Thr Val Thr Pro Thr Ala Leu Gly Asn Tyr Ala Val Ser<br>              100                      105                    110 | | 336 |
| gtt gct gag gtg acg tac aat gtt gag cag ggc aat act gcg acg gcc<br>Val Ala Glu Val Thr Tyr Asn Val Glu Gln Gly Asn Thr Ala Thr Ala<br>             115                      120                    125 | | 384 |
| cgc aag gct ctc agc aac ctg atc cgc gag ggc gag gcg tac tac tac<br>Arg Lys Ala Leu Ser Asn Leu Ile Arg Glu Gly Glu Ala Tyr Tyr Tyr<br>130                    135                     140 | | 432 |
| ggc gag ggt gtc gat gac gag agc ttt cgc ggc gtc atc tcc gtc ctc<br>Gly Glu Gly Val Asp Asp Glu Ser Phe Arg Gly Val Ile Ser Val Leu<br>145                      150                     155                 160 | | 480 |
| acc cgc gac cgt tac gac cgc ctg cac gcg cgc tac atc aag gag tcg<br>Thr Arg Asp Arg Tyr Asp Arg Leu His Ala Arg Tyr Ile Lys Glu Ser<br>                        165                      170                    175 | | 528 |
| acg gcg tac atc ttc cta ggc gcc atc ccg gcg ctg ttt ccc tac gta<br>Thr Ala Tyr Ile Phe Leu Gly Ala Ile Pro Ala Leu Phe Pro Tyr Val<br>             180                      185                    190 | | 576 |
| ctg tac cga gtg aag cag agc gag gtg gac gcg ctg ctc cgc cag cgc<br>Leu Tyr Arg Val Lys Gln Ser Glu Val Asp Ala Leu Leu Arg Gln Arg<br>             195                      200                    205 | | 624 |
| aag gcc agc aag tag<br>Lys Ala Ser Lys<br>    210 | | 639 |

<210> SEQ ID NO 62
<211> LENGTH: 212
<212> TYPE: PRT
<213> ORGANISM: Leishmania infantum

<400> SEQUENCE: 62

Met Ala Thr Leu Lys Val Leu Leu Leu Leu Cys Leu Ala Thr Leu Val
1               5                   10                  15

Ala Thr Thr Cys Phe Ala Gln Val Ala Gln Glu Ala Glu Ile Asn Pro
            20                  25                  30

His Pro Leu Leu Phe Val Ser Lys Thr Thr Ser Ser Asp Asp Ile Val
        35                  40                  45

Leu Gly Ser Ser Val Glu Val Val Thr Val Thr Asn Tyr Gly Gln
    50                  55                  60

Ser Pro Ala Phe Asp Val Gln Ile Ser Asp Leu Leu Glu Asp Gly Ser
65                  70                  75                  80

```
Leu Gln Ser Lys Ser Ile Ala Tyr Leu Pro Tyr Gly Ala Ser Glu Thr
            85                  90                  95

Leu Arg Tyr Thr Val Thr Pro Thr Ala Leu Gly Asn Tyr Ala Val Ser
        100                 105                 110

Val Ala Glu Val Thr Tyr Asn Val Gln Gly Asn Thr Ala Thr Ala
        115                 120                 125

Arg Lys Ala Leu Ser Asn Leu Ile Arg Glu Gly Ala Tyr Tyr Tyr
    130                 135                 140

Gly Glu Gly Val Asp Asp Glu Ser Phe Arg Gly Val Ile Ser Val Leu
145                 150                 155                 160

Thr Arg Asp Arg Tyr Asp Arg Leu His Ala Arg Tyr Ile Lys Glu Ser
                165                 170                 175

Thr Ala Tyr Ile Phe Leu Gly Ala Ile Pro Ala Leu Phe Pro Tyr Val
            180                 185                 190

Leu Tyr Arg Val Lys Gln Ser Glu Val Asp Ala Leu Leu Arg Gln Arg
        195                 200                 205

Lys Ala Ser Lys
    210

<210> SEQ ID NO 63
<211> LENGTH: 612
<212> TYPE: DNA
<213> ORGANISM: Trypanosoma brucei
<220> FEATURE:
<221> NAME/KEY: CDS
<222> LOCATION: (1)..(612)

<400> SEQUENCE: 63 atg cgg ctc ctc tat gtc atc ccg ctt ctt ttg gcc gct gct gcc gtc      48
Met Arg Leu Leu Tyr Val Ile Pro Leu Leu Leu Ala Ala Ala Ala Val
1               5                   10                  15 ggg tca ctg gct cag ccg gat ccc cag ccg ctt ctt ttc gtc tcg aaa      96
Gly Ser Leu Ala Gln Pro Asp Pro Gln Pro Leu Leu Phe Val Ser Lys
            20                  25                  30 atg atc tcg gat gac cac gtg gtg gtg ggc aac aac gtc gaa ttc act     144
Met Ile Ser Asp Asp His Val Val Val Gly Asn Asn Val Glu Phe Thr
        35                  40                  45 gtg act gtc tac aac tac ggt caa agc cct gcc ttt gat att acc att     192
Val Thr Val Tyr Asn Tyr Gly Gln Ser Pro Ala Phe Asp Ile Thr Ile
    50                  55                  60 act gac ttg cta cct gac ggt act acg cgc acg aag cag gtg gat tcg     240
Thr Asp Leu Leu Pro Asp Gly Thr Thr Arg Thr Lys Gln Val Asp Ser
65                  70                  75                  80 ctt gct ttc ggt gag tca gcc gaa ctt aag tac acc att gtc acc aag     288
Leu Ala Phe Gly Glu Ser Ala Glu Leu Lys Tyr Thr Ile Val Thr Lys
                85                  90                  95 gct ctt ggt ggt tat cac gtt ggg gtg acg gag gtg tta tac tcc ctg     336
Ala Leu Gly Gly Tyr His Val Gly Val Thr Glu Val Leu Tyr Ser Leu
            100                 105                 110 gag aga gga ggg aag aag aca gaa aaa gca tac agt aac atc atc cgc     384
Glu Arg Gly Gly Lys Lys Thr Glu Lys Ala Tyr Ser Asn Ile Ile Arg
        115                 120                 125 gaa ggt acg gca tat ttc tac gga gag gat tac gac gat aca aat ttc     432
Glu Gly Thr Ala Tyr Phe Tyr Gly Glu Asp Tyr Asp Asp Thr Asn Phe
    130                 135                 140 cgt ggt att gtg tcc gtg gtt acc cgc gag ttc tat gac cgc tta tac     480
Arg Gly Ile Val Ser Val Val Thr Arg Glu Phe Tyr Asp Arg Leu Tyr
145                 150                 155                 160 aag agc tat gtg cgg gag gcg gcg gtc tac gcc ttc cta tgt ctt gtt     528
Lys Ser Tyr Val Arg Glu Ala Ala Val Tyr Ala Phe Leu Cys Leu Val
```

```
Lys Ser Tyr Val Arg Glu Ala Ala Val Tyr Ala Phe Leu Cys Leu Val
                165                 170                 175 ccc gcc ttg ttt cct ctt gtt gtg tac cgt atg gag cag agc caa gtg    576
Pro Ala Leu Phe Pro Leu Val Val Tyr Arg Met Glu Gln Ser Gln Val
            180                 185                 190 gac ctc tta att cgt cgc tcc aag gca gtt aaa tga                    612
Asp Leu Leu Ile Arg Arg Ser Lys Ala Val Lys
            195                 200

<210> SEQ ID NO 64
<211> LENGTH: 203
<212> TYPE: PRT
<213> ORGANISM: Trypanosoma brucei

<400> SEQUENCE: 64

Met Arg Leu Leu Tyr Val Ile Pro Leu Leu Ala Ala Ala Val
1               5                   10                  15

Gly Ser Leu Ala Gln Pro Asp Pro Gln Pro Leu Leu Phe Val Ser Lys
            20                  25                  30

Met Ile Ser Asp Asp His Val Val Gly Asn Asn Val Glu Phe Thr
            35                  40                  45

Val Thr Val Tyr Asn Tyr Gly Gln Ser Pro Ala Phe Asp Ile Thr Ile
    50                  55                  60

Thr Asp Leu Leu Pro Asp Gly Thr Thr Arg Thr Lys Gln Val Asp Ser
65                  70                  75                  80

Leu Ala Phe Gly Glu Ser Ala Glu Leu Lys Tyr Thr Ile Val Thr Lys
                85                  90                  95

Ala Leu Gly Gly Tyr His Val Gly Val Thr Glu Val Leu Tyr Ser Leu
            100                 105                 110

Glu Arg Gly Gly Lys Lys Thr Glu Lys Ala Tyr Ser Asn Ile Ile Arg
        115                 120                 125

Glu Gly Thr Ala Tyr Phe Tyr Gly Glu Asp Tyr Asp Asp Thr Asn Phe
    130                 135                 140

Arg Gly Ile Val Ser Val Val Thr Arg Glu Phe Tyr Asp Arg Leu Tyr
145                 150                 155                 160

Lys Ser Tyr Val Arg Glu Ala Ala Val Tyr Ala Phe Leu Cys Leu Val
                165                 170                 175

Pro Ala Leu Phe Pro Leu Val Val Tyr Arg Met Glu Gln Ser Gln Val
            180                 185                 190

Asp Leu Leu Ile Arg Arg Ser Lys Ala Val Lys
            195                 200

<210> SEQ ID NO 65
<211> LENGTH: 687
<212> TYPE: DNA
<213> ORGANISM: Trypanosoma cruzi
<220> FEATURE:
<221> NAME/KEY: CDS
<222> LOCATION: (1)..(687)

<400> SEQUENCE: 65 atg aaa caa aaa atg cga cgc aaa ttt tgt gac gtt ctc ttc cct tta    48
Met Lys Gln Lys Met Arg Arg Lys Phe Cys Asp Val Leu Phe Pro Leu
1               5                   10                  15 ttg ttg gtg ttt ctc ttg acg acg atg gag cct gtg acg gct gag gtg    96
Leu Leu Val Phe Leu Leu Thr Thr Met Glu Pro Val Thr Ala Glu Val
            20                  25                  30 tac att cga ctt ttt ccc gga aaa gaa ttg tgc ttc aac tat gag ggc    144
Tyr Ile Arg Leu Phe Pro Gly Lys Glu Leu Cys Phe Asn Tyr Glu Gly
```

```
              35                  40                  45
tat cgt gac cca gag gat gac cca ccc acc gtg gac atc cgt cac cgt       192
Tyr Arg Asp Pro Glu Asp Asp Pro Pro Thr Val Asp Ile Arg His Arg
 50                  55                  60 gga att gac ccg cga aat gtc aac ata cgc acc cgc ctg tac gcc cca       240
Gly Ile Asp Pro Arg Asn Val Asn Ile Arg Thr Arg Leu Tyr Ala Pro
 65                  70                  75                  80 agt gga gcg cag gtg act ttg gat gag cgc att gac tct ttt ggt tcc       288
Ser Gly Ala Gln Val Thr Leu Asp Glu Arg Ile Asp Ser Phe Gly Ser
                 85                  90                  95 cca tcc tca ctt ttt ttt aag gtg aca gag act ggc act tat cgc ttt       336
Pro Ser Ser Leu Phe Phe Lys Val Thr Glu Thr Gly Thr Tyr Arg Phe
            100                 105                 110 tgt atg cgc aca cca ttg agt cag cct tcg tta cgt ttt gag atg cgc       384
Cys Met Arg Thr Pro Leu Ser Gln Pro Ser Leu Arg Phe Glu Met Arg
        115                 120                 125 ttt ctt gga gaa aag gat ctt ata gat ccg ata aca aca gca gag gga       432
Phe Leu Gly Glu Lys Asp Leu Ile Asp Pro Ile Thr Thr Ala Glu Gly
130                 135                 140 atg cct gct gtt gac aaa cca gta gac gct aaa gac tac gaa gcg cgg       480
Met Pro Ala Val Asp Lys Pro Val Asp Ala Lys Asp Tyr Glu Ala Arg
145                 150                 155                 160 ttg aat atg ttg gat att tgt gtg caa gtc gct ctt gac gaa gtt cgc       528
Leu Asn Met Leu Asp Ile Cys Val Gln Val Ala Leu Asp Glu Val Arg
                165                 170                 175 ata atc gaa aac cgt ctc cac atg ttt gat gaa gtc acg cag tcg acg       576
Ile Ile Glu Asn Arg Leu His Met Phe Asp Glu Val Thr Gln Ser Thr
            180                 185                 190 tac tac atc aca gtg ggg atg ctt ttt ctc aat gtg att ctc tct atc       624
Tyr Tyr Ile Thr Val Gly Met Leu Phe Leu Asn Val Ile Leu Ser Ile
        195                 200                 205 gta ctg acc gtg tgg tct gag aaa tac ctt gag cgc tac ttt aca aag       672
Val Leu Thr Val Trp Ser Glu Lys Tyr Leu Glu Arg Tyr Phe Thr Lys
210                 215                 220 aag aag aat gtc tag                                                    687
Lys Lys Asn Val
225

<210> SEQ ID NO 66
<211> LENGTH: 228
<212> TYPE: PRT
<213> ORGANISM: Trypanosoma cruzi

<400> SEQUENCE: 66

Met Lys Gln Lys Met Arg Arg Lys Phe Cys Asp Val Leu Phe Pro Leu
 1               5                  10                  15

Leu Leu Val Phe Leu Leu Thr Thr Met Glu Pro Val Thr Ala Glu Val
                20                  25                  30

Tyr Ile Arg Leu Phe Pro Gly Lys Glu Leu Cys Phe Asn Tyr Glu Gly
            35                  40                  45

Tyr Arg Asp Pro Glu Asp Asp Pro Pro Thr Val Asp Ile Arg His Arg
 50                  55                  60

Gly Ile Asp Pro Arg Asn Val Asn Ile Arg Thr Arg Leu Tyr Ala Pro
 65                  70                  75                  80

Ser Gly Ala Gln Val Thr Leu Asp Glu Arg Ile Asp Ser Phe Gly Ser
                 85                  90                  95

Pro Ser Ser Leu Phe Phe Lys Val Thr Glu Thr Gly Thr Tyr Arg Phe
            100                 105                 110
```

```
Cys Met Arg Thr Pro Leu Ser Gln Pro Ser Leu Arg Phe Glu Met Arg
            115                 120                 125

Phe Leu Gly Glu Lys Asp Leu Ile Asp Pro Ile Thr Thr Ala Glu Gly
        130                 135                 140

Met Pro Ala Val Asp Lys Pro Val Asp Ala Lys Asp Tyr Glu Ala Arg
145                 150                 155                 160

Leu Asn Met Leu Asp Ile Cys Val Gln Val Ala Leu Asp Glu Val Arg
                165                 170                 175

Ile Ile Glu Asn Arg Leu His Met Phe Asp Glu Val Thr Gln Ser Thr
            180                 185                 190

Tyr Tyr Ile Thr Val Gly Met Leu Phe Leu Asn Val Ile Leu Ser Ile
        195                 200                 205

Val Leu Thr Val Trp Ser Glu Lys Tyr Leu Glu Arg Tyr Phe Thr Lys
    210                 215                 220

Lys Lys Asn Val
225

<210> SEQ ID NO 67
<211> LENGTH: 747
<212> TYPE: DNA
<213> ORGANISM: Leishmania major
<220> FEATURE:
<221> NAME/KEY: CDS
<222> LOCATION: (1)..(747)

<400> SEQUENCE: 67 atg aac gct ctt gat ccg acg cgc gcg cac acg tct gta atg atg gcc      48
Met Asn Ala Leu Asp Pro Thr Arg Ala His Thr Ser Val Met Met Ala
1               5                   10                  15 gca tcg cgt gtc ctg ggg ctg ctg act gtt tgc ctg ctc tgc gcg ctg      96
Ala Ser Arg Val Leu Gly Leu Leu Thr Val Cys Leu Leu Cys Ala Leu
            20                  25                  30 tgc gca cgc gtc gtg gcg gcc gcg tcc atg cac gct ggc gtg tac gcg     144
Cys Ala Arg Val Val Ala Ala Ala Ser Met His Ala Gly Val Tyr Ala
        35                  40                  45 aag ctt ctg ccg gga aag gag ttc tgc gca gac tac cac gcc tac cgc     192
Lys Leu Leu Pro Gly Lys Glu Phe Cys Ala Asp Tyr His Ala Tyr Arg
    50                  55                  60 gat ccg cag agt gac cca gtg ccg gtg aca ttt cat cac cgc tgc atc     240
Asp Pro Gln Ser Asp Pro Val Pro Val Thr Phe His His Arg Cys Ile
65                  70                  75                  80 gat ccg cgc ctg gct ggc att act aca aag ctg tac ggt ccg agt agc     288
Asp Pro Arg Leu Ala Gly Ile Thr Thr Lys Leu Tyr Gly Pro Ser Ser
                85                  90                  95 gag ccg ctc aag cgc ggc ccg gag atc cct tta tca gaa acc atc gac     336
Glu Pro Leu Lys Arg Gly Pro Glu Ile Pro Leu Ser Glu Thr Ile Asp
            100                 105                 110 acc ttt ggc gac atc tcg cag att ttc ttc tac gcc gag aag acc ggc     384
Thr Phe Gly Asp Ile Ser Gln Ile Phe Phe Tyr Ala Glu Lys Thr Gly
        115                 120                 125 atc tat aag atg tgc ttt ctg ctt ccc ctc aag aag ccc gcc atg cgc     432
Ile Tyr Lys Met Cys Phe Leu Leu Pro Leu Lys Lys Pro Ala Met Arg
    130                 135                 140 ttc gag atg tcc ttc agc gcg gcc aac gac att gtc gag ccg ccc aag     480
Phe Glu Met Ser Phe Ser Ala Ala Asn Asp Ile Val Glu Pro Pro Lys
145                 150                 155                 160 gta gag gac ggg gcc ttc gtg gtg gac aaa ccg cca gag gtg gcc gac     528
Val Glu Asp Gly Ala Phe Val Val Asp Lys Pro Pro Glu Val Ala Asp
                165                 170                 175
```

```
tac gct gac cgc ctg cgc atg ttg aac ttg tcc gtg gag aca acc gtg    576
Tyr Ala Asp Arg Leu Arg Met Leu Asn Leu Ser Val Glu Thr Thr Val
            180                 185                 190 gac gag ctc cga atg tat cag acg cgg cga tac ttc ttc gac aag acg    624
Asp Glu Leu Arg Met Tyr Gln Thr Arg Arg Tyr Phe Phe Asp Lys Thr
        195                 200                 205 gtc aac tct gcc ttt tac gtt tgc gtc ttt agt gtg ctg ctg aac atc    672
Val Asn Ser Ala Phe Tyr Val Cys Val Phe Ser Val Leu Leu Asn Ile
    210                 215                 220 gcc atc gcc gtg ggg ctc acc ttg tgg tcg gag agg tat ctg aag cgg    720
Ala Ile Ala Val Gly Leu Thr Leu Trp Ser Glu Arg Tyr Leu Lys Arg
225                 230                 235                 240 tac ttt gta aag cag aag att gca taa                                747
Tyr Phe Val Lys Gln Lys Ile Ala
                245
```

<210> SEQ ID NO 68
<211> LENGTH: 248
<212> TYPE: PRT
<213> ORGANISM: Leishmania major

<400> SEQUENCE: 68

```
Met Asn Ala Leu Asp Pro Thr Arg Ala His Thr Ser Val Met Met Ala
1               5                   10                  15

Ala Ser Arg Val Leu Gly Leu Leu Thr Val Cys Leu Leu Cys Ala Leu
            20                  25                  30

Cys Ala Arg Val Val Ala Ala Ser Met His Ala Gly Val Tyr Ala
            35                  40                  45

Lys Leu Leu Pro Gly Lys Glu Phe Cys Ala Asp Tyr His Ala Tyr Arg
    50                  55                  60

Asp Pro Gln Ser Asp Pro Val Pro Val Thr Phe His His Arg Cys Ile
65                  70                  75                  80

Asp Pro Arg Leu Ala Gly Ile Thr Thr Lys Leu Tyr Gly Pro Ser Ser
                85                  90                  95

Glu Pro Leu Lys Arg Gly Pro Glu Ile Pro Leu Ser Glu Thr Ile Asp
            100                 105                 110

Thr Phe Gly Asp Ile Ser Gln Ile Phe Phe Tyr Ala Glu Lys Thr Gly
        115                 120                 125

Ile Tyr Lys Met Cys Phe Leu Leu Pro Leu Lys Pro Ala Met Arg
    130                 135                 140

Phe Glu Met Ser Phe Ser Ala Ala Asn Asp Ile Val Glu Pro Pro Lys
145                 150                 155                 160

Val Glu Asp Gly Ala Phe Val Val Asp Lys Pro Pro Glu Val Ala Asp
                165                 170                 175

Tyr Ala Asp Arg Leu Arg Met Leu Asn Leu Ser Val Glu Thr Thr Val
            180                 185                 190

Asp Glu Leu Arg Met Tyr Gln Thr Arg Arg Tyr Phe Phe Asp Lys Thr
        195                 200                 205

Val Asn Ser Ala Phe Tyr Val Cys Val Phe Ser Val Leu Leu Asn Ile
    210                 215                 220

Ala Ile Ala Val Gly Leu Thr Leu Trp Ser Glu Arg Tyr Leu Lys Arg
225                 230                 235                 240

Tyr Phe Val Lys Gln Lys Ile Ala
                245
```

<210> SEQ ID NO 69
<211> LENGTH: 708

```
<212> TYPE: DNA
<213> ORGANISM: Leishmania infantum
<220> FEATURE:
<221> NAME/KEY: CDS
<222> LOCATION: (1)..(708)

<400> SEQUENCE: 69 atg atg gcc gca tcg cgt gtc ctg gtg ctg gtg act gtg tgc ctg ctc      48
Met Met Ala Ala Ser Arg Val Leu Val Leu Val Thr Val Cys Leu Leu
1               5                  10                  15 tgc gcg ctg tgc gca cgc gtc gtc gcg gcc acc tcc gtg cac gct ggc      96
Cys Ala Leu Cys Ala Arg Val Val Ala Ala Thr Ser Val His Ala Gly
            20                  25                  30 gtg tac gcg aag ctg ctg cca gga aag gag ttc tgc gct gac tac cac     144
Val Tyr Ala Lys Leu Leu Pro Gly Lys Glu Phe Cys Ala Asp Tyr His
        35                  40                  45 gcc tac cgc gat ccg cag agt gac cca gtg ccg gtg aca ttt cat cac     192
Ala Tyr Arg Asp Pro Gln Ser Asp Pro Val Pro Val Thr Phe His His
    50                  55                  60 cgc tgc atc gat ccg cgc ctg gct ggc att act aca aag ctg tac ggc     240
Arg Cys Ile Asp Pro Arg Leu Ala Gly Ile Thr Thr Lys Leu Tyr Gly
65                  70                  75                  80 ccc agt agc gag ccg ctc aag cgc ggg ccg gag atc cct tta tca gaa     288
Pro Ser Ser Glu Pro Leu Lys Arg Gly Pro Glu Ile Pro Leu Ser Glu
                85                  90                  95 acc atc gac acc ttc ggc gac atc tcg cag ata ctc ttc tac gcc gag     336
Thr Ile Asp Thr Phe Gly Asp Ile Ser Gln Ile Leu Phe Tyr Ala Glu
            100                 105                 110 aag acc ggc atc tat aag atg tgc ttt ctg ctt ccc ctc aag aag ccc     384
Lys Thr Gly Ile Tyr Lys Met Cys Phe Leu Leu Pro Leu Lys Lys Pro
        115                 120                 125 gcc atg cgc ttc gag atg tcc ttc agc gcg gcc aac gac atc gtc gag     432
Ala Met Arg Phe Glu Met Ser Phe Ser Ala Ala Asn Asp Ile Val Glu
    130                 135                 140 ccg ccc aag gta gag gac ggg gcc ttc gtg gtg gac aag ccg cca gag     480
Pro Pro Lys Val Glu Asp Gly Ala Phe Val Val Asp Lys Pro Pro Glu
145                 150                 155                 160 atg gcc gac tac gcc gac cgc ctg cgc atg ttg aac ttg tcc gta gag     528
Met Ala Asp Tyr Ala Asp Arg Leu Arg Met Leu Asn Leu Ser Val Glu
                165                 170                 175 aca acc gtg gac gag ctc cgc atg tac cag acg cgg cgg tac ttc ttc     576
Thr Thr Val Asp Glu Leu Arg Met Tyr Gln Thr Arg Arg Tyr Phe Phe
            180                 185                 190 gac aag acg gtc aac tcc gcc ttt tgc gtt tgc gtc ttt agt gtg ctg     624
Asp Lys Thr Val Asn Ser Ala Phe Cys Val Cys Val Phe Ser Val Leu
        195                 200                 205 ctg aac atc gcc atc gcc gtg ggg ctc acc ttg tgg tcg gag aag tat     672
Leu Asn Ile Ala Ile Ala Val Gly Leu Thr Leu Trp Ser Glu Lys Tyr
    210                 215                 220 ctg aag cgg tac ttt gta aag cag aaa att gca taa                     708
Leu Lys Arg Tyr Phe Val Lys Gln Lys Ile Ala
225                 230                 235

<210> SEQ ID NO 70
<211> LENGTH: 235
<212> TYPE: PRT
<213> ORGANISM: Leishmania infantum

<400> SEQUENCE: 70

Met Met Ala Ala Ser Arg Val Leu Val Leu Val Thr Val Cys Leu Leu
1               5                  10                  15
```

```
Cys Ala Leu Cys Ala Arg Val Val Ala Thr Ser Val His Ala Gly
             20                  25                  30

Val Tyr Ala Lys Leu Leu Pro Gly Lys Glu Phe Cys Ala Asp Tyr His
         35                  40                  45

Ala Tyr Arg Asp Pro Gln Ser Asp Pro Val Pro Val Thr Phe His His
     50                  55                  60

Arg Cys Ile Asp Pro Arg Leu Ala Gly Ile Thr Thr Lys Leu Tyr Gly
 65                  70                  75                  80

Pro Ser Ser Glu Pro Leu Lys Arg Gly Pro Glu Ile Pro Leu Ser Glu
                 85                  90                  95

Thr Ile Asp Thr Phe Gly Asp Ile Ser Gln Ile Leu Phe Tyr Ala Glu
            100                 105                 110

Lys Thr Gly Ile Tyr Lys Met Cys Phe Leu Leu Pro Leu Lys Lys Pro
        115                 120                 125

Ala Met Arg Phe Glu Met Ser Phe Ser Ala Ala Asn Asp Ile Val Glu
    130                 135                 140

Pro Pro Lys Val Glu Asp Gly Ala Phe Val Val Asp Lys Pro Pro Glu
145                 150                 155                 160

Met Ala Asp Tyr Ala Asp Arg Leu Arg Met Leu Asn Leu Ser Val Glu
                165                 170                 175

Thr Thr Val Asp Glu Leu Arg Met Tyr Gln Thr Arg Arg Tyr Phe Phe
            180                 185                 190

Asp Lys Thr Val Asn Ser Ala Phe Cys Val Cys Val Phe Ser Val Leu
        195                 200                 205

Leu Asn Ile Ala Ile Ala Val Gly Leu Thr Leu Trp Ser Glu Lys Tyr
    210                 215                 220

Leu Lys Arg Tyr Phe Val Lys Gln Lys Ile Ala
225                 230                 235

<210> SEQ ID NO 71
<211> LENGTH: 699
<212> TYPE: DNA
<213> ORGANISM: Trypanosoma brucei
<220> FEATURE:
<221> NAME/KEY: CDS
<222> LOCATION: (1)..(699)

<400> SEQUENCE: 71 atg aag agt ttc cgc gta gtt tgc agg ttc ccc gcc atg ttg cag ctg      48
Met Lys Ser Phe Arg Val Val Cys Arg Phe Pro Ala Met Leu Gln Leu
  1               5                  10                  15 cta gca ctt gtg gga ctt gca ttg gtt ccg caa agc gct ctc agt tct      96
Leu Ala Leu Val Gly Leu Ala Leu Val Pro Gln Ser Ala Leu Ser Ser
             20                  25                  30 caa aac ggc gtg tac gta aaa ctc ttt ccc ggc cgt gag ttg tgt ttg     144
Gln Asn Gly Val Tyr Val Lys Leu Phe Pro Gly Arg Glu Leu Cys Leu
         35                  40                  45 agt tac gag ggg tac cgg gaa gtg gag gaa aca ccg cca aca gtt gcc     192
Ser Tyr Glu Gly Tyr Arg Glu Val Glu Glu Thr Pro Pro Thr Val Ala
     50                  55                  60 ttg cga cat cgc gcc ctc tcg cca cgt aac gtt aac gtg cga aca cgc     240
Leu Arg His Arg Ala Leu Ser Pro Arg Asn Val Asn Val Arg Thr Arg
 65                  70                  75                  80 ctc tac ggc cct gat gga aac att ata cga cat gat gac cgc atc gat     288
Leu Tyr Gly Pro Asp Gly Asn Ile Ile Arg His Asp Asp Arg Ile Asp
                 85                  90                  95 ccc ttt gga caa cca gcg tct ttc ttc ttt aag gta aca aag acg ggt     336
Pro Phe Gly Gln Pro Ala Ser Phe Phe Phe Lys Val Thr Lys Thr Gly
```

```
aca tat cgg gtt tgc atg cgt aca ccg ttg aac cac ccg ccg cta tcg      384
Thr Tyr Arg Val Cys Met Arg Thr Pro Leu Asn His Pro Pro Leu Ser
        115                 120                 125 ttt gac atg cgt ttc atc ggc gag cgc gat gtg gcg cag tca ccg gag      432
Phe Asp Met Arg Phe Ile Gly Glu Arg Asp Val Ala Gln Ser Pro Glu
    130                 135                 140 acc gtt gag gga gtg gaa gtt gct gac aaa cca ata gaa gcc tcc gac      480
Thr Val Glu Gly Val Glu Val Ala Asp Lys Pro Ile Glu Ala Ser Asp
145                 150                 155                 160 tat caa agt tca ctt cac atg ttg gac att tgt gtg caa gtg gct cta      528
Tyr Gln Ser Ser Leu His Met Leu Asp Ile Cys Val Gln Val Ala Leu
                165                 170                 175 gat gaa gtg cgt atg agt gag aac cgc ctt cat ctt ctt gat gag att      576
Asp Glu Val Arg Met Ser Glu Asn Arg Leu His Leu Leu Asp Glu Ile
            180                 185                 190 aca aac tct acg tac aac cgc gtt gtg gga ttc tta att ctg aac gtt      624
Thr Asn Ser Thr Tyr Asn Arg Val Val Gly Phe Leu Ile Leu Asn Val
        195                 200                 205 ctg ctt gtc att gtt gct agc gtt ggg tca gag aag tat ttg gaa cga      672
Leu Leu Val Ile Val Ala Ser Val Gly Ser Glu Lys Tyr Leu Glu Arg
    210                 215                 220 ttc ttt ata aag cag aag att gct taa                                  699
Phe Phe Ile Lys Gln Lys Ile Ala
225                 230

<210> SEQ ID NO 72
<211> LENGTH: 232
<212> TYPE: PRT
<213> ORGANISM: Trypanosoma brucei

<400> SEQUENCE: 72

Met Lys Ser Phe Arg Val Val Cys Arg Phe Pro Ala Met Leu Gln Leu
1               5                   10                  15

Leu Ala Leu Val Gly Leu Ala Leu Val Pro Gln Ser Ala Leu Ser Ser
            20                  25                  30

Gln Asn Gly Val Tyr Val Lys Leu Phe Pro Gly Arg Glu Leu Cys Leu
        35                  40                  45

Ser Tyr Glu Gly Tyr Arg Glu Val Glu Glu Thr Pro Thr Val Ala
    50                  55                  60

Leu Arg His Arg Ala Leu Ser Pro Arg Asn Val Asn Val Arg Thr Arg
65                  70                  75                  80

Leu Tyr Gly Pro Asp Gly Asn Ile Ile Arg His Asp Asp Arg Ile Asp
                85                  90                  95

Pro Phe Gly Gln Pro Ala Ser Phe Phe Lys Val Thr Lys Thr Gly
            100                 105                 110

Thr Tyr Arg Val Cys Met Arg Thr Pro Leu Asn His Pro Pro Leu Ser
        115                 120                 125

Phe Asp Met Arg Phe Ile Gly Glu Arg Asp Val Ala Gln Ser Pro Glu
    130                 135                 140

Thr Val Glu Gly Val Glu Val Ala Asp Lys Pro Ile Glu Ala Ser Asp
145                 150                 155                 160

Tyr Gln Ser Ser Leu His Met Leu Asp Ile Cys Val Gln Val Ala Leu
                165                 170                 175

Asp Glu Val Arg Met Ser Glu Asn Arg Leu His Leu Leu Asp Glu Ile
            180                 185                 190

Thr Asn Ser Thr Tyr Asn Arg Val Val Gly Phe Leu Ile Leu Asn Val
```

```
                195                 200                 205
Leu Leu Val Ile Val Ala Ser Val Gly Ser Glu Lys Tyr Leu Glu Arg
    210                 215                 220

Phe Phe Ile Lys Gln Lys Ile Ala
225                 230

<210> SEQ ID NO 73
<211> LENGTH: 2031
<212> TYPE: DNA
<213> ORGANISM: Trypanosoma cruzi
<220> FEATURE:
<221> NAME/KEY: CDS
<222> LOCATION: (1)..(2031)

<400> SEQUENCE: 73 atg tat tca tgt ttg tcg ctg agg ctg ttg gtg ggc gga ggg atg ggg    48
Met Tyr Ser Cys Leu Ser Leu Arg Leu Leu Val Gly Gly Gly Met Gly
1               5                   10                  15 ttt gct tcg cgg agg aga gct gct atg gtg ctg tcg ctc ttg gtc ttt    96
Phe Ala Ser Arg Arg Arg Ala Ala Met Val Leu Ser Leu Leu Val Phe
                20                  25                  30 ctt ctg gtt gtg cca tgc ggg gtc ttt tcg cag tat tct ttg gag tgc   144
Leu Leu Val Val Pro Cys Gly Val Phe Ser Gln Tyr Ser Leu Glu Cys
            35                  40                  45 cag aat gtg tgg gag ggt ccc aac gcc gaa aac gac att att gca tgc   192
Gln Asn Val Trp Glu Gly Pro Asn Ala Glu Asn Asp Ile Ile Ala Cys
        50                  55                  60 ctg tcg aat aag gat cgc ctg aag ggg caa tgg cgt ttg ttc att ctt   240
Leu Ser Asn Lys Asp Arg Leu Lys Gly Gln Trp Arg Leu Phe Ile Leu
65                  70                  75                  80 ccc gca ttg aac gtc att att ttg gct atg ctc ttg ttg agc ttt cct   288
Pro Ala Leu Asn Val Ile Ile Leu Ala Met Leu Leu Leu Ser Phe Pro
                85                  90                  95 ttg ttg ttt ttg tgt gct ctt tgt tgc cgt tgc tgc tgc aca cct ggt   336
Leu Leu Phe Leu Cys Ala Leu Cys Cys Arg Cys Cys Cys Thr Pro Gly
            100                 105                 110 act gcg gga agc acg aag cgt gcc cgt tgc tgc atg tgg ctg tgg att   384
Thr Ala Gly Ser Thr Lys Arg Ala Arg Cys Cys Met Trp Leu Trp Ile
        115                 120                 125 ttg tac gct gtc att tgg tcc ggg gtg atg ttt tat ctt gtc ttt ttt   432
Leu Tyr Ala Val Ile Trp Ser Gly Val Met Phe Tyr Leu Val Phe Phe
    130                 135                 140 ggt gcc ggg ctg ttg att gcg acg gcc cct cgc ctg ttg gaa gac ttt   480
Gly Ala Gly Leu Leu Ile Ala Thr Ala Pro Arg Leu Leu Glu Asp Phe
145                 150                 155                 160 gtc tcg ggt cca ctg gat tac ttt aat tct acc gcg gaa aga gtg ctt   528
Val Ser Gly Pro Leu Asp Tyr Phe Asn Ser Thr Ala Glu Arg Val Leu
                165                 170                 175 gac ttt gca tct gat tgg tcc acg ggt gaa cgc aag ccg ctt gat gcc   576
Asp Phe Ala Ser Asp Trp Ser Thr Gly Glu Arg Lys Pro Leu Asp Ala
            180                 185                 190 att cct ttg gac ctc tcg gat ttc aca acc gtc cac gaa cag gcc atg   624
Ile Pro Leu Asp Leu Ser Asp Phe Thr Thr Val His Glu Gln Ala Met
        195                 200                 205 gga ttt att gcc ctt gca agg aga tat tac ttc aac tac ctg gat aag   672
Gly Phe Ile Ala Leu Ala Arg Arg Tyr Tyr Phe Asn Tyr Leu Asp Lys
    210                 215                 220 gtt tct att gca acg ttc tgt gta tca agt gtg ggt ctt gtt ctg atc   720
Val Ser Ile Ala Thr Phe Cys Val Ser Ser Val Gly Leu Val Leu Ile
225                 230                 235                 240
```

```
atc ctc att ctg cca ttt gca tgc tgc cat tgc tgc att cca tgt ttt       768
Ile Leu Ile Leu Pro Phe Ala Cys Cys His Cys Cys Ile Pro Cys Phe
                245                 250                 255 cca ctt atc ctc tcg tgc ctt tac tgg gtg aca gga gtt ctt ttt gcg       816
Pro Leu Ile Leu Ser Cys Leu Tyr Trp Val Thr Gly Val Leu Phe Ala
                260                 265                 270 gtg ctt gga acc ctt gtg agt gtc ttg gca tat gct gca acc gtg ggc       864
Val Leu Gly Thr Leu Val Ser Val Leu Ala Tyr Ala Ala Thr Val Gly
                275                 280                 285 tgt gga gag ttg gag ctg caa tac aca cgt cag ccg gga gtt ttc cag       912
Cys Gly Glu Leu Glu Leu Gln Tyr Thr Arg Gln Pro Gly Val Phe Gln
                290                 295                 300 tgg tac gct gtg cct tac tgt cag aga cag ttc aat ttt tcg aac atc       960
Trp Tyr Ala Val Pro Tyr Cys Gln Arg Gln Phe Asn Phe Ser Asn Ile
305                 310                 315                 320 aac aag atg att cgc gag aag gaa ctt gag ctc tcc cga gaa gcc tgt      1008
Asn Lys Met Ile Arg Glu Lys Glu Leu Glu Leu Ser Arg Glu Ala Cys
                325                 330                 335 aac cag ctg ttg ggg gtg tgc gaa tcc gta acg ccg gag gag gct gca      1056
Asn Gln Leu Leu Gly Val Cys Glu Ser Val Thr Pro Glu Glu Ala Ala
                340                 345                 350 gcc gaa ccc atg aaa tta ctt gcg gcc ggt gtt att cct agt gct att      1104
Ala Glu Pro Met Lys Leu Leu Ala Ala Gly Val Ile Pro Ser Ala Ile
                355                 360                 365 ccc ggt gta att ccg gct gct gtt ccg gct gct gtt ccg gct gct ctt      1152
Pro Gly Val Ile Pro Ala Ala Val Pro Ala Ala Val Pro Ala Ala Leu
                370                 375                 380 cct gct ggt gtt ccc gga ggt ttt ccc gga ggt gtt gtt ccc gga ggt      1200
Pro Ala Gly Val Pro Gly Gly Phe Pro Gly Gly Val Val Pro Gly Gly
385                 390                 395                 400 gtt gcc gga ggt gct gct cca gga gtt gtt cct ggt gct gct act ggt      1248
Val Ala Gly Gly Ala Ala Pro Gly Val Val Pro Gly Ala Ala Thr Gly
                405                 410                 415 gat ggt gat tct gcg act ata gct gct ctt gcc gag tct ggc gcc ctt      1296
Asp Gly Asp Ser Ala Thr Ile Ala Ala Leu Ala Glu Ser Gly Ala Leu
                420                 425                 430 tct gga agt gac ggt gct ccc ctt gac atc agc agt ttg gcg gga tcg      1344
Ser Gly Ser Asp Gly Ala Pro Leu Asp Ile Ser Ser Leu Ala Gly Ser
                435                 440                 445 gat ggt gtt ggg ctg gct ggt ggg gct tcc agt gtt gag agc ttt gag      1392
Asp Gly Val Gly Leu Ala Gly Gly Ala Ser Ser Val Glu Ser Phe Glu
                450                 455                 460 ggt ttg cct ccc gga att gat tta tcc tcc atc aaa gac atg ccg ggt      1440
Gly Leu Pro Pro Gly Ile Asp Leu Ser Ser Ile Lys Asp Met Pro Gly
465                 470                 475                 480 gcg tcg gag agc atc aag aag gcc ttg gaa agc cgc aat atg tct gag      1488
Ala Ser Glu Ser Ile Lys Lys Ala Leu Glu Ser Arg Asn Met Ser Glu
                485                 490                 495 gac atc ctc cgt atg gtt ccc gga gaa gtg aac gcc gac ttg ctg aaa      1536
Asp Ile Leu Arg Met Val Pro Gly Glu Val Asn Ala Asp Leu Leu Lys
                500                 505                 510 atg tta agt aat gcc act gcg ctc tcg aat ctc ttc gca cgt ccc ttg      1584
Met Leu Ser Asn Ala Thr Ala Leu Ser Asn Leu Phe Ala Arg Pro Leu
                515                 520                 525 gtg tgc ggc aaa ggg ctc aaa agc gcc agt gag tgc ggg gac ttt ggc      1632
Val Cys Gly Lys Gly Leu Lys Ser Ala Ser Glu Cys Gly Asp Phe Gly
                530                 535                 540 acc atg gca agt att ctg ttg gac acc aag ctc cag aaa aac att ccg      1680
Thr Met Ala Ser Ile Leu Leu Asp Thr Lys Leu Gln Lys Asn Ile Pro
545                 550                 555                 560
```

```
ggc tgc gta tcc aaa aat ggc gac tgc acg ctt act gat tgt gcg gcg      1728
Gly Cys Val Ser Lys Asn Gly Asp Cys Thr Leu Thr Asp Cys Ala Ala
                565                 570                 575 acc tgc aca ata gat ttt ctt aag gat gcc gcc acg atg atc ttg tcg      1776
Thr Cys Thr Ile Asp Phe Leu Lys Asp Ala Ala Thr Met Ile Leu Ser
                580                 585                 590 aag ggg gaa atg gcc cgc aat gcg agt aat gcg ctt tcg tac gcc agg      1824
Lys Gly Glu Met Ala Arg Asn Ala Ser Asn Ala Leu Ser Tyr Ala Arg
                595                 600                 605 cct ttg ctt gag tgc aac ttt gtg att gat aag gtg gcc act ggt ctg      1872
Pro Leu Leu Glu Cys Asn Phe Val Ile Asp Lys Val Ala Thr Gly Leu
                610                 615                 620 gcg aag tgt gat gat ttg cgg aaa gga aca att atg ctc ggg atg gga      1920
Ala Lys Cys Asp Asp Leu Arg Lys Gly Thr Ile Met Leu Gly Met Gly
625                 630                 635                 640 ttc ctt gtg ggg gga atg ata ttt ggc ctg gcc atc tac att gca ttg      1968
Phe Leu Val Gly Gly Met Ile Phe Gly Leu Ala Ile Tyr Ile Ala Leu
                645                 650                 655 cgt gga gca tgc gtg tgg ggt gaa acg ttt cca aag ctc cga agg aaa      2016
Arg Gly Ala Cys Val Trp Gly Glu Thr Phe Pro Lys Leu Arg Arg Lys
                660                 665                 670 ccc aga gag gag taa                                                  2031
Pro Arg Glu Glu
        675
```

<210> SEQ ID NO 74
<211> LENGTH: 676
<212> TYPE: PRT
<213> ORGANISM: Trypanosoma cruzi

<400> SEQUENCE: 74

Met Tyr Ser Cys Leu Ser Leu Arg Leu Leu Val Gly Gly Gly Met Gly
1               5                   10                  15

Phe Ala Ser Arg Arg Arg Ala Ala Met Val Leu Ser Leu Leu Val Phe
            20                  25                  30

Leu Leu Val Val Pro Cys Gly Val Phe Ser Gln Tyr Ser Leu Glu Cys
        35                  40                  45

Gln Asn Val Trp Glu Gly Pro Asn Ala Glu Asn Asp Ile Ile Ala Cys
    50                  55                  60

Leu Ser Asn Lys Asp Arg Leu Lys Gly Gln Trp Arg Leu Phe Ile Leu
65                  70                  75                  80

Pro Ala Leu Asn Val Ile Ile Leu Ala Met Leu Leu Leu Ser Phe Pro
                85                  90                  95

Leu Leu Phe Leu Cys Ala Leu Cys Cys Arg Cys Cys Cys Thr Pro Gly
            100                 105                 110

Thr Ala Gly Ser Thr Lys Arg Ala Arg Cys Cys Met Trp Leu Trp Ile
        115                 120                 125

Leu Tyr Ala Val Ile Trp Ser Gly Val Met Phe Tyr Leu Val Phe Phe
    130                 135                 140

Gly Ala Gly Leu Leu Ile Ala Thr Ala Pro Arg Leu Leu Glu Asp Phe
145                 150                 155                 160

Val Ser Gly Pro Leu Asp Tyr Phe Asn Ser Thr Ala Glu Arg Val Leu
                165                 170                 175

Asp Phe Ala Ser Asp Trp Ser Thr Gly Glu Arg Lys Pro Leu Asp Ala
            180                 185                 190

Ile Pro Leu Asp Leu Ser Asp Phe Thr Thr Val His Glu Gln Ala Met
        195                 200                 205

```
Gly Phe Ile Ala Leu Ala Arg Arg Tyr Tyr Phe Asn Tyr Leu Asp Lys
    210                 215                 220

Val Ser Ile Ala Thr Phe Cys Val Ser Val Gly Leu Val Leu Ile
225                 230                 235                 240

Ile Leu Ile Leu Pro Phe Ala Cys Cys His Cys Cys Ile Pro Cys Phe
                245                 250                 255

Pro Leu Ile Leu Ser Cys Leu Tyr Trp Val Thr Gly Val Leu Phe Ala
                260                 265                 270

Val Leu Gly Thr Leu Val Ser Val Leu Ala Tyr Ala Ala Thr Val Gly
            275                 280                 285

Cys Gly Glu Leu Glu Leu Gln Tyr Thr Arg Gln Pro Gly Val Phe Gln
    290                 295                 300

Trp Tyr Ala Val Pro Tyr Cys Gln Arg Gln Phe Asn Phe Ser Asn Ile
305                 310                 315                 320

Asn Lys Met Ile Arg Glu Lys Glu Leu Glu Leu Ser Arg Glu Ala Cys
                325                 330                 335

Asn Gln Leu Leu Gly Val Cys Glu Ser Val Thr Pro Glu Glu Ala Ala
                340                 345                 350

Ala Glu Pro Met Lys Leu Leu Ala Ala Gly Val Ile Pro Ser Ala Ile
            355                 360                 365

Pro Gly Val Ile Pro Ala Ala Val Pro Ala Ala Val Pro Ala Ala Leu
    370                 375                 380

Pro Ala Gly Val Pro Gly Gly Phe Pro Gly Gly Val Val Pro Gly Gly
385                 390                 395                 400

Val Ala Gly Gly Ala Ala Pro Gly Val Val Pro Gly Ala Ala Thr Gly
                405                 410                 415

Asp Gly Asp Ser Ala Thr Ile Ala Ala Leu Ala Glu Ser Gly Ala Leu
                420                 425                 430

Ser Gly Ser Asp Gly Ala Pro Leu Asp Ile Ser Ser Leu Ala Gly Ser
    435                 440                 445

Asp Gly Val Gly Leu Ala Gly Gly Ala Ser Ser Val Glu Ser Phe Glu
    450                 455                 460

Gly Leu Pro Pro Gly Ile Asp Leu Ser Ser Ile Lys Asp Met Pro Gly
465                 470                 475                 480

Ala Ser Glu Ser Ile Lys Lys Ala Leu Glu Ser Arg Asn Met Ser Glu
                485                 490                 495

Asp Ile Leu Arg Met Val Pro Gly Glu Val Asn Ala Asp Leu Leu Lys
                500                 505                 510

Met Leu Ser Asn Ala Thr Ala Leu Ser Asn Leu Phe Ala Arg Pro Leu
    515                 520                 525

Val Cys Gly Lys Gly Leu Lys Ser Ala Ser Glu Cys Gly Asp Phe Gly
    530                 535                 540

Thr Met Ala Ser Ile Leu Leu Asp Thr Lys Leu Gln Lys Asn Ile Pro
545                 550                 555                 560

Gly Cys Val Ser Lys Asn Gly Asp Cys Thr Leu Thr Asp Cys Ala Ala
                565                 570                 575

Thr Cys Thr Ile Asp Phe Leu Lys Asp Ala Ala Thr Met Ile Leu Ser
                580                 585                 590

Lys Gly Glu Met Ala Arg Asn Ala Ser Asn Ala Leu Ser Tyr Ala Arg
            595                 600                 605

Pro Leu Leu Glu Cys Asn Phe Val Ile Asp Lys Val Ala Thr Gly Leu
    610                 615                 620
```

-continued

```
Ala Lys Cys Asp Asp Leu Arg Lys Gly Thr Ile Met Leu Gly Met Gly
625                 630                 635                 640

Phe Leu Val Gly Gly Met Ile Phe Gly Leu Ala Ile Tyr Ile Ala Leu
                645                 650                 655

Arg Gly Ala Cys Val Trp Gly Glu Thr Phe Pro Lys Leu Arg Arg Lys
            660                 665                 670

Pro Arg Glu Glu
        675
```

<210> SEQ ID NO 75
<211> LENGTH: 1647
<212> TYPE: DNA
<213> ORGANISM: Leishmania major
<220> FEATURE:
<221> NAME/KEY: CDS
<222> LOCATION: (1)..(1647)

<400> SEQUENCE: 75

| | | |
|---|---|---|
| atg gtg tgt ccc ttc tcc tgc ccg ccc ctc ccc gcc ccc tct ctc aac<br>Met Val Cys Pro Phe Ser Cys Pro Pro Leu Pro Ala Pro Ser Leu Asn<br>1               5                   10                  15 | 48 |
| tcg tcc cac ctc tca ttg ccg aag aag cag cgg tta aca gcg cgc gcg<br>Ser Ser His Leu Ser Leu Pro Lys Lys Gln Arg Leu Thr Ala Arg Ala<br>        20                  25                  30 | 96 |
| cac aca ccg aca cac aaa atg gcc aag aca acg ctt ctc gtg tgc gct<br>His Thr Pro Thr His Lys Met Ala Lys Thr Thr Leu Leu Val Cys Ala<br>            35                  40                  45 | 144 |
| ctg ctc gcc ctc gtc atg tgc ctg gca gcg aca gcc gtc tcg gcg cag<br>Leu Leu Ala Leu Val Met Cys Leu Ala Ala Thr Ala Val Ser Ala Gln<br>    50                  55                  60 | 192 |
| cag tcg ctg gcg tgc caa atg gtg tgg caa gct ccg tcc cct aac aac<br>Gln Ser Leu Ala Cys Gln Met Val Trp Gln Ala Pro Ser Pro Asn Asn<br>65                  70                  75                  80 | 240 |
| agc ctg ctg gag tgc ctg ggg aac acg gat cgc atc cgg tct cag tgg<br>Ser Leu Leu Glu Cys Leu Gly Asn Thr Asp Arg Ile Arg Ser Gln Trp<br>                85                  90                  95 | 288 |
| ccc tac tac ctg tat ccc gcc ttc gct gcg ctc atc ttc atc ttt acg<br>Pro Tyr Tyr Leu Tyr Pro Ala Phe Ala Ala Leu Ile Phe Ile Phe Thr<br>            100                 105                 110 | 336 |
| gtg att ggg ctg ccg att ctg ttc tgc tgc cac tgc tgc agc tgc tgc<br>Val Ile Gly Leu Pro Ile Leu Phe Cys Cys His Cys Cys Ser Cys Cys<br>        115                 120                 125 | 384 |
| gag gcg tat gtg aag ccg aag gcg gag acg gac ctc ggc gtt gcc cgc<br>Glu Ala Tyr Val Lys Pro Lys Ala Glu Thr Asp Leu Gly Val Ala Arg<br>    130                 135                 140 | 432 |
| tgc tgc cta tgg atg ctg atc gtg att tcg gtg ctt gtg gcg tgc ggc<br>Cys Cys Leu Trp Met Leu Ile Val Ile Ser Val Leu Val Ala Cys Gly<br>145                 150                 155                 160 | 480 |
| gtg tgc gtg ctg ctg gtg tat ggc tcc gtc tta ctg gag cag gca gcc<br>Val Cys Val Leu Leu Val Tyr Gly Ser Val Leu Leu Glu Gln Ala Ala<br>                165                 170                 175 | 528 |
| acg caa att atc cat gac acc gag tat cgc acg ctt aat tac ttc aac<br>Thr Gln Ile Ile His Asp Thr Glu Tyr Arg Thr Leu Asn Tyr Phe Asn<br>            180                 185                 190 | 576 |
| gac atc cgt gcg aac atc acg atg ctg ctg aca aac tac agc gcg gac<br>Asp Ile Arg Ala Asn Ile Thr Met Leu Leu Thr Asn Tyr Ser Ala Asp<br>        195                 200                 205 | 624 |
| cca ccg ata cca ccg tcg atc gac ctt agg acc ttt gac gct gtg aac<br>Pro Pro Ile Pro Pro Ser Ile Asp Leu Arg Thr Phe Asp Ala Val Asn<br>    210                 215                 220 | 672 |

-continued

| | | |
|---|---|---|
| gat gat att acc cac tac gtg cat ctg gcg cgc aac aac tac ctc cag<br>Asp Asp Ile Thr His Tyr Val His Leu Ala Arg Asn Asn Tyr Leu Gln<br>225 230 235 240 | 720 | |
| tac ttc cgc gct gcc gag att gtg gtg tgc tgt gtc ggc agc gtg ggt<br>Tyr Phe Arg Ala Ala Glu Ile Val Val Cys Cys Val Gly Ser Val Gly<br>245 250 255 | 768 | |
| gtt ttc ctg atg ctg tgc atg ctg gtt ttt gtg ctg tgc cgt tgc aat<br>Val Phe Leu Met Leu Cys Met Leu Val Phe Val Leu Cys Arg Cys Asn<br>260 265 270 | 816 | |
| ggg atc tgc ccg att gcg tgg agc tgc ctg tac ttc gtg ttc gcg ctt<br>Gly Ile Cys Pro Ile Ala Trp Ser Cys Leu Tyr Phe Val Phe Ala Leu<br>275 280 285 | 864 | |
| gca ttt gcg ttg ctt gcg gtg ttg ttc acg ata tgc atc tac gtg ctg<br>Ala Phe Ala Leu Leu Ala Val Leu Phe Thr Ile Cys Ile Tyr Val Leu<br>290 295 300 | 912 | |
| tcc gct ggc tgc ggc gag gtg ggc ctc cag cgt ggt cgt gag cct ggc<br>Ser Ala Gly Cys Gly Glu Val Gly Leu Gln Arg Gly Arg Glu Pro Gly<br>305 310 315 320 | 960 | |
| gtc ttc cag tgg tac ctg gtg ccg tgg tgc gag aag cag ttc aac ttc<br>Val Phe Gln Trp Tyr Leu Val Pro Trp Cys Glu Lys Gln Phe Asn Phe<br>325 330 335 | 1008 | |
| caa gcg ctg cgg gct cag gtg cag agc cag gag cag cag gtc tcg cag<br>Gln Ala Leu Arg Ala Gln Val Gln Ser Gln Glu Gln Gln Val Ser Gln<br>340 345 350 | 1056 | |
| agc gcc tgc gcg gag ctc ttg aac ttc tgt gac aac gat ccg cat tac<br>Ser Ala Cys Ala Glu Leu Leu Asn Phe Cys Asp Asn Asp Pro His Tyr<br>355 360 365 | 1104 | |
| tcg ttg gag act aaa aac cac atc ttc atg tgc ggc aac agc atc acc<br>Ser Leu Glu Thr Lys Asn His Ile Phe Met Cys Gly Asn Ser Ile Thr<br>370 375 380 | 1152 | |
| gat aag agc cag tgc gac tcg ctg gac gac gtg gtg gac gtt gtt ctg<br>Asp Lys Ser Gln Cys Asp Ser Leu Asp Asp Val Val Asp Val Val Leu<br>385 390 395 400 | 1200 | |
| agc aca tac gtg aag ccg atg ctg acg aac acg cta tgt gcc aac cag<br>Ser Thr Tyr Val Lys Pro Met Leu Thr Asn Thr Leu Cys Ala Asn Gln<br>405 410 415 | 1248 | |
| acg ggc atg gag tac ctg gag aag tgt aca gtg agg ttg tgc tca tcg<br>Thr Gly Met Glu Tyr Leu Glu Lys Cys Thr Val Arg Leu Cys Ser Ser<br>420 425 430 | 1296 | |
| cgg tgt gta aac tac gaa gcg ctg gat ctg cat gcc agg acg tac gcc<br>Arg Cys Val Asn Tyr Glu Ala Leu Asp Leu His Ala Arg Thr Tyr Ala<br>435 440 445 | 1344 | |
| att caa att ttg cag gct gcc gac ttt gct gcg aat gcg agc act gcg<br>Ile Gln Ile Leu Gln Ala Ala Asp Phe Ala Ala Asn Ala Ser Thr Ala<br>450 455 460 | 1392 | |
| ctg tcg tac gtg tgg ccg ctg ctg gac tgc aac ttc atc att gac aag<br>Leu Ser Tyr Val Trp Pro Leu Leu Asp Cys Asn Phe Ile Ile Asp Lys<br>465 470 475 480 | 1440 | |
| atc gcc aac aca gtc gag acg cag agc tac aac agc agc ttc acc acg<br>Ile Ala Asn Thr Val Glu Thr Gln Ser Tyr Asn Ser Ser Phe Thr Thr<br>485 490 495 | 1488 | |
| cag agc gaa tat gtc cgc agc tgc tct gcg gtc cgc act tcc tct gtg<br>Gln Ser Glu Tyr Val Arg Ser Cys Ser Ala Val Arg Thr Ser Ser Val<br>500 505 510 | 1536 | |
| atg ctg ggt acc ggg ttc ttt gtc ggg gcg ctc atg ttc att gtc ggc<br>Met Leu Gly Thr Gly Phe Phe Val Gly Ala Leu Met Phe Ile Val Gly<br>515 520 525 | 1584 | |
| att tat gtc ata cat cgc ggt tcg cgg atc acg gtg cca gtg aac aaa<br>Ile Tyr Val Ile His Arg Gly Ser Arg Ile Thr Val Pro Val Asn Lys<br>530 535 540 | 1632 | |

```
gag aag gat ttc tga                                          1647
Glu Lys Asp Phe
545

<210> SEQ ID NO 76
<211> LENGTH: 548
<212> TYPE: PRT
<213> ORGANISM: Leishmania major

<400> SEQUENCE: 76

Met Val Cys Pro Phe Ser Cys Pro Pro Leu Pro Ala Pro Ser Leu Asn
1               5                   10                  15

Ser Ser His Leu Ser Leu Pro Lys Lys Gln Arg Leu Thr Ala Arg Ala
            20                  25                  30

His Thr Pro Thr His Lys Met Ala Lys Thr Thr Leu Leu Val Cys Ala
        35                  40                  45

Leu Leu Ala Leu Val Met Cys Leu Ala Ala Thr Ala Val Ser Ala Gln
    50                  55                  60

Gln Ser Leu Ala Cys Gln Met Val Trp Gln Ala Pro Ser Pro Asn Asn
65                  70                  75                  80

Ser Leu Leu Glu Cys Leu Gly Asn Thr Asp Arg Ile Arg Ser Gln Trp
                85                  90                  95

Pro Tyr Tyr Leu Tyr Pro Ala Phe Ala Ala Leu Ile Phe Ile Phe Thr
            100                 105                 110

Val Ile Gly Leu Pro Ile Leu Phe Cys Cys His Cys Cys Ser Cys Cys
        115                 120                 125

Glu Ala Tyr Val Lys Pro Lys Ala Glu Thr Asp Leu Gly Val Ala Arg
    130                 135                 140

Cys Cys Leu Trp Met Leu Ile Val Ile Ser Val Leu Val Ala Cys Gly
145                 150                 155                 160

Val Cys Val Leu Leu Val Tyr Gly Ser Val Leu Leu Glu Gln Ala Ala
                165                 170                 175

Thr Gln Ile Ile His Asp Thr Glu Tyr Arg Thr Leu Asn Tyr Phe Asn
            180                 185                 190

Asp Ile Arg Ala Asn Ile Thr Met Leu Leu Thr Asn Tyr Ser Ala Asp
        195                 200                 205

Pro Pro Ile Pro Pro Ser Ile Asp Leu Arg Thr Phe Asp Ala Val Asn
    210                 215                 220

Asp Asp Ile Thr His Tyr Val His Leu Ala Arg Asn Asn Tyr Leu Gln
225                 230                 235                 240

Tyr Phe Arg Ala Ala Glu Ile Val Val Cys Val Gly Ser Val Gly
                245                 250                 255

Val Phe Leu Met Leu Cys Met Leu Val Phe Val Leu Cys Arg Cys Asn
            260                 265                 270

Gly Ile Cys Pro Ile Ala Trp Ser Cys Leu Tyr Phe Val Phe Ala Leu
        275                 280                 285

Ala Phe Ala Leu Leu Ala Val Leu Phe Thr Ile Cys Ile Tyr Val Leu
    290                 295                 300

Ser Ala Gly Cys Gly Glu Val Gly Leu Gln Arg Gly Arg Glu Pro Gly
305                 310                 315                 320

Val Phe Gln Trp Tyr Leu Val Pro Trp Cys Glu Lys Gln Phe Asn Phe
                325                 330                 335

Gln Ala Leu Arg Ala Gln Val Gln Ser Gln Glu Gln Val Ser Gln
            340                 345                 350
```

```
Ser Ala Cys Ala Glu Leu Leu Asn Phe Cys Asp Asn Asp Pro His Tyr
        355                 360                 365
Ser Leu Glu Thr Lys Asn His Ile Phe Met Cys Gly Asn Ser Ile Thr
    370                 375                 380
Asp Lys Ser Gln Cys Asp Ser Leu Asp Asp Val Val Asp Val Leu
385                 390                 395                 400
Ser Thr Tyr Val Lys Pro Met Leu Thr Asn Thr Leu Cys Ala Asn Gln
                405                 410                 415
Thr Gly Met Glu Tyr Leu Glu Lys Cys Thr Val Arg Leu Cys Ser Ser
            420                 425                 430
Arg Cys Val Asn Tyr Glu Ala Leu Asp Leu His Ala Arg Thr Tyr Ala
        435                 440                 445
Ile Gln Ile Leu Gln Ala Ala Asp Phe Ala Ala Asn Ala Ser Thr Ala
    450                 455                 460
Leu Ser Tyr Val Trp Pro Leu Leu Asp Cys Asn Phe Ile Ile Asp Lys
465                 470                 475                 480
Ile Ala Asn Thr Val Glu Thr Gln Ser Tyr Asn Ser Ser Phe Thr Thr
                485                 490                 495
Gln Ser Glu Tyr Val Arg Ser Cys Ser Ala Val Arg Thr Ser Ser Val
            500                 505                 510
Met Leu Gly Thr Gly Phe Phe Val Gly Ala Leu Met Phe Ile Val Gly
        515                 520                 525
Ile Tyr Val Ile His Arg Gly Ser Arg Ile Thr Val Pro Val Asn Lys
    530                 535                 540
Glu Lys Asp Phe
545

<210> SEQ ID NO 77
<211> LENGTH: 1590
<212> TYPE: DNA
<213> ORGANISM: Leishmania infantum
<220> FEATURE:
<221> NAME/KEY: CDS
<222> LOCATION: (1)..(1590)

<400> SEQUENCE: 77 atg gcc aaa aca gcg ctt ctc gtg ggc gct ctg ctc gcc ctc gtc atg        48
Met Ala Lys Thr Ala Leu Leu Val Gly Ala Leu Leu Ala Leu Val Met
1               5                   10                  15 tgc ctg gcg gcg acg gcc gtc tcg gcg cag cgg tcg ctg gag tgt caa        96
Cys Leu Ala Ala Thr Ala Val Ser Ala Gln Arg Ser Leu Glu Cys Gln
            20                  25                  30 atg gtg tgg caa ggt cct tcc tct aac aac agc ctg ctg gag tgc ctg       144
Met Val Trp Gln Gly Pro Ser Ser Asn Asn Ser Leu Leu Glu Cys Leu
        35                  40                  45 ggg aac acg gat cgc atc cgg tcc cag tgg ccc tac tac ctg tat ccc       192
Gly Asn Thr Asp Arg Ile Arg Ser Gln Trp Pro Tyr Tyr Leu Tyr Pro
    50                  55                  60 gcc ttc gct gcg ctc gtg ttc atc ttc acg gtg att ggg ctg ccg att       240
Ala Phe Ala Ala Leu Val Phe Ile Phe Thr Val Ile Gly Leu Pro Ile
65                  70                  75                  80 ctg ttc tgc tgc cac tgc tgc agc tgc tgc gag gcg tat gtg aag ccg       288
Leu Phe Cys Cys His Cys Cys Ser Cys Cys Glu Ala Tyr Val Lys Pro
                85                  90                  95 aag gcg gag acg gac ctc ggc gtt gcc cgc tgc tgc cta tgg atg tgg       336
Lys Ala Glu Thr Asp Leu Gly Val Ala Arg Cys Cys Leu Trp Met Trp
            100                 105                 110 atc gtg att tcg gtg ctt gtg gcg tgc ggc gtg tgc gtg ctg ctg gtg       384
```

```
Ile Val Ile Ser Val Leu Val Ala Cys Gly Val Cys Val Leu Leu Val
            115                 120                 125 tat ggc tcc gtc tta ctg gag cag gca gcc aaa caa att atc cac gac      432
Tyr Gly Ser Val Leu Leu Glu Gln Ala Ala Lys Gln Ile Ile His Asp
        130                 135                 140 acc gag tat cgc acg ctt gat tac ttc aac gac acc cgt gcg aac atc      480
Thr Glu Tyr Arg Thr Leu Asp Tyr Phe Asn Asp Thr Arg Ala Asn Ile
145                 150                 155                 160 gcg atg ctg ctg aca aac tac agc gcg gac cca ccg aca cca ccg tca      528
Ala Met Leu Leu Thr Asn Tyr Ser Ala Asp Pro Pro Thr Pro Pro Ser
                165                 170                 175 atc gac ctt agc gcc ttt gac gcc gtg aac gat aat gtt acc tac tac      576
Ile Asp Leu Ser Ala Phe Asp Ala Val Asn Asp Asn Val Thr Tyr Tyr
            180                 185                 190 gtg cac ctg gcg cgc aac aac tac ctc aag tac ttc cgc gct gcc gag      624
Val His Leu Ala Arg Asn Asn Tyr Leu Lys Tyr Phe Arg Ala Ala Glu
        195                 200                 205 att gtg gtc tgc tgc gtc ggc agc gtc ggt gtt ttc ctg atg ctg tgc      672
Ile Val Val Cys Cys Val Gly Ser Val Gly Val Phe Leu Met Leu Cys
210                 215                 220 atg ctg atc ttt gcg ctg tgc cgt tgc agt ggg atc tgc ccg att gtg      720
Met Leu Ile Phe Ala Leu Cys Arg Cys Ser Gly Ile Cys Pro Ile Val
225                 230                 235                 240 tgg agc tgc ctg tac ttc gtg ttc gcg ctt gca ttt gcg ttg ctt gcg      768
Trp Ser Cys Leu Tyr Phe Val Phe Ala Leu Ala Phe Ala Leu Leu Ala
                245                 250                 255 gtg ctg ttc acg ata tgc atc tac gtg atg tcc gcc ggc tgc ggc gag      816
Val Leu Phe Thr Ile Cys Ile Tyr Val Met Ser Ala Gly Cys Gly Glu
            260                 265                 270 gtg gac ctc cag tac agc cgt gag cct ggc gtc ttt cag tgg tac ctg      864
Val Asp Leu Gln Tyr Ser Arg Glu Pro Gly Val Phe Gln Trp Tyr Leu
        275                 280                 285 gtg ccg tgg tgc gag aag cag ttc gac ttc cag gcg ctg cgg gct cag      912
Val Pro Trp Cys Glu Lys Gln Phe Asp Phe Gln Ala Leu Arg Ala Gln
290                 295                 300 gtg cag agc cag gag cag cag gtc tcg cag agc gcc tgc ggg gcg ctc      960
Val Gln Ser Gln Glu Gln Gln Val Ser Gln Ser Ala Cys Gly Ala Leu
305                 310                 315                 320 ttg aac ttc tgt gac aac gat ccg aat tac tcg ttg gag aat aaa aac     1008
Leu Asn Phe Cys Asp Asn Asp Pro Asn Tyr Ser Leu Glu Asn Lys Asn
                325                 330                 335 cac atc ttc atg tgc ggc aac agc atc acc gac aaa agc cag tgc aac     1056
His Ile Phe Met Cys Gly Asn Ser Ile Thr Asp Lys Ser Gln Cys Asn
            340                 345                 350 tcg ctg gac gac gtg gtg gac gtt gtt ctg agc aca tac gtg aag ccg     1104
Ser Leu Asp Asp Val Val Asp Val Val Leu Ser Thr Tyr Val Lys Pro
        355                 360                 365 atg ctg acg aac acg cta tgt gcc aac cag acg ggc atg gag tac ctg     1152
Met Leu Thr Asn Thr Leu Cys Ala Asn Gln Thr Gly Met Glu Tyr Leu
370                 375                 380 gag aag tgt acg ttg atc tcc tgc gca tcg cgg tgt gtg gac tac caa     1200
Glu Lys Cys Thr Leu Ile Ser Cys Ala Ser Arg Cys Val Asp Tyr Gln
385                 390                 395                 400 ttc ccg ccc ctg cat gcc agg aca gaa gcc att caa att ctg cag gct     1248
Phe Pro Pro Leu His Ala Arg Thr Glu Ala Ile Gln Ile Leu Gln Ala
                405                 410                 415 gcc aac ttt gct gcg aat gcg agc act gcg ctg tca tac gtg tgg ccg     1296
Ala Asn Phe Ala Ala Asn Ala Ser Thr Ala Leu Ser Tyr Val Trp Pro
            420                 425                 430
```

-continued

| | | |
|---|---|---|
| ctg ctg gag tgc aac ttc atc att gac aag att gcc aac aca gtc gag<br>Leu Leu Glu Cys Asn Phe Ile Ile Asp Lys Ile Ala Asn Thr Val Glu<br>435                     440                 445 | 1344 |
| acg cgg aac tac aac agc agc ttc acc acg cag agc gat tat gtg cgc<br>Thr Arg Asn Tyr Asn Ser Ser Phe Thr Thr Gln Ser Asp Tyr Val Arg<br>450                     455                 460 | 1392 |
| agc tgc tct gcg gtc cgc gta tcc tcg gtg atg ctg ggt acc ggt ttc<br>Ser Cys Ser Ala Val Arg Val Ser Ser Val Met Leu Gly Thr Gly Phe<br>465                     470                 475                 480 | 1440 |
| ttt gtc ggg gcg ctc atg ttc atc ctc ggc att cac gtc atg cat cgc<br>Phe Val Gly Ala Leu Met Phe Ile Leu Gly Ile His Val Met His Arg<br>                 485                 490                 495 | 1488 |
| ggt gcg ttt atc tgg gct gcc ggc aag gag aat gat gcg gtg cag aag<br>Gly Ala Phe Ile Trp Ala Ala Gly Lys Glu Asn Asp Ala Val Gln Lys<br>500                     505                 510 | 1536 |
| aag gat gtt tca cca cct ggc aat gcc gtc tcg tca ccc ctg aga aca<br>Lys Asp Val Ser Pro Pro Gly Asn Ala Val Ser Ser Pro Leu Arg Thr<br>                 515                 520                 525 | 1584 |
| cct taa<br>Pro | 1590 |

<210> SEQ ID NO 78
<211> LENGTH: 529
<212> TYPE: PRT
<213> ORGANISM: Leishmania infantum

<400> SEQUENCE: 78

Met Ala Lys Thr Ala Leu Leu Val Gly Ala Leu Leu Ala Leu Val Met
1               5                   10                  15

Cys Leu Ala Ala Thr Ala Val Ser Ala Gln Arg Ser Leu Glu Cys Gln
                20                  25                  30

Met Val Trp Gln Gly Pro Ser Ser Asn Asn Ser Leu Leu Glu Cys Leu
            35                  40                  45

Gly Asn Thr Asp Arg Ile Arg Ser Gln Trp Pro Tyr Tyr Leu Tyr Pro
        50                  55                  60

Ala Phe Ala Ala Leu Val Phe Ile Phe Thr Val Ile Gly Leu Pro Ile
65                  70                  75                  80

Leu Phe Cys Cys His Cys Cys Ser Cys Cys Glu Ala Tyr Val Lys Pro
                85                  90                  95

Lys Ala Glu Thr Asp Leu Gly Val Ala Arg Cys Cys Leu Trp Met Trp
            100                 105                 110

Ile Val Ile Ser Val Leu Val Ala Cys Gly Val Cys Val Leu Leu Val
        115                 120                 125

Tyr Gly Ser Val Leu Leu Glu Gln Ala Ala Lys Gln Ile Ile His Asp
    130                 135                 140

Thr Glu Tyr Arg Thr Leu Asp Tyr Phe Asn Asp Thr Arg Ala Asn Ile
145                 150                 155                 160

Ala Met Leu Leu Thr Asn Tyr Ser Ala Asp Pro Pro Thr Pro Ser
                165                 170                 175

Ile Asp Leu Ser Ala Phe Asp Ala Val Asn Asp Asn Val Thr Tyr Tyr
            180                 185                 190

Val His Leu Ala Arg Asn Asn Tyr Leu Lys Tyr Phe Arg Ala Ala Glu
        195                 200                 205

Ile Val Val Cys Cys Val Gly Ser Val Gly Val Phe Leu Met Leu Cys
    210                 215                 220

Met Leu Ile Phe Ala Leu Cys Arg Cys Ser Gly Ile Cys Pro Ile Val
225                 230                 235                 240

```
Trp Ser Cys Leu Tyr Phe Val Phe Ala Leu Ala Phe Ala Leu Leu Ala
            245                 250                 255

Val Leu Phe Thr Ile Cys Ile Tyr Val Met Ser Ala Gly Cys Gly Glu
            260                 265                 270

Val Asp Leu Gln Tyr Ser Arg Glu Pro Gly Val Phe Gln Trp Tyr Leu
            275                 280                 285

Val Pro Trp Cys Glu Lys Gln Phe Asp Phe Gln Ala Leu Arg Ala Gln
            290                 295                 300

Val Gln Ser Gln Glu Gln Gln Val Ser Gln Ser Ala Cys Gly Ala Leu
305                 310                 315                 320

Leu Asn Phe Cys Asp Asn Asp Pro Asn Tyr Ser Leu Glu Asn Lys Asn
                325                 330                 335

His Ile Phe Met Cys Gly Asn Ser Ile Thr Asp Lys Ser Gln Cys Asn
            340                 345                 350

Ser Leu Asp Asp Val Val Asp Val Leu Ser Thr Tyr Val Lys Pro
            355                 360                 365

Met Leu Thr Asn Thr Leu Cys Ala Asn Gln Thr Gly Met Glu Tyr Leu
            370                 375                 380

Glu Lys Cys Thr Leu Ile Ser Cys Ala Ser Arg Cys Val Asp Tyr Gln
385                 390                 395                 400

Phe Pro Pro Leu His Ala Arg Thr Glu Ala Ile Gln Ile Leu Gln Ala
                405                 410                 415

Ala Asn Phe Ala Ala Asn Ala Ser Thr Ala Leu Ser Tyr Val Trp Pro
            420                 425                 430

Leu Leu Glu Cys Asn Phe Ile Ile Asp Lys Ile Ala Asn Thr Val Glu
            435                 440                 445

Thr Arg Asn Tyr Asn Ser Ser Phe Thr Thr Gln Ser Asp Tyr Val Arg
            450                 455                 460

Ser Cys Ser Ala Val Arg Val Ser Ser Val Met Leu Gly Thr Gly Phe
465                 470                 475                 480

Phe Val Gly Ala Leu Met Phe Ile Leu Gly Ile His Val Met His Arg
                485                 490                 495

Gly Ala Phe Ile Trp Ala Ala Gly Lys Glu Asn Asp Ala Val Gln Lys
            500                 505                 510

Lys Asp Val Ser Pro Pro Gly Asn Ala Val Ser Ser Pro Leu Arg Thr
            515                 520                 525

Pro

<210> SEQ ID NO 79
<211> LENGTH: 1644
<212> TYPE: DNA
<213> ORGANISM: Trypanosoma brucei
<220> FEATURE:
<221> NAME/KEY: CDS
<222> LOCATION: (1)..(1644)

<400> SEQUENCE: 79 atg tcc tcc gtt acc act ggc agc tct ttc tat gct gca gtg tta ttg      48
Met Ser Ser Val Thr Thr Gly Ser Ser Phe Tyr Ala Ala Val Leu Leu
1               5                   10                  15 gtg ctg ttg tta aca gtt acg caa tgc gga aac tcc aag ttt cca aat      96
Val Leu Leu Leu Thr Val Thr Gln Cys Gly Asn Ser Lys Phe Pro Asn
            20                  25                  30 ctt cac tgt gac aat gtc tgg gat ggg ccc agt gct cga aat gac cct     144
Leu His Cys Asp Asn Val Trp Asp Gly Pro Ser Ala Arg Asn Asp Pro
        35                  40                  45
```

```
ctt acg tgc att atg gat acc gac cgt atc tta gcg cag tgg cgt atg      192
Leu Thr Cys Ile Met Asp Thr Asp Arg Ile Leu Ala Gln Trp Arg Met
 50                  55                  60 tta gca atg cct gct ctc tgt gct ttc ctt ttc gtg gct gtg tta att      240
Leu Ala Met Pro Ala Leu Cys Ala Phe Leu Phe Val Ala Val Leu Ile
 65                  70                  75                  80 gct ttc ccc ata tct tgc ttt ctt aca tgc ctg tgt tcc tcc cgt tgc      288
Ala Phe Pro Ile Ser Cys Phe Leu Thr Cys Leu Cys Ser Ser Arg Cys
                     85                  90                  95 aag cct tcc tct aag gac gga ggt aag gaa caa cgt tgc tgc ctt tgg      336
Lys Pro Ser Ser Lys Asp Gly Gly Lys Glu Gln Arg Cys Cys Leu Trp
                100                 105                 110 atg tgg att atg ttt gct tta ata tgg gct ttt ggt gtt gct gca ttt      384
Met Trp Ile Met Phe Ala Leu Ile Trp Ala Phe Gly Val Ala Ala Phe
            115                 120                 125 gtg ttc ttt ggg gtg aag cag ttg tgg gca acc tca aat tat ttt ctc      432
Val Phe Phe Gly Val Lys Gln Leu Trp Ala Thr Ser Asn Tyr Phe Leu
        130                 135                 140 gat gta aca ttg atg aat ccg ttg aat gtt gtg aac tgc act gcg gaa      480
Asp Val Thr Leu Met Asn Pro Leu Asn Val Val Asn Cys Thr Ala Glu
145                 150                 155                 160 aaa gtt att gat ttt gcg tct aac tgg acc tct gga aat aga gag cca      528
Lys Val Ile Asp Phe Ala Ser Asn Trp Thr Ser Gly Asn Arg Glu Pro
                165                 170                 175 tac gct gat ggt gtt gat gtg agc ttt ttc tat gat ata tcg gaa aac      576
Tyr Ala Asp Gly Val Asp Val Ser Phe Phe Tyr Asp Ile Ser Glu Asn
                180                 185                 190 gcc gtt cgt gtt gtt gaa atg ttg aga ggt aga gcg gga gat tat att      624
Ala Val Arg Val Val Glu Met Leu Arg Gly Arg Ala Gly Asp Tyr Ile
            195                 200                 205 aag ttg tta cct gtt gtt tct tat gcg gtg ggt tcc gta tgt att gcg      672
Lys Leu Leu Pro Val Val Ser Tyr Ala Val Gly Ser Val Cys Ile Ala
        210                 215                 220 ttg atg gct ccg atg gtt att ctt gct tgc tgt cgc cga ggt cct ttg      720
Leu Met Ala Pro Met Val Ile Leu Ala Cys Cys Arg Arg Gly Pro Leu
225                 230                 235                 240 ata gtg ccc gaa tgc ttc gct tgt gca tat ttc gtt ttc ggg ctt gtt      768
Ile Val Pro Glu Cys Phe Ala Cys Ala Tyr Phe Val Phe Gly Leu Val
                245                 250                 255 ttt tca gtt ggc ggt gct gtt ttg ttc ctg ttg agc tat gct tct tca      816
Phe Ser Val Gly Gly Ala Val Leu Phe Leu Leu Ser Tyr Ala Ser Ser
                260                 265                 270 tct gtg tgt ggc gag att gca ctt cac cgt gag cga aag cct ggc att      864
Ser Val Cys Gly Glu Ile Ala Leu His Arg Glu Arg Lys Pro Gly Ile
            275                 280                 285 atc cag tgg tac gga atc cca tta tgc aat agc aag ttt cgc cct gat      912
Ile Gln Trp Tyr Gly Ile Pro Leu Cys Asn Ser Lys Phe Arg Pro Asp
        290                 295                 300 gct att aac aag aaa gtg aca gac gcg gag att ggc att tgt agg gag      960
Ala Ile Asn Lys Lys Val Thr Asp Ala Glu Ile Gly Ile Cys Arg Glu
305                 310                 315                 320 gct tgc aat tat ttg ctt gat aac tgt gat aat ctg gat atg cgt ggc     1008
Ala Cys Asn Tyr Leu Leu Asp Asn Cys Asp Asn Leu Asp Met Arg Gly
                325                 330                 335 cca agt atg agt cgt ttt tcg gga tca agt gta tct tat gat ggt tat     1056
Pro Ser Met Ser Arg Phe Ser Gly Ser Ser Val Ser Tyr Asp Gly Tyr
                340                 345                 350 gtg cct tct ggt tac ctc aaa gac aga aac ggt aag ccg aac acg cga     1104
Val Pro Ser Gly Tyr Leu Lys Asp Arg Asn Gly Lys Pro Asn Thr Arg
```

```
tct agc gac ata tcc cct gac gcc cct gct tct ttc ata gca agt ggg      1152
Ser Ser Asp Ile Ser Pro Asp Ala Pro Ala Ser Phe Ile Ala Ser Gly
370                 375                 380 ttt gta agt cat gcg gca gct agg aat gtg ggt ggt act ttt ccc gtg      1200
Phe Val Ser His Ala Ala Ala Arg Asn Val Gly Gly Thr Phe Pro Val
385                 390                 395                 400 aag gtt ctg act tgt gga aag aat atc acc tca tcc gat gag tgt cca      1248
Lys Val Leu Thr Cys Gly Lys Asn Ile Thr Ser Ser Asp Glu Cys Pro
                405                 410                 415 aac ttt ggc atc aca gca aca gta ctg gag gac aca cgg gtg aag gcc      1296
Asn Phe Gly Ile Thr Ala Thr Val Leu Glu Asp Thr Arg Val Lys Ala
            420                 425                 430 ttc gtt ggt tca tgc cct act ccc gga aat tct tgc acg gta gtg gag      1344
Phe Val Gly Ser Cys Pro Thr Pro Gly Asn Ser Cys Thr Val Val Glu
        435                 440                 445 tgt gcg gcc aat tgt acg gag ggc agg gca aag aac gtc tct atc gaa      1392
Cys Ala Ala Asn Cys Thr Glu Gly Arg Ala Lys Asn Val Ser Ile Glu
450                 455                 460 gtc gta cgt gtg gct gca cgg tcg cgt aac gtc agt gtt gca ctt tca      1440
Val Val Arg Val Ala Ala Arg Ser Arg Asn Val Ser Val Ala Leu Ser
465                 470                 475                 480 ata ggt cga ccg ctg ctg gaa tgt aat ttt atg ctc gac att gcg cta      1488
Ile Gly Arg Pro Leu Leu Glu Cys Asn Phe Met Leu Asp Ile Ala Leu
                485                 490                 495 act gcc atg ccg gac tgt gaa gat ata acg ccg ggt gtc ttc atg ctt      1536
Thr Ala Met Pro Asp Cys Glu Asp Ile Thr Pro Gly Val Phe Met Leu
            500                 505                 510 tcc gtc ggg ttt ctc ctt gga agt ctg atg ttt gcg gtc ggg att tat      1584
Ser Val Gly Phe Leu Leu Gly Ser Leu Met Phe Ala Val Gly Ile Tyr
        515                 520                 525 gtc atg ctc cgt ggt tct tgt gtt tgg ggt agt gcc aag acc tcg ccg      1632
Val Met Leu Arg Gly Ser Cys Val Trp Gly Ser Ala Lys Thr Ser Pro
530                 535                 540 gag gct tct taa                                                       1644
Glu Ala Ser
545

<210> SEQ ID NO 80
<211> LENGTH: 547
<212> TYPE: PRT
<213> ORGANISM: Trypanosoma brucei

<400> SEQUENCE: 80

Met Ser Ser Val Thr Thr Gly Ser Ser Phe Tyr Ala Ala Val Leu Leu
1               5                   10                  15

Val Leu Leu Leu Thr Val Thr Gln Cys Gly Asn Ser Lys Phe Pro Asn
            20                  25                  30

Leu His Cys Asp Asn Val Trp Asp Gly Pro Ser Ala Arg Asn Asp Pro
        35                  40                  45

Leu Thr Cys Ile Met Asp Thr Asp Arg Ile Leu Ala Gln Trp Arg Met
    50                  55                  60

Leu Ala Met Pro Ala Leu Cys Ala Phe Leu Phe Val Ala Val Leu Ile
65                  70                  75                  80

Ala Phe Pro Ile Ser Cys Phe Leu Thr Cys Leu Cys Ser Ser Arg Cys
                85                  90                  95

Lys Pro Ser Ser Lys Asp Gly Gly Lys Glu Gln Arg Cys Cys Leu Trp
            100                 105                 110
```

```
Met Trp Ile Met Phe Ala Leu Ile Trp Ala Phe Gly Val Ala Ala Phe
            115                 120                 125

Val Phe Phe Gly Val Lys Gln Leu Trp Ala Thr Ser Asn Tyr Phe Leu
130                 135                 140

Asp Val Thr Leu Met Asn Pro Leu Asn Val Val Asn Cys Thr Ala Glu
145                 150                 155                 160

Lys Val Ile Asp Phe Ala Ser Asn Trp Thr Ser Gly Asn Arg Glu Pro
                165                 170                 175

Tyr Ala Asp Gly Val Asp Val Ser Phe Phe Tyr Asp Ile Ser Glu Asn
            180                 185                 190

Ala Val Arg Val Val Glu Met Leu Arg Gly Arg Ala Gly Asp Tyr Ile
        195                 200                 205

Lys Leu Leu Pro Val Val Ser Tyr Ala Val Gly Ser Val Cys Ile Ala
    210                 215                 220

Leu Met Ala Pro Met Val Ile Leu Ala Cys Cys Arg Arg Gly Pro Leu
225                 230                 235                 240

Ile Val Pro Glu Cys Phe Ala Cys Ala Tyr Phe Val Phe Gly Leu Val
                245                 250                 255

Phe Ser Val Gly Gly Ala Val Leu Phe Leu Leu Ser Tyr Ala Ser Ser
            260                 265                 270

Ser Val Cys Gly Glu Ile Ala Leu His Arg Glu Arg Lys Pro Gly Ile
        275                 280                 285

Ile Gln Trp Tyr Gly Ile Pro Leu Cys Asn Ser Lys Phe Arg Pro Asp
    290                 295                 300

Ala Ile Asn Lys Lys Val Thr Asp Ala Glu Ile Gly Ile Cys Arg Glu
305                 310                 315                 320

Ala Cys Asn Tyr Leu Leu Asp Asn Cys Asp Asn Leu Asp Met Arg Gly
                325                 330                 335

Pro Ser Met Ser Arg Phe Ser Gly Ser Val Ser Tyr Asp Gly Tyr
            340                 345                 350

Val Pro Ser Gly Tyr Leu Lys Asp Arg Asn Gly Lys Pro Asn Thr Arg
        355                 360                 365

Ser Ser Asp Ile Ser Pro Asp Ala Pro Ala Ser Phe Ile Ala Ser Gly
    370                 375                 380

Phe Val Ser His Ala Ala Arg Asn Val Gly Gly Thr Phe Pro Val
385                 390                 395                 400

Lys Val Leu Thr Cys Gly Lys Asn Ile Thr Ser Ser Asp Glu Cys Pro
                405                 410                 415

Asn Phe Gly Ile Thr Ala Thr Val Leu Glu Asp Thr Arg Val Lys Ala
            420                 425                 430

Phe Val Gly Ser Cys Pro Thr Pro Gly Asn Ser Cys Thr Val Val Glu
        435                 440                 445

Cys Ala Ala Asn Cys Thr Glu Gly Arg Ala Lys Asn Val Ser Ile Glu
    450                 455                 460

Val Val Arg Val Ala Ala Arg Ser Arg Asn Val Ser Val Ala Leu Ser
465                 470                 475                 480

Ile Gly Arg Pro Leu Leu Glu Cys Asn Phe Met Leu Asp Ile Ala Leu
                485                 490                 495

Thr Ala Met Pro Asp Cys Glu Asp Ile Thr Pro Gly Val Phe Met Leu
            500                 505                 510

Ser Val Gly Phe Leu Leu Gly Ser Leu Met Phe Ala Val Gly Ile Tyr
        515                 520                 525

Val Met Leu Arg Gly Ser Cys Val Trp Gly Ser Ala Lys Thr Ser Pro
```

```
                  530               535               540
Glu Ala Ser
545

<210> SEQ ID NO 81
<211> LENGTH: 1713
<212> TYPE: DNA
<213> ORGANISM: Trypanosoma brucei
<220> FEATURE:
<221> NAME/KEY: CDS
<222> LOCATION: (1)..(1713)

<400> SEQUENCE: 81 atg tat aat gcc ctg agg tca gca gct ctg gca gtg ggg ttg gtg tta      48
Met Tyr Asn Ala Leu Arg Ser Ala Ala Leu Ala Val Gly Leu Val Leu
1               5                   10                  15 ctg ttt gcc gcc acg cca gca tcc gca act aga gag ggt tcg ttt caa      96
Leu Phe Ala Ala Thr Pro Ala Ser Ala Thr Arg Glu Gly Ser Phe Gln
            20                  25                  30 tgc gag aat gtg tgg gat ggc ccg agt acc agt aat gac gtt cag gcg     144
Cys Glu Asn Val Trp Asp Gly Pro Ser Thr Ser Asn Asp Val Gln Ala
        35                  40                  45 tgt ata ctc aat gca gag cgc atg cgg tct cag tgg aag ctc ttt gtt     192
Cys Ile Leu Asn Ala Glu Arg Met Arg Ser Gln Trp Lys Leu Phe Val
    50                  55                  60 ttg ccg ttt cta agt gct gta ctt ctt gca gta ctg ttg gta agc ttc     240
Leu Pro Phe Leu Ser Ala Val Leu Leu Ala Val Leu Leu Val Ser Phe
65                  70                  75                  80 cct ctt gta ttc att tgc tcc ata tgc tgt aac tgt tgc ggc tgt tgt     288
Pro Leu Val Phe Ile Cys Ser Ile Cys Cys Asn Cys Cys Gly Cys Cys
                85                  90                  95 ggt gca aac tgc tgt aaa ccg gaa acg aag aag agc agg aat cag gcc     336
Gly Ala Asn Cys Cys Lys Pro Glu Thr Lys Lys Ser Arg Asn Gln Ala
            100                 105                 110 cgt tgc tgt ttg tgg ttg tac atc gtg tat gcc cta ctt tgg agc gtt     384
Arg Cys Cys Leu Trp Leu Tyr Ile Val Tyr Ala Leu Leu Trp Ser Val
        115                 120                 125 atg gtt ttt ttt ctt atc gta tac ggg act cgg acg gtg acg aag gct     432
Met Val Phe Phe Leu Ile Val Tyr Gly Thr Arg Thr Val Thr Lys Ala
    130                 135                 140 gtt cca acg ttc gtc gac gac gca gtc tct gga ccc ttg tcg tac ttt     480
Val Pro Thr Phe Val Asp Asp Ala Val Ser Gly Pro Leu Ser Tyr Phe
145                 150                 155                 160 aat caa aca gca gaa agt gta atg gat tac aca tat gac tgg agc tcg     528
Asn Gln Thr Ala Glu Ser Val Met Asp Tyr Thr Tyr Asp Trp Ser Ser
                165                 170                 175 ggt gag cgg agg gaa cca ggt gac ttt acg att gac ttc tcc gag ttt     576
Gly Glu Arg Arg Glu Pro Gly Asp Phe Thr Ile Asp Phe Ser Glu Phe
            180                 185                 190 tcc agc atg cag aag aag gta atg gaa ggc gtg tcc gca gtc cgt gca     624
Ser Ser Met Gln Lys Lys Val Met Glu Gly Val Ser Ala Val Arg Ala
        195                 200                 205 aca gtc ttt gta cac ttt gac aag gtc tcc atc gcg tcc tac gtt gtc     672
Thr Val Phe Val His Phe Asp Lys Val Ser Ile Ala Ser Tyr Val Val
    210                 215                 220 gga agc ctt ggt ttc gtt atg gta ctt gtt att ctc cct ttt gcc atg     720
Gly Ser Leu Gly Phe Val Met Val Leu Val Ile Leu Pro Phe Ala Met
225                 230                 235                 240 ttc aag tgc tgc att ccg ggg ttt cca ata tgt atc tcg ttc gtc tat     768
Phe Lys Cys Cys Ile Pro Gly Phe Pro Ile Cys Ile Ser Phe Val Tyr
                245                 250                 255
```

```
tgg att ttt ggt ctt gcc ttc gcc gtg ctc gga ctg ttg acg att      816
Trp Ile Phe Gly Leu Ala Phe Ala Val Leu Gly Leu Leu Thr Ile
        260                 265                 270 ctg gcg tac ttc gcc acc ctt acc tgc ggc gaa gtg gag cga cac cat  864
Leu Ala Tyr Phe Ala Thr Leu Thr Cys Gly Glu Val Glu Arg His His
        275                 280                 285 ggg cgg gat cca ggg ctg att cag tgg tat ggc gtc cct gtt tgt aaa  912
Gly Arg Asp Pro Gly Leu Ile Gln Trp Tyr Gly Val Pro Val Cys Lys
        290                 295                 300 gag ttt ttt aat ttc caa cag tta aac aag ggc att atg gcc gct gag  960
Glu Phe Phe Asn Phe Gln Gln Leu Asn Lys Gly Ile Met Ala Ala Glu
305                 310                 315                 320 ttg cag ctg tct cag ggt gtc tgc aag gca gtt cta ccg ttc tgt gac  1008
Leu Gln Leu Ser Gln Gly Val Cys Lys Ala Val Leu Pro Phe Cys Asp
                325                 330                 335 aga cgt aag ctt cgg ggc ccc ggt ggc gta gtg gat cgt gct gat cct  1056
Arg Arg Lys Leu Arg Gly Pro Gly Gly Val Val Asp Arg Ala Asp Pro
            340                 345                 350 cac cct ggt gag aga aac agg ttg ctg cca ccc ggt ggc gaa tat cca  1104
His Pro Gly Glu Arg Asn Arg Leu Leu Pro Pro Gly Gly Glu Tyr Pro
        355                 360                 365 aat gaa aag gcc ttg gag aac aca agc cac aaa cac gga aat gtt cct  1152
Asn Glu Lys Ala Leu Glu Asn Thr Ser His Lys His Gly Asn Val Pro
370                 375                 380 cct gca agc gat agg gcg ggg ggt cca ccg cat cca aca cct gtg cgt  1200
Pro Ala Ser Asp Arg Ala Gly Gly Pro Pro His Pro Thr Pro Val Arg
385                 390                 395                 400 gac cac tcg ggt ctg cct gga att tcc gag ggg ccg aat ttt ccg gat  1248
Asp His Ser Gly Leu Pro Gly Ile Ser Glu Gly Pro Asn Phe Pro Asp
                405                 410                 415 ctt ccc gcg gtc cct gtg cta aac tgt caa gaa gga ttt aca gac gcc  1296
Leu Pro Ala Val Pro Val Leu Asn Cys Gln Glu Gly Phe Thr Asp Ala
            420                 425                 430 tcg cag tgt acg acg ttt gat gcg atg tcc gca ctt gtg ttg acg gcg  1344
Ser Gln Cys Thr Thr Phe Asp Ala Met Ser Ala Leu Val Leu Thr Ala
        435                 440                 445 gaa gtt aaa ggt tcc tta aac cca tgt gga gag gcc gga aag gcg tgc  1392
Glu Val Lys Gly Ser Leu Asn Pro Cys Gly Glu Ala Gly Lys Ala Cys
450                 455                 460 aac ctt acg gag tgt gcc gcg cgt tgt gaa aac gat caa tta cag gag  1440
Asn Leu Thr Glu Cys Ala Ala Arg Cys Glu Asn Asp Gln Leu Gln Glu
465                 470                 475                 480 ctt gcg gtt cgc gca aca agt cag att gag aga gtg cag aac gta acc  1488
Leu Ala Val Arg Ala Thr Ser Gln Ile Glu Arg Val Gln Asn Val Thr
                485                 490                 495 atc gcg tgg tcg tat gcc agg ccg cta ctt gag tgc aac ttc gta atc  1536
Ile Ala Trp Ser Tyr Ala Arg Pro Leu Leu Glu Cys Asn Phe Val Ile
            500                 505                 510 gac aag att gta gag tct cta gaa gca tgc ggg gac atc acg gca gga  1584
Asp Lys Ile Val Glu Ser Leu Glu Ala Cys Gly Asp Ile Thr Ala Gly
        515                 520                 525 acg atg gtg ttg ggt gca ggt ttt ttc att ggt gca att gtg ttt ggc  1632
Thr Met Val Leu Gly Ala Gly Phe Phe Ile Gly Ala Ile Val Phe Gly
    530                 535                 540 ctc ggt ata tat att atg ctc cgt ggt gct tgc gta tgg ggt gag ata  1680
Leu Gly Ile Tyr Ile Met Leu Arg Gly Ala Cys Val Trp Gly Glu Ile
545                 550                 555                 560 ccg atg ttc act agg gat gcg aaa gct tcg tag                      1713
Pro Met Phe Thr Arg Asp Ala Lys Ala Ser
```

<210> SEQ ID NO 82
<211> LENGTH: 570
<212> TYPE: PRT
<213> ORGANISM: Trypanosoma brucei

<400> SEQUENCE: 82

Met Tyr Asn Ala Leu Arg Ser Ala Ala Leu Ala Val Gly Leu Val Leu
1               5                   10                  15

Leu Phe Ala Ala Thr Pro Ala Ser Ala Thr Arg Glu Gly Ser Phe Gln
            20                  25                  30

Cys Glu Asn Val Trp Asp Gly Pro Ser Thr Ser Asn Asp Val Gln Ala
        35                  40                  45

Cys Ile Leu Asn Ala Glu Arg Met Arg Ser Gln Trp Lys Leu Phe Val
    50                  55                  60

Leu Pro Phe Leu Ser Ala Val Leu Leu Ala Val Leu Leu Val Ser Phe
65                  70                  75                  80

Pro Leu Val Phe Ile Cys Ser Ile Cys Cys Asn Cys Cys Gly Cys Cys
                85                  90                  95

Gly Ala Asn Cys Cys Lys Pro Glu Thr Lys Lys Ser Arg Asn Gln Ala
            100                 105                 110

Arg Cys Cys Leu Trp Leu Tyr Ile Val Tyr Ala Leu Leu Trp Ser Val
        115                 120                 125

Met Val Phe Phe Leu Ile Val Tyr Gly Thr Arg Thr Val Thr Lys Ala
    130                 135                 140

Val Pro Thr Phe Val Asp Asp Ala Val Ser Gly Pro Leu Ser Tyr Phe
145                 150                 155                 160

Asn Gln Thr Ala Glu Ser Val Met Asp Tyr Thr Tyr Asp Trp Ser Ser
                165                 170                 175

Gly Glu Arg Arg Glu Pro Gly Asp Phe Thr Ile Asp Phe Ser Glu Phe
            180                 185                 190

Ser Ser Met Gln Lys Lys Val Met Glu Gly Val Ser Ala Val Arg Ala
        195                 200                 205

Thr Val Phe Val His Phe Asp Lys Val Ser Ile Ala Ser Tyr Val Val
    210                 215                 220

Gly Ser Leu Gly Phe Val Met Val Leu Val Ile Leu Pro Phe Ala Met
225                 230                 235                 240

Phe Lys Cys Cys Ile Pro Gly Phe Pro Ile Cys Ile Ser Phe Val Tyr
                245                 250                 255

Trp Ile Phe Gly Leu Ala Phe Ala Val Leu Gly Leu Leu Thr Ile
            260                 265                 270

Leu Ala Tyr Phe Ala Thr Leu Thr Cys Gly Glu Val Glu Arg His His
    275                 280                 285

Gly Arg Asp Pro Gly Leu Ile Gln Trp Tyr Gly Val Pro Val Cys Lys
290                 295                 300

Glu Phe Phe Asn Phe Gln Gln Leu Asn Lys Gly Ile Met Ala Ala Glu
305                 310                 315                 320

Leu Gln Leu Ser Gln Gly Val Cys Lys Ala Val Leu Pro Phe Cys Asp
                325                 330                 335

Arg Arg Lys Leu Arg Gly Pro Gly Val Val Asp Arg Ala Asp Pro
            340                 345                 350

His Pro Gly Glu Arg Asn Arg Leu Leu Pro Gly Gly Glu Tyr Pro
        355                 360                 365

```
Asn Glu Lys Ala Leu Glu Asn Thr Ser His Lys His Gly Asn Val Pro
    370                 375                 380
Pro Ala Ser Asp Arg Ala Gly Pro Pro His Pro Thr Pro Val Arg
385                 390                 395                 400
Asp His Ser Gly Leu Pro Gly Ile Ser Glu Gly Pro Asn Phe Pro Asp
                    405                 410                 415
Leu Pro Ala Val Pro Val Leu Asn Cys Gln Glu Gly Phe Thr Asp Ala
                420                 425                 430
Ser Gln Cys Thr Thr Phe Asp Ala Met Ser Ala Leu Val Leu Thr Ala
            435                 440                 445
Glu Val Lys Gly Ser Leu Asn Pro Cys Gly Ala Gly Lys Ala Cys
450                 455                 460
Asn Leu Thr Glu Cys Ala Ala Arg Cys Glu Asn Asp Gln Leu Gln Glu
465                 470                 475                 480
Leu Ala Val Arg Ala Thr Ser Gln Ile Glu Arg Val Gln Asn Val Thr
                485                 490                 495
Ile Ala Trp Ser Tyr Ala Arg Pro Leu Leu Glu Cys Asn Phe Val Ile
                500                 505                 510
Asp Lys Ile Val Glu Ser Leu Glu Ala Cys Gly Asp Ile Thr Ala Gly
                515                 520                 525
Thr Met Val Leu Gly Ala Gly Phe Phe Ile Gly Ala Ile Val Phe Gly
                530                 535                 540
Leu Gly Ile Tyr Ile Met Leu Arg Gly Ala Cys Val Trp Gly Glu Ile
545                 550                 555                 560
Pro Met Phe Thr Arg Asp Ala Lys Ala Ser
                565                 570

<210> SEQ ID NO 83
<211> LENGTH: 1329
<212> TYPE: DNA
<213> ORGANISM: Trypanosoma cruzi
<220> FEATURE:
<221> NAME/KEY: CDS
<222> LOCATION: (1)..(1329)

<400> SEQUENCE: 83 atg cgt gag att gtg tgc gtt cag gcc ggc cag tgc ggc aac cag atc      48
Met Arg Glu Ile Val Cys Val Gln Ala Gly Gln Cys Gly Asn Gln Ile
1               5                   10                  15 ggc tcg aag ttc tgg gag gtg atc agc gac gaa cac ggt gtg gac cca      96
Gly Ser Lys Phe Trp Glu Val Ile Ser Asp Glu His Gly Val Asp Pro
            20                  25                  30 aca gga aca tac cag ggc gat tcg gac ctt cag ctg gag cgc atc aat     144
Thr Gly Thr Tyr Gln Gly Asp Ser Asp Leu Gln Leu Glu Arg Ile Asn
        35                  40                  45 gtg tac ttt gat gag gca acg ggc ggc cgc tac gtg ccc cgt gcg gtg     192
Val Tyr Phe Asp Glu Ala Thr Gly Gly Arg Tyr Val Pro Arg Ala Val
    50                  55                  60 ctt atc gac ctg gag ccc ggc acg atg gac tcc gtg cgc gct ggt cca     240
Leu Ile Asp Leu Glu Pro Gly Thr Met Asp Ser Val Arg Ala Gly Pro
65                  70                  75                  80 tac ggg cag atc ttc cgc ccg gac aac ttc atc ttt ggt cag tct ggc     288
Tyr Gly Gln Ile Phe Arg Pro Asp Asn Phe Ile Phe Gly Gln Ser Gly
                85                  90                  95 gca ggc aac aac tgg gcc cag ggc cac tac acg gag ggc gca gag ctg     336
Ala Gly Asn Asn Trp Ala Gln Gly His Tyr Thr Glu Gly Ala Glu Leu
            100                 105                 110 att gat tcc gtg ctg gac gtt tgc cgc aag gag gcg gag agc tgc gac     384
Ile Asp Ser Val Leu Asp Val Cys Arg Lys Glu Ala Glu Ser Cys Asp
```

```
Ile Asp Ser Val Leu Asp Val Cys Arg Lys Glu Ala Glu Ser Cys Asp
        115                 120                 125 tgc ctg cag ggc ttc cag atc tgc cac tct ctt ggc ggt ggt acg ggc       432
Cys Leu Gln Gly Phe Gln Ile Cys His Ser Leu Gly Gly Gly Thr Gly
        130                 135                 140 tct ggc atg gga act ctg ctc atc tcg aag ctg cgc gag gag tac cca       480
Ser Gly Met Gly Thr Leu Leu Ile Ser Lys Leu Arg Glu Glu Tyr Pro
145                 150                 155                 160 gac cgc atc atg atg acc ttc tcc atc att ccg tcc ccc aag gtg tcc       528
Asp Arg Ile Met Met Thr Phe Ser Ile Ile Pro Ser Pro Lys Val Ser
                165                 170                 175 gat acg gtc gtc gag ccg tac aat acg acg ctt tct gtg cat cag ctg       576
Asp Thr Val Val Glu Pro Tyr Asn Thr Thr Leu Ser Val His Gln Leu
                180                 185                 190 gtg gaa aac tca gac gaa tcg atg tgt att gac aat gag gct ctg tac       624
Val Glu Asn Ser Asp Glu Ser Met Cys Ile Asp Asn Glu Ala Leu Tyr
                195                 200                 205 gac att tgt ttt cgt acg ctg aaa ctg acg act cca acg ttc ggt gat       672
Asp Ile Cys Phe Arg Thr Leu Lys Leu Thr Thr Pro Thr Phe Gly Asp
210                 215                 220 ctg aac cac ttg gtg tcc gcg gtc gtc tcc ggc gtg acc tgc tgc ctg       720
Leu Asn His Leu Val Ser Ala Val Val Ser Gly Val Thr Cys Cys Leu
225                 230                 235                 240 cgc ttc cct ggc cag ctc aac tcc gac ctg cgc aag ctg gcg gtg aac       768
Arg Phe Pro Gly Gln Leu Asn Ser Asp Leu Arg Lys Leu Ala Val Asn
                245                 250                 255 ctg gtg ccg ttc cct cgt ctg cac ttc ttc atg atg ggc ttt gcc ccg       816
Leu Val Pro Phe Pro Arg Leu His Phe Phe Met Met Gly Phe Ala Pro
                260                 265                 270 ctc acg agc cgc ggc tcg cag cag tac cga ggt ctg tcc gtg cca gag       864
Leu Thr Ser Arg Gly Ser Gln Gln Tyr Arg Gly Leu Ser Val Pro Glu
                275                 280                 285 ctg acg cag cag atg ttc gat gca aag aac atg atg cag gct gca gac       912
Leu Thr Gln Gln Met Phe Asp Ala Lys Asn Met Met Gln Ala Ala Asp
                290                 295                 300 ccg cgc cac ggt cgc tac ctg acg gcg tct gcg ctc ttc cgc ggc cgc       960
Pro Arg His Gly Arg Tyr Leu Thr Ala Ser Ala Leu Phe Arg Gly Arg
305                 310                 315                 320 atg tcg acg aag gag gtg gac gag cag atg ctc aac gtg cag aac aag      1008
Met Ser Thr Lys Glu Val Asp Glu Gln Met Leu Asn Val Gln Asn Lys
                325                 330                 335 aac tcg tcc tac ttc att gag tgg atc ccg aac aac atc aag tcc tcc      1056
Asn Ser Ser Tyr Phe Ile Glu Trp Ile Pro Asn Asn Ile Lys Ser Ser
                340                 345                 350 atc tgc gac atc ccg ccc aag ggc ctg aag atg gcc gtc acc ttt gtc      1104
Ile Cys Asp Ile Pro Pro Lys Gly Leu Lys Met Ala Val Thr Phe Val
                355                 360                 365 ggc aac aac acc tgc atc cag gag atg ttt cgc cgc gtg ggc gag cag      1152
Gly Asn Asn Thr Cys Ile Gln Glu Met Phe Arg Arg Val Gly Glu Gln
370                 375                 380 ttc acg gcg atg ttc cgc cgc aag gcg ttc ttg cac tgg tac acg ggc      1200
Phe Thr Ala Met Phe Arg Arg Lys Ala Phe Leu His Trp Tyr Thr Gly
385                 390                 395                 400 gag ggc atg gac gag atg gag ttc acc gag gcg gag tcc aac atg aac      1248
Glu Gly Met Asp Glu Met Glu Phe Thr Glu Ala Glu Ser Asn Met Asn
                405                 410                 415 gat ctt gtg tcg gag tac cag cag tac cag gac gcc acc att gag gag      1296
Asp Leu Val Ser Glu Tyr Gln Gln Tyr Gln Asp Ala Thr Ile Glu Glu
                420                 425                 430
```

```
gaa ggt gag ttc gac gag gag gag cag tac tag                    1329
Glu Gly Glu Phe Asp Glu Glu Glu Gln Tyr
        435                 440
```

<210> SEQ ID NO 84
<211> LENGTH: 442
<212> TYPE: PRT
<213> ORGANISM: Trypanosoma cruzi

<400> SEQUENCE: 84

```
Met Arg Glu Ile Val Cys Val Gln Ala Gly Gln Cys Gly Asn Gln Ile
1               5                   10                  15

Gly Ser Lys Phe Trp Glu Val Ile Ser Asp Glu His Gly Val Asp Pro
            20                  25                  30

Thr Gly Thr Tyr Gln Gly Asp Ser Asp Leu Gln Leu Glu Arg Ile Asn
        35                  40                  45

Val Tyr Phe Asp Glu Ala Thr Gly Gly Arg Tyr Val Pro Arg Ala Val
    50                  55                  60

Leu Ile Asp Leu Glu Pro Gly Thr Met Asp Ser Val Arg Ala Gly Pro
65                  70                  75                  80

Tyr Gly Gln Ile Phe Arg Pro Asp Asn Phe Ile Phe Gly Gln Ser Gly
                85                  90                  95

Ala Gly Asn Asn Trp Ala Gln Gly His Tyr Thr Glu Gly Ala Glu Leu
            100                 105                 110

Ile Asp Ser Val Leu Asp Val Cys Arg Lys Glu Ala Glu Ser Cys Asp
        115                 120                 125

Cys Leu Gln Gly Phe Gln Ile Cys His Ser Leu Gly Gly Gly Thr Gly
    130                 135                 140

Ser Gly Met Gly Thr Leu Leu Ile Ser Lys Leu Arg Glu Glu Tyr Pro
145                 150                 155                 160

Asp Arg Ile Met Met Thr Phe Ser Ile Ile Pro Ser Pro Lys Val Ser
                165                 170                 175

Asp Thr Val Val Glu Pro Tyr Asn Thr Thr Leu Ser Val His Gln Leu
            180                 185                 190

Val Glu Asn Ser Asp Glu Ser Met Cys Ile Asp Asn Glu Ala Leu Tyr
        195                 200                 205

Asp Ile Cys Phe Arg Thr Leu Lys Leu Thr Thr Pro Thr Phe Gly Asp
    210                 215                 220

Leu Asn His Leu Val Ser Ala Val Val Ser Gly Val Thr Cys Cys Leu
225                 230                 235                 240

Arg Phe Pro Gly Gln Leu Asn Ser Asp Leu Arg Lys Leu Ala Val Asn
                245                 250                 255

Leu Val Pro Phe Pro Arg Leu His Phe Phe Met Met Gly Phe Ala Pro
            260                 265                 270

Leu Thr Ser Arg Gly Ser Gln Gln Tyr Arg Gly Leu Ser Val Pro Glu
        275                 280                 285

Leu Thr Gln Gln Met Phe Asp Ala Lys Asn Met Met Gln Ala Ala Asp
    290                 295                 300

Pro Arg His Gly Arg Tyr Leu Thr Ala Ser Ala Leu Phe Arg Gly Arg
305                 310                 315                 320

Met Ser Thr Lys Glu Val Asp Glu Gln Met Leu Asn Val Gln Asn Lys
                325                 330                 335

Asn Ser Ser Tyr Phe Ile Glu Trp Ile Pro Asn Asn Ile Lys Ser Ser
            340                 345                 350

Ile Cys Asp Ile Pro Pro Lys Gly Leu Lys Met Ala Val Thr Phe Val
```

```
                      355                 360                 365
Gly Asn Asn Thr Cys Ile Gln Glu Met Phe Arg Arg Val Gly Glu Gln
        370                 375                 380

Phe Thr Ala Met Phe Arg Arg Lys Ala Phe Leu His Trp Tyr Thr Gly
385                 390                 395                 400

Glu Gly Met Asp Glu Met Glu Phe Thr Glu Ala Glu Ser Asn Met Asn
                405                 410                 415

Asp Leu Val Ser Glu Tyr Gln Gln Tyr Gln Asp Ala Thr Ile Glu Glu
            420                 425                 430

Glu Gly Glu Phe Asp Glu Glu Glu Gln Tyr
        435                 440

<210> SEQ ID NO 85
<211> LENGTH: 1227
<212> TYPE: DNA
<213> ORGANISM: Trypanosoma cruzi
<220> FEATURE:
<221> NAME/KEY: CDS
<222> LOCATION: (1)..(1227)

<400> SEQUENCE: 85 atg tac gtc gtg ctt ttt ttc gtt tta tta ctc tcc gtg ctt ggc gtt       48
Met Tyr Val Val Leu Phe Phe Val Leu Leu Leu Ser Val Leu Gly Val
1               5                   10                  15 gat gca gaa gag gag gac gtg agg aga aac gat gag gtg gta gcg cgt       96
Asp Ala Glu Glu Glu Asp Val Arg Arg Asn Asp Glu Val Val Ala Arg
            20                  25                  30 ctg cgc gag gag ttg gcg gag gag ggc gtt gag ccg ttg cca gaa ccg      144
Leu Arg Glu Glu Leu Ala Glu Glu Gly Val Glu Pro Leu Pro Glu Pro
        35                  40                  45 ccc cga gaa ctt ggt gtt cat gcc gcc tgc gtg agg cac ggc gtg gga      192
Pro Arg Glu Leu Gly Val His Ala Ala Cys Val Arg His Gly Val Gly
    50                  55                  60 tgc ccg gac gaa tac gtg gaa ttt ttg gag tcg ctg cag agg acc cca      240
Cys Pro Asp Glu Tyr Val Glu Phe Leu Glu Ser Leu Gln Arg Thr Pro
65                  70                  75                  80 cac act ttt ccg gag acg aaa ccg aga aac gat gca atg agt gcg gaa      288
His Thr Phe Pro Glu Thr Lys Pro Arg Asn Asp Ala Met Ser Ala Glu
                85                  90                  95 cgg agc gga aat atg cgg cgc caa acg cca ctc cat ggc gct gga gag      336
Arg Ser Gly Asn Met Arg Arg Gln Thr Pro Leu His Gly Ala Gly Glu
            100                 105                 110 aga agg gcc tat tca att aag ggc gag gat gct gtt att gag gtt caa      384
Arg Arg Ala Tyr Ser Ile Lys Gly Glu Asp Ala Val Ile Glu Val Gln
        115                 120                 125 ctg gag aat atg cgg cgc ctg cgt gat gta atg cgt gag cgg ttg gcc      432
Leu Glu Asn Met Arg Arg Leu Arg Asp Val Met Arg Glu Arg Leu Ala
    130                 135                 140 aag cag cag tcg ccc gag caa cag tgg aag tgc aaa gag ttt ttg tgg      480
Lys Gln Gln Ser Pro Glu Gln Gln Trp Lys Cys Lys Glu Phe Leu Trp
145                 150                 155                 160 atc agc aga ggg ctg aaa atg gtt gag gcc atg cat tcc gta tta ttg      528
Ile Ser Arg Gly Leu Lys Met Val Glu Ala Met His Ser Val Leu Leu
                165                 170                 175 caa aag tac tgg aat ttt gtc atg aat cag ctt ctt cca tgc gtc ctg      576
Gln Lys Tyr Trp Asn Phe Val Met Asn Gln Leu Leu Pro Cys Val Leu
            180                 185                 190 ctt gtt ttt gtg aca gtg tgg gtc ttt act ggc aac cgt att ccg cgt      624
Leu Val Phe Val Thr Val Trp Val Phe Thr Gly Asn Arg Ile Pro Arg
        195                 200                 205
```

```
gag cac ttg cgc agt ctc ctt gcc gat gat ccc gtc cct gtc ttc aat    672
Glu His Leu Arg Ser Leu Leu Ala Asp Asp Pro Val Pro Val Phe Asn
    210                 215                 220 gag gtt ata atc cgc cgc aag tcg cca caa tcc gtg gcg cag ctt gtg    720
Glu Val Ile Ile Arg Arg Lys Ser Pro Gln Ser Val Ala Gln Leu Val
225                 230                 235                 240 atg gag cgt gaa agc cac aat ttc tcc agt atg gtt gac atc gat gat    768
Met Glu Arg Glu Ser His Asn Phe Ser Ser Met Val Asp Ile Asp Asp
                245                 250                 255 ggt agc agc agc ccc tct gcc gtc cct aat ggc ttt gcg aag gaa aaa    816
Gly Ser Ser Ser Pro Ser Ala Val Pro Asn Gly Phe Ala Lys Glu Lys
            260                 265                 270 gag gac tcc atg cgg gcg att ata aat tat cgc cgt gat cgt tgg ttt    864
Glu Asp Ser Met Arg Ala Ile Ile Asn Tyr Arg Arg Asp Arg Trp Phe
        275                 280                 285 gct acc cgc ttt gcc ctg ctt gag gcg tac cat gag gcc cac att gcg    912
Ala Thr Arg Phe Ala Leu Leu Glu Ala Tyr His Glu Ala His Ile Ala
    290                 295                 300 ggg gta gtt ttg aga ctt cgc cta gcg tta agt gca gct gtt ttg ctg    960
Gly Val Val Leu Arg Leu Arg Leu Ala Leu Ser Ala Ala Val Leu Leu
305                 310                 315                 320 atg ctt tgc tgg act ctt ttc tcc ctc gtg ctg cga gct tcc gag gtg    1008
Met Leu Cys Trp Thr Leu Phe Ser Leu Val Leu Arg Ala Ser Glu Val
                325                 330                 335 cgc aga aac agt gac ggt gga ata ata caa cac cta ttg gtt atg ctc    1056
Arg Arg Asn Ser Asp Gly Gly Ile Ile Gln His Leu Leu Val Met Leu
            340                 345                 350 ttt ccg tca tgg gtg acg acc tct ttc gta ctg tac att ggc tgg tcg    1104
Phe Pro Ser Trp Val Thr Thr Ser Phe Val Leu Tyr Ile Gly Trp Ser
        355                 360                 365 tgg att ggc ggc atg gtg gcg tac gcc gcg tgg gag cta gtg tct act    1152
Trp Ile Gly Gly Met Val Ala Tyr Ala Ala Trp Glu Leu Val Ser Thr
    370                 375                 380 ggg gag gct ctg gtg cgc acg ggt gag cgt gcg gct gct ctt cat gag    1200
Gly Glu Ala Leu Val Arg Thr Gly Glu Arg Ala Ala Ala Leu His Glu
385                 390                 395                 400 aag att ctg gag cgc tgg tgc ggc tga                                1227
Lys Ile Leu Glu Arg Trp Cys Gly
                405

<210> SEQ ID NO 86
<211> LENGTH: 408
<212> TYPE: PRT
<213> ORGANISM: Trypanosoma cruzi

<400> SEQUENCE: 86

Met Tyr Val Val Leu Phe Phe Val Leu Leu Ser Val Leu Gly Val
1               5                   10                  15

Asp Ala Glu Glu Glu Asp Val Arg Arg Asn Asp Glu Val Val Ala Arg
            20                  25                  30

Leu Arg Glu Glu Leu Ala Glu Glu Gly Val Glu Pro Leu Pro Glu Pro
        35                  40                  45

Pro Arg Glu Leu Gly Val His Ala Ala Cys Val Arg His Gly Val Gly
    50                  55                  60

Cys Pro Asp Glu Tyr Val Glu Phe Leu Glu Ser Leu Gln Arg Thr Pro
65                  70                  75                  80

His Thr Phe Pro Glu Thr Lys Pro Arg Asn Asp Ala Met Ser Ala Glu
                85                  90                  95
```

```
Arg Ser Gly Asn Met Arg Arg Gln Thr Pro Leu His Gly Ala Gly Glu
                100                 105                 110

Arg Arg Ala Tyr Ser Ile Lys Gly Glu Asp Ala Val Ile Glu Val Gln
            115                 120                 125

Leu Glu Asn Met Arg Arg Leu Arg Asp Val Met Arg Glu Arg Leu Ala
        130                 135                 140

Lys Gln Gln Ser Pro Glu Gln Gln Trp Lys Cys Lys Glu Phe Leu Trp
145                 150                 155                 160

Ile Ser Arg Gly Leu Lys Met Val Glu Ala Met His Ser Val Leu Leu
                165                 170                 175

Gln Lys Tyr Trp Asn Phe Val Met Asn Gln Leu Leu Pro Cys Val Leu
            180                 185                 190

Leu Val Phe Val Thr Val Trp Val Phe Thr Gly Asn Arg Ile Pro Arg
        195                 200                 205

Glu His Leu Arg Ser Leu Leu Ala Asp Asp Pro Val Pro Val Phe Asn
210                 215                 220

Glu Val Ile Ile Arg Arg Lys Ser Pro Gln Ser Val Ala Gln Leu Val
225                 230                 235                 240

Met Glu Arg Glu Ser His Asn Phe Ser Ser Met Val Asp Ile Asp Asp
                245                 250                 255

Gly Ser Ser Ser Pro Ser Ala Val Pro Asn Gly Phe Ala Lys Glu Lys
            260                 265                 270

Glu Asp Ser Met Arg Ala Ile Ile Asn Tyr Arg Arg Asp Arg Trp Phe
        275                 280                 285

Ala Thr Arg Phe Ala Leu Leu Glu Ala Tyr His Glu Ala His Ile Ala
290                 295                 300

Gly Val Val Leu Arg Leu Arg Leu Ala Leu Ser Ala Ala Val Leu Leu
305                 310                 315                 320

Met Leu Cys Trp Thr Leu Phe Ser Leu Val Leu Arg Ala Ser Glu Val
                325                 330                 335

Arg Arg Asn Ser Asp Gly Gly Ile Ile Gln His Leu Leu Val Met Leu
            340                 345                 350

Phe Pro Ser Trp Val Thr Thr Ser Phe Val Leu Tyr Ile Gly Trp Ser
        355                 360                 365

Trp Ile Gly Gly Met Val Ala Tyr Ala Ala Trp Glu Leu Val Ser Thr
370                 375                 380

Gly Glu Ala Leu Val Arg Thr Gly Glu Arg Ala Ala Ala Leu His Glu
385                 390                 395                 400

Lys Ile Leu Glu Arg Trp Cys Gly
                405

<210> SEQ ID NO 87
<211> LENGTH: 1824
<212> TYPE: DNA
<213> ORGANISM: Leishmania major
<220> FEATURE:
<221> NAME/KEY: CDS
<222> LOCATION: (1)..(1824)

<400> SEQUENCE: 87 atg cag ccg ctt atg gct tac cct ggc ttc ttt cgc ttg act gct gcg    48
Met Gln Pro Leu Met Ala Tyr Pro Gly Phe Phe Arg Leu Thr Ala Ala
1               5                   10                  15 gcg cgg gtg gcg ctc gtg gcg ttg tgt ctt gct ctc gcc ttc ctg agt    96
Ala Arg Val Ala Leu Val Ala Leu Cys Leu Ala Leu Ala Phe Leu Ser
            20                  25                  30
```

```
gtg gcc gct gtt gct gcg cct acc ttc tcc gca tcg gcc aca gcc cag     144
Val Ala Ala Val Ala Ala Pro Thr Phe Ser Ala Ser Ala Thr Ala Gln
         35                  40                  45 cag tat agg gac agg cgc gtc gcg cac ttg cgc gct gct ttg ctc gac     192
Gln Tyr Arg Asp Arg Arg Val Ala His Leu Arg Ala Ala Leu Leu Asp
 50                  55                  60 aag gca ccg tat cat gta ggg gcc cta ccc gat cca ccg ctg gag tgg     240
Lys Ala Pro Tyr His Val Gly Ala Leu Pro Asp Pro Pro Leu Glu Trp
 65                  70                  75                  80 ggc ctt cat acg gcg tgc aaa aag ttc ggc cgt ggc tgc ccg gac acc     288
Gly Leu His Thr Ala Cys Lys Lys Phe Gly Arg Gly Cys Pro Asp Thr
                 85                  90                  95 tac gta cag ttt ctc gag gag ctc gta gcc tta cta gag ggt gag gtc     336
Tyr Val Gln Phe Leu Glu Glu Leu Val Ala Leu Leu Glu Gly Glu Val
                100                 105                 110 gcc gat gga gac ggt tgc gac gtc gca ggc gcg gtc gca gcg aag agg     384
Ala Asp Gly Asp Gly Cys Asp Val Ala Gly Ala Val Ala Ala Lys Arg
            115                 120                 125 aaa ggg gcg gag cat gcg aca tgc cag gct caa ccg gag ctg ggc agt     432
Lys Gly Ala Glu His Ala Thr Cys Gln Ala Gln Pro Glu Leu Gly Ser
130                 135                 140 atc gcg gtg aca cga gtc gcg tct gtt gtt gag gcc ccc gag cgg tgc     480
Ile Ala Val Thr Arg Val Ala Ser Val Val Glu Ala Pro Glu Arg Cys
145                 150                 155                 160 atc aac ggc gtg gac gac ggc gtt gcc gac gct gct gtc tct ctt gcc     528
Ile Asn Gly Val Asp Asp Gly Val Ala Asp Ala Ala Val Ser Leu Ala
                165                 170                 175 gca ctc ctg ccg tgc gat ctt cga ctt ccg ctg cag ttg tcg tgg ctg     576
Ala Leu Leu Pro Cys Asp Leu Arg Leu Pro Leu Gln Leu Ser Trp Leu
                180                 185                 190 tac gag gcg cgg aag cgt ctt gag aac ctg ctc cat ctc ctt gcc att     624
Tyr Glu Ala Arg Lys Arg Leu Glu Asn Leu Leu His Leu Leu Ala Ile
            195                 200                 205 cgc gag tct gag ctc cgc aga gac ggt gtc gcg ccg gcg ccg ttg cag     672
Arg Glu Ser Glu Leu Arg Arg Asp Gly Val Ala Pro Ala Pro Leu Gln
210                 215                 220 cga ctc tac cat gta cca tct gcc gag cac att cac ttg gtg gag gac     720
Arg Leu Tyr His Val Pro Ser Ala Glu His Ile His Leu Val Glu Asp
225                 230                 235                 240 cta gac ggc gcc gta acg gcg cgg ctg cac acc gct tgc gct atc ggc     768
Leu Asp Gly Ala Val Thr Ala Arg Leu His Thr Ala Cys Ala Ile Gly
                245                 250                 255 tca gcg tcg tcg tcg gcg ccc ctg cca gcg ggg tgg acg ctg cag aag     816
Ser Ala Ser Ser Ser Ala Pro Leu Pro Ala Gly Trp Thr Leu Gln Lys
                260                 265                 270 tgg gaa gac gtg tac ggc ttg tgg tgt cga cat gtc gag caa cag cat     864
Trp Glu Asp Val Tyr Gly Leu Trp Cys Arg His Val Glu Gln Gln His
            275                 280                 285 cga aat cga cga gat gat agc ttg ggc gca act agc gtg ata gca gca     912
Arg Asn Arg Arg Asp Asp Ser Leu Gly Ala Thr Ser Val Ile Ala Ala
290                 295                 300 tct ccc tcc agc ttg gtg cct ctt cct cgc aag gcg tgg tat tgc gtt     960
Ser Pro Ser Ser Leu Val Pro Leu Pro Arg Lys Ala Trp Tyr Cys Val
305                 310                 315                 320 gca ctc cac cac gct acg ctg tac ctg cag ttg ctc gtg cgc gca gat    1008
Ala Leu His His Ala Thr Leu Tyr Leu Gln Leu Leu Val Arg Ala Asp
                325                 330                 335 cag ctt ctc gcc tgg gct tgg gac tgg acc ttt tac acc gca gta ccg    1056
Gln Leu Leu Ala Trp Ala Trp Asp Trp Thr Phe Tyr Thr Ala Val Pro
                340                 345                 350
```

```
agc gcg ttt ctg gtg tgc gtt ctt ctc tgg ctc tgc gtg gga gat gca      1104
Ser Ala Phe Leu Val Cys Val Leu Leu Trp Leu Cys Val Gly Asp Ala
        355                 360                 365 tgg aca gaa gcg gct gag gcc ttt gtg gtg aat gcg tcc gcg gtt aca      1152
Trp Thr Glu Ala Ala Glu Ala Phe Val Val Asn Ala Ser Ala Val Thr
370                 375                 380 gct gat gcc gca ggg caa ggc gac ggt gtg gtg aag gag gct agt gcg      1200
Ala Asp Ala Ala Gly Gln Gly Asp Gly Val Val Lys Glu Ala Ser Ala
385                 390                 395                 400 agt agg gac acc aca cct agc gca aca ccg cac gag tgt cgg ccg ccc      1248
Ser Arg Asp Thr Thr Pro Ser Ala Thr Pro His Glu Cys Arg Pro Pro
                405                 410                 415 tcg gcg acc aca gga tct ccc tcg act ctg acc gcg agc tct gcc gtg      1296
Ser Ala Thr Thr Gly Ser Pro Ser Thr Leu Thr Ala Ser Ser Ala Val
            420                 425                 430 cgt ggg ggc gaa gca gcg ccg tcg ctg tcc ccc atg gcg tct gtc gcc      1344
Arg Gly Gly Glu Ala Ala Pro Ser Leu Ser Pro Met Ala Ser Val Ala
        435                 440                 445 ctc gca gag ggg cgg cgt gac acc ccg ctg gca ggg tac ggc gcg gtg      1392
Leu Ala Glu Gly Arg Arg Asp Thr Pro Leu Ala Gly Tyr Gly Ala Val
450                 455                 460 ccc gcc tcg gag cat tgc ccc cat caa cac caa gga cag ctg gaa ggg      1440
Pro Ala Ser Glu His Cys Pro His Gln His Gln Gly Gln Leu Glu Gly
465                 470                 475                 480 cag cag cag cgt cgc gct gct ctg cta cgc cgg cgt ttt gcc gta tct      1488
Gln Gln Gln Arg Arg Ala Ala Leu Leu Arg Arg Arg Phe Ala Val Ser
                485                 490                 495 gct ctc cat cgc tcc ccg aca ctc ttt ctt ctc aag tta cgg ctg ctc      1536
Ala Leu His Arg Ser Pro Thr Leu Phe Leu Leu Lys Leu Arg Leu Leu
            500                 505                 510 ctg tgc ctc ctt gtg gcg ggt caa ctg ctg tgg agc ctg tgg cgt gtc      1584
Leu Cys Leu Leu Val Ala Gly Gln Leu Leu Trp Ser Leu Trp Arg Val
        515                 520                 525 ttg gct gcc agc tat gac gtg acc gcc tca gct gcc ccg ctc gtg cag      1632
Leu Ala Ala Ser Tyr Asp Val Thr Ala Ser Ala Ala Pro Leu Val Gln
530                 535                 540 ttc ttt ctc ccg tcc tgg ctg ctg gtg tgc ctg agc gcg tat ctc gtt      1680
Phe Phe Leu Pro Ser Trp Leu Leu Val Cys Leu Ser Ala Tyr Leu Val
545                 550                 555                 560 gtg cca ctg cag atg atg gtg ctg ggg aca gcg ttg aag ggc gcc cta      1728
Val Pro Leu Gln Met Met Val Leu Gly Thr Ala Leu Lys Gly Ala Leu
                565                 570                 575 aac gcg cac gaa gaa cta ctg tct ttc caa gcc aag tgc gca gct gag      1776
Asn Ala His Glu Glu Leu Leu Ser Phe Gln Ala Lys Cys Ala Ala Glu
            580                 585                 590 cag cgt gct ctt ctg aac gct gct ggc gtg ctt cca ttg ggt ggc tga      1824
Gln Arg Ala Leu Leu Asn Ala Ala Gly Val Leu Pro Leu Gly Gly
        595                 600                 605

<210> SEQ ID NO 88
<211> LENGTH: 607
<212> TYPE: PRT
<213> ORGANISM: Leishmania major

<400> SEQUENCE: 88

Met Gln Pro Leu Met Ala Tyr Pro Gly Phe Phe Arg Leu Thr Ala Ala
1               5                   10                  15

Ala Arg Val Ala Leu Val Ala Leu Cys Leu Ala Leu Ala Phe Leu Ser
            20                  25                  30
```

```
Val Ala Ala Val Ala Ala Pro Thr Phe Ser Ala Ser Ala Thr Ala Gln
             35                  40                  45

Gln Tyr Arg Asp Arg Arg Val Ala His Leu Arg Ala Ala Leu Leu Asp
 50                  55                  60

Lys Ala Pro Tyr His Val Gly Ala Leu Pro Asp Pro Pro Leu Glu Trp
 65                  70                  75                  80

Gly Leu His Thr Ala Cys Lys Lys Phe Gly Arg Gly Cys Pro Asp Thr
                 85                  90                  95

Tyr Val Gln Phe Leu Glu Glu Leu Val Ala Leu Leu Glu Gly Glu Val
                100                 105                 110

Ala Asp Gly Asp Gly Cys Asp Val Ala Gly Ala Val Ala Ala Lys Arg
                115                 120                 125

Lys Gly Ala Glu His Ala Thr Cys Gln Ala Gln Pro Glu Leu Gly Ser
130                 135                 140

Ile Ala Val Thr Arg Val Ala Ser Val Val Glu Ala Pro Glu Arg Cys
145                 150                 155                 160

Ile Asn Gly Val Asp Asp Gly Val Ala Asp Ala Val Ser Leu Ala
                165                 170                 175

Ala Leu Leu Pro Cys Asp Leu Arg Leu Pro Leu Gln Leu Ser Trp Leu
                180                 185                 190

Tyr Glu Ala Arg Lys Arg Leu Glu Asn Leu Leu His Leu Leu Ala Ile
                195                 200                 205

Arg Glu Ser Glu Leu Arg Arg Asp Gly Val Ala Pro Ala Pro Leu Gln
                210                 215                 220

Arg Leu Tyr His Val Pro Ser Ala Glu His Ile His Leu Val Glu Asp
225                 230                 235                 240

Leu Asp Gly Ala Val Thr Ala Arg Leu His Thr Ala Cys Ala Ile Gly
                245                 250                 255

Ser Ala Ser Ser Ser Ala Pro Leu Pro Ala Gly Trp Thr Leu Gln Lys
                260                 265                 270

Trp Glu Asp Val Tyr Gly Leu Trp Cys Arg His Val Glu Gln Gln His
                275                 280                 285

Arg Asn Arg Arg Asp Asp Ser Leu Gly Ala Thr Ser Val Ile Ala Ala
290                 295                 300

Ser Pro Ser Ser Leu Val Pro Leu Pro Arg Lys Ala Trp Tyr Cys Val
305                 310                 315                 320

Ala Leu His His Ala Thr Leu Tyr Leu Gln Leu Leu Val Arg Ala Asp
                325                 330                 335

Gln Leu Leu Ala Trp Ala Trp Asp Trp Thr Phe Tyr Thr Ala Val Pro
                340                 345                 350

Ser Ala Phe Leu Val Cys Val Leu Leu Trp Leu Cys Val Gly Asp Ala
                355                 360                 365

Trp Thr Glu Ala Ala Glu Ala Phe Val Val Asn Ala Ser Ala Val Thr
                370                 375                 380

Ala Asp Ala Ala Gly Gln Gly Asp Gly Val Val Lys Glu Ala Ser Ala
385                 390                 395                 400

Ser Arg Asp Thr Thr Pro Ser Ala Thr Pro His Glu Cys Arg Pro Pro
                405                 410                 415

Ser Ala Thr Thr Gly Ser Pro Ser Thr Leu Thr Ala Ser Ser Ala Val
                420                 425                 430

Arg Gly Gly Glu Ala Ala Pro Ser Leu Ser Pro Met Ala Ser Val Ala
                435                 440                 445

Leu Ala Glu Gly Arg Arg Asp Thr Pro Leu Ala Gly Tyr Gly Ala Val
```

```
                        450                 455                 460
Pro Ala Ser Glu His Cys Pro His Gln His Gln Gly Gln Leu Glu Gly
465                 470                 475                 480

Gln Gln Gln Arg Arg Ala Ala Leu Leu Arg Arg Phe Ala Val Ser
                485                 490                 495

Ala Leu His Arg Ser Pro Thr Leu Phe Leu Leu Lys Leu Arg Leu Leu
                500                 505                 510

Leu Cys Leu Leu Val Ala Gly Gln Leu Leu Trp Ser Leu Trp Arg Val
            515                 520                 525

Leu Ala Ala Ser Tyr Asp Val Thr Ala Ser Ala Ala Pro Leu Val Gln
            530                 535                 540

Phe Phe Leu Pro Ser Trp Leu Leu Val Cys Leu Ser Ala Tyr Leu Val
545                 550                 555                 560

Val Pro Leu Gln Met Met Val Leu Gly Thr Ala Leu Lys Gly Ala Leu
                565                 570                 575

Asn Ala His Glu Glu Leu Leu Ser Phe Gln Ala Lys Cys Ala Ala Glu
                580                 585                 590

Gln Arg Ala Leu Leu Asn Ala Ala Gly Val Leu Pro Leu Gly Gly
                595                 600                 605

<210> SEQ ID NO 89
<211> LENGTH: 1812
<212> TYPE: DNA
<213> ORGANISM: Leishmania infantum
<220> FEATURE:
<221> NAME/KEY: CDS
<222> LOCATION: (1)..(1812)

<400> SEQUENCE: 89 atg gct tac cct ggc ttc ttt cgc ttg act gct gcg gcc cgg gtg gcg      48
Met Ala Tyr Pro Gly Phe Phe Arg Leu Thr Ala Ala Ala Arg Val Ala
1               5                   10                  15 ctc atg gcg ttg tgt ctt gct cta gca ctc atc tgc gtg gcc gct gtt      96
Leu Met Ala Leu Cys Leu Ala Leu Ala Leu Ile Cys Val Ala Ala Val
                20                  25                  30 gct gcg cct acc ttc tcc gca tcg tcc gca gcc cag cag tat agg gac     144
Ala Ala Pro Thr Phe Ser Ala Ser Ser Ala Ala Gln Gln Tyr Arg Asp
            35                  40                  45 agg cgc gtc gcg cac ttg cgc gct gct ttg ctc gac aag gca ccg tat     192
Arg Arg Val Ala His Leu Arg Ala Ala Leu Leu Asp Lys Ala Pro Tyr
        50                  55                  60 cat gca gag gcg tta ccc gat ccg cca ctg gag tgg ggc gtt cac acg     240
His Ala Glu Ala Leu Pro Asp Pro Pro Leu Glu Trp Gly Val His Thr
65                  70                  75                  80 gcg tgc aag aag ttc ggc cgt ggc tgc ccg gac tcg tac gtt gag ttt     288
Ala Cys Lys Lys Phe Gly Arg Gly Cys Pro Asp Ser Tyr Val Glu Phe
                85                  90                  95 ctc gag gag ctc gta gcc tca ctg aag ggt gag gtc gct gat gga gac     336
Leu Glu Glu Leu Val Ala Ser Leu Lys Gly Glu Val Ala Asp Gly Asp
                100                 105                 110 ggt cgc gac gtc gca gac gcg gtc gcg gag aag agg aaa ggg acg gag     384
Gly Arg Asp Val Ala Asp Ala Val Ala Glu Lys Arg Lys Gly Thr Glu
            115                 120                 125 cat gcg aca tgc cag gct cag acg gag ctg ggc aat aac gcg gcg aca     432
His Ala Thr Cys Gln Ala Gln Thr Glu Leu Gly Asn Asn Ala Ala Thr
        130                 135                 140 cga gtc gcg tct gtc gtt gag gcc ccc gag cgg tgc atc agc ggc gtg     480
Arg Val Ala Ser Val Val Glu Ala Pro Glu Arg Cys Ile Ser Gly Val
145                 150                 155                 160
```

```
gac gac cgc gtt gcc gac gct gct gtc tct ctt gcc gca ctc ctg ccg      528
Asp Asp Arg Val Ala Asp Ala Ala Val Ser Leu Ala Ala Leu Leu Pro
            165                 170                 175 ggt gat ctc cga ctt cct ctg cag ttg acg tgg ccg tac gag gcg cgg      576
Gly Asp Leu Arg Leu Pro Leu Gln Leu Thr Trp Pro Tyr Glu Ala Arg
        180                 185                 190 aag cgt ctt gag aac ctg ctc cat cta ctt gcc act cgc gag tct gag      624
Lys Arg Leu Glu Asn Leu Leu His Leu Leu Ala Thr Arg Glu Ser Glu
        195                 200                 205 ctc cgc aga gac ggt gtc gcg ccg gcg ccg tta cag cga ctc tac cat      672
Leu Arg Arg Asp Gly Val Ala Pro Ala Pro Leu Gln Arg Leu Tyr His
    210                 215                 220 gta cca tct gcc gag cac att cac ttg gtg gag gac cta gac ggc gcc      720
Val Pro Ser Ala Glu His Ile His Leu Val Glu Asp Leu Asp Gly Ala
225                 230                 235                 240 gta acg gcg cgg ctg cac acc gct tgc gct atc ggc tca gcg tcg tcg      768
Val Thr Ala Arg Leu His Thr Ala Cys Ala Ile Gly Ser Ala Ser Ser
                245                 250                 255 tcg gcg cca ctg cca gcg ggg tgg aca ctg caa aag tgg gaa gac atg      816
Ser Ala Pro Leu Pro Ala Gly Trp Thr Leu Gln Lys Trp Glu Asp Met
            260                 265                 270 tac ggc ttg tgg tgt cga cat gtc gag caa cag cat caa aat cga cga      864
Tyr Gly Leu Trp Cys Arg His Val Glu Gln Gln His Gln Asn Arg Arg
        275                 280                 285 gat gat agc ttg ggc gca act agc gtg ata gca gca cct cca tcc agc      912
Asp Asp Ser Leu Gly Ala Thr Ser Val Ile Ala Ala Pro Pro Ser Ser
        290                 295                 300 ttg gtg cct ctt cct cgc aag gca ttg cat tgc act gca ctc cac cac      960
Leu Val Pro Leu Pro Arg Lys Ala Leu His Cys Thr Ala Leu His His
305                 310                 315                 320 gcg aca ctg tac ctg cag ctg ctc gtg cgc gca gat cag ctt ctc acc     1008
Ala Thr Leu Tyr Leu Gln Leu Leu Val Arg Ala Asp Gln Leu Leu Thr
                325                 330                 335 tgg gct tgg ggc tgg act ttt tac atc gca gta cca agt gcg ttt ctg     1056
Trp Ala Trp Gly Trp Thr Phe Tyr Ile Ala Val Pro Ser Ala Phe Leu
            340                 345                 350 gtg tgc gtt ctt ctt tgg ctc tgc gtg gga gat gca tgg aca gaa gcg     1104
Val Cys Val Leu Leu Trp Leu Cys Val Gly Asp Ala Trp Thr Glu Ala
        355                 360                 365 gct gag gcc ttc gtg gtg aat gcg tcc gcg gtt aca gct gat gcc gca     1152
Ala Glu Ala Phe Val Val Asn Ala Ser Ala Val Thr Ala Asp Ala Ala
        370                 375                 380 ggg caa gac gac ggc gtg gtg aag gag gct agt gcg agt agg ggc acg     1200
Gly Gln Asp Asp Gly Val Val Lys Glu Ala Ser Ala Ser Arg Gly Thr
385                 390                 395                 400 aca cct agc gca aca ccg cac gag tgt cgg ccg ccc tcg gcg acc aca     1248
Thr Pro Ser Ala Thr Pro His Glu Cys Arg Pro Pro Ser Ala Thr Thr
                405                 410                 415 gga tct ccc tcg act ctg acc gcg agt tct gcc gtg cat ggg gcc gag     1296
Gly Ser Pro Ser Thr Leu Thr Ala Ser Ser Ala Val His Gly Ala Glu
            420                 425                 430 gca gcg ccg tcg acg tcc ccc gta acc tct gta gcc ctc gca gag ggg     1344
Ala Ala Pro Ser Thr Ser Pro Val Thr Ser Val Ala Leu Ala Glu Gly
        435                 440                 445 cgg cgt gac acc cct ccg gca ggg tac ggc gcg gtg ccc gcc tcg gag     1392
Arg Arg Asp Thr Pro Pro Ala Gly Tyr Gly Ala Val Pro Ala Ser Glu
        450                 455                 460 cat tgc ccc cac caa cac caa ggg cag ctc gaa ggg cag cgg cag cgt     1440
His Cys Pro His Gln His Gln Gly Gln Leu Glu Gly Gln Arg Gln Arg
```

```
                465                 470                 475                 480
cgc gct gct ctg cta cgc cgg cgt ttt gct cta tct gct ctc cac cgc      1488
Arg Ala Ala Leu Leu Arg Arg Arg Phe Ala Leu Ser Ala Leu His Arg
                        485                 490                 495 tcc ccc aca ctc ttt ttc ctc aag tta cgg ctg ctg tgc ctc ctt          1536
Ser Pro Thr Leu Phe Phe Leu Lys Leu Arg Leu Leu Cys Leu Leu
                500                 505                 510 gtg gca ggc caa ctg ctg tgg agc ctg tgg cgt gtc tta gct gcc agc      1584
Val Ala Gly Gln Leu Leu Trp Ser Leu Trp Arg Val Leu Ala Ala Ser
            515                 520                 525 tat gac gtg acc gcc tca gct gct cca ctt gtg cag ttc ttt ctc ccg      1632
Tyr Asp Val Thr Ala Ser Ala Ala Pro Leu Val Gln Phe Phe Leu Pro
        530                 535                 540 tcc tgg ctt ctg ggg tgc ctg agc gtg tat ctc gtt gtg cca ctg cag      1680
Ser Trp Leu Leu Gly Cys Leu Ser Val Tyr Leu Val Val Pro Leu Gln
545                 550                 555                 560 atg atg gtg ctg ggg aca gcg ttg aag ggt gcc cta agc gcg cac gaa      1728
Met Met Val Leu Gly Thr Ala Leu Lys Gly Ala Leu Ser Ala His Glu
                565                 570                 575 gaa cta ctg tct ttc caa gcc aag tgc gca gct gag cag cgt gct cta      1776
Glu Leu Leu Ser Phe Gln Ala Lys Cys Ala Ala Glu Gln Arg Ala Leu
                580                 585                 590 ctg aac gct gct ggc gtg ctt cca ttg ggt ggc taa                      1812
Leu Asn Ala Ala Gly Val Leu Pro Leu Gly Gly
            595                 600

<210> SEQ ID NO 90
<211> LENGTH: 603
<212> TYPE: PRT
<213> ORGANISM: Leishmania infantum

<400> SEQUENCE: 90

Met Ala Tyr Pro Gly Phe Phe Arg Leu Thr Ala Ala Arg Val Ala
1               5                   10                  15

Leu Met Ala Leu Cys Leu Ala Leu Ala Leu Ile Cys Val Ala Val
                20                  25                  30

Ala Ala Pro Thr Phe Ser Ala Ser Ser Ala Ala Gln Gln Tyr Arg Asp
            35                  40                  45

Arg Arg Val Ala His Leu Arg Ala Ala Leu Leu Asp Lys Ala Pro Tyr
    50                  55                  60

His Ala Glu Ala Leu Pro Asp Pro Pro Leu Glu Trp Gly Val His Thr
65                  70                  75                  80

Ala Cys Lys Lys Phe Gly Arg Gly Cys Pro Asp Ser Tyr Val Glu Phe
                85                  90                  95

Leu Glu Glu Leu Val Ala Ser Leu Lys Gly Glu Val Ala Asp Gly Asp
            100                 105                 110

Gly Arg Asp Val Ala Asp Ala Val Ala Glu Lys Arg Lys Gly Thr Glu
        115                 120                 125

His Ala Thr Cys Gln Ala Gln Thr Glu Leu Gly Asn Asn Ala Ala Thr
    130                 135                 140

Arg Val Ala Ser Val Val Glu Ala Pro Glu Arg Cys Ile Ser Gly Val
145                 150                 155                 160

Asp Asp Arg Val Ala Asp Ala Val Ser Leu Ala Ala Leu Leu Pro
                165                 170                 175

Gly Asp Leu Arg Leu Pro Leu Gln Leu Thr Trp Pro Tyr Glu Ala Arg
            180                 185                 190

Lys Arg Leu Glu Asn Leu Leu His Leu Leu Ala Thr Arg Glu Ser Glu
```

```
                195                 200                 205
Leu Arg Arg Asp Gly Val Ala Pro Ala Pro Leu Gln Arg Leu Tyr His
    210                 215                 220

Val Pro Ser Ala Glu His Ile His Leu Val Glu Asp Leu Asp Gly Ala
225                 230                 235                 240

Val Thr Ala Arg Leu His Thr Ala Cys Ala Ile Gly Ser Ala Ser Ser
                245                 250                 255

Ser Ala Pro Leu Pro Ala Gly Trp Thr Leu Gln Lys Trp Glu Asp Met
            260                 265                 270

Tyr Gly Leu Trp Cys Arg His Val Glu Gln Gln His Gln Asn Arg Arg
        275                 280                 285

Asp Asp Ser Leu Gly Ala Thr Ser Val Ile Ala Ala Pro Pro Ser Ser
    290                 295                 300

Leu Val Pro Leu Pro Arg Lys Ala Leu His Cys Thr Ala Leu His His
305                 310                 315                 320

Ala Thr Leu Tyr Leu Gln Leu Leu Val Arg Ala Asp Gln Leu Leu Thr
                325                 330                 335

Trp Ala Trp Gly Trp Thr Phe Tyr Ile Ala Val Pro Ser Ala Phe Leu
            340                 345                 350

Val Cys Val Leu Leu Trp Leu Cys Val Gly Asp Ala Trp Thr Glu Ala
        355                 360                 365

Ala Glu Ala Phe Val Val Asn Ala Ser Ala Val Thr Ala Asp Ala Ala
    370                 375                 380

Gly Gln Asp Asp Gly Val Val Lys Glu Ala Ser Ala Ser Arg Gly Thr
385                 390                 395                 400

Thr Pro Ser Ala Thr Pro His Glu Cys Arg Pro Ser Ala Thr Thr
                405                 410                 415

Gly Ser Pro Ser Thr Leu Thr Ala Ser Ser Ala Val His Gly Ala Glu
            420                 425                 430

Ala Ala Pro Ser Thr Ser Pro Val Thr Ser Val Ala Leu Ala Glu Gly
        435                 440                 445

Arg Arg Asp Thr Pro Pro Ala Gly Tyr Gly Ala Val Pro Ala Ser Glu
    450                 455                 460

His Cys Pro His Gln His Gln Gly Gln Leu Glu Gly Gln Arg Gln Arg
465                 470                 475                 480

Arg Ala Ala Leu Leu Arg Arg Phe Ala Leu Ser Ala Leu His Arg
                485                 490                 495

Ser Pro Thr Leu Phe Phe Leu Lys Leu Arg Leu Leu Cys Leu Leu
            500                 505                 510

Val Ala Gly Gln Leu Leu Trp Ser Leu Trp Arg Val Leu Ala Ala Ser
        515                 520                 525

Tyr Asp Val Thr Ala Ser Ala Pro Leu Val Gln Phe Phe Leu Pro
    530                 535                 540

Ser Trp Leu Leu Gly Cys Leu Ser Val Tyr Leu Val Pro Leu Gln
545                 550                 555                 560

Met Met Val Leu Gly Thr Ala Leu Lys Gly Ala Leu Ser Ala His Glu
                565                 570                 575

Glu Leu Leu Ser Phe Gln Ala Lys Cys Ala Ala Glu Gln Arg Ala Leu
            580                 585                 590

Leu Asn Ala Ala Gly Val Leu Pro Leu Gly Gly
    595                 600

<210> SEQ ID NO 91
```

```
<211> LENGTH: 1221
<212> TYPE: DNA
<213> ORGANISM: Trypanosoma brucei
<220> FEATURE:
<221> NAME/KEY: CDS
<222> LOCATION: (1)..(1221)

<400> SEQUENCE: 91 atg tac caa agc aga aca atg gta tct ttt ttg atg gct gca act ctt      48
Met Tyr Gln Ser Arg Thr Met Val Ser Phe Leu Met Ala Ala Thr Leu
1               5                   10                  15 ttt gcg ttg tat ttg ttt cca ttt ggg gcc cga gga gac gac ccg agg      96
Phe Ala Leu Tyr Leu Phe Pro Phe Gly Ala Arg Gly Asp Asp Pro Arg
            20                  25                  30 cgg aac gat aaa tta gtg gag gcc ctg aga gca gag ttt acg tca tct     144
Arg Asn Asp Lys Leu Val Glu Ala Leu Arg Ala Glu Phe Thr Ser Ser
        35                  40                  45 ggc ctc gct gca cca ccc gag cca ccg tcc gat ttg ggt gtg cat gcg     192
Gly Leu Ala Ala Pro Pro Glu Pro Pro Ser Asp Leu Gly Val His Ala
50                  55                  60 act tgc gta aag ttt gga ctc gcg tgc tcc gac gcg tat gtg gac ttt     240
Thr Cys Val Lys Phe Gly Leu Ala Cys Ser Asp Ala Tyr Val Asp Phe
65                  70                  75                  80 ctt aag gat gaa gtc gca aaa ctg cat ggc act gcc ggt ggg att cct     288
Leu Lys Asp Glu Val Ala Lys Leu His Gly Thr Ala Gly Gly Ile Pro
                85                  90                  95 cct tca cag gca gag aag ccg aag cga gtg cca cca acc agt gca ggt     336
Pro Ser Gln Ala Glu Lys Pro Lys Arg Val Pro Pro Thr Ser Ala Gly
            100                 105                 110 aag gaa cga cga act ccg aag tcc cca gtg gag gat aac gat ccc acg     384
Lys Glu Arg Arg Thr Pro Lys Ser Pro Val Glu Asp Asn Asp Pro Thr
        115                 120                 125 cgt gac gta aaa ctg gag aag cta cag cgt ttg cga aat gtg tat cgt     432
Arg Asp Val Lys Leu Glu Lys Leu Gln Arg Leu Arg Asn Val Tyr Arg
130                 135                 140 gat aaa ttg ctg gag cta cat tcg tca gaa aag agg tgg gaa tgt ttc     480
Asp Lys Leu Leu Glu Leu His Ser Ser Glu Lys Arg Trp Glu Cys Phe
145                 150                 155                 160 ttc aca agg att agc agt gta ttg agt tct tta tta ctc tct cat gtt     528
Phe Thr Arg Ile Ser Ser Val Leu Ser Ser Leu Leu Leu Ser His Val
                165                 170                 175 tcc tcg ttc gtg ttg tgg ttc tgg act gcc ttt gcg cct cat gtt ccc     576
Ser Ser Phe Val Leu Trp Phe Trp Thr Ala Phe Ala Pro His Val Pro
            180                 185                 190 gtt gcc atg ctt ctc atg gcg gta ctt acg tgg gta ttt ttc ggc act     624
Val Ala Met Leu Leu Met Ala Val Leu Thr Trp Val Phe Phe Gly Thr
        195                 200                 205 cac atc ccc aac gag cac att tgc tgc ctt cgt gct gcg aga cct gca     672
His Ile Pro Asn Glu His Ile Cys Cys Leu Arg Ala Ala Arg Pro Ala
210                 215                 220 ttc gca atg gat caa ctc ctt gcc cgc agt gcc cct ccg aaa tcg gtt     720
Phe Ala Met Asp Gln Leu Leu Ala Arg Ser Ala Pro Pro Lys Ser Val
225                 230                 235                 240 gcg agc ctc gtg att gag cgg gag cgg tgc tct ggt tat gat gat ttc     768
Ala Ser Leu Val Ile Glu Arg Glu Arg Cys Ser Gly Tyr Asp Asp Phe
                245                 250                 255 ggt gaa ttt aac gac tcc gct acc ggt gct tca gca gag ggg gag gtg     816
Gly Glu Phe Asn Asp Ser Ala Thr Gly Ala Ser Ala Glu Gly Glu Val
            260                 265                 270 caa ggg cac gag gtg gaa cgc cgc gat gaa tat tgg gat ctt gtg cgg     864
Gln Gly His Glu Val Glu Arg Arg Asp Glu Tyr Trp Asp Leu Val Arg
```

```
                     275                 280                 285
ttt tcc ctg att gaa gcg tat gac atg tac cac gcg gag gtg ata gtc         912
Phe Ser Leu Ile Glu Ala Tyr Asp Met Tyr His Ala Glu Val Ile Val
290                 295                 300 ttg aag ttg aga ttg gtg ctg agt ctg ttg gca ttg cta atg ctc att         960
Leu Lys Leu Arg Leu Val Leu Ser Leu Leu Ala Leu Leu Met Leu Ile
305                 310                 315                 320 tgg agc gtt att tct ctg ccg ctg caa act gtt gat ctg cag aat ggt        1008
Trp Ser Val Ile Ser Leu Pro Leu Gln Thr Val Asp Leu Gln Asn Gly
                325                 330                 335 gga ttt gta aag act ctg gtg tcc agt gtt ttg ccg gag tgg gtg ccc        1056
Gly Phe Val Lys Thr Leu Val Ser Ser Val Leu Pro Glu Trp Val Pro
            340                 345                 350 gct gtg gcg ggg ctt cac ttt gcg tgg tca tgc gtt ggt gga ttg gtt        1104
Ala Val Ala Gly Leu His Phe Ala Trp Ser Cys Val Gly Gly Leu Val
        355                 360                 365 gct ttc gcc tgc tgg gag gtg ttt gcc gct ggc gag atg ctt tgc cgt        1152
Ala Phe Ala Cys Trp Glu Val Phe Ala Ala Gly Glu Met Leu Cys Arg
    370                 375                 380 ttg aat gcg cgt tcc gcc acc atg tgc gac agc atc ctt aag gaa tgg        1200
Leu Asn Ala Arg Ser Ala Thr Met Cys Asp Ser Ile Leu Lys Glu Trp
385                 390                 395                 400 agt tgg aaa ctt gat gga taa                                            1221
Ser Trp Lys Leu Asp Gly
                405

<210> SEQ ID NO 92
<211> LENGTH: 406
<212> TYPE: PRT
<213> ORGANISM: Trypanosoma brucei

<400> SEQUENCE: 92

Met Tyr Gln Ser Arg Thr Met Val Ser Phe Leu Met Ala Ala Thr Leu
1               5                   10                  15

Phe Ala Leu Tyr Leu Phe Pro Phe Gly Ala Arg Gly Asp Asp Pro Arg
            20                  25                  30

Arg Asn Asp Lys Leu Val Glu Ala Leu Arg Ala Glu Phe Thr Ser Ser
        35                  40                  45

Gly Leu Ala Ala Pro Pro Glu Pro Pro Ser Asp Leu Gly Val His Ala
    50                  55                  60

Thr Cys Val Lys Phe Gly Leu Ala Cys Ser Asp Ala Tyr Val Asp Phe
65                  70                  75                  80

Leu Lys Asp Glu Val Ala Lys Leu His Gly Thr Ala Gly Gly Ile Pro
            85                  90                  95

Pro Ser Gln Ala Glu Lys Pro Lys Arg Val Pro Pro Thr Ser Ala Gly
        100                 105                 110

Lys Glu Arg Arg Thr Pro Lys Ser Pro Val Glu Asp Asn Asp Pro Thr
    115                 120                 125

Arg Asp Val Lys Leu Glu Lys Leu Gln Arg Leu Arg Asn Val Tyr Arg
130                 135                 140

Asp Lys Leu Leu Glu Leu His Ser Ser Glu Lys Arg Trp Glu Cys Phe
145                 150                 155                 160

Phe Thr Arg Ile Ser Ser Val Leu Ser Ser Leu Leu Ser His Val
            165                 170                 175

Ser Ser Phe Val Leu Trp Phe Trp Thr Ala Phe Ala Pro His Val Pro
        180                 185                 190

Val Ala Met Leu Leu Met Ala Val Leu Thr Trp Val Phe Phe Gly Thr
```

```
                195                 200                 205
His Ile Pro Asn Glu His Ile Cys Cys Leu Arg Ala Ala Arg Pro Ala
            210                 215                 220

Phe Ala Met Asp Gln Leu Leu Ala Arg Ser Ala Pro Pro Lys Ser Val
225                 230                 235                 240

Ala Ser Leu Val Ile Glu Arg Glu Arg Cys Ser Gly Tyr Asp Asp Phe
                245                 250                 255

Gly Glu Phe Asn Asp Ser Ala Thr Gly Ala Ser Ala Glu Gly Glu Val
            260                 265                 270

Gln Gly His Glu Val Glu Arg Arg Asp Glu Tyr Trp Asp Leu Val Arg
        275                 280                 285

Phe Ser Leu Ile Glu Ala Tyr Asp Met Tyr His Ala Glu Val Ile Val
    290                 295                 300

Leu Lys Leu Arg Leu Val Leu Ser Leu Leu Ala Leu Leu Met Leu Ile
305                 310                 315                 320

Trp Ser Val Ile Ser Leu Pro Leu Gln Thr Val Asp Leu Gln Asn Gly
                325                 330                 335

Gly Phe Val Lys Thr Leu Val Ser Ser Val Leu Pro Glu Trp Val Pro
            340                 345                 350

Ala Val Ala Gly Leu His Phe Ala Trp Ser Cys Val Gly Gly Leu Val
        355                 360                 365

Ala Phe Ala Cys Trp Glu Val Phe Ala Ala Gly Glu Met Leu Cys Arg
    370                 375                 380

Leu Asn Ala Arg Ser Ala Thr Met Cys Asp Ser Ile Leu Lys Glu Trp
385                 390                 395                 400

Ser Trp Lys Leu Asp Gly
                405

<210> SEQ ID NO 93
<211> LENGTH: 1488
<212> TYPE: DNA
<213> ORGANISM: Trypanosmacruzi
<220> FEATURE:
<221> NAME/KEY: CDS
<222> LOCATION: (1)..(1488)

<400> SEQUENCE: 93 atg ccc tct ggc aaa gca act gcg ctt gca gcg gcg aca ctg ctg gcg      48
Met Pro Ser Gly Lys Ala Thr Ala Leu Ala Ala Ala Thr Leu Leu Ala
1               5                   10                  15 ctt ctc gtg gtc gcg ccc gcc gtt gca tct gcc cag cgc tca ctc gac      96
Leu Leu Val Val Ala Pro Ala Val Ala Ser Ala Gln Arg Ser Leu Asp
                20                  25                  30 tgc caa aag gtg tgg gat ggc ccc agc atc gac aac gac ttc tta aaa     144
Cys Gln Lys Val Trp Asp Gly Pro Ser Ile Asp Asn Asp Phe Leu Lys
            35                  40                  45 tgc ctg tcc aac acc gac cgc ata aag ggg cag tgg cgc tac ctt gtt     192
Cys Leu Ser Asn Thr Asp Arg Ile Lys Gly Gln Trp Arg Tyr Leu Val
        50                  55                  60 tat ccg ggg gtt tgt gcg ctg ctg ttc gtg act ttg ctg agc ttc         240
Tyr Pro Gly Val Cys Ala Leu Leu Phe Val Val Thr Leu Leu Ser Phe
65                  70                  75                  80 ccg ctt gtt ttt ctc agc gtt gtc tgt tgt cgc tcc tgc ggt cag ccg     288
Pro Leu Val Phe Leu Ser Val Val Cys Cys Arg Ser Cys Gly Gln Pro
                85                  90                  95 aaa cca ggg cgg agc agt gac gcg tcc cgc tgc ttt ctc tgg atg tgg     336
Lys Pro Gly Arg Ser Ser Asp Ala Ser Arg Cys Phe Leu Trp Met Trp
            100                 105                 110
```

| | | | | | | | | | | | | | | | | |
|---|---|---|---|---|---|---|---|---|---|---|---|---|---|---|---|---|
| gtc | att | tac | gtc | gtg | ctg | tgg | agc | gct | gcc | atg | gct | gtt | ctc | gtg | ata | 384 |
| Val | Ile | Tyr | Val | Val | Leu | Trp | Ser | Ala | Ala | Met | Ala | Val | Leu | Val | Ile | |
| | | 115 | | | | 120 | | | | | 125 | | | | | |
| ttg | ggc | gcc | aag | ctg | ctg | gcg | acg | tcc | gcc | cac | agt | atc | att | gac | aac | 432 |
| Leu | Gly | Ala | Lys | Leu | Leu | Ala | Thr | Ser | Ala | His | Ser | Ile | Ile | Asp | Asn | |
| 130 | | | | | 135 | | | | | 140 | | | | | | |
| acg | ctg | gat | ggt | ccg | ctg | cag | tac | ttc | aat | aac | acg | gct | gag | agg | atc | 480 |
| Thr | Leu | Asp | Gly | Pro | Leu | Gln | Tyr | Phe | Asn | Asn | Thr | Ala | Glu | Arg | Ile | |
| 145 | | | | 150 | | | | | 155 | | | | | 160 | | |
| att | gat | ttc | acg | tcc | aac | tgg | tcc | tcg | ggt | aag | cgt | gag | ccc | ata | cat | 528 |
| Ile | Asp | Phe | Thr | Ser | Asn | Trp | Ser | Ser | Gly | Lys | Arg | Glu | Pro | Ile | His | |
| | | | | 165 | | | | | 170 | | | | | 175 | | |
| tcc | atc | gac | ctg | gac | atc | act | gcc | ttc | acc | aac | atc | agc | acc | aat | gtg | 576 |
| Ser | Ile | Asp | Leu | Asp | Ile | Thr | Ala | Phe | Thr | Asn | Ile | Ser | Thr | Asn | Val | |
| | | | 180 | | | | | 185 | | | | | 190 | | | |
| acc | gat | tta | ctc | atg | gat | gcc | aag | cag | aag | att | tcg | aag | tac | att | gga | 624 |
| Thr | Asp | Leu | Leu | Met | Asp | Ala | Lys | Gln | Lys | Ile | Ser | Lys | Tyr | Ile | Gly | |
| | | 195 | | | | | 200 | | | | | 205 | | | | |
| tgg | gta | ccg | att | gtg | tcg | tac | tgt | gtc | ggt | ggc | gtg | ggt | gtt | gtg | cta | 672 |
| Trp | Val | Pro | Ile | Val | Ser | Tyr | Cys | Val | Gly | Gly | Val | Gly | Val | Val | Leu | |
| | 210 | | | | | 215 | | | | | 220 | | | | | |
| atg | ctt | ctt | gtg | gtt | ttt | ttg | gcc | tgt | tgc | cgc | tgc | ggc | atc | ccg | tgc | 720 |
| Met | Leu | Leu | Val | Val | Phe | Leu | Ala | Cys | Cys | Arg | Cys | Gly | Ile | Pro | Cys | |
| 225 | | | | | 230 | | | | | 235 | | | | | 240 | |
| aca | aca | tat | tta | ttc | tcc | tgc | gtc | tac | tgg | ctc | ttc | ggg | gtt | gtg | ttc | 768 |
| Thr | Thr | Tyr | Leu | Phe | Ser | Cys | Val | Tyr | Trp | Leu | Phe | Gly | Val | Val | Phe | |
| | | | | 245 | | | | | 250 | | | | | 255 | | |
| gca | ctg | ctc | gcg | gtt | gtg | gtg | acg | gtg | ctg | gcg | tat | ctc | tct | tgg | gcc | 816 |
| Ala | Leu | Leu | Ala | Val | Val | Val | Thr | Val | Leu | Ala | Tyr | Leu | Ser | Trp | Ala | |
| | | | 260 | | | | | 265 | | | | | 270 | | | |
| gcc | tgt | ggc | gag | gtg | gag | ctg | cag | caa | caa | cgg | cag | ccg | ggt | gtg | ttc | 864 |
| Ala | Cys | Gly | Glu | Val | Glu | Leu | Gln | Gln | Gln | Arg | Gln | Pro | Gly | Val | Phe | |
| | | 275 | | | | | 280 | | | | | 285 | | | | |
| cag | tgg | tat | ctt | gtg | ccg | tac | tgt | gag | cag | aca | ttt | gac | ttt | gct | gat | 912 |
| Gln | Trp | Tyr | Leu | Val | Pro | Tyr | Cys | Glu | Gln | Thr | Phe | Asp | Phe | Ala | Asp | |
| | 290 | | | | | 295 | | | | | 300 | | | | | |
| atc | aac | agg | gag | gcg | gat | gat | gcg | gag | cgg | cgg | ttc | tcc | aaa | gag | gcg | 960 |
| Ile | Asn | Arg | Glu | Ala | Asp | Asp | Ala | Glu | Arg | Arg | Phe | Ser | Lys | Glu | Ala | |
| 305 | | | | | 310 | | | | | 315 | | | | | 320 | |
| tgc | aaa | aat | ttg | ctc | aaa | tct | tgc | gat | aac | aat | acc | att | tca | ttt | aag | 1008 |
| Cys | Lys | Asn | Leu | Leu | Lys | Ser | Cys | Asp | Asn | Asn | Thr | Ile | Ser | Phe | Lys | |
| | | | | 325 | | | | | 330 | | | | | 335 | | |
| ccc | ttg | ctg | tgc | ggc | aac | gac | atc | aca | tcg | gag | gat | cag | tgc | ccc | aac | 1056 |
| Pro | Leu | Leu | Cys | Gly | Asn | Asp | Ile | Thr | Ser | Glu | Asp | Gln | Cys | Pro | Asn | |
| | | | 340 | | | | | 345 | | | | | 350 | | | |
| ttt | ggc | acc | atg | gcc | agc | gtg | ctg | agt | gct | acc | cgg | atc | aaa | gct | ttc | 1104 |
| Phe | Gly | Thr | Met | Ala | Ser | Val | Leu | Ser | Ala | Thr | Arg | Ile | Lys | Ala | Phe | |
| | | | | 355 | | | | | 360 | | | | | 365 | | |
| aca | atg | gcg | tgt | ccc | gtg | gcg | ggc | gaa | tcg | tgc | acg | ctg | ttt | gag | tgc | 1152 |
| Thr | Met | Ala | Cys | Pro | Val | Ala | Gly | Glu | Ser | Cys | Thr | Leu | Phe | Glu | Cys | |
| | 370 | | | | | 375 | | | | | 380 | | | | | |
| gcc | gcc | aac | tgc | acc | aac | aca | gac | gtc | aaa | gca | gtg | gcg | tca | ggg | att | 1200 |
| Ala | Ala | Asn | Cys | Thr | Asn | Thr | Asp | Val | Lys | Ala | Val | Ala | Ser | Gly | Ile | |
| 385 | | | | | 390 | | | | | 395 | | | | | 400 | |
| ctg | cag | ctt | gcg | gcg | cag | gca | agc | aat | gcg | agc | att | gct | ctg | tcg | tac | 1248 |
| Leu | Gln | Leu | Ala | Ala | Gln | Ala | Ser | Asn | Ala | Ser | Ile | Ala | Leu | Ser | Tyr | |
| | | | | 405 | | | | | 410 | | | | | 415 | | |
| gcc | agg | ccg | ttg | ctc | gac | tgc | aat | ttt | gtg | gtg | gac | aag | ctt | ctg | gga | 1296 |
| Ala | Arg | Pro | Leu | Leu | Asp | Cys | Asn | Phe | Val | Val | Asp | Lys | Leu | Leu | Gly | |

|  |  |  |  |  |  |  |  |  |  |  |  | | |
|---|---|---|---|---|---|---|---|---|---|---|---|---|---|
|  |  | 420 |  |  |  | 425 |  |  |  | 430 |  | | |
| gcc | atg | agt | gac | tgc | aac | gaa | ctg | aag | gcg | ggg | acc | ctg | atg | ctt | ggc | 1344 |
| Ala | Met | Ser | Asp | Cys | Asn | Glu | Leu | Lys | Ala | Gly | Thr | Leu | Met | Leu | Gly |  |
|  |  | 435 |  |  |  | 440 |  |  |  | 445 |  | | |
| act | ggc | ttc | ttt | gtt | ggg | gga | ctg | atg | ttc | ggt | ctg | gcc | atc | tac | atc | 1392 |
| Thr | Gly | Phe | Phe | Val | Gly | Gly | Leu | Met | Phe | Gly | Leu | Ala | Ile | Tyr | Ile |  |
| 450 |  |  |  |  | 455 |  |  |  |  | 460 |  | | |
| atg | ttc | cgc | ggc | tcc | tgc | att | tgg | gac | gcc | cgg | ttc | atc | aaa | cag | ggt | 1440 |
| Met | Phe | Arg | Gly | Ser | Cys | Ile | Trp | Asp | Ala | Arg | Phe | Ile | Lys | Gln | Gly |  |
| 465 |  |  |  |  | 470 |  |  |  |  | 475 |  |  |  |  | 480 |
| acg | agc | cct | cgt | ggc | tta | aat | ggg | tca | ggg | tcg | gta | aat | gct | gcc | tag | 1488 |
| Thr | Ser | Pro | Arg | Gly | Leu | Asn | Gly | Ser | Gly | Ser | Val | Asn | Ala | Ala |  |  |
|  |  |  |  |  | 485 |  |  |  |  | 490 |  |  |  | 495 |  |  |

<210> SEQ ID NO 94
<211> LENGTH: 495
<212> TYPE: PRT
<213> ORGANISM: Trypanosmacruzi

<400> SEQUENCE: 94

Met Pro Ser Gly Lys Ala Thr Ala Leu Ala Ala Ala Thr Leu Leu Ala
1               5                   10                  15

Leu Leu Val Val Ala Pro Ala Val Ala Ser Ala Gln Arg Ser Leu Asp
                20                  25                  30

Cys Gln Lys Val Trp Asp Gly Pro Ser Ile Asp Asn Asp Phe Leu Lys
            35                  40                  45

Cys Leu Ser Asn Thr Asp Arg Ile Lys Gly Gln Trp Arg Tyr Leu Val
        50                  55                  60

Tyr Pro Gly Val Cys Ala Leu Leu Phe Val Val Thr Leu Leu Ser Phe
65                  70                  75                  80

Pro Leu Val Phe Leu Ser Val Val Cys Cys Arg Ser Cys Gly Gln Pro
                85                  90                  95

Lys Pro Gly Arg Ser Ser Asp Ala Ser Arg Cys Phe Leu Trp Met Trp
            100                 105                 110

Val Ile Tyr Val Val Leu Trp Ser Ala Ala Met Ala Val Leu Val Ile
        115                 120                 125

Leu Gly Ala Lys Leu Leu Ala Thr Ser Ala His Ser Ile Ile Asp Asn
130                 135                 140

Thr Leu Asp Gly Pro Leu Gln Tyr Phe Asn Asn Thr Ala Glu Arg Ile
145                 150                 155                 160

Ile Asp Phe Thr Ser Asn Trp Ser Ser Gly Lys Arg Glu Pro Ile His
                165                 170                 175

Ser Ile Asp Leu Asp Ile Thr Ala Phe Thr Asn Ile Ser Thr Asn Val
            180                 185                 190

Thr Asp Leu Leu Met Asp Ala Lys Gln Lys Ile Ser Lys Tyr Ile Gly
        195                 200                 205

Trp Val Pro Ile Val Ser Tyr Cys Val Gly Val Gly Val Val Leu
210                 215                 220

Met Leu Leu Val Val Phe Leu Ala Cys Cys Arg Cys Gly Ile Pro Cys
225                 230                 235                 240

Thr Thr Tyr Leu Phe Ser Cys Val Tyr Trp Leu Phe Gly Val Val Phe
                245                 250                 255

Ala Leu Leu Ala Val Val Val Thr Val Leu Ala Tyr Leu Ser Trp Ala
            260                 265                 270

Ala Cys Gly Glu Val Glu Leu Gln Gln Gln Arg Gln Pro Gly Val Phe
        275                 280                 285

```
Gln Trp Tyr Leu Val Pro Tyr Cys Glu Gln Thr Phe Asp Phe Ala Asp
        290                 295                 300

Ile Asn Arg Glu Ala Asp Asp Ala Glu Arg Arg Phe Ser Lys Glu Ala
305                 310                 315                 320

Cys Lys Asn Leu Leu Lys Ser Cys Asp Asn Thr Ile Ser Phe Lys
            325                 330                 335

Pro Leu Leu Cys Gly Asn Asp Ile Thr Ser Glu Asp Gln Cys Pro Asn
                340                 345                 350

Phe Gly Thr Met Ala Ser Val Leu Ser Ala Thr Arg Ile Lys Ala Phe
            355                 360                 365

Thr Met Ala Cys Pro Val Ala Gly Glu Ser Cys Thr Leu Phe Glu Cys
370                 375                 380

Ala Ala Asn Cys Thr Asn Thr Asp Val Lys Ala Val Ala Ser Gly Ile
385                 390                 395                 400

Leu Gln Leu Ala Ala Gln Ala Ser Asn Ala Ser Ile Ala Leu Ser Tyr
                405                 410                 415

Ala Arg Pro Leu Leu Asp Cys Asn Phe Val Val Asp Lys Leu Leu Gly
                420                 425                 430

Ala Met Ser Asp Cys Asn Glu Leu Lys Ala Gly Thr Leu Met Leu Gly
            435                 440                 445

Thr Gly Phe Phe Val Gly Gly Leu Met Phe Gly Leu Ala Ile Tyr Ile
            450                 455                 460

Met Phe Arg Gly Ser Cys Ile Trp Asp Ala Arg Phe Ile Lys Gln Gly
465                 470                 475                 480

Thr Ser Pro Arg Gly Leu Asn Gly Ser Gly Ser Val Asn Ala Ala
                485                 490                 495

<210> SEQ ID NO 95
<211> LENGTH: 1647
<212> TYPE: DNA
<213> ORGANISM: Leishmania major
<220> FEATURE:
<221> NAME/KEY: CDS
<222> LOCATION: (1)..(1647)

<400> SEQUENCE: 95 atg gtg tgt ccc ttc tcc tgc ccg ccc ctc ccc gcc ccc tct ctc aac      48
Met Val Cys Pro Phe Ser Cys Pro Pro Leu Pro Ala Pro Ser Leu Asn
1               5                   10                  15 tcg tcc cac ctc tca ttg ccg aag aag cag cgg tta aca gcg cgc gcg      96
Ser Ser His Leu Ser Leu Pro Lys Lys Gln Arg Leu Thr Ala Arg Ala
            20                  25                  30 cac aca ccg aca cac aaa atg gcc aag aca acg ctt ctc gtg tgc gct     144
His Thr Pro Thr His Lys Met Ala Lys Thr Thr Leu Leu Val Cys Ala
        35                  40                  45 ctg ctc gcc ctc gtc atg tgc ctg gca gcg aca gcc gtc tcg gcg cag     192
Leu Leu Ala Leu Val Met Cys Leu Ala Ala Thr Ala Val Ser Ala Gln
50                  55                  60 cag tcg ctg gcg tgc caa atg gtg tgg caa gct ccg tcc cct aac aac     240
Gln Ser Leu Ala Cys Gln Met Val Trp Gln Ala Pro Ser Pro Asn Asn
65                  70                  75                  80 agc ctg ctg gag tgc ctg ggg aac acg gat cgc atc cgg tct cag tgg     288
Ser Leu Leu Glu Cys Leu Gly Asn Thr Asp Arg Ile Arg Ser Gln Trp
                85                  90                  95 ccc tac tac ctg tat ccc gcc ttc gct gcg ctc atc ttc atc ttt acg     336
Pro Tyr Tyr Leu Tyr Pro Ala Phe Ala Ala Leu Ile Phe Ile Phe Thr
            100                 105                 110
```

| | | |
|---|---|---|
| gtg att ggg ctg ccg att ctg ttc tgc tgc cac tgc tgc agc tgc tgc<br>Val Ile Gly Leu Pro Ile Leu Phe Cys Cys His Cys Cys Ser Cys Cys<br>115                          120                      125 | | 384 |
| gag gcg tat gtg aag ccg aag gcg gag acg gac ctc ggc gtt gcc cgc<br>Glu Ala Tyr Val Lys Pro Lys Ala Glu Thr Asp Leu Gly Val Ala Arg<br>130                          135                      140 | | 432 |
| tgc tgc cta tgg atg ctg atc gtg att tcg gtg ctt gtg gcg tgc ggc<br>Cys Cys Leu Trp Met Leu Ile Val Ile Ser Val Leu Val Ala Cys Gly<br>145                          150                      155                      160 | | 480 |
| gtg tgc gtg ctg ctg gtg tat ggc tcc gtc tta ctg gag cag gca gcc<br>Val Cys Val Leu Leu Val Tyr Gly Ser Val Leu Leu Glu Gln Ala Ala<br>                  165                      170                      175 | | 528 |
| acg caa att atc cat gac acc gag tat cgc acg ctt aat tac ttc aac<br>Thr Gln Ile Ile His Asp Thr Glu Tyr Arg Thr Leu Asn Tyr Phe Asn<br>180                          185                      190 | | 576 |
| gac atc cgt gcg aac atc acg atg ctg ctg aca aac tac agc gcg gac<br>Asp Ile Arg Ala Asn Ile Thr Met Leu Leu Thr Asn Tyr Ser Ala Asp<br>                  195                      200                      205 | | 624 |
| cca ccg ata cca ccg tcg atc gac ctt agg acc ttt gac gct gtg aac<br>Pro Pro Ile Pro Pro Ser Ile Asp Leu Arg Thr Phe Asp Ala Val Asn<br>210                          215                      220 | | 672 |
| gat gat att acc cac tac gtg cat ctg gcg cgc aac aac tac ctc cag<br>Asp Asp Ile Thr His Tyr Val His Leu Ala Arg Asn Asn Tyr Leu Gln<br>225                          230                      235                      240 | | 720 |
| tac ttc cgc gct gcc gag att gtg gtg tgc tgt gtc ggc agc gtg ggt<br>Tyr Phe Arg Ala Ala Glu Ile Val Val Cys Cys Val Gly Ser Val Gly<br>                  245                      250                      255 | | 768 |
| gtt ttc ctg atg ctg tgc atg ctg gtt ttt gtg ctg tgc cgt tgc aat<br>Val Phe Leu Met Leu Cys Met Leu Val Phe Val Leu Cys Arg Cys Asn<br>                  260                      265                      270 | | 816 |
| ggg atc tgc ccg att gcg tgg agc tgc ctg tac ttc gtg ttc gcg ctt<br>Gly Ile Cys Pro Ile Ala Trp Ser Cys Leu Tyr Phe Val Phe Ala Leu<br>                  275                      280                      285 | | 864 |
| gca ttt gcg ttg ctt gcg gtg ttg ttc acg ata tgc atc tac gtg ctg<br>Ala Phe Ala Leu Leu Ala Val Leu Phe Thr Ile Cys Ile Tyr Val Leu<br>290                          295                      300 | | 912 |
| tcc gct ggc tgc ggc gag gtg ggc ctc cag cgt ggt cgt gag cct ggc<br>Ser Ala Gly Cys Gly Glu Val Gly Leu Gln Arg Gly Arg Glu Pro Gly<br>305                          310                      315                      320 | | 960 |
| gtc ttc cag tgg tac ctg gtg ccg tgg tgc gag aag cag ttc aac ttc<br>Val Phe Gln Trp Tyr Leu Val Pro Trp Cys Glu Lys Gln Phe Asn Phe<br>                  325                      330                      335 | | 1008 |
| caa gcg ctg cgg gct cag gtg cag agc cag gag cag cag gtc tcg cag<br>Gln Ala Leu Arg Ala Gln Val Gln Ser Gln Glu Gln Gln Val Ser Gln<br>                  340                      345                      350 | | 1056 |
| agc gcc tgc gcg gag ctc ttg aac ttc tgt gac aac gat ccg cat tac<br>Ser Ala Cys Ala Glu Leu Leu Asn Phe Cys Asp Asn Asp Pro His Tyr<br>                  355                      360                      365 | | 1104 |
| tcg ttg gag act aaa aac cac atc ttc atg tgc ggc aac agc atc acc<br>Ser Leu Glu Thr Lys Asn His Ile Phe Met Cys Gly Asn Ser Ile Thr<br>                  370                      375                      380 | | 1152 |
| gat aag agc cag tgc gac tcg ctg gac gac gtg gtg gac gtt gtt ctg<br>Asp Lys Ser Gln Cys Asp Ser Leu Asp Asp Val Val Asp Val Val Leu<br>385                          390                      395                      400 | | 1200 |
| agc aca tac gtg aag ccg atg ctg acg aac acg cta tgt gcc aac cag<br>Ser Thr Tyr Val Lys Pro Met Leu Thr Asn Thr Leu Cys Ala Asn Gln<br>                  405                      410                      415 | | 1248 |
| acg ggc atg gag tac ctg gag aag tgt aca gtg agg ttg tgc tca tcg<br>Thr Gly Met Glu Tyr Leu Glu Lys Cys Thr Val Arg Leu Cys Ser Ser<br>                  420                      425                      430 | | 1296 |

```
cgg tgt gta aac tac gaa gcg ctg gat ctg cat gcc agg acg tac gcc    1344
Arg Cys Val Asn Tyr Glu Ala Leu Asp Leu His Ala Arg Thr Tyr Ala
        435                 440                 445 att caa att ttg cag gct gcc gac ttt gct gcg aat gcg agc act gcg    1392
Ile Gln Ile Leu Gln Ala Ala Asp Phe Ala Ala Asn Ala Ser Thr Ala
450                 455                 460 ctg tcg tac gtg tgg ccg ctg ctg gac tgc aac ttc atc att gac aag    1440
Leu Ser Tyr Val Trp Pro Leu Leu Asp Cys Asn Phe Ile Ile Asp Lys
465                 470                 475                 480 atc gcc aac aca gtc gag acg cag agc tac aac agc agc ttc acc acg    1488
Ile Ala Asn Thr Val Glu Thr Gln Ser Tyr Asn Ser Ser Phe Thr Thr
            485                 490                 495 cag agc gaa tat gtc cgc agc tgc tct gcg gtc cgc act tcc tct gtg    1536
Gln Ser Glu Tyr Val Arg Ser Cys Ser Ala Val Arg Thr Ser Ser Val
        500                 505                 510 atg ctg ggt acc ggg ttc ttt gtc ggg gcg ctc atg ttc att gtc ggc    1584
Met Leu Gly Thr Gly Phe Phe Val Gly Ala Leu Met Phe Ile Val Gly
        515                 520                 525 att tat gtc ata cat cgc ggt tcg cgg atc acg gtg cca gtg aac aaa    1632
Ile Tyr Val Ile His Arg Gly Ser Arg Ile Thr Val Pro Val Asn Lys
530                 535                 540 gag aag gat ttc tga                                                 1647
Glu Lys Asp Phe
545

<210> SEQ ID NO 96
<211> LENGTH: 548
<212> TYPE: PRT
<213> ORGANISM: Leishmania major

<400> SEQUENCE: 96

Met Val Cys Pro Phe Ser Cys Pro Pro Leu Pro Ala Pro Ser Leu Asn
1               5                   10                  15

Ser Ser His Leu Ser Leu Pro Lys Lys Gln Arg Leu Thr Ala Arg Ala
            20                  25                  30

His Thr Pro Thr His Lys Met Ala Lys Thr Thr Leu Leu Val Cys Ala
        35                  40                  45

Leu Leu Ala Leu Val Met Cys Leu Ala Ala Thr Ala Val Ser Ala Gln
    50                  55                  60

Gln Ser Leu Ala Cys Gln Met Val Trp Gln Ala Pro Ser Pro Asn Asn
65                  70                  75                  80

Ser Leu Leu Glu Cys Leu Gly Asn Thr Asp Arg Ile Arg Ser Gln Trp
                85                  90                  95

Pro Tyr Tyr Leu Tyr Pro Ala Phe Ala Ala Leu Ile Phe Ile Phe Thr
            100                 105                 110

Val Ile Gly Leu Pro Ile Leu Phe Cys Cys His Cys Cys Ser Cys Cys
        115                 120                 125

Glu Ala Tyr Val Lys Pro Lys Ala Glu Thr Asp Leu Gly Val Ala Arg
    130                 135                 140

Cys Cys Leu Trp Met Leu Ile Val Ile Ser Val Leu Val Ala Cys Gly
145                 150                 155                 160

Val Cys Val Leu Leu Val Tyr Gly Ser Val Leu Leu Glu Gln Ala Ala
                165                 170                 175

Thr Gln Ile Ile His Asp Thr Glu Tyr Arg Thr Leu Asn Tyr Phe Asn
            180                 185                 190

Asp Ile Arg Ala Asn Ile Thr Met Leu Leu Thr Asn Tyr Ser Ala Asp
        195                 200                 205
```

```
Pro Pro Ile Pro Pro Ser Ile Asp Leu Arg Thr Phe Asp Ala Val Asn
            210                 215                 220
Asp Asp Ile Thr His Tyr Val His Leu Ala Arg Asn Asn Tyr Leu Gln
225                 230                 235                 240
Tyr Phe Arg Ala Ala Glu Ile Val Val Cys Cys Val Gly Ser Val Gly
                245                 250                 255
Val Phe Leu Met Leu Cys Met Leu Val Phe Val Leu Cys Arg Cys Asn
                260                 265                 270
Gly Ile Cys Pro Ile Ala Trp Ser Cys Leu Tyr Phe Val Phe Ala Leu
            275                 280                 285
Ala Phe Ala Leu Leu Ala Val Leu Phe Thr Ile Cys Ile Tyr Val Leu
        290                 295                 300
Ser Ala Gly Cys Gly Glu Val Gly Leu Gln Arg Gly Arg Glu Pro Gly
305                 310                 315                 320
Val Phe Gln Trp Tyr Leu Val Pro Trp Cys Glu Lys Gln Phe Asn Phe
                325                 330                 335
Gln Ala Leu Arg Ala Gln Val Gln Ser Gln Glu Gln Val Ser Gln
            340                 345                 350
Ser Ala Cys Ala Glu Leu Leu Asn Phe Cys Asp Asn Asp Pro His Tyr
        355                 360                 365
Ser Leu Glu Thr Lys Asn His Ile Phe Met Cys Gly Asn Ser Ile Thr
370                 375                 380
Asp Lys Ser Gln Cys Asp Ser Leu Asp Asp Val Asp Val Val Leu
                385                 390                 395                 400
Ser Thr Tyr Val Lys Pro Met Leu Thr Asn Thr Leu Cys Ala Asn Gln
                405                 410                 415
Thr Gly Met Glu Tyr Leu Glu Lys Cys Thr Val Arg Leu Cys Ser Ser
            420                 425                 430
Arg Cys Val Asn Tyr Glu Ala Leu Asp Leu His Ala Arg Thr Tyr Ala
        435                 440                 445
Ile Gln Ile Leu Gln Ala Ala Asp Phe Ala Ala Asn Ala Ser Thr Ala
        450                 455                 460
Leu Ser Tyr Val Trp Pro Leu Leu Asp Cys Asn Phe Ile Ile Asp Lys
465                 470                 475                 480
Ile Ala Asn Thr Val Glu Thr Gln Ser Tyr Asn Ser Ser Phe Thr Thr
                485                 490                 495
Gln Ser Glu Tyr Val Arg Ser Cys Ser Ala Val Arg Thr Ser Ser Val
            500                 505                 510
Met Leu Gly Thr Gly Phe Phe Val Gly Ala Leu Met Phe Ile Val Gly
        515                 520                 525
Ile Tyr Val Ile His Arg Gly Ser Arg Ile Thr Val Pro Val Asn Lys
    530                 535                 540
Glu Lys Asp Phe
545

<210> SEQ ID NO 97
<211> LENGTH: 1590
<212> TYPE: DNA
<213> ORGANISM: Leishmania infantum
<220> FEATURE:
<221> NAME/KEY: CDS
<222> LOCATION: (1)..(1590)

<400> SEQUENCE: 97 atg gcc aaa aca gcg ctt ctc gtg ggc gct ctg ctc gcc ctc gtc atg         48
```

-continued

| | |
|---|---|
| Met Ala Lys Thr Ala Leu Leu Val Gly Ala Leu Leu Ala Leu Val Met<br>1                5                        10                        15 | |
| tgc ctg gcg gcg acg gcc gtc tcg gcg cag cgg tcg ctg gag tgt caa<br>Cys Leu Ala Ala Thr Ala Val Ser Ala Gln Arg Ser Leu Glu Cys Gln<br>                   20                      25                      30 | 96 |
| atg gtg tgg caa ggt cct tcc tct aac aac agc ctg ctg gag tgc ctg<br>Met Val Trp Gln Gly Pro Ser Ser Asn Asn Ser Leu Leu Glu Cys Leu<br>         35                      40                      45 | 144 |
| ggg aac acg gat cgc atc cgg tcc cag tgg ccc tac tac ctg tat ccc<br>Gly Asn Thr Asp Arg Ile Arg Ser Gln Trp Pro Tyr Tyr Leu Tyr Pro<br>      50                      55                      60 | 192 |
| gcc ttc gct gcg ctc gtg ttc atc ttc acg gtg att ggg ctg ccg att<br>Ala Phe Ala Ala Leu Val Phe Ile Phe Thr Val Ile Gly Leu Pro Ile<br>65                      70                      75                      80 | 240 |
| ctg ttc tgc tgc cac tgc tgc agc tgc tgc gag gcg tat gtg aag ccg<br>Leu Phe Cys Cys His Cys Cys Ser Cys Cys Glu Ala Tyr Val Lys Pro<br>                   85                      90                      95 | 288 |
| aag gcg gag acg gac ctc ggc gtt gcc cgc tgc tgc cta tgg atg tgg<br>Lys Ala Glu Thr Asp Leu Gly Val Ala Arg Cys Cys Leu Trp Met Trp<br>                100                      105                      110 | 336 |
| atc gtg att tcg gtg ctt gtg gcg tgc ggc gtg tgc gtg ctg ctg gtg<br>Ile Val Ile Ser Val Leu Val Ala Cys Gly Val Cys Val Leu Leu Val<br>                115                      120                      125 | 384 |
| tat ggc tcc gtc tta ctg gag cag gca gcc aaa caa att atc cac gac<br>Tyr Gly Ser Val Leu Leu Glu Gln Ala Ala Lys Gln Ile Ile His Asp<br>130                      135                      140 | 432 |
| acc gag tat cgc acg ctt gat tac ttc aac gac acc cgt gcg aac atc<br>Thr Glu Tyr Arg Thr Leu Asp Tyr Phe Asn Asp Thr Arg Ala Asn Ile<br>145                      150                      155                      160 | 480 |
| gcg atg ctg ctg aca aac tac agc gcg gac cca ccg aca cca ccg tca<br>Ala Met Leu Leu Thr Asn Tyr Ser Ala Asp Pro Pro Thr Pro Pro Ser<br>                165                      170                      175 | 528 |
| atc gac ctt agc gcc ttt gac gcc gtg aac gat aat gtt acc tac tac<br>Ile Asp Leu Ser Ala Phe Asp Ala Val Asn Asp Asn Val Thr Tyr Tyr<br>                  180                      185                      190 | 576 |
| gtg cac ctg gcg cgc aac aac tac ctc aag tac ttc cgc gct gcc gag<br>Val His Leu Ala Arg Asn Asn Tyr Leu Lys Tyr Phe Arg Ala Ala Glu<br>                195                      200                      205 | 624 |
| att gtg gtc tgc tgc gtc ggc agc gtc ggt gtt ttc ctg atg ctg tgc<br>Ile Val Val Cys Cys Val Gly Ser Val Gly Val Phe Leu Met Leu Cys<br>210                      215                      220 | 672 |
| atg ctg atc ttt gcg ctg tgc cgt tgc agt ggg atc tgc ccg att gtg<br>Met Leu Ile Phe Ala Leu Cys Arg Cys Ser Gly Ile Cys Pro Ile Val<br>225                      230                      235                      240 | 720 |
| tgg agc tgc ctg tac ttc gtg ttc gcg ctt gca ttt gcg ttg ctt gcg<br>Trp Ser Cys Leu Tyr Phe Val Phe Ala Leu Ala Phe Ala Leu Leu Ala<br>                245                      250                      255 | 768 |
| gtg ctg ttc acg ata tgc atc tac gtg atg tcc gcc ggc tgc ggc gag<br>Val Leu Phe Thr Ile Cys Ile Tyr Val Met Ser Ala Gly Cys Gly Glu<br>                260                      265                      270 | 816 |
| gtg gac ctc cag tac agc cgt gag cct ggc gtc ttt cag tgg tac ctg<br>Val Asp Leu Gln Tyr Ser Arg Glu Pro Gly Val Phe Gln Trp Tyr Leu<br>                275                      280                      285 | 864 |
| gtg ccg tgg tgc gag aag cag ttc gac ttc cag gcg ctg cgg gct cag<br>Val Pro Trp Cys Glu Lys Gln Phe Asp Phe Gln Ala Leu Arg Ala Gln<br>290                      295                      300 | 912 |
| gtg cag agc cag gag cag cag gtc tcg cag agc gcc tgc ggg gcg ctc<br>Val Gln Ser Gln Glu Gln Gln Val Ser Gln Ser Ala Cys Gly Ala Leu<br>305                      310                      315                      320 | 960 |

```
ttg aac ttc tgt gac aac gat ccg aat tac tcg ttg gag aat aaa aac    1008
Leu Asn Phe Cys Asp Asn Asp Pro Asn Tyr Ser Leu Glu Asn Lys Asn
                325                 330                 335 cac atc ttc atg tgc ggc aac agc atc acc gac aaa agc cag tgc aac    1056
His Ile Phe Met Cys Gly Asn Ser Ile Thr Asp Lys Ser Gln Cys Asn
            340                 345                 350 tcg ctg gac gac gtg gtg gac gtt gtt ctg agc aca tac gtg aag ccg    1104
Ser Leu Asp Asp Val Val Asp Val Val Leu Ser Thr Tyr Val Lys Pro
        355                 360                 365 atg ctg acg aac acg cta tgt gcc aac cag acg ggc atg gag tac ctg    1152
Met Leu Thr Asn Thr Leu Cys Ala Asn Gln Thr Gly Met Glu Tyr Leu
    370                 375                 380 gag aag tgt acg ttg atc tcc tgc gca tcg cgg tgt gtg gac tac caa    1200
Glu Lys Cys Thr Leu Ile Ser Cys Ala Ser Arg Cys Val Asp Tyr Gln
385                 390                 395                 400 ttc ccg ccc ctg cat gcc agg aca gaa gcc att caa att ctg cag gct    1248
Phe Pro Pro Leu His Ala Arg Thr Glu Ala Ile Gln Ile Leu Gln Ala
                405                 410                 415 gcc aac ttt gct gcg aat gcg agc act gcg ctg tca tac gtg tgg ccg    1296
Ala Asn Phe Ala Ala Asn Ala Ser Thr Ala Leu Ser Tyr Val Trp Pro
            420                 425                 430 ctg ctg gag tgc aac ttc atc att gac aag att gcc aac aca gtc gag    1344
Leu Leu Glu Cys Asn Phe Ile Ile Asp Lys Ile Ala Asn Thr Val Glu
        435                 440                 445 acg cgg aac tac aac agc agc ttc acc acg cag agc gat tat gtg cgc    1392
Thr Arg Asn Tyr Asn Ser Ser Phe Thr Thr Gln Ser Asp Tyr Val Arg
    450                 455                 460 agc tgc tct gcg gtc cgc gta tcc tcg gtg atg ctg ggt acc ggt ttc    1440
Ser Cys Ser Ala Val Arg Val Ser Ser Val Met Leu Gly Thr Gly Phe
465                 470                 475                 480 ttt gtc ggg gcg ctc atg ttc atc ctc ggc att cac gtc atg cat cgc    1488
Phe Val Gly Ala Leu Met Phe Ile Leu Gly Ile His Val Met His Arg
                485                 490                 495 ggt gcg ttt atc tgg gct gcc ggc aag gag aat gat gcg gtg cag aag    1536
Gly Ala Phe Ile Trp Ala Ala Gly Lys Glu Asn Asp Ala Val Gln Lys
            500                 505                 510 aag gat gtt tca cca cct ggc aat gcc gtc tcg tca ccc ctg aga aca    1584
Lys Asp Val Ser Pro Pro Gly Asn Ala Val Ser Ser Pro Leu Arg Thr
        515                 520                 525 cct taa                                                            1590
Pro

<210> SEQ ID NO 98
<211> LENGTH: 529
<212> TYPE: PRT
<213> ORGANISM: Leishmania infantum

<400> SEQUENCE: 98

Met Ala Lys Thr Ala Leu Leu Val Gly Ala Leu Leu Ala Leu Val Met
1               5                   10                  15

Cys Leu Ala Ala Thr Ala Val Ser Ala Gln Arg Ser Leu Glu Cys Gln
            20                  25                  30

Met Val Trp Gln Gly Pro Ser Ser Asn Asn Ser Leu Leu Glu Cys Leu
        35                  40                  45

Gly Asn Thr Asp Arg Ile Arg Ser Gln Trp Pro Tyr Tyr Leu Tyr Pro
    50                  55                  60

Ala Phe Ala Ala Leu Val Phe Ile Phe Thr Val Ile Gly Leu Pro Ile
65                  70                  75                  80

Leu Phe Cys Cys His Cys Cys Ser Cys Cys Glu Ala Tyr Val Lys Pro
```

-continued

```
                85                  90                  95
Lys Ala Glu Thr Asp Leu Gly Val Ala Arg Cys Cys Leu Trp Met Trp
                100                 105                 110

Ile Val Ile Ser Val Leu Val Ala Cys Gly Val Cys Val Leu Leu Val
                115                 120                 125

Tyr Gly Ser Val Leu Leu Glu Gln Ala Ala Lys Gln Ile Ile His Asp
            130                 135                 140

Thr Glu Tyr Arg Thr Leu Asp Tyr Phe Asn Asp Thr Arg Ala Asn Ile
145                 150                 155                 160

Ala Met Leu Leu Thr Asn Tyr Ser Ala Asp Pro Pro Thr Pro Pro Ser
                165                 170                 175

Ile Asp Leu Ser Ala Phe Asp Ala Val Asn Asp Asn Val Thr Tyr Tyr
                180                 185                 190

Val His Leu Ala Arg Asn Asn Tyr Leu Lys Tyr Phe Arg Ala Ala Glu
                195                 200                 205

Ile Val Val Cys Cys Val Gly Ser Val Gly Val Phe Leu Met Leu Cys
                210                 215                 220

Met Leu Ile Phe Ala Leu Cys Arg Cys Ser Gly Ile Cys Pro Ile Val
225                 230                 235                 240

Trp Ser Cys Leu Tyr Phe Val Phe Ala Leu Ala Phe Ala Leu Leu Ala
                245                 250                 255

Val Leu Phe Thr Ile Cys Ile Tyr Val Met Ser Ala Gly Cys Gly Glu
                260                 265                 270

Val Asp Leu Gln Tyr Ser Arg Glu Pro Gly Val Phe Gln Trp Tyr Leu
                275                 280                 285

Val Pro Trp Cys Glu Lys Gln Phe Asp Phe Gln Ala Leu Arg Ala Gln
                290                 295                 300

Val Gln Ser Gln Glu Gln Val Ser Gln Ser Ala Cys Gly Ala Leu
305                 310                 315                 320

Leu Asn Phe Cys Asp Asn Asp Pro Asn Tyr Ser Leu Glu Asn Lys Asn
                325                 330                 335

His Ile Phe Met Cys Gly Asn Ser Ile Thr Asp Lys Ser Gln Cys Asn
                340                 345                 350

Ser Leu Asp Asp Val Val Asp Val Leu Ser Thr Tyr Val Lys Pro
                355                 360                 365

Met Leu Thr Asn Thr Leu Cys Ala Asn Gln Thr Gly Met Glu Tyr Leu
                370                 375                 380

Glu Lys Cys Thr Leu Ile Ser Cys Ala Ser Arg Cys Val Asp Tyr Gln
385                 390                 395                 400

Phe Pro Pro Leu His Ala Arg Thr Glu Ala Ile Gln Ile Leu Gln Ala
                405                 410                 415

Ala Asn Phe Ala Ala Asn Ala Ser Thr Ala Leu Ser Tyr Val Trp Pro
                420                 425                 430

Leu Leu Glu Cys Asn Phe Ile Ile Asp Lys Ile Ala Asn Thr Val Glu
                435                 440                 445

Thr Arg Asn Tyr Asn Ser Ser Phe Thr Thr Gln Ser Asp Tyr Val Arg
                450                 455                 460

Ser Cys Ser Ala Val Arg Val Ser Val Met Leu Gly Thr Gly Phe
465                 470                 475                 480

Phe Val Gly Ala Leu Met Phe Ile Leu Gly Ile His Val Met His Arg
                485                 490                 495

Gly Ala Phe Ile Trp Ala Ala Gly Lys Glu Asn Asp Ala Val Gln Lys
                500                 505                 510
```

```
Lys Asp Val Ser Pro Pro Gly Asn Ala Val Ser Ser Pro Leu Arg Thr
        515                 520                 525
Pro

<210> SEQ ID NO 99
<211> LENGTH: 1644
<212> TYPE: DNA
<213> ORGANISM: Trypanosoma brucei
<220> FEATURE:
<221> NAME/KEY: CDS
<222> LOCATION: (1)..(1644)

<400> SEQUENCE: 99 atg tcc tcc gtt acc act ggc agc tct ttc tat gct gca gtg tta ttg      48
Met Ser Ser Val Thr Thr Gly Ser Ser Phe Tyr Ala Ala Val Leu Leu
1               5                   10                  15 gtg ctg ttg tta aca gtt acg caa tgc gga aac tcc aag ttt cca aat      96
Val Leu Leu Leu Thr Val Thr Gln Cys Gly Asn Ser Lys Phe Pro Asn
            20                  25                  30 ctt cac tgt gac aat gtc tgg gat ggg ccc agt gct cga aat gac cct     144
Leu His Cys Asp Asn Val Trp Asp Gly Pro Ser Ala Arg Asn Asp Pro
        35                  40                  45 ctt acg tgc att atg gat acc gac cgt atc tta gcg cag tgg cgt atg     192
Leu Thr Cys Ile Met Asp Thr Asp Arg Ile Leu Ala Gln Trp Arg Met
    50                  55                  60 tta gca atg cct gct ctc tgt gct ttc ctt ttc gtg gct gtg tta att     240
Leu Ala Met Pro Ala Leu Cys Ala Phe Leu Phe Val Ala Val Leu Ile
65                  70                  75                  80 gct ttc ccc ata tct tgc ttt ctt aca tgc ctg tgt tcc tcc cgt tgc     288
Ala Phe Pro Ile Ser Cys Phe Leu Thr Cys Leu Cys Ser Ser Arg Cys
                85                  90                  95 aag cct tcc tct aag gac gga ggt aag gaa caa cgt tgc tgc ctt tgg     336
Lys Pro Ser Ser Lys Asp Gly Gly Lys Glu Gln Arg Cys Cys Leu Trp
            100                 105                 110 atg tgg att atg ttt gct tta ata tgg gct ttt ggt gtt gct gca ttt     384
Met Trp Ile Met Phe Ala Leu Ile Trp Ala Phe Gly Val Ala Ala Phe
        115                 120                 125 gtg ttc ttt ggg gtg aag cag ttg tgg gca acc tca aat tat ttt ctc     432
Val Phe Phe Gly Val Lys Gln Leu Trp Ala Thr Ser Asn Tyr Phe Leu
    130                 135                 140 gat gta aca ttg atg aat ccg ttg aat gtt gtg aac tgc act gcg gaa     480
Asp Val Thr Leu Met Asn Pro Leu Asn Val Val Asn Cys Thr Ala Glu
145                 150                 155                 160 aaa gtt att gat ttt gcg tct aac tgg acc tct gga aat aga gag cca     528
Lys Val Ile Asp Phe Ala Ser Asn Trp Thr Ser Gly Asn Arg Glu Pro
                165                 170                 175 tac gct gat ggt gtt gat gtg agc ttt ttc tat gat ata tcg gaa aac     576
Tyr Ala Asp Gly Val Asp Val Ser Phe Phe Tyr Asp Ile Ser Glu Asn
            180                 185                 190 gcc gtt cgt gtt gtt gaa atg ttg aga ggt aga gcg gga gat tat att     624
Ala Val Arg Val Val Glu Met Leu Arg Gly Arg Ala Gly Asp Tyr Ile
        195                 200                 205 aag ttg tta cct gtt gtt tct tat gcg gtg ggt tcc gta tgt att gcg     672
Lys Leu Leu Pro Val Val Ser Tyr Ala Val Gly Ser Val Cys Ile Ala
    210                 215                 220 ttg atg gct ccg atg gtt att ctt gct tgt cgc cga ggt cct ttg         720
Leu Met Ala Pro Met Val Ile Leu Ala Cys Cys Arg Arg Gly Pro Leu
225                 230                 235                 240 ata gtg ccc gaa tgc ttc gct tgt gca tat ttc gtt ttc ggg ctt gtt     768
Ile Val Pro Glu Cys Phe Ala Cys Ala Tyr Phe Val Phe Gly Leu Val
```

```
                             245                 250                 255
ttt tca gtt ggc ggt gct gtt ttg ttc ctg ttg agc tat gct tct tca     816
Phe Ser Val Gly Gly Ala Val Leu Phe Leu Leu Ser Tyr Ala Ser Ser
        260                 265                 270 tct gtg tgt ggc gag att gca ctt cac cgt gag cga aag cct ggc att     864
Ser Val Cys Gly Glu Ile Ala Leu His Arg Glu Arg Lys Pro Gly Ile
            275                 280                 285 atc cag tgg tac gga atc cca tta tgc aat agc aag ttt cgc cct gat     912
Ile Gln Trp Tyr Gly Ile Pro Leu Cys Asn Ser Lys Phe Arg Pro Asp
        290                 295                 300 gct att aac aag aaa gtg aca gac gcg gag att ggc att tgt agg gag     960
Ala Ile Asn Lys Lys Val Thr Asp Ala Glu Ile Gly Ile Cys Arg Glu
305                 310                 315                 320 gct tgc aat tat ttg ctt gat aac tgt gat aat ctg gat atg cgt ggc    1008
Ala Cys Asn Tyr Leu Leu Asp Asn Cys Asp Asn Leu Asp Met Arg Gly
                325                 330                 335 cca agt atg agt cgt ttt tcg gga tca agt gta tct tat gat ggt tat    1056
Pro Ser Met Ser Arg Phe Ser Gly Ser Ser Val Ser Tyr Asp Gly Tyr
            340                 345                 350 gtg cct tct ggt tac ctc aaa gac aga aac ggt aag ccg aac acg cga    1104
Val Pro Ser Gly Tyr Leu Lys Asp Arg Asn Gly Lys Pro Asn Thr Arg
        355                 360                 365 tct agc gac ata tcc cct gac gcc cct gct tct ttc ata gca agt ggg    1152
Ser Ser Asp Ile Ser Pro Asp Ala Pro Ala Ser Phe Ile Ala Ser Gly
370                 375                 380 ttt gta agt cat gcg gca gct agg aat gtg ggt ggt act ttt ccc gtg    1200
Phe Val Ser His Ala Ala Ala Arg Asn Val Gly Gly Thr Phe Pro Val
385                 390                 395                 400 aag gtt ctg act tgt gga aag aat atc acc tca tcc gat gag tgt cca    1248
Lys Val Leu Thr Cys Gly Lys Asn Ile Thr Ser Ser Asp Glu Cys Pro
                405                 410                 415 aac ttt ggc atc aca gca aca gta ctg gag gac aca cgg gtg aag gcc    1296
Asn Phe Gly Ile Thr Ala Thr Val Leu Glu Asp Thr Arg Val Lys Ala
            420                 425                 430 ttc gtt ggt tca tgc cct act ccc gga aat tct tgc acg gta gtg gag    1344
Phe Val Gly Ser Cys Pro Thr Pro Gly Asn Ser Cys Thr Val Val Glu
        435                 440                 445 tgt gcg gcc aat tgt acg gag ggc agg gca aag aac gtc tct atc gaa    1392
Cys Ala Ala Asn Cys Thr Glu Gly Arg Ala Lys Asn Val Ser Ile Glu
450                 455                 460 gtc gta cgt gtg gct gca cgg tcg cgt aac gtc agt gtt gca ctt tca    1440
Val Val Arg Val Ala Ala Arg Ser Arg Asn Val Ser Val Ala Leu Ser
465                 470                 475                 480 ata ggt cga ccg ctg ctg gaa tgt aat ttt atg ctc gac att gcg cta    1488
Ile Gly Arg Pro Leu Leu Glu Cys Asn Phe Met Leu Asp Ile Ala Leu
                485                 490                 495 act gcc atg ccg gac tgt gaa gat ata acg ccg ggt gtc ttc atg ctt    1536
Thr Ala Met Pro Asp Cys Glu Asp Ile Thr Pro Gly Val Phe Met Leu
            500                 505                 510 tcc gtc ggg ttt ctc ctt gga agt ctg atg ttt gcg gtc ggg att tat    1584
Ser Val Gly Phe Leu Leu Gly Ser Leu Met Phe Ala Val Gly Ile Tyr
        515                 520                 525 gtc atg ctc cgt ggt tct tgt gtt tgg ggt agt gcc aag acc tcg ccg    1632
Val Met Leu Arg Gly Ser Cys Val Trp Gly Ser Ala Lys Thr Ser Pro
530                 535                 540 gag gct tct taa                                                    1644
Glu Ala Ser
545
```

<210> SEQ ID NO 100
<211> LENGTH: 547
<212> TYPE: PRT
<213> ORGANISM: Trypanosoma brucei

<400> SEQUENCE: 100

```
Met Ser Ser Val Thr Thr Gly Ser Ser Phe Tyr Ala Ala Val Leu Leu
1               5                   10                  15

Val Leu Leu Thr Val Thr Gln Cys Gly Asn Ser Lys Phe Pro Asn
                20                  25                  30

Leu His Cys Asp Asn Val Trp Asp Gly Pro Ser Ala Arg Asn Asp Pro
            35                  40                  45

Leu Thr Cys Ile Met Asp Thr Asp Arg Ile Leu Ala Gln Trp Arg Met
        50                  55                  60

Leu Ala Met Pro Ala Leu Cys Ala Phe Leu Phe Val Ala Val Leu Ile
65                  70                  75                  80

Ala Phe Pro Ile Ser Cys Phe Leu Thr Cys Leu Cys Ser Ser Arg Cys
                85                  90                  95

Lys Pro Ser Ser Lys Asp Gly Gly Lys Glu Gln Arg Cys Cys Leu Trp
            100                 105                 110

Met Trp Ile Met Phe Ala Leu Ile Trp Ala Phe Gly Val Ala Ala Phe
        115                 120                 125

Val Phe Phe Gly Val Lys Gln Leu Trp Ala Thr Ser Asn Tyr Phe Leu
    130                 135                 140

Asp Val Thr Leu Met Asn Pro Leu Asn Val Val Asn Cys Thr Ala Glu
145                 150                 155                 160

Lys Val Ile Asp Phe Ala Ser Asn Trp Thr Ser Gly Asn Arg Glu Pro
                165                 170                 175

Tyr Ala Asp Gly Val Asp Val Ser Phe Phe Tyr Asp Ile Ser Glu Asn
            180                 185                 190

Ala Val Arg Val Val Glu Met Leu Arg Gly Arg Ala Gly Asp Tyr Ile
        195                 200                 205

Lys Leu Leu Pro Val Val Ser Tyr Ala Val Gly Ser Val Cys Ile Ala
210                 215                 220

Leu Met Ala Pro Met Val Ile Leu Ala Cys Cys Arg Arg Gly Pro Leu
225                 230                 235                 240

Ile Val Pro Glu Cys Phe Ala Cys Ala Tyr Phe Val Phe Gly Leu Val
                245                 250                 255

Phe Ser Val Gly Gly Ala Val Leu Phe Leu Leu Ser Tyr Ala Ser Ser
            260                 265                 270

Ser Val Cys Gly Glu Ile Ala Leu His Arg Glu Arg Lys Pro Gly Ile
        275                 280                 285

Ile Gln Trp Tyr Gly Ile Pro Leu Cys Asn Ser Lys Phe Arg Pro Asp
    290                 295                 300

Ala Ile Asn Lys Lys Val Thr Asp Ala Glu Ile Gly Ile Cys Arg Glu
305                 310                 315                 320

Ala Cys Asn Tyr Leu Leu Asp Asn Cys Asp Asn Leu Asp Met Arg Gly
                325                 330                 335

Pro Ser Met Ser Arg Phe Ser Gly Ser Ser Val Ser Tyr Asp Gly Tyr
            340                 345                 350

Val Pro Ser Gly Tyr Leu Lys Asp Arg Asn Gly Lys Pro Asn Thr Arg
        355                 360                 365

Ser Ser Asp Ile Ser Pro Asp Ala Pro Ala Ser Phe Ile Ala Ser Gly
    370                 375                 380
```

```
Phe Val Ser His Ala Ala Ala Arg Asn Val Gly Gly Thr Phe Pro Val
385                 390                 395                 400

Lys Val Leu Thr Cys Gly Lys Asn Ile Thr Ser Ser Asp Glu Cys Pro
            405                 410                 415

Asn Phe Gly Ile Thr Ala Thr Val Leu Glu Asp Thr Arg Val Lys Ala
        420                 425                 430

Phe Val Gly Ser Cys Pro Thr Pro Gly Asn Ser Cys Thr Val Val Glu
        435                 440                 445

Cys Ala Asn Cys Thr Glu Gly Arg Ala Lys Asn Val Ser Ile Glu
    450                 455                 460

Val Val Arg Val Ala Ala Arg Ser Arg Asn Val Ser Val Ala Leu Ser
465                 470                 475                 480

Ile Gly Arg Pro Leu Leu Glu Cys Asn Phe Met Leu Asp Ile Ala Leu
            485                 490                 495

Thr Ala Met Pro Asp Cys Glu Asp Ile Thr Pro Gly Val Phe Met Leu
            500                 505                 510

Ser Val Gly Phe Leu Leu Gly Ser Leu Met Phe Ala Val Gly Ile Tyr
            515                 520                 525

Val Met Leu Arg Gly Ser Cys Val Trp Gly Ser Ala Lys Thr Ser Pro
530                 535                 540

Glu Ala Ser
545

<210> SEQ ID NO 101
<211> LENGTH: 1713
<212> TYPE: DNA
<213> ORGANISM: Trypanosoma brucei
<220> FEATURE:
<221> NAME/KEY: CDS
<222> LOCATION: (1)..(1713)

<400> SEQUENCE: 101 atg tat aat gcc ctg agg tca gca gct ctg gca gtg ggg ttg gtg tta      48
Met Tyr Asn Ala Leu Arg Ser Ala Ala Leu Ala Val Gly Leu Val Leu
1               5                   10                  15 ctg ttt gcc gcc acg cca gca tcc gca act aga gag ggt tcg ttt caa     96
Leu Phe Ala Ala Thr Pro Ala Ser Ala Thr Arg Glu Gly Ser Phe Gln
            20                  25                  30 tgc gag aat gtg tgg gat ggc ccg agt acc agt aat gac gtt cag gcg    144
Cys Glu Asn Val Trp Asp Gly Pro Ser Thr Ser Asn Asp Val Gln Ala
        35                  40                  45 tgt ata ctc aat gca gag cgc atg cgg tct cag tgg aag ctc ttt gtt    192
Cys Ile Leu Asn Ala Glu Arg Met Arg Ser Gln Trp Lys Leu Phe Val
50                  55                  60 ttg ccg ttt cta agt gct gta ctt ctt gca gta ctg ttg gta agc ttc    240
Leu Pro Phe Leu Ser Ala Val Leu Leu Ala Val Leu Leu Val Ser Phe
65                  70                  75                  80 cct ctt gta ttc att tgc tcc ata tgc tgt aac tgt tgc ggc tgt tgt    288
Pro Leu Val Phe Ile Cys Ser Ile Cys Cys Asn Cys Cys Gly Cys Cys
                85                  90                  95 ggt gca aac tgc tgt aaa ccg gaa acg aag aag agc agg aat cag gcc    336
Gly Ala Asn Cys Cys Lys Pro Glu Thr Lys Lys Ser Arg Asn Gln Ala
            100                 105                 110 cgt tgc tgt ttg tgg ttg tac atc gtg tat gcc cta ctt tgg agc gtt    384
Arg Cys Cys Leu Trp Leu Tyr Ile Val Tyr Ala Leu Leu Trp Ser Val
        115                 120                 125 atg gtt ttt ttt ctt atc gta tac ggg act cgg acg gtg acg aag gct    432
Met Val Phe Phe Leu Ile Val Tyr Gly Thr Arg Thr Val Thr Lys Ala
    130                 135                 140
```

```
gtt cca acg ttc gtc gac gac gca gtc tct gga ccc ttg tcg tac ttt      480
Val Pro Thr Phe Val Asp Asp Ala Val Ser Gly Pro Leu Ser Tyr Phe
145             150                 155                 160 aat caa aca gca gaa agt gta atg gat tac aca tat gac tgg agc tcg      528
Asn Gln Thr Ala Glu Ser Val Met Asp Tyr Thr Tyr Asp Trp Ser Ser
                165                 170                 175 ggt gag cgg agg gaa cca ggt gac ttt acg att gac ttc tcc gag ttt      576
Gly Glu Arg Arg Glu Pro Gly Asp Phe Thr Ile Asp Phe Ser Glu Phe
            180                 185                 190 tcc agc atg cag aag aag gta atg gaa ggc gtg tcc gca gtc cgt gca      624
Ser Ser Met Gln Lys Lys Val Met Glu Gly Val Ser Ala Val Arg Ala
        195                 200                 205 aca gtc ttt gta cac ttt gac aag gtc tcc atc gcg tcc tac gtt gtc      672
Thr Val Phe Val His Phe Asp Lys Val Ser Ile Ala Ser Tyr Val Val
    210                 215                 220 gga agc ctt ggt ttc gtt atg gta ctt gtt att ctc cct ttt gcc atg      720
Gly Ser Leu Gly Phe Val Met Val Leu Val Ile Leu Pro Phe Ala Met
225                 230                 235                 240 ttc aag tgc tgc att ccg ggg ttt cca ata tgt atc tcg ttc gtc tat      768
Phe Lys Cys Cys Ile Pro Gly Phe Pro Ile Cys Ile Ser Phe Val Tyr
                245                 250                 255 tgg att ttt ggt ctt gcc ttc gcc gtg ctc gga ctt ctg ttg acg att      816
Trp Ile Phe Gly Leu Ala Phe Ala Val Leu Gly Leu Leu Leu Thr Ile
            260                 265                 270 ctg gcg tac ttc gcc acc ctt acc tgc ggc gaa gtg gag cga cac cat      864
Leu Ala Tyr Phe Ala Thr Leu Thr Cys Gly Glu Val Glu Arg His His
        275                 280                 285 ggg cgg gat cca ggg ctg att cag tgg tat ggc gtc cct gtt tgt aaa      912
Gly Arg Asp Pro Gly Leu Ile Gln Trp Tyr Gly Val Pro Val Cys Lys
    290                 295                 300 gag ttt ttt aat ttc caa cag tta aac aag ggc att atg gcc gct gag      960
Glu Phe Phe Asn Phe Gln Gln Leu Asn Lys Gly Ile Met Ala Ala Glu
305                 310                 315                 320 ttg cag ctg tct cag ggt gtc tgc aag gca gtt cta ccg ttc tgt gac     1008
Leu Gln Leu Ser Gln Gly Val Cys Lys Ala Val Leu Pro Phe Cys Asp
                325                 330                 335 aga cgt aag ctt cgg ggc ccc ggt ggc gta gtg gat cgt gct gat cct     1056
Arg Arg Lys Leu Arg Gly Pro Gly Gly Val Val Asp Arg Ala Asp Pro
            340                 345                 350 cac cct ggt gag aga aac agg ttg ctg cca ccc ggt ggc gaa tat cca     1104
His Pro Gly Glu Arg Asn Arg Leu Leu Pro Pro Gly Gly Glu Tyr Pro
        355                 360                 365 aat gaa aag gcc ttg gag aac aca agc cac aaa cac gga aat gtt cct     1152
Asn Glu Lys Ala Leu Glu Asn Thr Ser His Lys His Gly Asn Val Pro
    370                 375                 380 cct gca agc gat agg gcg ggg ggt cca ccg cat cca aca cct gtg cgt     1200
Pro Ala Ser Asp Arg Ala Gly Gly Pro Pro His Pro Thr Pro Val Arg
385                 390                 395                 400 gac cac tcg ggt ctg cct gga att tcc gag ggg ccg aat ttt ccg gat     1248
Asp His Ser Gly Leu Pro Gly Ile Ser Glu Gly Pro Asn Phe Pro Asp
                405                 410                 415 ctt ccc gcg gtc cct gtg cta aac tgt caa gaa gga ttt aca gac gcc     1296
Leu Pro Ala Val Pro Val Leu Asn Cys Gln Glu Gly Phe Thr Asp Ala
            420                 425                 430 tcg cag tgt acg acg ttt gat gcg atg tcc gca ctt gtg ttg acg gcg     1344
Ser Gln Cys Thr Thr Phe Asp Ala Met Ser Ala Leu Val Leu Thr Ala
        435                 440                 445 gaa gtt aaa ggt tcc tta aac cca tgt gga gag gcc gga aag gcg tgc     1392
Glu Val Lys Gly Ser Leu Asn Pro Cys Gly Glu Ala Gly Lys Ala Cys
```

```
                450               455               460
aac ctt acg gag tgt gcc gcg cgt tgt gaa aac gat caa tta cag gag   1440
Asn Leu Thr Glu Cys Ala Ala Arg Cys Glu Asn Asp Gln Leu Gln Glu
465                 470                 475                 480 ctt gcg gtt cgc gca aca agt cag att gag aga gtg cag aac gta acc   1488
Leu Ala Val Arg Ala Thr Ser Gln Ile Glu Arg Val Gln Asn Val Thr
                485                 490                 495 atc gcg tgg tcg tat gcc agg ccg cta ctt gag tgc aac ttc gta atc   1536
Ile Ala Trp Ser Tyr Ala Arg Pro Leu Leu Glu Cys Asn Phe Val Ile
            500                 505                 510 gac aag att gta gag tct cta gaa gca tgc ggg gac atc acg gca gga   1584
Asp Lys Ile Val Glu Ser Leu Glu Ala Cys Gly Asp Ile Thr Ala Gly
        515                 520                 525 acg atg gtg ttg ggt gca ggt ttt ttc att ggt gca att gtg ttt ggc   1632
Thr Met Val Leu Gly Ala Gly Phe Phe Ile Gly Ala Ile Val Phe Gly
    530                 535                 540 ctc ggt ata tat att atg ctc cgt ggt gct tgc gta tgg ggt gag ata   1680
Leu Gly Ile Tyr Ile Met Leu Arg Gly Ala Cys Val Trp Gly Glu Ile
545                 550                 555                 560 ccg atg ttc act agg gat gcg aaa gct tcg tag                       1713
Pro Met Phe Thr Arg Asp Ala Lys Ala Ser
                565                 570

<210> SEQ ID NO 102
<211> LENGTH: 570
<212> TYPE: PRT
<213> ORGANISM: Trypanosoma brucei

<400> SEQUENCE: 102

Met Tyr Asn Ala Leu Arg Ser Ala Ala Leu Ala Val Gly Leu Val Leu
1               5                   10                  15

Leu Phe Ala Ala Thr Pro Ala Ser Ala Thr Arg Glu Gly Ser Phe Gln
            20                  25                  30

Cys Glu Asn Val Trp Asp Gly Pro Ser Thr Ser Asn Asp Val Gln Ala
        35                  40                  45

Cys Ile Leu Asn Ala Glu Arg Met Arg Ser Gln Trp Lys Leu Phe Val
    50                  55                  60

Leu Pro Phe Leu Ser Ala Val Leu Leu Ala Val Leu Leu Val Ser Phe
65                  70                  75                  80

Pro Leu Val Phe Ile Cys Ser Ile Cys Cys Asn Cys Cys Gly Cys Cys
                85                  90                  95

Gly Ala Asn Cys Cys Lys Pro Glu Thr Lys Lys Ser Arg Asn Gln Ala
            100                 105                 110

Arg Cys Cys Leu Trp Leu Tyr Ile Val Tyr Ala Leu Leu Trp Ser Val
        115                 120                 125

Met Val Phe Phe Leu Ile Val Tyr Gly Thr Arg Thr Val Thr Lys Ala
    130                 135                 140

Val Pro Thr Phe Val Asp Asp Ala Val Ser Gly Pro Leu Ser Tyr Phe
145                 150                 155                 160

Asn Gln Thr Ala Glu Ser Val Met Asp Tyr Thr Tyr Asp Trp Ser Ser
                165                 170                 175

Gly Glu Arg Arg Glu Pro Gly Asp Phe Thr Ile Asp Phe Ser Glu Phe
            180                 185                 190

Ser Ser Met Gln Lys Lys Val Met Glu Gly Val Ser Ala Val Arg Ala
        195                 200                 205

Thr Val Phe Val His Phe Asp Lys Val Ser Ile Ala Ser Tyr Val Val
    210                 215                 220
```

Gly Ser Leu Gly Phe Val Met Val Leu Val Ile Leu Pro Phe Ala Met
225                 230                 235                 240

Phe Lys Cys Cys Ile Pro Gly Phe Pro Ile Cys Ile Ser Phe Val Tyr
            245                 250                 255

Trp Ile Phe Gly Leu Ala Phe Ala Val Leu Gly Leu Leu Leu Thr Ile
        260                 265                 270

Leu Ala Tyr Phe Ala Thr Leu Thr Cys Gly Glu Val Glu Arg His His
            275                 280                 285

Gly Arg Asp Pro Gly Leu Ile Gln Trp Tyr Gly Val Pro Val Cys Lys
        290                 295                 300

Glu Phe Phe Asn Phe Gln Gln Leu Asn Lys Gly Ile Met Ala Ala Glu
305                 310                 315                 320

Leu Gln Leu Ser Gln Gly Val Cys Lys Ala Val Leu Pro Phe Cys Asp
            325                 330                 335

Arg Arg Lys Leu Arg Gly Pro Gly Val Val Asp Arg Ala Asp Pro
        340                 345                 350

His Pro Gly Glu Arg Asn Arg Leu Leu Pro Pro Gly Gly Glu Tyr Pro
            355                 360                 365

Asn Glu Lys Ala Leu Glu Asn Thr Ser His Lys His Gly Asn Val Pro
370                 375                 380

Pro Ala Ser Asp Arg Ala Gly Gly Pro Pro His Pro Thr Pro Val Arg
385                 390                 395                 400

Asp His Ser Gly Leu Pro Gly Ile Ser Glu Gly Pro Asn Phe Pro Asp
            405                 410                 415

Leu Pro Ala Val Pro Val Leu Asn Cys Gln Glu Gly Phe Thr Asp Ala
        420                 425                 430

Ser Gln Cys Thr Thr Phe Asp Ala Met Ser Ala Leu Val Leu Thr Ala
            435                 440                 445

Glu Val Lys Gly Ser Leu Asn Pro Cys Gly Glu Ala Gly Lys Ala Cys
450                 455                 460

Asn Leu Thr Glu Cys Ala Ala Arg Cys Glu Asn Asp Gln Leu Gln Glu
465                 470                 475                 480

Leu Ala Val Arg Ala Thr Ser Gln Ile Glu Arg Val Gln Asn Val Thr
            485                 490                 495

Ile Ala Trp Ser Tyr Ala Arg Pro Leu Leu Glu Cys Asn Phe Val Ile
        500                 505                 510

Asp Lys Ile Val Glu Ser Leu Glu Ala Cys Gly Asp Ile Thr Ala Gly
            515                 520                 525

Thr Met Val Leu Gly Ala Gly Phe Phe Ile Gly Ala Ile Val Phe Gly
        530                 535                 540

Leu Gly Ile Tyr Ile Met Leu Arg Gly Ala Cys Val Trp Gly Glu Ile
545                 550                 555                 560

Pro Met Phe Thr Arg Asp Ala Lys Ala Ser
            565                 570

<210> SEQ ID NO 103
<211> LENGTH: 735
<212> TYPE: DNA
<213> ORGANISM: Trypanosoma cruzi
<220> FEATURE:
<221> NAME/KEY: CDS
<222> LOCATION: (1)..(735)

<400> SEQUENCE: 103 atg cgg tgg att ttt ttg tta ctt gcc gta ctg agt gtg ttg aag ccg        48

```
Met Arg Trp Ile Phe Leu Leu Leu Ala Val Leu Ser Val Leu Lys Pro
 1               5                  10                  15 aca gat gca act ccc gat cct ctg gag cat gcc atg gga ctg aac tac    96
Thr Asp Ala Thr Pro Asp Pro Leu Glu His Ala Met Gly Leu Asn Tyr
             20                  25                  30 aag gtt gcc ttt tct cag aag ccc cca ccg cgg ggg ctt agc aag gaa   144
Lys Val Ala Phe Ser Gln Lys Pro Pro Pro Arg Gly Leu Ser Lys Glu
         35                  40                  45 caa tat tac tca atg cgt ctt aga aat gga tct ttt ttt gtg tgt gtc   192
Gln Tyr Tyr Ser Met Arg Leu Arg Asn Gly Ser Phe Phe Val Cys Val
     50                  55                  60 ttg ccg gag gtg cta tta gag cag cgg agc tcc gcg gca ctt ttt gaa   240
Leu Pro Glu Val Leu Leu Glu Gln Arg Ser Ser Ala Ala Leu Phe Glu
 65                  70                  75                  80 gca aac agt gaa gtt cca gtg aaa ttt att gag cgc att cat gaa cgg   288
Ala Asn Ser Glu Val Pro Val Lys Phe Ile Glu Arg Ile His Glu Arg
                 85                  90                  95 ttt aaa aaa gta tgt att aat tta ctt gag ggg tgg tgg acg tat cgg   336
Phe Lys Lys Val Cys Ile Asn Leu Leu Glu Gly Trp Trp Thr Tyr Arg
            100                 105                 110 ctc tgt tgg aat gat gcg ata gtg caa gtg cac ttg ccg aca gtg att   384
Leu Cys Trp Asn Asp Ala Ile Val Gln Val His Leu Pro Thr Val Ile
        115                 120                 125 tta agc gat ggg gta ttg ttg aca aca gag ccg cag ggg cca cag aca   432
Leu Ser Asp Gly Val Leu Leu Thr Thr Glu Pro Gln Gly Pro Gln Thr
    130                 135                 140 caa ttc ctt ctt gga aca tct cca tcg aag gat gat tta aac ttt cgt   480
Gln Phe Leu Leu Gly Thr Ser Pro Ser Lys Asp Asp Leu Asn Phe Arg
145                 150                 155                 160 tac ggt gtg gat gcc ctt gga aat cgt tac atc ttc aca aaa tat cca   528
Tyr Gly Val Asp Ala Leu Gly Asn Arg Tyr Ile Phe Thr Lys Tyr Pro
                165                 170                 175 aac ggc gaa gtc tgc gac ctc aca aat gca cca aga gaa acg gaa gtt   576
Asn Gly Glu Val Cys Asp Leu Thr Asn Ala Pro Arg Glu Thr Glu Val
            180                 185                 190 cgc ctg tat tgt gca cgt gat aat gag gag gaa aag atg aca tta cgc   624
Arg Leu Tyr Cys Ala Arg Asp Asn Glu Glu Glu Lys Met Thr Leu Arg
        195                 200                 205 gag gtg gag gtt tgt cgt tat gtg gtg agt ttg acc tcg aga cat gcc   672
Glu Val Glu Val Cys Arg Tyr Val Val Ser Leu Thr Ser Arg His Ala
    210                 215                 220 tgc att cag gaa ctg cag caa gaa gta acg cag aga aca att aca tgc   720
Cys Ile Gln Glu Leu Gln Gln Glu Val Thr Gln Arg Thr Ile Thr Cys
225                 230                 235                 240 cac gaa ctt gtc taa                                                735
His Glu Leu Val <210> SEQ ID NO 104
<211> LENGTH: 244
<212> TYPE: PRT
<213> ORGANISM: Trypanosoma cruzi

<400> SEQUENCE: 104

Met Arg Trp Ile Phe Leu Leu Leu Ala Val Leu Ser Val Leu Lys Pro
 1               5                  10                  15

Thr Asp Ala Thr Pro Asp Pro Leu Glu His Ala Met Gly Leu Asn Tyr
             20                  25                  30

Lys Val Ala Phe Ser Gln Lys Pro Pro Pro Arg Gly Leu Ser Lys Glu
         35                  40                  45
```

```
Gln Tyr Tyr Ser Met Arg Leu Arg Asn Gly Ser Phe Val Cys Val
         50                  55                  60

Leu Pro Glu Val Leu Leu Glu Gln Arg Ser Ser Ala Ala Leu Phe Glu
 65                  70                  75                  80

Ala Asn Ser Glu Val Pro Val Lys Phe Ile Glu Arg Ile His Glu Arg
                 85                  90                  95

Phe Lys Lys Val Cys Ile Asn Leu Leu Glu Gly Trp Trp Thr Tyr Arg
            100                 105                 110

Leu Cys Trp Asn Asp Ala Ile Val Gln Val His Leu Pro Thr Val Ile
            115                 120                 125

Leu Ser Asp Gly Val Leu Leu Thr Thr Glu Pro Gln Gly Pro Gln Thr
130                 135                 140

Gln Phe Leu Leu Gly Thr Ser Pro Ser Lys Asp Asp Leu Asn Phe Arg
145                 150                 155                 160

Tyr Gly Val Asp Ala Leu Gly Asn Arg Tyr Ile Phe Thr Lys Tyr Pro
                165                 170                 175

Asn Gly Glu Val Cys Asp Leu Thr Asn Ala Pro Arg Glu Thr Glu Val
            180                 185                 190

Arg Leu Tyr Cys Ala Arg Asp Asn Glu Glu Lys Met Thr Leu Arg
        195                 200                 205

Glu Val Glu Val Cys Arg Tyr Val Val Ser Leu Thr Ser Arg His Ala
    210                 215                 220

Cys Ile Gln Glu Leu Gln Gln Glu Val Thr Gln Arg Thr Ile Thr Cys
225                 230                 235                 240

His Glu Leu Val

<210> SEQ ID NO 105
<211> LENGTH: 738
<212> TYPE: DNA
<213> ORGANISM: Leishmania major
<220> FEATURE:
<221> NAME/KEY: CDS
<222> LOCATION: (1)..(738)

<400> SEQUENCE: 105 atg ggg cgc cgc agt ggc tgt gtg ttg tgg ctt gct gcc gca gcg ttg      48
Met Gly Arg Arg Ser Gly Cys Val Leu Trp Leu Ala Ala Ala Ala Leu
 1               5                  10                  15 gcc att ttt aca ctt cag ctg cgt agc gct gtc gca gcg ccg atg gat      96
Ala Ile Phe Thr Leu Gln Leu Arg Ser Ala Val Ala Ala Pro Met Asp
             20                  25                  30 ctt tcc aat cct gta gag cgc aat cat ttt ctt tta tta gca ccc tac     144
Leu Ser Asn Pro Val Glu Arg Asn His Phe Leu Leu Leu Ala Pro Tyr
         35                  40                  45 ggt gtt cgt cat cga tca ggc gcc aac gct cac gga gaa aac aca gcg     192
Gly Val Arg His Arg Ser Gly Ala Asn Ala His Gly Glu Asn Thr Ala
     50                  55                  60 cga tat gtg cag ctg agc aac ggc tct cga ttt gtg tgc gac aca acg     240
Arg Tyr Val Gln Leu Ser Asn Gly Ser Arg Phe Val Cys Asp Thr Thr
 65                  70                  75                  80 ggc aca aag cgc cgc gat ccc ctc gac gcc aaa aac tac ccg ctg cga     288
Gly Thr Lys Arg Arg Asp Pro Leu Asp Ala Lys Asn Tyr Pro Leu Arg
                 85                  90                  95 cat caa atg gag tcc ttg atg acc ttt atg cgg ggt tcc gac cat ccg     336
His Gln Met Glu Ser Leu Met Thr Phe Met Arg Gly Ser Asp His Pro
            100                 105                 110 tgc gtg cac tac gca gag gag agc tac gtg aca gtc tac tgc tgg gac     384
Cys Val His Tyr Ala Glu Glu Ser Tyr Val Thr Val Tyr Cys Trp Asp
```

|   |   |   | 115 |   |   |   | 120 |   |   |   | 125 |   |   |   |   |
|---|---|---|---|---|---|---|---|---|---|---|---|---|---|---|---|

```
aac gag gtg cgc gag gat gct ctt tca gag aac aag gcc tcc tcc ctg       432
Asn Glu Val Arg Glu Asp Ala Leu Ser Glu Asn Lys Ala Ser Ser Leu
    130                 135                 140 ggg agg cgg cgg acc gac gga cct caa atg tac tgg gcc tcc aac gac       480
Gly Arg Arg Arg Thr Asp Gly Pro Gln Met Tyr Trp Ala Ser Asn Asp
145                 150                 155                 160 gcg ttc ggc cgg tac gcc gca acc gtc tac gga gat ggt gac gag tgt       528
Ala Phe Gly Arg Tyr Ala Ala Thr Val Tyr Gly Asp Gly Asp Glu Cys
                165                 170                 175 ccg tac gac aag gga cgc cgc ata gag aca gag gtg cgc ttc tac tgc       576
Pro Tyr Asp Lys Gly Arg Arg Ile Glu Thr Glu Val Arg Phe Tyr Cys
            180                 185                 190 cgg tac tcc gag ttc gag aac ccg att ccg tac atg agt atc cac gag       624
Arg Tyr Ser Glu Phe Glu Asn Pro Ile Pro Tyr Met Ser Ile His Glu
        195                 200                 205 tcg tcg cag tgc cgc tat atg ctg cgc ctt ctg tca agt aag ttc tgt       672
Ser Ser Gln Cys Arg Tyr Met Leu Arg Leu Leu Ser Ser Lys Phe Cys
    210                 215                 220 tcc gtg cac cag cta gat cac cca agc gag gag gag acg gtg cag tgc       720
Ser Val His Gln Leu Asp His Pro Ser Glu Glu Glu Thr Val Gln Cys
225                 230                 235                 240 cag atg ttg gct gat tag                                               738
Gln Met Leu Ala Asp
                245
```

<210> SEQ ID NO 106
<211> LENGTH: 245
<212> TYPE: PRT
<213> ORGANISM: Leishmania major

<400> SEQUENCE: 106

```
Met Gly Arg Arg Ser Gly Cys Val Leu Trp Leu Ala Ala Ala Leu
1               5                   10                  15

Ala Ile Phe Thr Leu Gln Leu Arg Ser Ala Val Ala Ala Pro Met Asp
                20                  25                  30

Leu Ser Asn Pro Val Glu Arg Asn His Phe Leu Leu Leu Ala Pro Tyr
            35                  40                  45

Gly Val Arg His Arg Ser Gly Ala Asn Ala His Gly Glu Asn Thr Ala
        50                  55                  60

Arg Tyr Val Gln Leu Ser Asn Gly Ser Arg Phe Val Cys Asp Thr Thr
65                  70                  75                  80

Gly Thr Lys Arg Arg Asp Pro Leu Asp Ala Lys Asn Tyr Pro Leu Arg
                85                  90                  95

His Gln Met Glu Ser Leu Met Thr Phe Met Arg Gly Ser Asp His Pro
            100                 105                 110

Cys Val His Tyr Ala Glu Glu Ser Tyr Val Thr Val Tyr Cys Trp Asp
        115                 120                 125

Asn Glu Val Arg Glu Asp Ala Leu Ser Glu Asn Lys Ala Ser Ser Leu
    130                 135                 140

Gly Arg Arg Arg Thr Asp Gly Pro Gln Met Tyr Trp Ala Ser Asn Asp
145                 150                 155                 160

Ala Phe Gly Arg Tyr Ala Ala Thr Val Tyr Gly Asp Gly Asp Glu Cys
                165                 170                 175

Pro Tyr Asp Lys Gly Arg Arg Ile Glu Thr Glu Val Arg Phe Tyr Cys
            180                 185                 190

Arg Tyr Ser Glu Phe Glu Asn Pro Ile Pro Tyr Met Ser Ile His Glu
```

```
                195                 200                 205
Ser Ser Gln Cys Arg Tyr Met Leu Arg Leu Leu Ser Ser Lys Phe Cys
    210                 215                 220

Ser Val His Gln Leu Asp His Pro Ser Glu Glu Glu Thr Val Gln Cys
225                 230                 235                 240

Gln Met Leu Ala Asp
                245

<210> SEQ ID NO 107
<211> LENGTH: 738
<212> TYPE: DNA
<213> ORGANISM: Leishmania infantum
<220> FEATURE:
<221> NAME/KEY: CDS
<222> LOCATION: (1)..(738)

<400> SEQUENCE: 107 atg ggg tgc cgc agt agc tgt atg ctg tgg ctt gct gtc gca gct ttg      48
Met Gly Cys Arg Ser Ser Cys Met Leu Trp Leu Ala Val Ala Ala Leu
1               5                   10                  15 gcc gtt ttg aca ctt cag ctg cgt agc gct gcc gca gcg ccc atg gat      96
Ala Val Leu Thr Leu Gln Leu Arg Ser Ala Ala Ala Ala Pro Met Asp
                20                  25                  30 ctt tcc aac cct gtc gag cac aat cat ttt ctt ctg tta gca ccc tat     144
Leu Ser Asn Pro Val Glu His Asn His Phe Leu Leu Leu Ala Pro Tyr
            35                  40                  45 ggc gct agt cat cga tcg ggc acc ggc gct gac ggg gaa aac aca gcg     192
Gly Ala Ser His Arg Ser Gly Thr Gly Ala Asp Gly Glu Asn Thr Ala
        50                  55                  60 cga tat gtg cag ctg agc aac ggc tct cga ttt gtg tgc gag acc gcg     240
Arg Tyr Val Gln Leu Ser Asn Gly Ser Arg Phe Val Cys Glu Thr Ala
65                  70                  75                  80 agc aca agg cgc cgt gag ccc ctc gac gcc aaa agc tac cca ctg cga     288
Ser Thr Arg Arg Arg Glu Pro Leu Asp Ala Lys Ser Tyr Pro Leu Arg
                85                  90                  95 cat caa atg gag tcc ttg atg acc gtt atg cgg cgt tcc gac cat ccg     336
His Gln Met Glu Ser Leu Met Thr Val Met Arg Arg Ser Asp His Pro
            100                 105                 110 tgc gtg cac tac gca gag gag aac tac gtg acg gtc tac tgc tgg gac     384
Cys Val His Tyr Ala Glu Glu Asn Tyr Val Thr Val Tyr Cys Trp Asp
        115                 120                 125 aac gag gtg cgc gag gat gct ctt tca gaa aac aaa ggc cgc tcc ctg     432
Asn Glu Val Arg Glu Asp Ala Leu Ser Glu Asn Lys Gly Arg Ser Leu
130                 135                 140 ggg agg cgg cgg atc gac gga cct caa atc tac tgg acc tcc aac gac     480
Gly Arg Arg Arg Ile Asp Gly Pro Gln Ile Tyr Trp Thr Ser Asn Asp
145                 150                 155                 160 gcg ttc ggc cgg tac gtc gca acc gtc tac ggc gac ggt gac gag tgc     528
Ala Phe Gly Arg Tyr Val Ala Thr Val Tyr Gly Asp Gly Asp Glu Cys
                165                 170                 175 ccc tac gac aag gga cgc cgc ata gag acg gag gtg cgc ttc cac tgc     576
Pro Tyr Asp Lys Gly Arg Arg Ile Glu Thr Glu Val Arg Phe His Cys
            180                 185                 190 cgg tac tcc gag ttc gag aac ccg att ccg tac atg agt ctt cac gag     624
Arg Tyr Ser Glu Phe Glu Asn Pro Ile Pro Tyr Met Ser Leu His Glu
        195                 200                 205 tcg tcg cag tgc cgc tat atg ctg cgc ctt ctg tca agt aag ttc tgt     672
Ser Ser Gln Cys Arg Tyr Met Leu Arg Leu Leu Ser Ser Lys Phe Cys
210                 215                 220 tcc gtg ccc cag ctg gat cac cca agc gag gag gag acg gtg cgg tgc     720
Ser Val Pro Gln Leu Asp His Pro Ser Glu Glu Glu Thr Val Arg Cys
```

```
Ser Val Pro Gln Leu Asp His Pro Ser Glu Glu Thr Val Arg Cys
225                 230                 235                 240 cag atg ttg gat gat tag                                              738
Gln Met Leu Asp Asp
                245
```

<210> SEQ ID NO 108
<211> LENGTH: 245
<212> TYPE: PRT
<213> ORGANISM: Leishmania infantum

<400> SEQUENCE: 108

```
Met Gly Cys Arg Ser Ser Cys Met Leu Trp Leu Ala Val Ala Ala Leu
1               5                   10                  15

Ala Val Leu Thr Leu Gln Leu Arg Ser Ala Ala Ala Pro Met Asp
            20                  25                  30

Leu Ser Asn Pro Val Glu His Asn His Phe Leu Leu Leu Ala Pro Tyr
            35                  40                  45

Gly Ala Ser His Arg Ser Gly Thr Gly Ala Asp Gly Glu Asn Thr Ala
50                  55                  60

Arg Tyr Val Gln Leu Ser Asn Gly Ser Arg Phe Val Cys Glu Thr Ala
65                  70                  75                  80

Ser Thr Arg Arg Glu Pro Leu Asp Ala Lys Ser Tyr Pro Leu Arg
                85                  90                  95

His Gln Met Glu Ser Leu Met Thr Val Met Arg Arg Ser Asp His Pro
            100                 105                 110

Cys Val His Tyr Ala Glu Glu Asn Tyr Val Thr Val Tyr Cys Trp Asp
            115                 120                 125

Asn Glu Val Arg Glu Asp Ala Leu Ser Glu Asn Lys Gly Arg Ser Leu
            130                 135                 140

Gly Arg Arg Arg Ile Asp Gly Pro Gln Ile Tyr Trp Thr Ser Asn Asp
145                 150                 155                 160

Ala Phe Gly Arg Tyr Val Ala Thr Val Tyr Gly Asp Gly Asp Glu Cys
                165                 170                 175

Pro Tyr Asp Lys Gly Arg Arg Ile Glu Thr Glu Val Arg Phe His Cys
            180                 185                 190

Arg Tyr Ser Glu Phe Glu Asn Pro Ile Pro Tyr Met Ser Leu His Glu
            195                 200                 205

Ser Ser Gln Cys Arg Tyr Met Leu Arg Leu Leu Ser Ser Lys Phe Cys
            210                 215                 220

Ser Val Pro Gln Leu Asp His Pro Ser Glu Glu Thr Val Arg Cys
225                 230                 235                 240

Gln Met Leu Asp Asp
                245
```

<210> SEQ ID NO 109
<211> LENGTH: 789
<212> TYPE: DNA
<213> ORGANISM: Trypanosoma brucei
<220> FEATURE:
<221> NAME/KEY: CDS
<222> LOCATION: (1)..(789)

<400> SEQUENCE: 109

```
atg tat gcg act cgt gct aag gtg ctg ttg ttc cgg tta gcg act ttc      48
Met Tyr Ala Thr Arg Ala Lys Val Leu Leu Phe Arg Leu Ala Thr Phe
1               5                   10                  15 gtg ctt gtg tct gtt gtg cgt ggc caa gag gaa gtc act gaa cac aaa      96
```

```
Val Leu Val Ser Val Val Arg Gly Gln Glu Glu Val Thr Glu His Lys
         20                  25                  30 tac aac atc gtg ttc tct cgc gac cca gtc ccc agt gga cta agt gag      144
Tyr Asn Ile Val Phe Ser Arg Asp Pro Val Pro Ser Gly Leu Ser Glu
             35                  40                  45 gaa cag tac tat cca atg cgg ctt agc aac ggt tcg gcc tac ttg tgc      192
Glu Gln Tyr Tyr Pro Met Arg Leu Ser Asn Gly Ser Ala Tyr Leu Cys
     50                  55                  60 gtg ctg cct gac att act gtc gaa gag aag aag aca ctt cag gcc gag      240
Val Leu Pro Asp Ile Thr Val Glu Glu Lys Lys Thr Leu Gln Ala Glu
 65                  70                  75                  80 gac agt gaa cta gat gtt ccg ctc tcc tta gaa cat gtg gct gtg gtt      288
Asp Ser Glu Leu Asp Val Pro Leu Ser Leu Glu His Val Ala Val Val
                 85                  90                  95 aac aga gcg ctg aag aac atg tgc tac acg atg gag gaa tcg tgg tgg      336
Asn Arg Ala Leu Lys Asn Met Cys Tyr Thr Met Glu Glu Ser Trp Trp
            100                 105                 110 acg tac cga tta tgt tgg ggg tca ggt gtg gag cag ttt cac cgt tct      384
Thr Tyr Arg Leu Cys Trp Gly Ser Gly Val Glu Gln Phe His Arg Ser
        115                 120                 125 gcg gtt gcc ggg gat agc aaa tcg aat gct ccg aag caa atg aaa gag      432
Ala Val Ala Gly Asp Ser Lys Ser Asn Ala Pro Lys Gln Met Lys Glu
    130                 135                 140 gac ccg cac ttc gtg ttg gga gtg gcc cca cct gcg gac gtg ttg gac      480
Asp Pro His Phe Val Leu Gly Val Ala Pro Pro Ala Asp Val Leu Asp
145                 150                 155                 160 ttg cgc tac ggc gtg aac aca aaa ggc ttg cga tat att tac acc ata      528
Leu Arg Tyr Gly Val Asn Thr Lys Gly Leu Arg Tyr Ile Tyr Thr Ile
                165                 170                 175 tac agc gat ggt tta acg tgt gat ctc aca caa ctc ccc cgg aca acg      576
Tyr Ser Asp Gly Leu Thr Cys Asp Leu Thr Gln Leu Pro Arg Thr Thr
            180                 185                 190 gag gtg cag ttg tac tgc gca cgc gag ggc gaa ggt aac agt cca act      624
Glu Val Gln Leu Tyr Cys Ala Arg Glu Gly Glu Gly Asn Ser Pro Thr
        195                 200                 205 atg cgt gtg cga gag gca gaa gtg tgt cgc tac atc gtt agt tta aca      672
Met Arg Val Arg Glu Ala Glu Val Cys Arg Tyr Ile Val Ser Leu Thr
    210                 215                 220 gcc aaa gag gtg tgt cta cta ggg ttg aag gaa att caa cag cgg tat      720
Ala Lys Glu Val Cys Leu Leu Gly Leu Lys Glu Ile Gln Gln Arg Tyr
225                 230                 235                 240 ggt gtg att acg tgt cat gaa aca aaa ccc acg aac aca gta gat tgg      768
Gly Val Ile Thr Cys His Glu Thr Lys Pro Thr Asn Thr Val Asp Trp
                245                 250                 255 aac aat aaa caa cag ggt tag                                          789
Asn Asn Lys Gln Gln Gly
            260

<210> SEQ ID NO 110
<211> LENGTH: 262
<212> TYPE: PRT
<213> ORGANISM: Trypanosoma brucei

<400> SEQUENCE: 110

Met Tyr Ala Thr Arg Ala Lys Val Leu Leu Phe Arg Leu Ala Thr Phe
1               5                   10                  15

Val Leu Val Ser Val Arg Gly Gln Glu Glu Val Thr Glu His Lys
         20                  25                  30

Tyr Asn Ile Val Phe Ser Arg Asp Pro Val Pro Ser Gly Leu Ser Glu
         35                  40                  45
```

```
Glu Gln Tyr Tyr Pro Met Arg Leu Ser Asn Gly Ser Ala Tyr Leu Cys
             50                  55                  60

Val Leu Pro Asp Ile Thr Val Glu Glu Lys Lys Thr Leu Gln Ala Glu
 65                  70                  75                  80

Asp Ser Glu Leu Asp Val Pro Leu Ser Leu Glu His Val Ala Val Val
                 85                  90                  95

Asn Arg Ala Leu Lys Asn Met Cys Tyr Thr Met Glu Glu Ser Trp Trp
            100                 105                 110

Thr Tyr Arg Leu Cys Trp Gly Ser Gly Val Glu Gln Phe His Arg Ser
            115                 120                 125

Ala Val Ala Gly Asp Ser Lys Ser Asn Ala Pro Lys Gln Met Lys Glu
            130                 135                 140

Asp Pro His Phe Val Leu Gly Val Ala Pro Ala Asp Val Leu Asp
145                 150                 155                 160

Leu Arg Tyr Gly Val Asn Thr Lys Gly Leu Arg Tyr Ile Tyr Thr Ile
                165                 170                 175

Tyr Ser Asp Gly Leu Thr Cys Asp Leu Thr Gln Leu Pro Arg Thr Thr
            180                 185                 190

Glu Val Gln Leu Tyr Cys Ala Arg Glu Gly Gly Asn Ser Pro Thr
            195                 200                 205

Met Arg Val Arg Glu Ala Glu Val Cys Arg Tyr Ile Val Ser Leu Thr
210                 215                 220

Ala Lys Glu Val Cys Leu Leu Gly Leu Lys Glu Ile Gln Gln Arg Tyr
225                 230                 235                 240

Gly Val Ile Thr Cys His Glu Thr Lys Pro Thr Asn Thr Val Asp Trp
                245                 250                 255

Asn Asn Lys Gln Gln Gly
            260

<210> SEQ ID NO 111
<211> LENGTH: 17
<212> TYPE: PRT
<213> ORGANISM: Artificial sequence
<220> FEATURE:
<223> OTHER INFORMATION: signal peptide

<400> SEQUENCE: 111

Met Leu Ser Leu Ala Glu Val Cys Leu Cys Pro Ala Val Arg Gly
 1               5                  10                  15

Val

<210> SEQ ID NO 112
<211> LENGTH: 20
<212> TYPE: PRT
<213> ORGANISM: Artificial Sequence
<220> FEATURE:
<223> OTHER INFORMATION: peptide signal

<400> SEQUENCE: 112

Met Arg Trp Ile Phe Leu Leu Leu Ala Val Leu Ser Val Leu Lys Pro
 1               5                  10                  15

Thr Asp Ala Thr
             20

<210> SEQ ID NO 113
<211> LENGTH: 31
<212> TYPE: PRT
<213> ORGANISM: Artificial Sequence
```

```
<220> FEATURE:
<223> OTHER INFORMATION: peptide signal

<400> SEQUENCE: 113

Met Ile Val Leu Asn Gly Ile Ser Glu Glu Gln Lys Lys Leu Ala Val
1               5                   10                  15

Val Gly Ala Ala Ala Phe Phe Ser Ser Ala Val Thr Ala Ala
            20                  25                  30

<210> SEQ ID NO 114
<211> LENGTH: 29
<212> TYPE: PRT
<213> ORGANISM: Artificial Sequence
<220> FEATURE:
<223> OTHER INFORMATION: peptide signal

<400> SEQUENCE: 114

Met Phe Pro Ala Gln Glu Phe Leu Arg Tyr Ser Met Lys Ser Leu Leu
1               5                   10                  15

Leu Ala Ser Ser Leu Ala Val Ala Ala Gly Trp Ala Tyr
            20                  25

<210> SEQ ID NO 115
<211> LENGTH: 18
<212> TYPE: PRT
<213> ORGANISM: Artificial Sequence
<220> FEATURE:
<223> OTHER INFORMATION: peptide signal

<400> SEQUENCE: 115

Met Arg Arg Thr Leu Phe Cys Leu Ser Thr Leu Val Lys Ile Gly Arg
1               5                   10                  15

Gly Ala

<210> SEQ ID NO 116
<211> LENGTH: 28
<212> TYPE: PRT
<213> ORGANISM: Artificial Sequence
<220> FEATURE:
<223> OTHER INFORMATION: peptide signal

<400> SEQUENCE: 116

Met Pro Ser Gly Lys Ala Thr Ala Leu Ala Ala Ala Thr Leu Leu Ala
1               5                   10                  15

Leu Leu Val Val Ala Pro Ala Val Ala Ser Ala Gln
            20                  25

<210> SEQ ID NO 117
<211> LENGTH: 27
<212> TYPE: PRT
<213> ORGANISM: Artificial Sequence
<220> FEATURE:
<223> OTHER INFORMATION: peptide signal

<400> SEQUENCE: 117

Met Arg Thr Ser Ser Ala Val Ser Phe Phe Leu Leu Ala Val Ala Ala
1               5                   10                  15

Val Leu Phe Ser Pro Phe Val Ala Asp Ala Phe
            20                  25

<210> SEQ ID NO 118
<211> LENGTH: 25
<212> TYPE: PRT
<213> ORGANISM: Artificial Sequence
```

```
<220> FEATURE:
<223> OTHER INFORMATION: peptide signal

<400> SEQUENCE: 118

Met Ser Ala Lys Ala Ser Arg Arg Cys Asn Arg Leu Ile Val Leu Phe
1               5                   10                  15

Ser Ser Ile Asn Gly Val Thr Ala Trp
            20                  25

<210> SEQ ID NO 119
<211> LENGTH: 25
<212> TYPE: PRT
<213> ORGANISM: Artificial Sequence
<220> FEATURE:
<223> OTHER INFORMATION: peptide signal

<400> SEQUENCE: 119

Met Ser Val Lys Ala Ser Arg Arg Cys Asn Arg Leu Ile Val Leu Phe
1               5                   10                  15

Ser Ser Ile Asn Asp Val Thr Ala Trp
            20                  25

<210> SEQ ID NO 120
<211> LENGTH: 32
<212> TYPE: PRT
<213> ORGANISM: Artificial Sequence
<220> FEATURE:
<223> OTHER INFORMATION: peptide signal

<400> SEQUENCE: 120

Met Ile His Thr Ala Arg Lys Lys Gln Phe Gly Leu Ser Ala Leu Ala
1               5                   10                  15

Leu Phe Val Leu Leu Leu Phe Leu Leu Val Cys Ile Thr Leu Gly Leu
            20                  25                  30

<210> SEQ ID NO 121
<211> LENGTH: 31
<212> TYPE: PRT
<213> ORGANISM: Artificial Sequence
<220> FEATURE:
<223> OTHER INFORMATION: peptide signal

<400> SEQUENCE: 121

Met Lys Gln Lys Met Arg Arg Lys Phe Cys Asp Val Leu Phe Pro Leu
1               5                   10                  15

Leu Leu Val Phe Leu Leu Thr Thr Met Glu Pro Val Thr Ala Glu
            20                  25                  30

<210> SEQ ID NO 122
<211> LENGTH: 43
<212> TYPE: PRT
<213> ORGANISM: Artificial Sequence
<220> FEATURE:
<223> OTHER INFORMATION: peptide signal

<400> SEQUENCE: 122

Met Tyr Ser Cys Leu Ser Leu Arg Leu Leu Val Gly Gly Met Gly
1               5                   10                  15

Phe Ala Ser Arg Arg Arg Ala Ala Met Val Leu Ser Leu Leu Val Phe
            20                  25                  30

Leu Leu Val Val Pro Cys Gly Val Phe Ser Gln
            35                  40
```

```
<210> SEQ ID NO 123
<211> LENGTH: 19
<212> TYPE: PRT
<213> ORGANISM: Artificial Sequence
<220> FEATURE:
<223> OTHER INFORMATION: peptide signal

<400> SEQUENCE: 123

Met Tyr Val Val Leu Phe Phe Val Leu Leu Ser Val Leu Gly Val
1               5                   10                  15

Asp Ala Glu

<210> SEQ ID NO 124
<211> LENGTH: 39
<212> TYPE: DNA
<213> ORGANISM: Artificial Sequence
<220> FEATURE:
<223> OTHER INFORMATION: oligonucleotide primer

<400> SEQUENCE: 124
catgagctta ctagtatgtt gtctctggca gaagtgtgt                      39

<210> SEQ ID NO 125
<211> LENGTH: 20
<212> TYPE: DNA
<213> ORGANISM: Artificial sequence
<220> FEATURE:
<223> OTHER INFORMATION: oligonucleotide primer

<400> SEQUENCE: 125
acggtgccca aaggcgtgta                                           20

<210> SEQ ID NO 126
<211> LENGTH: 55
<212> TYPE: DNA
<213> ORGANISM: Artificial sequence
<220> FEATURE:
<223> OTHER INFORMATION: oligonucleotide primer

<400> SEQUENCE: 126
cacacggaag ctttcaatga tgatgatgat gatggcgacc aaacctagcc ataag    55

<210> SEQ ID NO 127
<211> LENGTH: 39
<212> TYPE: DNA
<213> ORGANISM: Artificial sequence
<220> FEATURE:
<223> OTHER INFORMATION: oligonucleotide primer

<400> SEQUENCE: 127
ctgggggaat tcatgcggtg gattttttg ttacttgcc                       39

<210> SEQ ID NO 128
<211> LENGTH: 21
<212> TYPE: DNA
<213> ORGANISM: Artificial sequence
<220> FEATURE:
<223> OTHER INFORMATION: oligonucleotide primer

<400> SEQUENCE: 128
ccgatacgtc caccacccct c                                         21

<210> SEQ ID NO 129
<211> LENGTH: 56
<212> TYPE: DNA
<213> ORGANISM: Artificial sequence
```

<220> FEATURE:
<223> OTHER INFORMATION: oligonucleotide primer

<400> SEQUENCE: 129
cgtcggaagc ttctagtgat ggtggtggtg atggacaagt tcgtggcatg taattg      56

<210> SEQ ID NO 130
<211> LENGTH: 39
<212> TYPE: DNA
<213> ORGANISM: Artificial sequence
<220> FEATURE:
<223> OTHER INFORMATION: oligonucleotide primer

<400> SEQUENCE: 130
acacggacta gtatgattgt attgaatgga atttctgag                         39

<210> SEQ ID NO 131
<211> LENGTH: 22
<212> TYPE: DNA
<213> ORGANISM: Artificial sequence
<220> FEATURE:
<223> OTHER INFORMATION: oligonucleotide primer

<400> SEQUENCE: 131
ctaatagtcc gaagtcgttg cg                                           22

<210> SEQ ID NO 132
<211> LENGTH: 53
<212> TYPE: DNA
<213> ORGANISM: Artificial sequence
<220> FEATURE:
<223> OTHER INFORMATION: oligonucleotide primer

<400> SEQUENCE: 132
ctacacaagc ttttagtgat ggtgatggtg atggctgcgc ctccacaccg tgc         53

<210> SEQ ID NO 133
<211> LENGTH: 38
<212> TYPE: DNA
<213> ORGANISM: Artificial sequence
<220> FEATURE:
<223> OTHER INFORMATION: oligonucleotide primer

<400> SEQUENCE: 133
ctgataggca ctagtatgtt tccggcgcag gaattcct                          38

<210> SEQ ID NO 134
<211> LENGTH: 26
<212> TYPE: DNA
<213> ORGANISM: Artificial sequence
<220> FEATURE:
<223> OTHER INFORMATION: oligonucleotide primer

<400> SEQUENCE: 134
cccctttcag gtgaccatta caagag                                       26

<210> SEQ ID NO 135
<211> LENGTH: 55
<212> TYPE: DNA
<213> ORGANISM: Artificial sequence
<220> FEATURE:
<223> OTHER INFORMATION: oligonucleotide primer

<400> SEQUENCE: 135
gccgtcaagc ttttagtggt ggtggtggtg atgctccgct cccaacttca aacga       55

```
<210> SEQ ID NO 136
<211> LENGTH: 39
<212> TYPE: DNA
<213> ORGANISM: Artificial sequence
<220> FEATURE:
<223> OTHER INFORMATION: oligonucleotide primer

<400> SEQUENCE: 136
ctgataggca ctagtatgcg tcgcacttta ttttgtctg                        39

<210> SEQ ID NO 137
<211> LENGTH: 20
<212> TYPE: DNA
<213> ORGANISM: Artificial sequence
<220> FEATURE:
<223> OTHER INFORMATION: oligonucleotide primer

<400> SEQUENCE: 137
ctctccaact cgtacggcga                                             20

<210> SEQ ID NO 138
<211> LENGTH: 59
<212> TYPE: DNA
<213> ORGANISM: Artificial sequence
<220> FEATURE:
<223> OTHER INFORMATION: oligonucleotide primer

<400> SEQUENCE: 138
ctgcaggcaa gcttctaatg gtggtgatgg tgatgttatg ataccggcat caagtcccc   59

<210> SEQ ID NO 139
<211> LENGTH: 35
<212> TYPE: DNA
<213> ORGANISM: Artificial sequence
<220> FEATURE:
<223> OTHER INFORMATION: oligonucleotide primer

<400> SEQUENCE: 139
cgcactcact agtatgccct ctggcaaagc aactg                            35

<210> SEQ ID NO 140
<211> LENGTH: 21
<212> TYPE: DNA
<213> ORGANISM: Artificial sequence
<220> FEATURE:
<223> OTHER INFORMATION: oligonucleotide primer

<400> SEQUENCE: 140
tcactgctcc gccctggttt c                                           21

<210> SEQ ID NO 141
<211> LENGTH: 54
<212> TYPE: DNA
<213> ORGANISM: Artificial sequence
<220> FEATURE:
<223> OTHER INFORMATION: oligonucleotide primer

<400> SEQUENCE: 141
cgctccctcg agttagtggt gatggtggtg atgggcagca tttaccgacc ctga        54

<210> SEQ ID NO 142
<211> LENGTH: 36
<212> TYPE: DNA
<213> ORGANISM: Artificial sequence
<220> FEATURE:
<223> OTHER INFORMATION: oligonucleotide primer
```

<400> SEQUENCE: 142
gctcagccaa gcttatgcgc acttcttctg ccgtgt                                   36

<210> SEQ ID NO 143
<211> LENGTH: 25
<212> TYPE: DNA
<213> ORGANISM: Artificial sequence
<220> FEATURE:
<223> OTHER INFORMATION: oligonucleotide primer

<400> SEQUENCE: 143
atcggggagt tttgtgcagg ttgag                                               25

<210> SEQ ID NO 144
<211> LENGTH: 58
<212> TYPE: DNA
<213> ORGANISM: Artificial sequence
<220> FEATURE:
<223> OTHER INFORMATION: oligonucleotide primer

<400> SEQUENCE: 144
gtggtcttct cgagttagtg atggtggtgg tgatggtcga ctttaatgct cgcgtata          58

<210> SEQ ID NO 145
<211> LENGTH: 37
<212> TYPE: DNA
<213> ORGANISM: Artificial sequence
<220> FEATURE:
<223> OTHER INFORMATION: oligonucleotide primer

<400> SEQUENCE: 145
ctgcccagta ctagtatgtc tgctaaagcc tcacggc                                  37

<210> SEQ ID NO 146
<211> LENGTH: 23
<212> TYPE: DNA
<213> ORGANISM: Artificial sequence
<220> FEATURE:
<223> OTHER INFORMATION: oligonucleotide primer

<400> SEQUENCE: 146
tccaggtagt cacccattcc gtg                                                 23

<210> SEQ ID NO 147
<211> LENGTH: 54
<212> TYPE: DNA
<213> ORGANISM: Artificial sequence
<220> FEATURE:
<223> OTHER INFORMATION: oligonucleotide primer

<400> SEQUENCE: 147
ctcagccaag cttttaatga tgatgatgat ggtgtcgtct cgcctcacag tgct               54

<210> SEQ ID NO 148
<211> LENGTH: 38
<212> TYPE: DNA
<213> ORGANISM: Artificial sequence
<220> FEATURE:
<223> OTHER INFORMATION: oligonucleotide primer

<400> SEQUENCE: 148
ctgcgctgga ctagtatgtc tgttaaagcc tcacggcg                                 38

<210> SEQ ID NO 149

```
<211> LENGTH: 22
<212> TYPE: DNA
<213> ORGANISM: Artificial sequence
<220> FEATURE:
<223> OTHER INFORMATION: oligonucleotide primer

<400> SEQUENCE: 149
ccattccgtg accgccgtag ac                                              22

<210> SEQ ID NO 150
<211> LENGTH: 53
<212> TYPE: DNA
<213> ORGANISM: Artificial sequence
<220> FEATURE:
<223> OTHER INFORMATION: oligonucleotide primer

<400> SEQUENCE: 150
ctcggtaagc ttttaatgat gatgatgatg gtgtcgtctc gcctcacagt gct            53

<210> SEQ ID NO 151
<211> LENGTH: 39
<212> TYPE: DNA
<213> ORGANISM: Artificial sequence
<220> FEATURE:
<223> OTHER INFORMATION: oligonucleotide primer

<400> SEQUENCE: 151
ctcgctggaa ttcatgcggt gggtgatagt tgtatttgc                            39

<210> SEQ ID NO 152
<211> LENGTH: 22
<212> TYPE: DNA
<213> ORGANISM: Artificial sequence
<220> FEATURE:
<223> OTHER INFORMATION: oligonucleotide primer

<400> SEQUENCE: 152
cgccaacaac gtagttgcca ag                                              22

<210> SEQ ID NO 153
<211> LENGTH: 54
<212> TYPE: DNA
<213> ORGANISM: Artificial sequence
<220> FEATURE:
<223> OTHER INFORMATION: oligonucleotide primer

<400> SEQUENCE: 153
acggacctcg agttagtgat ggtggtggtg atgcttgttg agtttggagc ggcg           54

<210> SEQ ID NO 154
<211> LENGTH: 39
<212> TYPE: DNA
<213> ORGANISM: Artificial sequence
<220> FEATURE:
<223> OTHER INFORMATION: oligonucleotide primer

<400> SEQUENCE: 154
cgcgggacta gtatgaaaca aaaaatgcga cgcaaattg                            39

<210> SEQ ID NO 155
<211> LENGTH: 25
<212> TYPE: DNA
<213> ORGANISM: Artificial sequence
<220> FEATURE:
<223> OTHER INFORMATION: oligonucleotide primer

<400> SEQUENCE: 155
```
gtgaggatgg ggaaccaaaa gagtc                                        25

<210> SEQ ID NO 156
<211> LENGTH: 57
<212> TYPE: DNA
<213> ORGANISM: Artificial sequence
<220> FEATURE:
<223> OTHER INFORMATION: oligonucleotide primer

<400> SEQUENCE: 156
cagccaagct tctagtgatg gtgatgatga tggacattct tcttctttgt aaagtag       57

<210> SEQ ID NO 157
<211> LENGTH: 37
<212> TYPE: DNA
<213> ORGANISM: Artificial sequence
<220> FEATURE:
<223> OTHER INFORMATION: oligonucleotide primer

<400> SEQUENCE: 157
cgcggcacta gtatgtattc atgtttgtcg ctgaggc                            37

<210> SEQ ID NO 158
<211> LENGTH: 21
<212> TYPE: DNA
<213> ORGANISM: Artificial sequence
<220> FEATURE:
<223> OTHER INFORMATION: oligonucleotide primer

<400> SEQUENCE: 158
gcagcaacgg caacaaagag c                                             21

<210> SEQ ID NO 159
<211> LENGTH: 54
<212> TYPE: DNA
<213> ORGANISM: Artificial sequence
<220> FEATURE:
<223> OTHER INFORMATION: oligonucleotide primer

<400> SEQUENCE: 159
catggcaagc ttttagtgat ggtggtggtg atgctcctct ctgggtttcc ttcg          54

<210> SEQ ID NO 160
<211> LENGTH: 37
<212> TYPE: DNA
<213> ORGANISM: Artificial sequence
<220> FEATURE:
<223> OTHER INFORMATION: oligonucleotide primer

<400> SEQUENCE: 160
cgcgccacta gtatgtacgt cgtgcttttt ttcgttt                            37

<210> SEQ ID NO 161
<211> LENGTH: 21
<212> TYPE: DNA
<213> ORGANISM: Artificial sequence
<220> FEATURE:
<223> OTHER INFORMATION: oligonucleotide primer

<400> SEQUENCE: 161
cgcatatttc cgctccgttc c                                             21

<210> SEQ ID NO 162
<211> LENGTH: 55
<212> TYPE: DNA

```
<213> ORGANISM: Artificial sequence
<220> FEATURE:
<223> OTHER INFORMATION: oligonucleotide primer

<400> SEQUENCE: 162
agcagtccaa gcttttagtg atggtgatga tgatggccgc accagcgctc cagaa         55

<210> SEQ ID NO 163
<211> LENGTH: 37
<212> TYPE: DNA
<213> ORGANISM: Artificial sequence
<220> FEATURE:
<223> OTHER INFORMATION: oligonucleotide primer

<400> SEQUENCE: 163
gggtgccact agtatgcgtg agattgtgtg cgttcag                             37

<210> SEQ ID NO 164
<211> LENGTH: 22
<212> TYPE: DNA
<213> ORGANISM: Artificial sequence
<220> FEATURE:
<223> OTHER INFORMATION: oligonucleotide primer

<400> SEQUENCE: 164
gggcggaaga tctgcccgta tg                                             22

<210> SEQ ID NO 165
<211> LENGTH: 57
<212> TYPE: DNA
<213> ORGANISM: Artificial sequence
<220> FEATURE:
<223> OTHER INFORMATION: oligonucleotide primer

<400> SEQUENCE: 165
agcgctcaag cttttagtga tggtggtggt gatggtactg ctcctcctcg tcgaact       57

<210> SEQ ID NO 166
<211> LENGTH: 34
<212> TYPE: DNA
<213> ORGANISM: Artificial sequence
<220> FEATURE:
<223> OTHER INFORMATION: oligonucleotide primer

<400> SEQUENCE: 166
catgaccact agtatggcca aaacagcgct tctc                                34

<210> SEQ ID NO 167
<211> LENGTH: 55
<212> TYPE: DNA
<213> ORGANISM: Artificial sequence
<220> FEATURE:
<223> OTHER INFORMATION: oligonucleotide primer

<400> SEQUENCE: 167
gcagtccaag cttttagtga tggtgatgat gatgaggtgt tctcaggggt gacga         55

<210> SEQ ID NO 168
<211> LENGTH: 34
<212> TYPE: DNA
<213> ORGANISM: Artificial sequence
<220> FEATURE:
<223> OTHER INFORMATION: oligonucleotide primer

<400> SEQUENCE: 168
catgctcgac tagtatgggg tgccgcagta gctg                                34
```

<210> SEQ ID NO 169
<211> LENGTH: 56
<212> TYPE: DNA
<213> ORGANISM: Artificial sequence
<220> FEATURE:
<223> OTHER INFORMATION: oligonucleotide primer

<400> SEQUENCE: 169
gcagtccaag cttttaatga tgatggtggt gatgatcatc caacatctgg caccgc        56

<210> SEQ ID NO 170
<211> LENGTH: 29
<212> TYPE: DNA
<213> ORGANISM: Artificial sequence
<220> FEATURE:
<223> OTHER INFORMATION: oligonucleotide primer

<400> SEQUENCE: 170
atgattgaac aagatggatt gcacgcagg                                       29

<210> SEQ ID NO 171
<211> LENGTH: 20
<212> TYPE: DNA
<213> ORGANISM: Artificial sequence
<220> FEATURE:
<223> OTHER INFORMATION: oligonucleotide primer

<400> SEQUENCE: 171
tcagaagaac tcgtcaagaa                                                 20

<210> SEQ ID NO 172
<211> LENGTH: 1593
<212> TYPE: DNA
<213> ORGANISM: Leishmania major
<220> FEATURE:
<221> NAME/KEY: CDS
<222> LOCATION: (1)..(1593)

<400> SEQUENCE: 172

```
atg gcc aag aca acg ctt ctc gtg tgc gct ctg ctc gcc ctc gtc atg       48
Met Ala Lys Thr Thr Leu Leu Val Cys Ala Leu Leu Ala Leu Val Met
1               5                   10                  15 tgc ctg gca gcg aca gcc gtc tcg gcg cag cag tcg ctg gcg tgc caa       96
Cys Leu Ala Ala Thr Ala Val Ser Ala Gln Gln Ser Leu Ala Cys Gln
            20                  25                  30 atg gtg tgg caa gct ccg tcc cct aac aac agc ctg ctg gag tgc ctg      144
Met Val Trp Gln Ala Pro Ser Pro Asn Asn Ser Leu Leu Glu Cys Leu
        35                  40                  45 ggg aac acg gat cgc atc cgg tct cag tgg ccc tac tac ctg tat ccc      192
Gly Asn Thr Asp Arg Ile Arg Ser Gln Trp Pro Tyr Tyr Leu Tyr Pro
    50                  55                  60 gcc ttc gct gcg ctc atc ttc atc ttt acg gtg att ggg ctg ccg att      240
Ala Phe Ala Ala Leu Ile Phe Ile Phe Thr Val Ile Gly Leu Pro Ile
65                  70                  75                  80 ctg ttc tgc tgc cac tgc tgc agc tgc tgc gag gcg tat gtg aag ccg      288
Leu Phe Cys Cys His Cys Cys Ser Cys Cys Glu Ala Tyr Val Lys Pro
                85                  90                  95 aag gcg gag acg gac ctc ggc gtt gcc cgc tgc tgc cta tgg atg ctg      336
Lys Ala Glu Thr Asp Leu Gly Val Ala Arg Cys Cys Leu Trp Met Leu
            100                 105                 110 atc gtg att tcg gtg ctt gtg gcg tgc ggc gtg tgc gtg ctg ctg gtg      384
Ile Val Ile Ser Val Leu Val Ala Cys Gly Val Cys Val Leu Leu Val
        115                 120                 125
```

-continued

| | | |
|---|---|---|
| tat ggc tcc gtc tta ctg gag cag gca gcc acg caa att atc cat gac<br>Tyr Gly Ser Val Leu Leu Glu Gln Ala Ala Thr Gln Ile Ile His Asp<br>    130                       135                       140 | 432 |
| acc gag tat cgc acg ctt gat tac ttc aac gac atc cgt gcg aac atc<br>Thr Glu Tyr Arg Thr Leu Asp Tyr Phe Asn Asp Ile Arg Ala Asn Ile<br>145                     150                     155                160 | 480 |
| acg atg ctg ctg aca aac tac agc gcg gac cca ccg ata cca ccg tcg<br>Thr Met Leu Leu Thr Asn Tyr Ser Ala Asp Pro Pro Ile Pro Pro Ser<br>                  165                      170                   175 | 528 |
| atc gac ctt agg acc ttt gac gct gtg aac gat gat att acc cac tac<br>Ile Asp Leu Arg Thr Phe Asp Ala Val Asn Asp Asp Ile Thr His Tyr<br>            180                       185                   190 | 576 |
| gtg cat gtg gcg cgc aac aac tac ctc cag tac ttc cgc gct gcc gag<br>Val His Val Ala Arg Asn Asn Tyr Leu Gln Tyr Phe Arg Ala Ala Glu<br>       195                       200                   205 | 624 |
| att gtg gcg tgc tgt gtc ggc agc gtg ggt gtt ttc ctg atg ctg tgc<br>Ile Val Ala Cys Cys Val Gly Ser Val Gly Val Phe Leu Met Leu Cys<br>210                     215                     220 | 672 |
| atg ctg gtt ttt gcg ctg tgc cgt tgc aat ggg atc tgc ccg att gcg<br>Met Leu Val Phe Ala Leu Cys Arg Cys Asn Gly Ile Cys Pro Ile Ala<br>225                     230                     235                240 | 720 |
| tgg agc tgc ctg tac ttc gtg ttc gcg ctt gca ttt gcg ttg ctt gcg<br>Trp Ser Cys Leu Tyr Phe Val Phe Ala Leu Ala Phe Ala Leu Leu Ala<br>                    245                       250                   255 | 768 |
| gtg ttg ttc acg ata tgc atc tac gtg ctg tcc gct ggc tgc ggc gag<br>Val Leu Phe Thr Ile Cys Ile Tyr Val Leu Ser Ala Gly Cys Gly Glu<br>            260                       265                   270 | 816 |
| gtg ggc ctc cag cat ggt cgt gag cct ggc gtc ttc cag tgg tac ctg<br>Val Gly Leu Gln His Gly Arg Glu Pro Gly Val Phe Gln Trp Tyr Leu<br>       275                       280                   285 | 864 |
| gtg ccg tgg tgc gag aag gag ttc aac ttc caa gcg ctg cgg gct cag<br>Val Pro Trp Cys Glu Lys Glu Phe Asn Phe Gln Ala Leu Arg Ala Gln<br>            290                       295                   300 | 912 |
| gtg cag agc cag gag cag cag gtc tcg cag agc gcc tgc gcg gag ctc<br>Val Gln Ser Gln Glu Gln Gln Val Ser Gln Ser Ala Cys Ala Glu Leu<br>305                     310                     315                320 | 960 |
| ttg aac ttc tgt gac aac gat ccg cat tac tcg ttg gag act aaa aac<br>Leu Asn Phe Cys Asp Asn Asp Pro His Tyr Ser Leu Glu Thr Lys Asn<br>                    325                      330                   335 | 1008 |
| cac atc ttc atg tgc ggc aac agc atc acc gat aag agc cag tgc gac<br>His Ile Phe Met Cys Gly Asn Ser Ile Thr Asp Lys Ser Gln Cys Asp<br>            340                       345                   350 | 1056 |
| tcg ctg gac gac gtg gtg gac gtt gtt ctg agc aca tac gtg aag ccg<br>Ser Leu Asp Asp Val Val Asp Val Val Leu Ser Thr Tyr Val Lys Pro<br>       355                       360                   365 | 1104 |
| atg ctg acg aac acg cta tgt gcc aac cag acg ggc atg gag tac ctg<br>Met Leu Thr Asn Thr Leu Cys Ala Asn Gln Thr Gly Met Glu Tyr Leu<br>            370                       375                   380 | 1152 |
| gag aag tgt acg ctg atc tcc tgc tca tcg cgg tgt gta aac tac aaa<br>Glu Lys Cys Thr Leu Ile Ser Cys Ser Ser Arg Cys Val Asn Tyr Lys<br>385                     390                     395                400 | 1200 |
| ttc ccg gcc ctg gat gcc agg acg tac gcc att caa att ttg cag gct<br>Phe Pro Ala Leu Asp Ala Arg Thr Tyr Ala Ile Gln Ile Leu Gln Ala<br>                    405                      410                   415 | 1248 |
| gcc gac ttt gct gcg aat gcg agc act gcg ctg tcg tac gtg tgg ccg<br>Ala Asp Phe Ala Ala Asn Ala Ser Thr Ala Leu Ser Tyr Val Trp Pro<br>            420                       425                   430 | 1296 |
| ctg ctg gac tgc aac ttc atc att gac aag atc gcc aac aca gtc gag<br>Leu Leu Asp Cys Asn Phe Ile Ile Asp Lys Ile Ala Asn Thr Val Glu | 1344 |

```
                435                 440                 445
acg cag agc tac aac agc agc ttc acc acg cag agc gaa tat gtc cgc      1392
Thr Gln Ser Tyr Asn Ser Ser Phe Thr Thr Gln Ser Glu Tyr Val Arg
    450                 455                 460 agc tgc tct gcg gtc cgc act tcc tct gtg atg ctg ggt acc ggg ttc      1440
Ser Cys Ser Ala Val Arg Thr Ser Ser Val Met Leu Gly Thr Gly Phe
465                 470                 475                 480 ttt gtc ggg gcg ctc atg ttc att ctc ggc att cac gtc atg cat cgt      1488
Phe Val Gly Ala Leu Met Phe Ile Leu Gly Ile His Val Met His Arg
                485                 490                 495 ggt gcg ttt atc tgg gct gcc ggc aag aag aac ggt gca gtg cag aaa      1536
Gly Ala Phe Ile Trp Ala Ala Gly Lys Lys Asn Gly Ala Val Gln Lys
            500                 505                 510 acg aag gat gtt tca cca ccg gac aat gct gcc tcg tcg aat ccg cga      1584
Thr Lys Asp Val Ser Pro Pro Asp Asn Ala Ala Ser Ser Asn Pro Arg
        515                 520                 525 aca cct taa                                                           1593
Thr Pro
    530

<210> SEQ ID NO 173
<211> LENGTH: 530
<212> TYPE: PRT
<213> ORGANISM: Leishmania major

<400> SEQUENCE: 173

Met Ala Lys Thr Thr Leu Leu Val Cys Ala Leu Leu Ala Leu Val Met
1               5                   10                  15

Cys Leu Ala Ala Thr Ala Val Ser Ala Gln Gln Ser Leu Ala Cys Gln
                20                  25                  30

Met Val Trp Gln Ala Pro Ser Pro Asn Asn Ser Leu Leu Glu Cys Leu
            35                  40                  45

Gly Asn Thr Asp Arg Ile Arg Ser Gln Trp Pro Tyr Tyr Leu Tyr Pro
        50                  55                  60

Ala Phe Ala Ala Leu Ile Phe Ile Phe Thr Val Ile Gly Leu Pro Ile
65                  70                  75                  80

Leu Phe Cys Cys His Cys Cys Ser Cys Cys Glu Ala Tyr Val Lys Pro
                85                  90                  95

Lys Ala Glu Thr Asp Leu Gly Val Ala Arg Cys Cys Leu Trp Met Leu
                100                 105                 110

Ile Val Ile Ser Val Leu Val Ala Cys Gly Val Cys Val Leu Leu Val
            115                 120                 125

Tyr Gly Ser Val Leu Leu Glu Gln Ala Ala Thr Gln Ile Ile His Asp
        130                 135                 140

Thr Glu Tyr Arg Thr Leu Asp Tyr Phe Asn Asp Ile Arg Ala Asn Ile
145                 150                 155                 160

Thr Met Leu Leu Thr Asn Tyr Ser Ala Asp Pro Pro Ile Pro Pro Ser
                165                 170                 175

Ile Asp Leu Arg Thr Phe Asp Ala Val Asn Asp Ile Thr His Tyr
            180                 185                 190

Val His Val Ala Arg Asn Asn Tyr Leu Gln Tyr Phe Arg Ala Ala Glu
        195                 200                 205

Ile Val Ala Cys Cys Val Gly Ser Val Gly Val Phe Leu Met Leu Cys
    210                 215                 220

Met Leu Val Phe Ala Leu Cys Arg Cys Asn Gly Ile Cys Pro Ile Ala
225                 230                 235                 240
```

```
Trp Ser Cys Leu Tyr Phe Val Phe Ala Leu Ala Phe Ala Leu Leu Ala
            245             250             255

Val Leu Phe Thr Ile Cys Ile Tyr Val Leu Ser Ala Gly Cys Gly Glu
            260             265             270

Val Gly Leu Gln His Gly Arg Glu Pro Gly Val Phe Gln Trp Tyr Leu
            275             280             285

Val Pro Trp Cys Glu Lys Glu Phe Asn Phe Gln Ala Leu Arg Ala Gln
            290             295             300

Val Gln Ser Gln Glu Gln Gln Val Ser Gln Ser Ala Cys Ala Glu Leu
305             310             315             320

Leu Asn Phe Cys Asp Asn Asp Pro His Tyr Ser Leu Glu Thr Lys Asn
            325             330             335

His Ile Phe Met Cys Gly Asn Ser Ile Thr Asp Lys Ser Gln Cys Asp
            340             345             350

Ser Leu Asp Asp Val Val Asp Val Val Leu Ser Thr Tyr Val Lys Pro
            355             360             365

Met Leu Thr Asn Thr Leu Cys Ala Asn Gln Thr Gly Met Glu Tyr Leu
            370             375             380

Glu Lys Cys Thr Leu Ile Ser Cys Ser Ser Arg Cys Val Asn Tyr Lys
385             390             395             400

Phe Pro Ala Leu Asp Ala Arg Thr Tyr Ala Ile Gln Ile Leu Gln Ala
            405             410             415

Ala Asp Phe Ala Ala Asn Ala Ser Thr Ala Leu Ser Tyr Val Trp Pro
            420             425             430

Leu Leu Asp Cys Asn Phe Ile Ile Asp Lys Ile Ala Asn Thr Val Glu
            435             440             445

Thr Gln Ser Tyr Asn Ser Ser Phe Thr Thr Gln Ser Glu Tyr Val Arg
    450             455             460

Ser Cys Ser Ala Val Arg Thr Ser Ser Val Met Leu Gly Thr Gly Phe
465             470             475             480

Phe Val Gly Ala Leu Met Phe Ile Leu Gly Ile His Val Met His Arg
            485             490             495

Gly Ala Phe Ile Trp Ala Ala Gly Lys Lys Asn Gly Ala Val Gln Lys
            500             505             510

Thr Lys Asp Val Ser Pro Pro Asp Asn Ala Ala Ser Ser Asn Pro Arg
            515             520             525

Thr Pro
530
```

METHOD FOR THE SCREENING OF CONSERVED SECRETED PROTEINS

The present invention relates to conserved secreted protein in protozoan parasites, to a method for the screening said proteins and to therapeutical applications thereof. More particularly, the present invention relates to excreted/secreted polypeptides and polynucleotides encoding same, compositions comprising the same, and methods of vaccination against protozoan parasites causing important diseases in humans.

The Trypanosomatidae comprise a large group of parasitic protozoa, some of which cause important diseases in humans. The three model organisms that have been most extensively studied are *Trypanosoma brucei*, the causative agent of African sleeping sickness, *T. cruzi*, responsible for Chagas disease in South America, and *Leishmania*, which causes Leishmaniasis in Asia, South America and Mediterranean countries. Half a billion people, primarily in tropical and subtropical areas of the world, are at risk of contracting these diseases. It is estimated that more than 20 million individuals are infected, resulting in extensive suffering and more than 100,000 deaths per year.

Chagas disease is one of the most important parasitic diseases and affects 15 million people in Central and South America. The annual worldwide incidence of new cases is estimated at around 50,000-200,000.

The diagnosis of *T. cruzi* infection is difficult because the symptoms of the infection are often absent or non-specific, and because the parasites themselves are usually below the level of detection in the infected subjects (Tarleton et al., 2007). Therefore, diagnosis generally depends on the measurement of *T. cruzi*-specific antibodies produced in response to the infection.

Conventional serological tests, such as the indirect hemagglutination assay, indirect immunofluorescence assay, and enzyme-linked immunosorbent assay (ELISA), are used widely in the countries where the infection is endemic. Most are based on the use of whole or semi-purified antigenic fractions from *T. cruzi* epimastigotes grown in axenic culture. A persistent problem with the conventional assays is the occurrence of inconclusive and false-positive results. Thus, there is no consensus on which parasite antigen preparation is best for detecting antibodies to *T. cruzi*. The World Health Organization and other expert groups recommend using at least two tests in parallel to confirm *T. cruzi* infection. Due to the lack of a true gold standard for the serologic diagnosis of *T. cruzi* infection, development of new diagnostic tools remains a challenge for Chagas disease.

High-sensitivity and high specificity ELISA methods using recombinant or synthetic peptides as antigens have been reported. The inclusion of recombinant antigens and synthetic peptides for the serological diagnosis of *T. cruzi* infection has been an advantage in terms of specificity increase. Nevertheless, single recombinant antigens display lower sensitivity when compared with conventional test using whole parasite extracts. The use of cocktails of recombinant antigens, mixtures of synthetic peptides or multi-epitope antigens have shown to increase sensitivity.

It is widely assumed that secreted/excreted factors in *T. cruzi* are highly immunogenic. Indeed, trypomastigote forms release several antigens into the supernatant of infected cell cultures. This complex mixture of antigens, termed TESA (trypomastigote excretory-secretory antigens), is highly immunogenic and has been used for the diagnosis of both acute and chronic Chagas. Remarkably, the components of the TESA mixture are currently unknown.

In order to complete their life cycle, these parasites have to adapt and develop in an insect vector (a tsetse fly, a triatomine bug, or a sandfly, respectively), and in a vertebrate host. These single-celled organisms have developed several strategies to modify their surrounding environment, modulate host immune responses, or interfere with the host's anti-microbial activity. Materials secreted by the parasite play pivotal roles in these processes. Secreted proteases belonging to the family of cystein- or metallo-proteases are generally thought to be involved in the manipulation of host immune responses in insect and vertebrate hosts. Biochemical analysis of the extracellular gp63 of *Leishmania* has revealed two forms of the protein, one released from the cell surface and another that is apparently directly secreted. The secreted form provides protection for *Leishmania* against insect-derived antimicrobial peptides. Parasites can also secrete enzymes involved in nutritional processes. *Leishmania*, like other trypanosomatids, are purine auxotrophs, and therefore are entirely dependent upon salvaging these essential nutrients from their hosts. To satisfy its essential purine requirements, *Leishmania* secretes a nuclease that may function externally of the parasite to hydrolyze and access host-derived nucleic acids. Secreted materials can also be directly involved in the invasion of target cells. Tc-TOX, a pore-forming protein of *T. cruzi*, allows the parasite to escape the endosome and reach the cytoplasm, its natural cellular environment. Experimental evidence suggests that *Leishmania* also possess a pore-forming protein that contributes to their release from host macrophages.

Together, these findings demonstrate that secreted materials are involved in processes that help the parasite survive in an environment more favorable for its own development. However, all of the factors in these processes are currently not clearly identified.

In eukaryotes, soluble secreted proteins typically contain N-terminal signal peptides that direct them to the translocation apparatus of the endoplasmic reticulum (ER). Following vesicular transport from the ER via the Golgi apparatus to the cell surface, lumenal proteins are released into the extracellular space by fusion of Golgi-derived secretory vesicles with the plasma membrane.

In trypanosomatids, it is presumed that molecules destined for the cell surface and secretion follow a typical eukaryotic pathway traveling from the ER to the Golgi apparatus, then to the cell surface via a flagellar reservoir membrane called the flagellar pocket. Nevertheless, a recent proteomic approach applied to the *Leishmania* secretome suggested that this parasite predominantly uses non-classical secretion pathways to directly export proteins, including the release of microvesicles (Silverman J M, Chan S K, Robinson D P, Dwyer D M, Nandan D, Foster L J, Reiner N E: Proteomic analysis of the secretome of *Leishmania donovani*. Genome Biol 2008, 9 (2):R35).

Comparative analyses have revealed that genomes of the trypanosomatid parasites causing disease in humans, *Leishmania major*, *Trypanosoma cruzi* and *Trypanosoma brucei* are highly conserved. In addition, about 50% of predicted proteins in the genome were annotated as "hypothetical proteins even if for many of them some evidence of protein expression exists (El-Sayed N M, Myler P J, Blandin G, Berriman M, Crabtree J, Aggarwal G, Caler E, Renauld H, Worthey E A, Hertz-Fowler C et al: Comparative genomics of trypanosomatid parasitic protozoa. Science 2005, 309 (5733):404-409; Atwood J A, 3rd, Weatherly D B, Minning T A, Bundy B, Cavola C, Opperdoes F R, Orlando R, Tarleton R L: The *Trypanosoma cruzi* proteome. Science 2005, 309 (5733):473-476; Jones A, Faldas A, Foucher A, Hunt E, Tait A, Wastling J M, Turner C M: Visualisation and analysis of proteomic data from the procyclic form of *Trypanosoma brucei*. Proteomics 2006, 6 (1):259-267). Progress in controlling infections caused by these pathogens requires an improved understanding of the biology of these parasites so as to design novel treatment strategies. It is widely assumed that excreted/secreted factors play crucial roles in the biology or virulence of trypanosomatid parasites and may therefore represent targets for vaccines or rational drug design. In trypanosomatids the secretion process is not fully understood and various pathways may contribute to the formation of the "extracellular proteome". Identification of secreted materials would enhance efforts towards understanding mechanisms of protein secretion in these medically important parasites The availability of three draft trypanosomatid genome sequences provides valuable data for protein-mining using bioinformatic tools, especially for the localization or prediction of function for hypothetical proteins. Given that a significant number of trypanosomatid protein-coding genes are annotated as hypothetical, additional studies are needed to ascertain their function.

Various approaches aimed at characterizing such extracellular material were developed. Even if collecting a culture's supernatant is relatively easy to perform, identification of the different factors can be difficult because of the relatively low abundance of the constituents. Additionally, the in vitro growth of mammalian stages for trypanosomatids is impossible or laborious. Moreover, even if parasites are grown in cell-free and serum-free media, the culture's supernatant can be contaminated with materials that are not primarily "secreted" by the parasite. These materials may be shed from the parasite surface or can originate from dead organisms. Thus to avoid such pitfalls it is best to limit the parasite's incubation time in a serum-free media to a few hours. Further characterization by screening cDNA libraries with sera raised against culture medium supernatants has also been performed. However, using this approach proteins with a low abundance or that are poorly immunogenic are likely to be missed. Recently, the secretome of *L. donovani* promastigotes was analyzed by using a quantitative proteomic approach based on the SILAC methodology (Silverman et al., Genome Biology (2008), 9, R35). Although the authors identified a total of 358 proteins secreted into a promastigote conditioned medium, the SILAC methodology was unable to detect proteins that are well known to be secreted, e.g., chitinase and SAcP (secreted acid phosphatase). This may be explained by the relative ratios (extracellular versus cell-associated protein) used by the SILAC approach to identify extracellular proteins. For example, this methodology is limited in its ability to detect proteins for which the large majority is secreted (extracellular) and almost nothing remains within the cell. Consequently, no reliable ratio can be calculated. The methodology developed in WO 2006/108720 is totally different from the one of the instant invention. It is based on immunogenicity properties of materials released in the culture supernatants by the promastigote forms of *L. major*, and a cDNA library screening. By using this method only the immunogenic proteins released by the parasite in the culture supernatant may be identified. A subset of these proteins is potentially secreted by the classical secretory pathway, based on the predictions of the signal peptide in the polypeptide sequence. Another subset might be exported by other ways, since they do not carry a predicted signal peptide. Another difference with the instant invention is the stage-dependent identification: their starting point is the materials released by the stationary-phase promastigotes, whereas the instant invention is stage-independent, since the starting point is genomic-based (the sequences might be expressed by any stage of the parasite life-cycle) and transgenic parasites are used for overexpression of the target proteins. Van Ooij et a.l (Ploss Pathogens, 2008, 4 (6), 1-15) use a bioinformatic analysis for prediction of signal peptide, but specific for *Plasmodium* species, and their functional validation is only performed on *Plasmodium*. This methodology aimed to detect and study the function of secreted proteins that bear ER retention motif and the PEXEL (Plasmodium Export Element) motif, not described in trypanosomatids.

In view of this, the inventors designed a new experimental approach based on bioinformatics genome screening to identify new proteins conserved among protozoan parasites, particularly those conserved among the three main trypanosomatid pathogens and that are secreted via the classical pathway. Said methodology possesses two main advantages Firstly, detection of secreted proteins is not limited to a particular parasite stage since the approach relies on the use of transgenic *Leishmania* parasites to detect extracellular proteins. Secondly, it allows the detection of small quantities of extracellular proteins that otherwise may be missed by other methodologies, such as, quantitative mass spectrometry.

Consequently the invention relates to an isolated or purified conserved secreted polypeptide said polypeptide comprising an amino acid sequence substantially identical to a sequence selected from the group consisting of SEQ ID NOS: 86 and 98 and functional derivatives thereof selected from the group comprising SEQ ID NOS: 88, 90, 92, 94, 96, 100, 102 and 173.

More specifically, the invention relates to an isolated or purified conserved secreted polypeptide according to claim 1 consisting of SEQ ID NOS: 86 or 98 and functional derivatives thereof selected from the group comprising SEQ ID NOS: 88, 90, 92, 94, 96, 100, 102 and 173.

According to the invention, said polypeptides may be identified by a method for identifying conserved polypeptides from protozoan parasitic species which are secreted through the endoplasmic reticulum/Golgi dependent secretory pathway, said method comprising the following steps:

a. analysing a putative conserved polypeptide from protozoan parasitic species to determine if said polypeptide has a secretion signal peptide at the N-terminus and a cleavage site just behind said signal peptide, b. searching for orthologue, in related family members, of said polypeptide, said orthologue having a secretion signal peptide and a cleavage site just behind said signal peptide, c. analyzing said orthologue to determine if said orthologue has a secretion signal peptide at the N-terminus and a cleavage site just behind said signal peptide, d. selecting the conserved polypeptide and its corresponding orthologue having a secretion signal peptide and a cleavage site just behind said signal peptide, e. cloning the encoding genes for the polypeptide selected in step d) by mean of an expression vector, f. transfecting replicative protozoan parasitic cells, g. in vitro cultivating said cells under pH and temperature conditions naturally found in a host infected by a protozoan parasitic strain, h. analysing the presence of secreted polypeptides in the proliferative protozoan parasitic cells and i. identifying said secreted polypeptides by a protein identification method.

According to the invention, "conserved proteins" are defined by the presence of orthologous genes in the family members. For example for the three trypanosomatids, *Leishmania*, *Trypanosoma cruzi* and *Trypanosoma brucei*, (tri Tryp) the orthologous genes are defined by "Jaccard COG Clustering". The orthology between the 'tri Tryp' organisms is predicted using a method known as Jaccard COG clustering. Briefly, this firstly involves the proteins within each organism's data set being grouped into clusters using reciprocal BLASTP searches, with an assigned cut off score. Representatives of each cluster for each organism are then chosen and three way reciprocal BLASTP searches are run again on these data sets. A clustered orthologous group (COG) is a group of proteins which contains reciprocal best hits between the genomes. (Aslett M et al, Int J Parasitol. 2005 35:481-93).

According to the invention "family members" is defined as organisms belonging to the same genera.

According to the invention, "protozoan parasites" generally refers to any protozoan organisms that are eukaryotic, unicellular, parasitic and characterized by at least one developmental stage within its vertebrate host. Parasites used in the methods of the invention include, but are not limited to, protozoan parasites that are members of the genera *Toxoplasma, Neospora, Eimeria, Theileria, Sarcocystis, Cryptosporidium* and Trypanosomatidae family (*Trypanosoma* and *Leishmania*).

In an advantageous embodiment of the invention, the putative conserved polypeptide has been identified by screening a database of information.

More specifically the instant invention concerns a method for identifying conserved secreted polypeptides from trypanosomatid parasites.

In an advantageous embodiment said trypanosomatid parasites are selected from the group comprising *Leishmania major, Leishmania infantum, Leishmania tropica, Leishmania braziliensis, Leishmania donovani, Leishmania amazonensis, Leishmania chagasi, Trypanosoma cruzi, Trypanosoma brucei, Trypanosoma vivax, Trypanosoma congolense, Trypanosoma brucei rhodesiense* and *Trypanosoma brucei gambiense*.

Other objects of the invention concern a method for identifying conserved polypeptides from trypanosomatid parasites which are secreted through the endoplasmic reticulum/Golgi dependent secretory pathway, said method comprising the following steps:

a. analyzing a putative conserved polypeptide from a trypanosomatid parasite to determine if said polypeptide has a secretion signal peptide at the N-terminus and a cleavage site just behind said signal peptide, b. searching for orthologue, in related family members, of said identified polypeptide having a secretion signal peptide and a cleavage site just behind said signal peptide c. analyzing said orthologue to determine if said orthologue has a secretion signal peptide at the N-terminus and a cleavage site just behind said signal peptide, d. selecting the conserved polypeptide and its corresponding orthologue having a secretion signal peptide and a cleavage site just behind said signal peptide, e. cloning the encoding genes for the polypeptide selected in step d) by mean of an expression vector, f. transfecting replicative trypanosomatid cells at the promastigotes stage, g. in vitro cultivating said cells under pH and temperature conditions naturally found in a host cell infected by a trypanosomatid strain, h. collecting replicative transfected cells obtained in step g), i. incubating said cells in a serum free medium during 1 to 10 hours, preferably during 5 to 6 hours, at a temperature comprised between 25-27° C., j. analysing the presence of secreted polypeptides by said cells and k. identifying said secreted polypeptides by a protein identification method.

More specifically the instant invention concerns a method for identifying conserved polypeptides wherein the putative conserved polypeptide is identified by screening a genome selected from the accessible genome from of *Trypanosoma cruzi, Trypanosoma brucei, Trypanosoma vivax, Leishmania major, Leishmania braziliensis*, in particular by screening the integrated *Trypanosoma cruzi*, genome resource TcruziDB.

In yet another embodiment of the invention, the replicative trypanosomatid cells used in step f) are promastigotes of *Leishmania infantum*.

In yet another embodiment of the invention, the primers used in step e) are selected from the group comprising SEQ ID NO 124 to 165.

A further object of the invention is an isolated or purified conserved secreted polypeptide identified by the method of the invention, said polypeptide comprising an amino acid sequence substantially identical to a sequence selected from the group consisting of SEQ ID NOS: 86, 88, 90, 92, 94, 96, 98, 100, 102, 104, 106, 108, 110, 173 and functional derivatives or fragments thereof.

A "functional derivative", as is generally understood and used herein, refers to a protein/peptide sequence that possesses a functional biological activity that is substantially similar to the biological activity of the whole protein/peptide sequence. A functional derivative of a protein/peptide may or may not contain post-translational modifications such as covalently linked carbohydrate, if such modification is not necessary for the performance of a specific function. The term "functional derivative" is intended to the "fragments", "segments", "variants", "analogs" or "chemical derivatives" of a protein/peptide. As used herein, the term "polypeptide(s)" refers to any peptide or protein comprising two or more amino acids joined to each other by peptide bonds or modified peptide bonds. "Polypeptide(s)" refers to both short chains, commonly referred to as peptides, oligopeptides and oligomers and to longer chains generally referred to as proteins. Polypeptides may contain amino acids other than the 20 gene-encoded amino acids. "Polypeptide(s)" include those modified either by natural processes, such as processing and other post-translational modifications, but also by chemical modification techniques. Such modifications are well described in basic texts and in more detailed monographs, as well as in a voluminous research literature and they are well known to those of skill in the art. It will be appreciated that the same type of modification may be present in the same or varying degree at several sites in a given polypeptide. Also, a given polypeptide may contain many types of modifications. Modifications can occur anywhere in a polypeptide, including the peptide backbone, the amino acid side-chains, and the amino or carboxyl termini. Modifications include, for example, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of cysteine, formation of pyroglutamate, formylation, gamma-carboxylation, GPI anchor formation, hydroxylation, iodination, methylation, myristoylation, oxidation, proteolytic processing, phosphorylation, prenylation, racemization, glycosylation, lipid attachment, sulfation, gamma-carboxylation of glutamic acid residues, hydroxylation, selenoylation, sulfation and transfer-RNA mediated addition of amino acids to proteins, such as arginylation, and ubiquitination. See, for instance: PROTEINS-STRUCTURE AND MOLECULAR PROPERTIES, 2nd Ed., T. E. Creighton, W.K Freeman and Company, New York (1993); Wold, F., Posttranslational Protein Modifications: Perspectives and Prospects, pgs. 1-12 in POSTTRANSLATIONAL COVALENT MODIFICATION OF PROTEINS, B. C. Johnson, Ed., Academic Press, New York (1983); Seifter et al., Meth. Enzymol. 182:626-646 (1990); and Rattan et al., Protein Synthesis: Posttranslational Modifications and Aging, Ann. N.Y. Acad. Sci. 663: 48-62 (1992). Polypeptides may be branched or cyclic, with or without branching. Cyclic, branched and branched circular polypeptides may result from posttranslational natural processes and may be made by entirely synthetic methods, as well.

By the term "substantially identical", it is meant that the polypeptide of the present invention preferably has an amino sequence having at least 80% homology, or even preferably 85% homology to part or all of SEQ ID NO: 86, 88, 90, 92, 94, 96, 98, 100, 102, 104, 106, 108, 110, 173.

Yet an other object of the invention concerns an isolated polynucleotide comprising a sequence encoding a secreted polypeptide according to the invention, said sequence comprising a nucleotide sequence substantially identical to a sequence selected from the group consisting of SEQ ID NOS 85, 89, 91, 93, 97, 99, 101, 103, 107 or 109 and functional fragments thereof selected from SEQ ID NOS 87, 89, 91, 93, 95, 99, 101 and 172

According to the invention "functional derivatives or fragments" refers to polypeptides which possess biological function or activity that is identified through a defined functional assay and which is associated with a particular biologic, morphologic, or phenotypic alteration in a cell or cell mechanism. By the term "substantially identical", it is meant that the polynucleotide of the invention has a nucleic acid sequence which is at least 65% identical, more particularly 80% identical and even more particularly 95% identical to any one of SEQ ID NO: 85, 87, 89, 91, 93, 95, 97, 99, 101, 103, 105, 107, 109, 172.

Amino acid or nucleotide sequence "identity" and "similarity" are determined from an optimal global alignment between the two sequences being compared. "Identity" means that an amino acid or nucleotide at a particular position in a first polypeptide or polynucleotide is identical to a corresponding amino acid or nucleotide in a second polypeptide or polynucleotide that is in an optimal global alignment with the first polypeptide or polynucleotide. In contrast to identity, "similarity" encompasses amino acids that are conservative substitutions. A "conservative" substitution is any substitution that has a positive score in the blosum62 substitution matrix (Hentikoff and Hentikoff, 1992, Proc. Natl. Acad. Sci. USA 89: 10915-10919). By the statement "sequence A is n % similar to sequence B" is meant that n % of the positions of an optimal global alignment between sequences A and B consists of identical residues or nucleotides and conservative substitutions. By the statement "sequence A is n % identical to sequence B" is meant that n % of the positions of an optimal global alignment between sequences A and B consists of identical residues or nucleotides.

According to the invention, the terms "Isolated or Purified" means altered "by the hand of man" from its natural state, i.e., if it occurs in nature, it has been changed or removed from its original environment, or both. For example, a polynucleotide or a protein/peptide naturally present in a living organism is neither "isolated" nor purified, the same polynucleotide separated from the coexisting materials of its natural state, obtained by cloning, amplification and/or chemical synthesis is "isolated" as the term is employed herein. Moreover, a polynucleotide or a protein/peptide that is introduced into an organism by transformation, genetic manipulation or by any other recombinant method is "isolated" even if it is still present in said organism.

According to the invention, the term "polynucleotide(s)" generally refers to any polyribonucleotide or poly-deoxyribonucleotide, which may be unmodified RNA or DNA or modified RNA or DNA. This definition includes, without limitation, single- and double-stranded DNA, DNA that is a mixture of single- and double-stranded regions or single-, double- and triple-stranded regions, single- and double-stranded RNA, and RNA that is mixture of single- and double-stranded regions, hybrid molecules comprising DNA and RNA that may be single-stranded or, more typically, double-stranded, or triple-stranded regions, or a mixture of single- and double-stranded regions. In addition, "polynucleotide" as used herein refers to triple-stranded regions comprising RNA or DNA or both RNA and DNA. The strands in such regions may be from the same molecule or from different molecules. The regions may include all of one or more of the molecules, but more typically involve only a region of some of the molecules. One of the molecules of a triple-helical region often is an oligonucleotide. As used herein, the term "polynucleotide(s)" also includes DNAs or RNAs as described above that contain one or more modified bases. Thus, DNAs or RNAs with backbones modified for stability or for other reasons are "polynucleotide(s)" as that term is intended herein. Moreover, DNAs or RNAs comprising unusual bases, such as inosine, or modified bases, such as tritylated bases, to name just two examples, are polynucleotides as the term is used herein, it will be appreciated that a great variety of modifications have been made to DNA and RNA that serve many useful purposes known to those of skill in the art. "Polynucleotide(s)" embraces short polynucleotides or fragments often referred to as oligonucleotide(s). The term "polynucleotide(s)" as it is employed herein thus embraces such chemically, enzymatically or metabolically modified forms of polynucleotides, as well as the chemical forms of DNA and RNA characteristic of viruses and cells, including, for example, simple and complex cells which exhibits the same biological function as the polypeptide encoded by SEQ ID NOS 86, 88, 90, 92, 94, 96, 98, 100, 102, 104, 106, 108, 110, 173. The term "polynucleotide(s)" also embraces short nucleotides or fragments, often referred to as "oligonucleotides", that due to mutagenesis are not 100% identical but nevertheless code for the same amino acid sequence or sequence with high similarity.

Yet another object of the invention concerns an immunogenic composition generating an immune response against a leishmaniasis, comprising a polynucleotide corresponding to SEQ ID NOS 89, 97 or 107 or a polypeptide corresponding to SEQ ID NOS 90, 98 or 108 and an acceptable carrier.

Yet another object of the present invention concerns an immunogenic composition generating an immune response against a Chagas disease, comprising a polynucleotide corresponding to SEQ ID NOS 85, 93 or 103 or a polypeptide corresponding to SEQ ID NOS 86, 94 or 104 and an acceptable carrier.

Yet another object of the instant invention concerns an immunogenic composition generating an immune response against a sleeping sickness comprising a polynucleotide corresponding to SEQ ID NOS 91, 99, 101 or 109 or a polypeptide corresponding to SEQ ID NOS 92, 100, 102 or 110 and an acceptable carrier.

Thanks to the method of the invention it is possible to select a conserved protein from one organism selected from *Trypa-* nosoma cruzi, Trypanosoma brucei and Leishamia major and to use said protein or its corresponding nucleotide to treat one or more diseases selected from leishmaniasis, Chagas disease and sleeping sickness, i.e. the method according to the invention allows to treat two of them or the three together.

Consequently another object of the instant invention concerns an immunogenic composition generating an immune response against at least one disease selected from leishmaniasis, Chagas disease and sleeping sickness, comprising a polynucleotide corresponding to SEQ ID NOS 85, 87, 89, 91, 93, 95, 97, 99, 101, 103, 105, 107, 109, 172 or a polypeptide corresponding to SEQ ID NOS 86, 88, 90, 92, 94, 96, 98, 100, 102, 104, 106, 108, 110, 173.

Advantageously, the immunogenic composition according to the invention leads to an immune response which generates a cellular and/or humoral response, preferably a cellular response.

Yet another object of the invention is a vaccine composition generating a protecting response against a leishmaniasis, comprising a polynucleotide corresponding to SEQ ID NOS 89, 97 or 107 or a polypeptide corresponding to SEQ ID NOS 90, 98 or 108 and an acceptable carrier.

Yet another object of the invention is a vaccine composition generating a protecting response against a Chagas disease, comprising a polynucleotide corresponding to SEQ ID NOS 85, 93 or 103 or a polypeptide corresponding to SEQ ID NOS 86, 94 or 104 and an acceptable carrier.

Yet another object of the invention is a vaccine composition generating a protecting response against a sleeping sickness comprising a polynucleotide corresponding to SEQ ID NOS 91, 99, 101 or 109 or a polypeptide corresponding to SEQ ID NOS 92, 100, 102 or 110 and an acceptable carrier.

Yet another object of the invention is a vaccine composition generating a protecting response against a leishmaniasis, a Chagas disease or a sleeping sickness comprising a polynucleotide corresponding to SEQ ID NOS 85, 87, 89, 91, 93, 95, 97, 99, 101, 103, 105, 107, 109, 172 or a polypeptide corresponding to SEQ ID NOS 86, 88, 90, 92, 94, 96, 98, 100, 102, 104, 106, 108, 110, 173 and an acceptable carrier.

Yet another object of the instant invention is an antibody obtainable by the immunization of an animal with a polypeptide according to the invention.

The antibodies of the invention may be prepared by a variety of methods using the polypeptides described above. For example, the polypeptide, or antigenic fragments thereof, may be administered to an animal in order to induce the production of polyclonal antibodies. Alternatively, antibodies used as described herein may be monoclonal antibodies, which are prepared using hybridoma technology. As mentioned above, the present invention is preferably directed to antibodies that specifically bind to trypanosomatids excreted/secreted polypeptides, or fragments thereof as defined above. In particular, the invention features "neutralizing" antibodies. By "neutralizing" antibodies is meant antibodies that interfere with any of the biological activities of any of the trypanosomatids excreted/secreted polypeptides. Any standard assay known to one skilled in the art may be used to assess potentially neutralizing antibodies. Once produced, monoclonal and polyclonal antibodies are preferably tested for specific trypanosomatids excreted/secreted polypeptides recognition by Western blot, immunoprecipitation analysis or any other suitable method.

With respect to antibodies of the invention, the term "specifically binds to" refers to antibodies that bind with a relatively high affinity to one or more epitopes of a protein of interest, but which do not substantially recognize and bind molecules other than the one(s) of interest. As used herein, the term "relatively high affinity" means a binding affinity between the antibody and the protein of interest of at least $10^6$ $M^{-1}$, and preferably of at least about $10^7$ $M^{-1}$ and even more preferably $10^8$ $M^{-1}$ to $10^{10}$ $M^{-1}$. Determination of such affinity is preferably conducted under standard competitive binding immunoassay conditions which is common knowledge to one skilled in the art. As used herein, "antibody" and "antibodies" include all of the possibilities mentioned hereinafter: antibodies or fragments thereof obtained by purification, proteolytic treatment or by genetic engineering, artificial constructs comprising antibodies or fragments thereof and artificial constructs designed to mimic the binding of antibodies or fragments thereof. They include complete antibodies, F(ab')2 fragments, Fab fragments, Fv fragments, scFv fragments, other fragments, CDR peptides and mimetics. These can easily be obtained and prepared by those skilled in the art. For example, enzyme digestion can be used to obtain F(ab')2 and Fab fragments by subjecting an IgG molecule to pepsin or papain cleavage respectively. Recombinant antibodies are also covered by the present invention.

Preferably, the antibody of the invention is a human or animal immunoglobulin such as IgG1, IgG2, IgG3, IgG4, IgM, IgA, IgE or IgD carrying rat or mouse variable regions (chimeric) or CDRs (humanized or "animalized"). Furthermore, the antibody of the invention may also be conjugated to any suitable carrier known to one skilled in the art in order to provide, for instance, a specific delivery and prolonged retention of the antibody, either in a targeted local area or for a systemic application.

The term "humanized antibody" refers to an antibody derived from a non-human antibody, typically murine, that retains or substantially retains the antigen-binding properties of the parent antibody but which is less immunogenic in humans. This may be achieved by various methods including (a) grafting only the non-human CDRs onto human framework and constant regions with or without retention of critical framework residues, or (b) transplanting the entire non-human variable domains, but "cloaking" them with a human-like section by replacement of surface residues. Such methods are well known to one skilled in the art.

As mentioned above, the antibody of the invention is immunologically specific to the polypeptide of the present invention and immunological derivatives thereof. As used herein, the term "immunological derivative" refers to a polypeptide that possesses an immunological activity that is substantially similar to the immunological activity of the whole polypeptide, and such immunological activity refers to the capacity of stimulating the production of antibodies immunologically specific to the trypanosomatids secreted polypeptides or derivative thereof. The term "immunological derivative" therefore encompasses "fragments", "segments", "variants", or "analogs" of a polypeptide.

Yet another object of the invention is an expression or a cloning vector containing a polynucleotide of the invention and more preferably a host capable of expressing the polypeptide encoded by this polynucleotide.

As used herein, the term "vector" refers to a polynucleotide construct designed for transduction/transfection of one or more cell types. Vectors may be, for example, "cloning vectors" which are designed for isolation, propagation and replication of inserted nucleotides, "expression vectors" which are designed for expression of a nucleotide sequence in a host cell, or a "viral vector" which is designed to result in the production of a recombinant virus or virus-like particle, or "shuttle vectors", which comprise the attributes of more than one type of vector. A number of vectors suitable for stable transfection of cells and bacteria are available to the public (e.g. plasmids, adenoviruses, baculoviruses, yeast baculoviruses, plant viruses, adeno-associated viruses, retroviruses, Herpes Simplex Viruses, Alphaviruses, Lentiviruses), as are methods for constructing such cell lines. It will be understood that the present invention encompasses any type of vector comprising any of the polynucleotide molecule of the invention.

Yet another object of the invention concerns a method for preventing and/or treating a patient suffering from one or more diseases selected from leishmaniasis, Chagas disease and sleeping sickness, said method comprising the step of administering to the patient a therapeutically effective amount of a composition as defined above or of an antibody as defined above.

In another embodiment, the invention features the use of a polynucleotide according to the invention and/or a polypeptide according to the invention as a target for identifying a molecule capable of preventing a disease selected from leishmaniasis, Chagas disease and sleeping sickness or two of them or the three together.

In another embodiment, the invention proposes an in vitro diagnostic method for the detection of the presence or absence of antibodies indicative of one or more diseases selected from leishmaniasis, Chagas disease and sleeping sickness which bind to a polypeptide according to the invention to form an immune complex, comprising the steps of:
  a. contacting said polypeptide with a biological sample for a time and under conditions sufficient to form an immune complex; and
  b. detecting the presence or absence of the immune complex formed in a).

In another embodiment a diagnostic kit for the detection of the presence or absence of antibodies indicative of one or more diseases selected from leishmaniasis, Chagas disease and sleeping sickness is provided. Accordingly said kit comprises:
  a. a polypeptide according to the invention;
  b. a reagent to detect polypeptide-antibody immune complex; optionally a biological reference sample lacking antibodies that immunologically bind with said peptide; and
  c. optionally a comparison sample comprising antibodies which can specifically bind to said peptide;
wherein said polypeptide, reagent, biological reference sample, and comparison sample are present in an amount sufficient to perform said detection.

The invention also proposes an in vitro diagnostic method for the detection of the presence or absence of polypeptides indicative of one or more diseases selected from leishmaniasis, Chagas disease and sleeping sickness which bind to an antibody of the invention to form an immune complex, comprising the steps of:
  a. contacting said antibody with a biological sample for a time and under conditions sufficient to form an immune complex; and
  b. detecting the presence or absence of the immune complex formed in a).

The invention further provides a diagnostic kit for the detection of the presence or absence of polypeptides indicative of one or more diseases selected from leishmaniasis, Chagas disease and sleeping sickness, comprising:
  a. an antibody according to the invention;
  b. a reagent to detect polypeptide-antibody immune complex; and
  c. optionally a biological reference sample lacking polypeptides that immunologically bind with said antibody; and
  d. optionally a comparison sample comprising polypeptides which can specifically bind to said antibody;
wherein said antibody, reagent, biological reference sample, and comparison sample are present in an amount sufficient to perform said detection A further object of the invention concerns a transformed or transfected cell that contains a vector as defined above, more preferably a transformed or transfected cell that contains a polynucleotide according to the invention, preferably a polynucleotide as defined above.

Transformed or transfected cells preferably contemplated by the present invention contain a polynucleotide having a sequence comprising a nucleotide sequence substantially identical to a sequence selected from the group consisting of SEQ ID NOS 85, 87, 89, 91, 93, 95, 97, 99, 101, 103, 105, 107, 109, 172 and functional fragments thereof. Examples of such cells are those consisting of replicative protozoan parasitic cells (egg *Leishmania* promastigotes, *T. cruzi* epimastigotes) transfected with a recombinant expression vector such as pTEX, widely used to express heterologous DNA sequences in the trypanosome genetic environment, containing sequence selected from the group consisting of SEQ ID NOS 85, 87, 89, 91, 93, 95, 97, 99, 101, 103, 105, 107, 109, 172 and functional fragments thereof.

Another further object of the invention is a method for detecting the presence or absence of lymphocytic stimulation in a subject suspected of one or more diseases selected from leishmaniasis, Chagas disease and sleeping sickness, comprising the steps of:
  a. obtaining a sample containing T Lymphocytes from said subject;
  b. contacting the T lymphocytes with a polypeptide; and
  c. detecting the presence or absence of a proliferative response of said T lymphocyte to the polypeptide.

The instant invention also provides a method for detecting the presence or absence of lymphocytic stimulation in a subject suspected of one or more diseases selected from leishmaniasis, Chagas disease and sleeping sickness, comprising the steps of:
  a. obtaining a sample containing T Lymphocytes from said subject;
  b. contacting the T lymphocytes with a polypeptide as defined above; and
  c. detecting the presence or absence of cytokines indicative of lymphocytic stimulation.

The present invention will be more readily understood by referring to the following examples 1 to 3 and to FIGS. 1 to 11.

FIG. 1 illustrates the *T. cruzi* genes selected by in silico analysis. The 13 proteins bears the highest probability for the presence of the signal peptide and were selected for functional confirmation of bona fide secretion. The beta-tubulin *T. cruzi* gene (GeneID Tc00.1047053506563) was added to our sample as a potential negative control for protein.

SPP Signal peptide probability predicted by SignalP 3.0; CSP Maximal cleavage site probability predicted by SignalP.

FIG. 2 illustrates the primer design of the 13 *T. cruzi* putative secreted proteins conserved in trypanosomatids and *T. cruzi*. Tubulin is taken as negative control. F: Forward primer including the start codon; Rint: Internal reverse primer for RT-PCR; R: Reverse primer used for the amplification of the full-length ORF. In the column "Primer sequences" restriction sites used for cloning in the pTEX vector are in italics and the His-Tag sequence is in bold. Column "MW" corresponds to the expected molecular weight of the proteins. In the first column, last line Tc00.1047053506563.40 corresponds to Beta-tubulin gene.

FIG. 3 illustrates the ID of *L. infantum* orthologous genes and primers used for cloning. F: Forward primer including the start codon; R: Reverse primer used for the amplification of the full-length ORF. In the column "Primer sequences" restriction sites used for cloning in the pTEX vector are in italics and the His-Tag sequence is in bold. Column "MW" corresponds to the expected molecular weight of the proteins.

FIG. 4 illustrates the expression analysis of potentially secreted proteins during the life cycle of *T. cruzi*. RT-PCR analysis of total RNA from *T. cruzi* (clone derived from the Y strain) epimastigotes (E), trypomastigotes (T) and amastigotes (A), respectively, using cDNA obtained by gene-specific PCR primers listed in FIG. 2. Gene ID and expected lengths of cDNA are listed in order in FIG. 2. B: Blank. M: Molecular marker: Smart Ladder SF.

Figure 5:
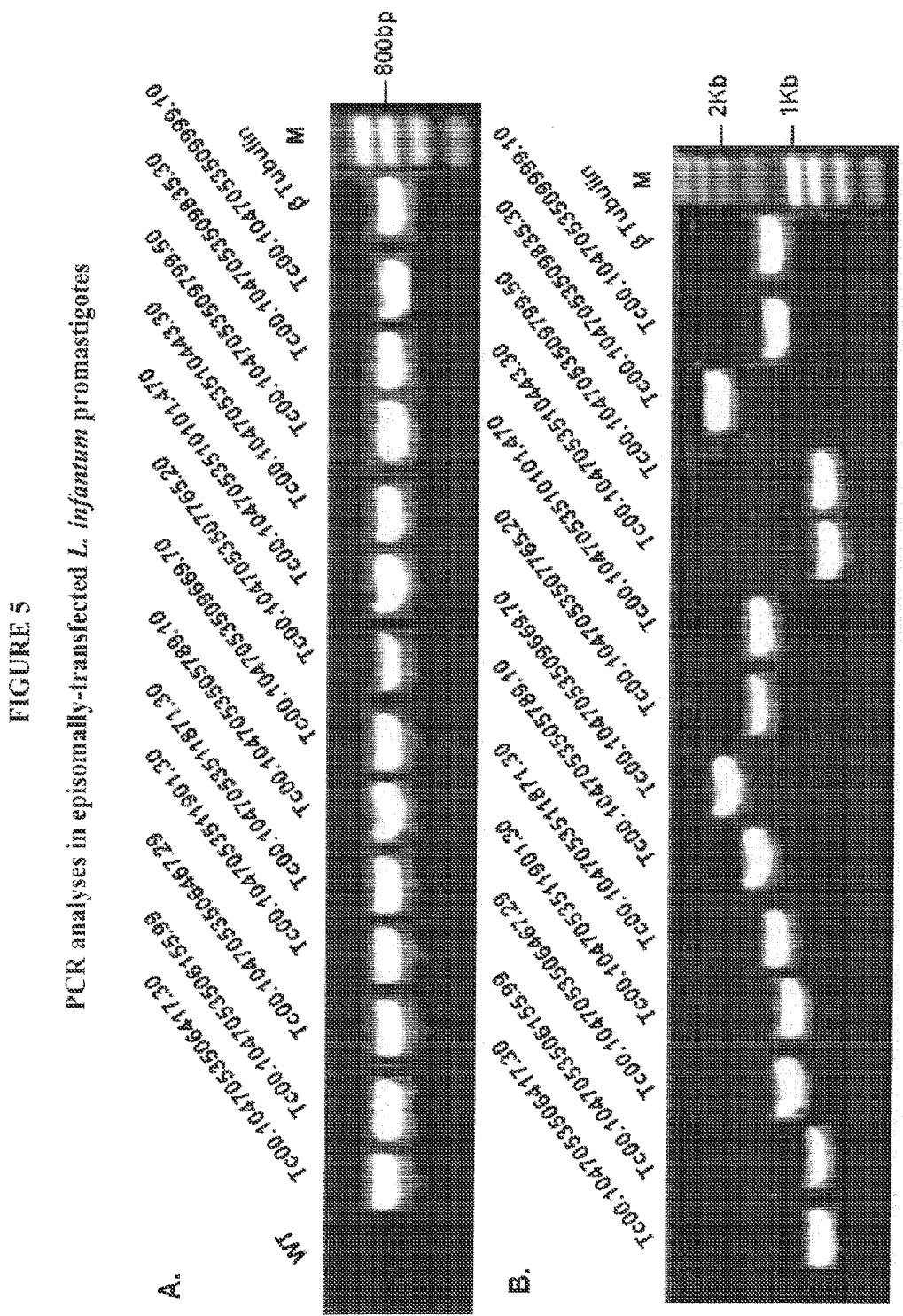

FIG. 5 illustrates PCR analyses in episomally-transfected *L. infantum* promastigotes (A) Amplification of NEO gene fragment in *L. infantum* episomally transfected promastigotes. (B) Amplification of full length transfected genes in *L. infantum* promastigotes. Specific forward and Reverse PCR primers and gene lengths are listed in order in FIG. 2. WT: Wild Type Parasites. M: Molecular marker: Smart Ladder SL.

Figure 6:
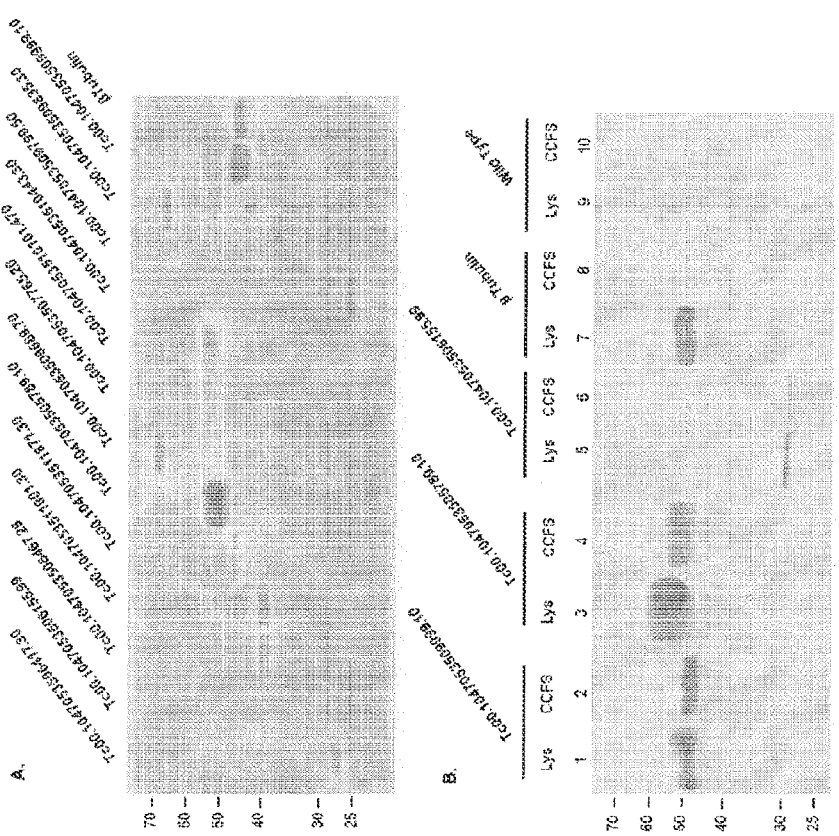

FIG. 6 illustrates the protein expression in *L. infantum* episomally transfected promastigotes during the exponential phase of development (A) Western blot analysis of His-tagged proteins detected in whole cell lysate. Equal amounts of total protein (35 μg) were resolved by electrophoresis in 4-12% gradient gels (Invitrogen), blotted, and developed with anti-HisTag antibody followed by ECL (Amersham). Gene ID and theoretical molecular weight of detected proteins are listed in order in FIG. 2. (B) Identification of secreted proteins in whole cell lysate (Lys) and concentrated cell-free culture supernatant (CCFS) obtained from promastigotes incubated for 6 h in serum-free medium. Note the absence of β Tubulin in the concentrated supernatant of Line 8. Non-transfected *L. infantum* promastigotes (Wild Type) were used as a negative control. Protein molecular mass standards in kDa are shown on the left of each panel.

Figure 7:
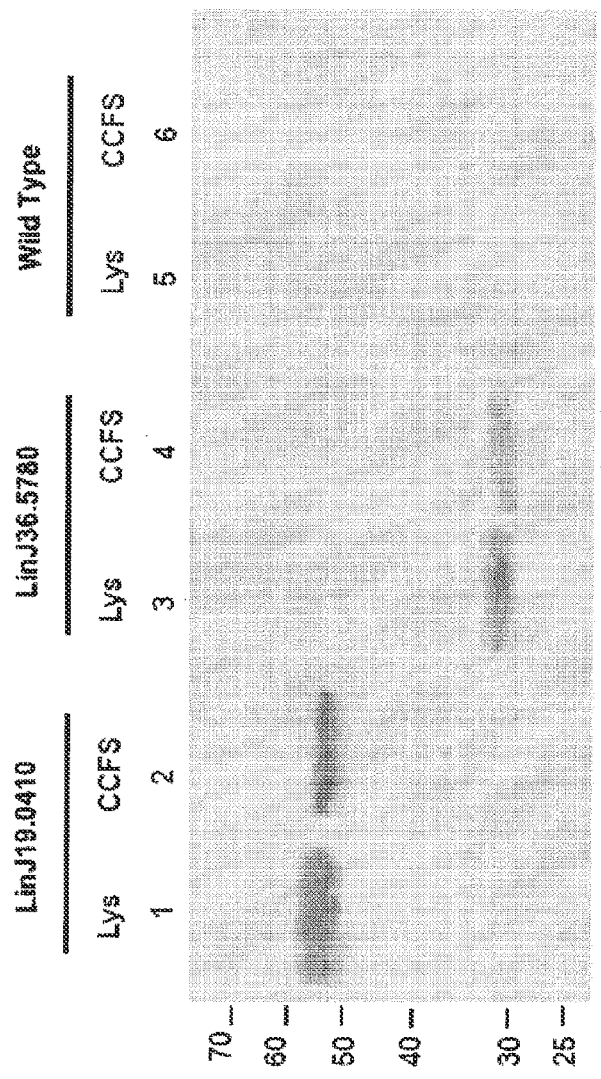

FIG. 7 illustrates the homologous expression of secreted proteins in *L. infantum* episomally transfected promastigotes according to the example. *L. infantum* promastigotes were transfected with genes: LinJ19.0410 and LinJ36.5780 corresponding to secreted proteins Tc00.1047053505789.10 (SEQ ID NO 93) and Tc00.1047053506155.99 (SEQ ID NO 103), respectively. Cell whole lysate (Lys) and concentrated cell-free culture supernatant (CCFS) were obtained as in FIG. 6. Tagged proteins were detected only in recombinant parasites transfected with LinJ19.0410 (58 kDa) (Line 1 and 2) and LinJ36.5780 (28 kDa) (Line 3 and 4). Non-transfected *L. infantum* promastigotes (Wild Type) were used as negative controls (Line 5 and 6). Protein molecular mass standards in kDa are shown on the left. Cell whole lysate (Lys), concentrated cell-free culture supernatant (CCFS) and electrophoresis procedure were as mentioned in FIG. 6. Non-transfected *L. infantum* promastigotes (Wild Type) were used as negative controls (Line 5 and 6). Protein molecular mass standards in kDa are shown on the left.

Figure 8:
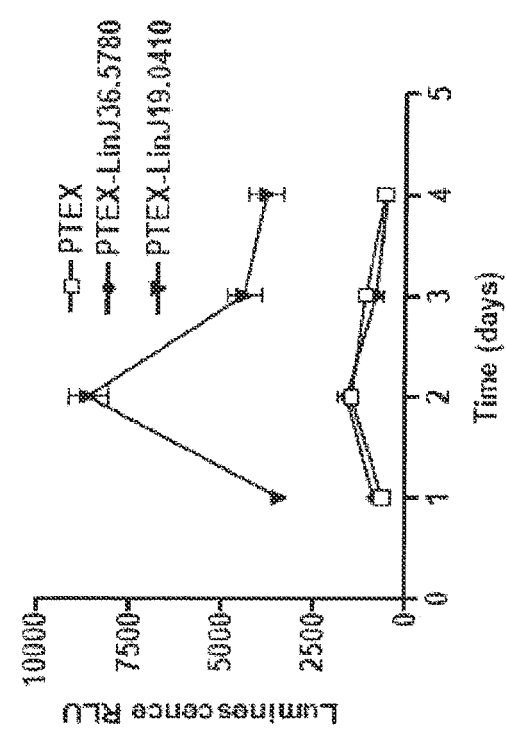

FIG. 8 illustrates the bioluminescence activity of intracellular *Leishmania* expressing episomal luciferase in infected macrophages in vitro. Recombinant *L. infantum* promastigotes over-expressing the secreted proteins pTEX734 LinJ19.0410 (▼) or pTEX-LinJ36.5780 (●) were co-transfected with the pSP735 YαHYGROαLUC carrying the firefly-luciferase gene. Survival of luciferase-expressing parasites was monitored in infected human monocyte cell line THP-1 differentiated into macrophages as indicated in the Methods section. Promastigotes transfected with the pTEX vector alone and the pSP-αHYGαLUC (□) were used as control for infection experiments. RLU (Relative Luminescence Units) were measured at various time points post-infection using the Steady Glo reagent. Results are expressed as the mean of three independent experiments, each carried out in triplicate.

Figure 9:
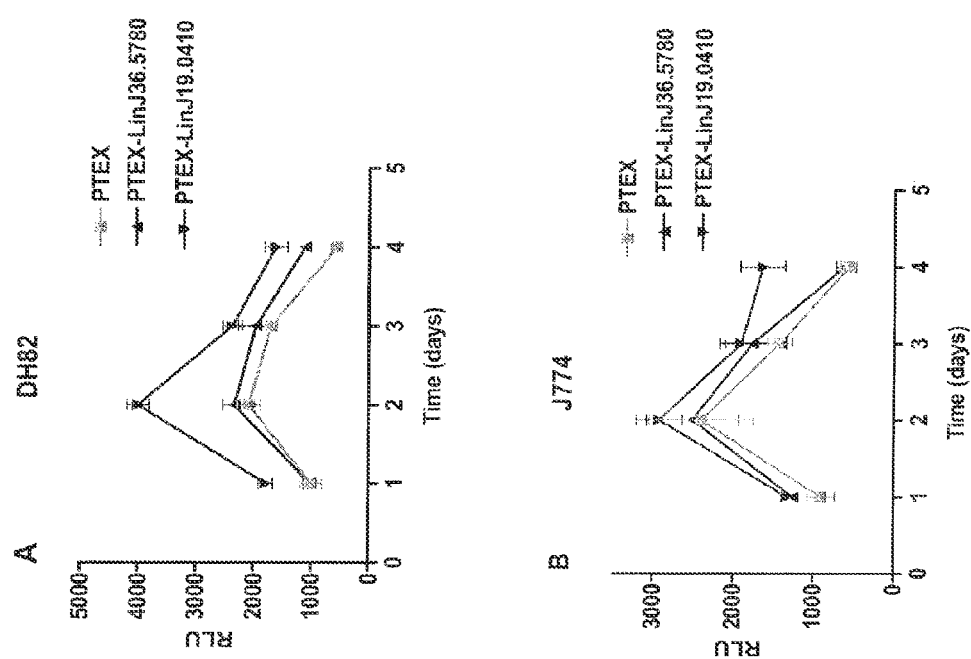

FIG. 9 illustrates the bioluminescence activity of intracellular *Leishmania* expressing episomal luciferase in infected macrophages in vitro. Transgenic *L. infantum* promastigotes over-expressing the secreted proteins pTEX-LinJ19.0410 (▼) or pTEX-LinJ36.5780 (▲) were co-transfected with the pSP-YαHYGROαLUC carrying the firefly-luciferase gene. Survival of luciferase-expressing parasites was monitored in infected canine monocyte-macrophage cell line DH-82 (A) and murine macrophage cell line J774 (B). Promastigotes transfected with the pTEX vector alone and pSP-αHYGα-LUC (■) were used as controls for infection experiments. RLU (Relative Luminescence Units) were measured at various time points post-infection using the Steady Glo reagent. Results are expressed as the mean of three independent experiments, each carried out in triplicate.

Figure 10:
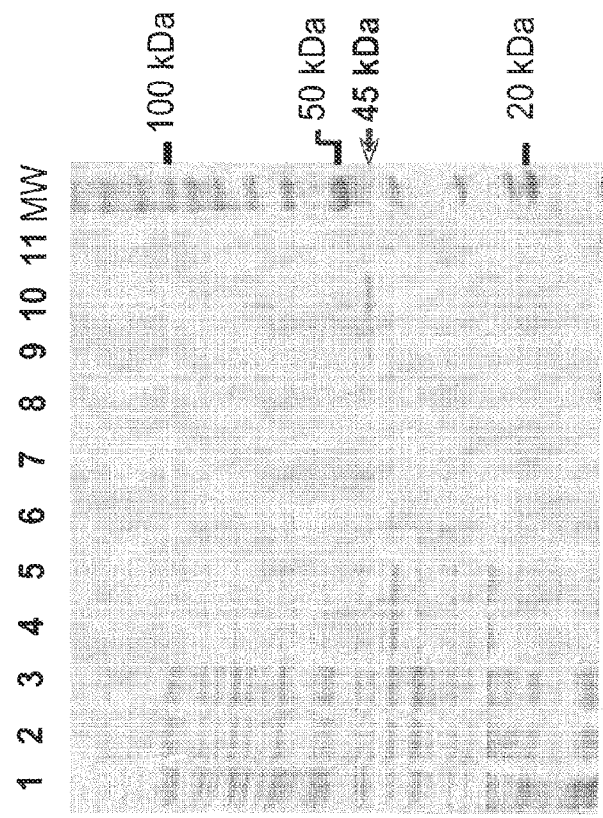

FIG. 10 illustrates the purification of the recombinant protein rTc00.1047053509999.10 ((SEQ ID NO 85). Lane 1: cleared bacterial lysate; lane 2: flow-through; lanes 3-5: washes; lanes 6-8: eluates at pH 5,9; lanes 9-11: eluates at pH 4,5. MW: Molecular marker (BenchMark Protein Ladder, Invitrogen). The proteins were resolved by electrophoresis in a 4-12% gradient gel and visualized by Coomassie staining. The purified protein appeared in the pH 4.5 eluates as a band of 45 kDa corresponding to the theoretical molecular weight of the recombinant protein.

Figure 11:
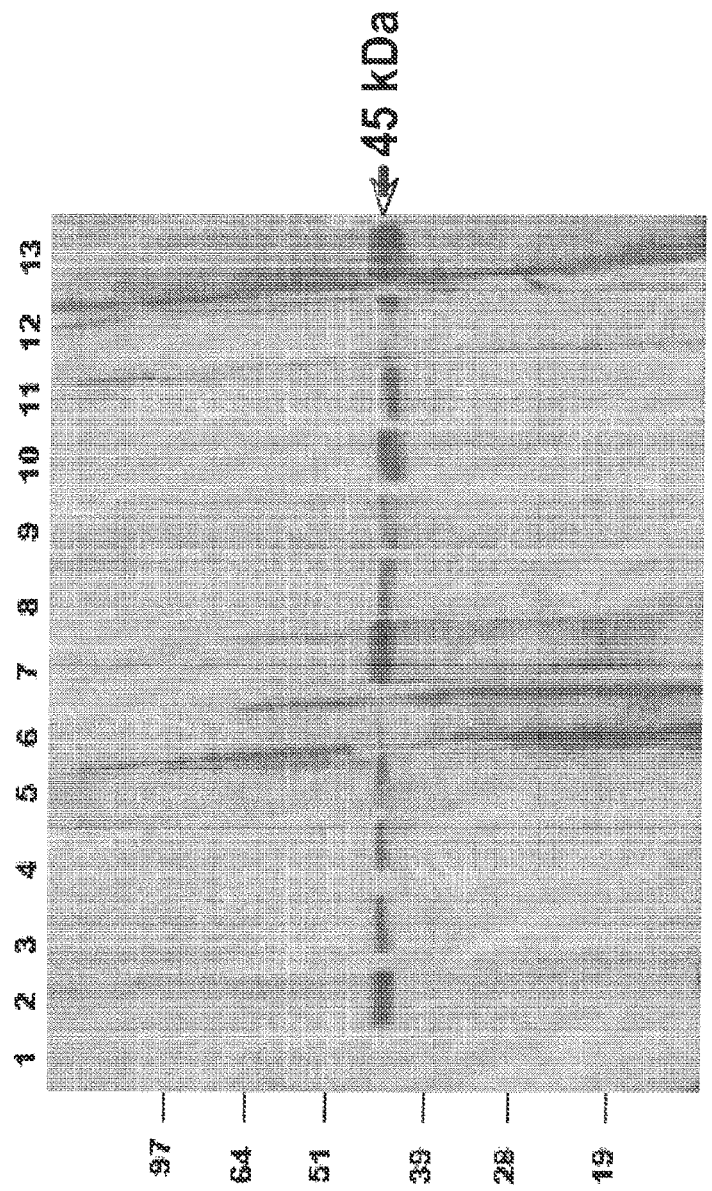

FIG. 11 represents the Western blot of the recombinant protein rTc00.1047053509999.10 (SEQ ID NO 85) with sera from non chagasic individuals (lane 1) and sera from chagasic patients (lanes 2-13)

EXAMPLE 1

Identification of Conserved Secreted Proteins in Trypanosomatids 1.1. Methods 1.1.1. In Silico Sequence Analysis Release V 5.0 of the *T. cruzi* genome was extracted from the integrated *T. cruzi* genome resource TcruziDB. Protein sequences that do not bear an initial methionine amino acid were removed manually. Proteins belonging to large families of surface molecules, which include trans-sialidases, mucins, gp63s and mucin-associated surface proteins were also discarded. Finally ORFs encoding proteins bearing a molecular weight (MW) above 90 kDa were also eliminated. The software SignalP 3.0 was used to predict the presence of a secretion signal peptide and a cleavage site in amino acid sequences. Protein sequences having a secretion signal peptide probability greater than 0.8 associated with a cleavage site probability greater than 0.7 were analyzed for the presence of orthologs in the related *Trypanosoma brucei* and *Leishmania* major parasite databases.

1.1.2 Parasite Strains and Cultures

The *T. cruzi* TcY7 (or Y c17) clone derived from the Y strain (Allaoui A, Francois C, Zemzoumi K, Guilvard E, Ouaissi A: Intracellular growth and metacyclogenesis defects in *Trypanosoma cruzi* carrying a targeted deletion of a Tc52 protein-encoding allele. *Mol Microbiol* 1999, 32 (6):1273-1286; Garzon E, Borges M C, Cordeiro-da-Silva A, Nacife V, Meirelles Mde N, Guilvard E, Bosseno M F, Guevara A G, Breniere S F, Ouaissi A: *Trypanosoma cruzi* carrying a targeted deletion of a Tc52 protein-encoding allele elicits attenuated Chagas' disease in mice. *Immunol Lett* 2003, 89 (1):67-80) was used throughout this study. Epimastigotes were grown in liver infusion tryptose (LIT) medium supplemented with 10% FCS at 28° C. in standard conditions as described by Camargo E P (Growth And Differentiation In *Trypanosoma Cruzi*. I. Origin Of Metacyclic Trypanosomes In Liquid Media. *Rev Inst Med Trop Sao Paulo* 1964, 12:93-100) and harvested during the logarithmic growth phase. Metacyclic trypomastigotes, obtained from the differentiation of late stationary phase epimastigotes, were used to initiate infection of mouse fibroblasts (L929). Trypomastigotes and amastigotes were produced and harvested as previously described by the inventors (Mathieu-Daude F, Bosseno M F, Garzon E, Lelievre J, Sereno D, Ouaissi A, Breniere S F: Sequence diversity and differential expression of Tc52 immuno-regulatory protein in *Trypanosoma cruzi*: potential implications in the biological variability of strains. *Parasitol Res* 2007, 101 (5):1355-1363). Pellets for RNA purification were processed immediately in lysis buffer. The wild-type (WT) promastigote clone from *L. infantum* (MHOM/MA/67/ITMAP-263) was maintained at 26° C. by weekly sub-passages in SDM 79 medium supplemented with 10% heat-inactivated FCS, 100 U/ml penicillin and 100 µg/ml streptomycin according to Brun R, Schonenberger (Cultivation and in vitro cloning or procyclic culture forms of *Trypanosoma brucei* in a semi-defined medium. Short communication. *Acta Trop* 1979, 36 (3):289-292).

1.1.3. Reverse Transcription and PCR Amplifications

Total RNA was extracted from epimastigotes, amastigotes and trypomastigotes with the RNeasy kit (Qiagen, Hilden, Germany) according to the manufacturers' instructions, and treated with DNase I (DNA-free kit, Ambion Inc., Austin, Tex.). Reverse transcription was performed for 1 µg of total RNA using random hexamers and Superscript II reverse transcriptase (Invitrogen, Carlsbad, Calif.) according to the manufacturers' instructions. The cDNA (4 µl of 1/10 dilutions) from each stage was amplified by PCR in a 20 µl reaction volume using 10 µl of Master Mix 1× (Promega, Madison, Wis.), 0.5 µM gene-specific forward and internal reverse primers (listed in FIG. 2) using the following cycling conditions: 94° C. for 3 min followed by 30 cycles of 94° C. for 30 s, 55° C. to 58° C. (according to the primer pair) for 30 s, 72° C. for 45 s and a final elongation at 72° C. for 5 min. Amplicons were electrophoresed on 2% agarose gels stained with ethidium bromide.

1.1.4. Cloning and Sequencing

The encoding genes selected through the in silico analysis were cloned into the pTEX expression vector, carrying the Neomycin resistance gene (NEO). Full length ORFs were amplified from genomic DNA with specific reverse and forward primers including different restriction sites and a 6-Histidine-Tag in the C-terminal region (see FIGS. 2 and 3). PCR reactions were carried out in 20 µl using 0.5 µM of each primer, 0.2 mM dNTP, 0.4 U of Phusion high-fidelity polymerase (Finnzymes, Espoo, Finland) and the following cycling conditions: 98° C. for 30 s followed by 25 cycles of 98° C. for 10 s, 64° C. to 68° C. for 15 s, 72° C. for 25 to 60 s (according to gene size), and a 72° C. elongation for 5 min. Digested and purified fragments were inserted into the dephosphorylated pTEX vector digested with the corresponding restriction enzymes. Cloned sequences were confirmed by restriction digestion and sequencing. Large scale preparations of the different constructs were performed using the plasmid midi kit (Promega).

1.1.5. Transfection Procedures

Promastigotes of the *Leishmania infantum* clone were electroporated as described elsewhere (Sereno D, Roy G, Lemesre J L, Papadopoulou B, Ouellette M: DNA transformation of *Leishmania infantum* axenic amastigotes and their use in drug screening. *Antimicrob Agents Chemother* 2001, 45 (4):1168-1173). Briefly, promastigotes were washed twice with HEPES-NaCl buffer saline (21 mM HEPES, 5 mM KCl, 0.7 mM NaH2PO4, 137 mM NaCl), resuspended at $10^8$ cells/ml in HEPES-NaCl electroporation buffer (pH 7.2) supplemented with 6 mM glucose and cooled on ice for 10 min. Cells ($10^8$) were combined with 15 µg of vector, left on ice for 10 additional min, and electroporated using an Easyject Plus (Eurogentec, Liege, Belgium) apparatus set at 450 V and 450 µF, for one pulse. The cells were left on ice for a further 10 min and transferred to 4 ml of growth medium. The antibiotic G-418 (20 µg/ml) was added 24 h later, and parasites were sub-cultured at a dilution of 1/10 in 5 ml SDM in the presence of 20 µg/ml G418. Drug-resistant cells were observed 15-20 days later. Parasites were grown in the presence of gradually increasing concentrations of G418 and were routinely maintained in SDM containing 150 µg/ml of G418.

1.1.6. PCR Amplifications in Transfected Parasites

PCR amplifications were carried out to check for the presence of the NEO gene and the corresponding gene in transfected parasites. A fragment of 800 bp corresponding to the NEO gene was amplified with specific forward and reverse primers (SEQ ID NO 170 F5'ATGATTGAACAAGATGGATTGCACGCAGG3' and SEQ ID NO 171 R5' TCAGAAGAACTCGTCAAGAA 3'). Full length ORFs of the specific genes were amplified with primers listed in FIG. 2. PCR reactions were carried out in a 20 µl reaction volume using 10 µl of Master Mix 1× (Promega, Madison, Wis.), 0.5 µM NEO and gene-specific forward and reverse primers using the following cycling conditions: 94° C. for 3 min followed by 30 cycles of 94° C. for 30 s, 55° C. to 58° C. (according to the primer pair) for 30 s, 72° C. for 45 s to 2 min (according to gene size) and a final elongation at 72° C. for 5 min.

1.1.7. Production of Cell Free Culture Supernatants

To analyze the presence of secreted proteins in the supernatant, $1\times10^9$ *L. infantum* promastigotes from log-phase culture were collected by centrifugation, washed twice in HEPES-NaCl buffer, re-suspended in 40 ml of HEPES-NaCl (pH 7.2), 11 mM glucose, 200 µg/ml G-418 and incubated for 6 h at 27° C. Parasite viability was then assessed as previously described (Vergnes B, Sereno D, Madjidian-Sereno N, Lemesre J L, Ouaissi A: Cytoplasmic SIR2 homologue overexpression promotes survival of *Leishmania* parasites by preventing programmed cell death. *Gene* 2002, 296 (1-2):139-150) and harvested by centrifugation at 2,100×g for 10 min at 4° C. The parasite pellet was stored at −80° C. for subsequent SDS-PAGE analysis and the supernatant filtered through a low retention 0.45 µm PVDF filter membrane (Millipore, Boston, Mass.). After addition of protease inhibitor cocktail (Sigma-Aldrich) the filtrate was concentrated up to 80-fold using an Amicon Ultra-Centrifugal Filter device, according to manufacturers' instructions (Amicon Bioseparations, MilliporeCorp). The concentrated cell-free culture supernatant was frozen and stored at −80° C.

1.1.8. Production of Parasite Lysates

Cell pellets of wild-type and episomally-transfected *L. infantum* promastigotes were re-suspended in RIPA buffer (25 mM Tris-HCl pH 7.6, 150 mM NaCl, 1% NP-40, 1% Sodium deoxycholate and 0.1% SDS), incubated on ice for 30 min and sonicated three times for 20 s. The soluble phase was recovered by centrifugation at 10,000 g for 30 min (4° C.) and the protein concentration was determined using a Bradford protein assay (Bio-Rad Laboratories, Hercules, Calif.).

1.1.9. Gel Electrophoresis and Western Blot Analysis

Proteins from parasite lysates (35 µg) or from 80× concentrated cell-free supernatants (2 µg) were separated on a NuPAGE Bis-Tris gel (4-12%) in MOPS-SDS running buffer (Invitrogen) under reducing conditions (50 mM DTT), and transferred to a PVDF membrane (Hybond-P, Amersham). The membrane was rinsed twice in TBS and incubated for 1 h in the anti-His HRP conjugate blocking buffer (Qiagen). The membrane was then incubated in 1/3000 anti-His HRP conjugate antibody (Qiagen) for 1 h and washed seven times for 5 min in TBS-T buffer (TBS-0.5% Tween 20). Signals were detected by chemiluminescence emission using the ECL Plus Western blotting detection system and ECL Hyperfilms (GE Healthcare, UK).

1.2. Results 1.2.1. Bioinformatic Selection for Secreted Proteins in Trypanosomatids The preliminary screening of the *T. cruzi* gene bank was performed to discard; (i) uncompleted sequences, (ii) housekeeping genes and sequences belonging to large gene families like the trans-sialidases, mucins, Mucin Associated Surface Proteins (MASPs), (iii) sequences encoding proteins with a molecular weight above 90 kDa, in order to facilitate subsequent gene cloning. The remaining coding sequences were screened for the presence of both the signal peptide and a secretion signal peptide peptidase (SPP) cleavage site. Only 216 sequences bore a 0.8 and 0.7 probability of carrying both the secretion signal peptide and the peptidase cleavage site, respectively. Among them, 91 (42%) were annotated as "hypothetical proteins, conserved" in the data bank. The final criterion for selected proteins likely to be secreted by the classical eukaryotic pathway was the presence of the signal peptide and the signal peptidase site in orthologous members of the related parasites; *Leishmania major, L. infantum* and *T. brucei*. Among the 91 sequences, only 45 showed orthologous members with the signal peptide criteria. The 13 proteins bearing the highest probability for the presence of the signal peptide were selected (FIG. 1) for functional confirmation of bona fide secretion. The beta-tubulin *T. cruzi* gene (GeneID Tc00.1047053506563—SEQ ID NO 83) was added to the sample as a potential negative control for protein secretion.

1.2.2. Expression Analysis of Potentially Secreted Proteins During the Life Cycle of *T. cruzi*

The expression of the 13 different encoding genes was analysed throughout the developmental life cycle of *T. cruzi*. The beta-tubulin *T. cruzi* gene (GeneID Tc00.1047053506563—SEQ ID NO 83), constitutively expressed in all the three stages of *T. cruzi* was used as a positive control. The expression of each gene was supported by positive RT-PCR amplification in the infective trypomastigote and amastigote forms. Nevertheless two genes (Gene ID Tc00.1047053511901.30 (SEQ ID NO 17) and Tc00.1047053509999.10 (SEQ ID NO 85)) were negative for the amplification of cDNA in the non-infective epimastigote form, suggesting a possible stage-specific expression of these genes (FIG. 4).

1.2.3. Experimental Approach for the Detection of Secreted Proteins

A functional test to confirm the presence of selected proteins in the extracellular environment by detection of target proteins in cell-free supernatants was set-up. Thus the 13 selected encoding genes of *T. cruzi* and the gene encoding the beta-tubulin negative control were amplified from genomic DNA. A sequence encoding a 6×His-Tag was added at the C-terminal end of each of the encoded genes. This would allow to detect the protein in total parasite protein extracts or in cell-free supernatants. Amplified PCR products were cloned into the pTEX shuttle vector that is widely used for expression in trypanosomatids (Kelly J M, Ward H M, Miles M A, Kendall G: A shuttle vector which facilitates the expression of transfected genes in *Trypanosoma cruzi* and *Leishmania. Nucleic Acids Res* 1992, 20 (15):3963-3969). Transformation and selection of *T. cruzi* is not as easy to perform as for *Leishmania*, mainly due to longer periods required for selecting drug-resistant parasites. Since the inventors were aimed to develop a fast and reliable approach to identify trypanosomatid conserved secreted proteins, they used *Leishmania* as the recipient organism for the experimental validation of their selected proteins. Thus, *Leishmania* infantum promastigotes were transformed with pTEX carrying the 14 selected *T. cruzi* genes (including the beta-tubulin gene), and recombinant parasites were selected for resistance to Geneticin G418. Each parasite population was checked for the presence of both the $NEO^R$ gene and the selected gene whose secretion was to be analyzed. A specific 800 bp fragment, indicative of the presence of the $NEO^R$ gene, was detected in the transfected promastigotes and not in wild-type parasites (FIG. 5A). Moreover, the presence of each candidate gene in recombinant parasites was confirmed using specific primers (FIG. 5B). PCR were negative in Wild type parasites, demonstrating that the amplification for each gene is specific although they are conserved in trypanosomatids (data not shown). The expression of these genes was screened using an antibody directed against the His-Tag carried by the recombinant proteins (FIG. 6A). Western blot analysis demonstrated that; (i) the inventors were able to easily and specifically detect the 6×His tag protein in the extract derived from recombinant parasites, (ii) recombinant *Leishmania* expressed a relatively high level of *T. cruzi* protein, and (iii) the molecular weight of the detected tagged protein corresponded to the expected MW (see FIG. 2). The inventors thus set up an approach to detect recombinant proteins in cell-free supernatants. In order to limit potential contamination by proteins derived from dying organisms, they restricted incubation in serum-free mediums to 6 hours, and they checked the viability of parasite populations before and after this incubation period. Parasites and cell-free supernatants were collected if the viability of the cell population was above 98%. Western Blot analyses of the concentrated cell-free supernatants revealed that among the 14 proteins only 3 were actively secreted (Tc00.1047053506155.99 (SEQ ID NO 103), Tc00.1047053505789.10 (SEQ ID NO 93) and Tc00.1047053509999.10 (SEQ ID NO 85)) (FIG. 6B). These proteins represent genuine secreted material, since; (i) the over-expression of the beta-tubulin gene does not induce translocation of the beta-tubulin protein into the extracellular space (difference between Lys and CCFS in FIG. 6B), and (ii) the detection of the tagged protein in the cell-free supernatant is not related to the level of its expression by *Leishmania* (low abundance of Tc00.1047053506155.99 (SEQ ID NO 103) in FIG. 6B). As expected, for the three proteins it was observed a slight molecular weight difference between the tagged protein detected into the whole soluble extract and that detected in the cell-free supernatant. This observation could be explained by a loss of the Signal Peptide (FIG. 6B). As anticipated, no band was detected in wild-type parasites (FIG. 6B). Furthermore, to verify that secretion is not related to the heterologous expression system, two *Leishmania* genes (GenID LinJ19.0410 (SEQ ID NO 77) and LinJ36.5780 (SEQ ID NO 107)) corresponding to the orthologous of Tc00.1047053506155.99 gene (SEQ ID N0103) and Tc00.1047053505789.10 gene (SEQ ID NO 93), were selected to validate said approach. By using the same protocol as above, parasites expressing the 6×His tagged proteins were produced (See FIG. 3). As expected, the presence of the tagged protein in the extracellular medium was detected only in the episomally transfected parasites (FIG. 7).

Together, these results demonstrate that the approach used by the inventors allowed them to identify new and genuinely secreted proteins which are conserved between different species and are involved in the endoplasmic reticulum/Golgi-dependent secretory pathway.

EXAMPLE 2

Generation of Bioluminescent *L. infantum* Promastigotes and In Vitro Infection of Human, Canine and Murine Macrophages 2.1. Material and Methods A homologous episomal expression system was devised to further examine the infection in vitro of two secreted proteins from *L. infantum*. The vector pSP-αHYGαLUC disclosed by El Fadili et al. (Mol Biochem Parasitol, 2002, 124:63-71) carrying the firefly-luciferase gene was used to co-transfect *L. infantum* promastigotes over-expressing the secreted proteins LinJ19.0410 (SEQ ID NO 97) ortholog of Tc00.1047053505789.10 (SEQ ID NO 93 or LinJ36.5780 (ortholog of. Tc00.1047053506155.99=SEQ ID NO 103). Recombinant parasites were selected for their growth in increasing concentrations of Hygromycin (up to 300 μg/ml) over a period of several weeks. Promastigotes transfected with the pTEX vector alone and the pSP-αHYGαLUC were used as controls for infection experiments. The survival of transfected parasites was evaluated within human leukemia monocyte cell line (THP-1 cells). THP-1 cells were cultured in RPMI 1640 medium supplemented with 10% FCS, 2 mM glutamine, 100 IU of penicillin/ml, and 100 μg of streptomycin/ml. THP-1 cells in the log phase of growth were differentiated into macrophages by incubation for 2 days in a medium containing 20 ng/ml of phorbol myristate acetate (Sigma-Aldrich). THP-1 cells treated with PMA were washed with prewarmed medium and then infected with stationary-phase promastigotes of transfected-*Leishmania* in a 24-well plate at a parasite/macrophage ratio of 10:1 for 4 h at 37° C. with 5% CO2. Non internalized parasites were removed. After different incubation periods (24 h to 96 h) Luciferase activity was determined using the Steady Glo reagent (Promega, Madison, Wis.), according to the manufacturers' instructions. After 5 min, the plate was read using a Multilabel Counter VICTOR2258 model 1420 (Perkin Elmer). Results are expressed as the mean of RLU (Relative Luminescence Units) activity of three independent experiments, each performed in triplicate. Statistical significance was analyzed by the Mann-Whitney U-test.

To further evaluate these secreted proteins (LinJ19.0410 and LinJ36.5780), the infectivity of the transgenic parasites in different cell cultures was assessed. By using the same infection protocol with slight modifications, the survival of transfected parasites within murine macrophage cell line J774 and the canine monocyte-macrophage cell line DH82 were evaluated.

Briefly, both lines were cultured in RPMI 1640 complete medium (RPMI 1640 supplemented with 10% heat-inactivated FCS, 2 mM L-glutamine, 2 mM sodium pyruvate, 100 units/ml gentamycin). Cell suspensions in the log phase of growth (107 cells/ml RPMI 1640) were treated with 25 ug/ml mitomycin for 20 min at 37° C., washed with PBS, and distributed into 24-well microplates at 2×105 cells/well in 500 μl of culture medium. The cells were infected with stationary-phase promastigotes (10 promastigotes/cell) and infection was determined by measuring luciferase activity as described before.

2.2. Results

Results are given in FIGS. 8 and 9.

We attempted to determine whether the expression of *Leishmania* secreted proteins could interfere with the capacity of recombinant parasites to replicate within human macrophages in vitro. Both confirmed secreted proteins (LinJ19.0410 and LinJ36.5780) from *L. infantum* were tested by using the luciferase reporter system in transfected parasites over-expressing these proteins. We used bioluminescence as a quantitative indicator of the viability and multiplication of parasites. The number of promastigotes cells and luciferase activity were linearly correlated for the different recombinant parasites before macrophage infection (data not shown). Results of in vitro infection showed that over-expression of secreted protein LinJ19.0410 (ortholog of Tc00.1047053505789.10) increases the capacity of *Leishmania* to survive in THP-1 differentiated macrophages as early as 24 h post-infection (FIG. 8). Furthermore, a statistically significant increase in luciferase activity of recombinant parasites expressing LinJ19.0410 was maintained throughout the experiments ($P<0.05$). This effect was not observed in parasites over-expressing LinJ36.5780 (ortholog of Tc00.1047053506155.99) where infectivity levels were similar to the control parasites transfected with the pTEX vector alone and the pSP-αHYGαLUC (FIG. 8). Results of these assays showed a significant survival advantage to *Leishmania* parasites over-expressing the gene LinJ19.0410 (Ortholog gene of Tc00.1047053505789.10) suggesting that this protein is involved in a process increasing survival and replication of the parasite inside its target cell.

As shown in FIG. 9, parasites expressing the protein LinJ19.0410 displayed higher luciferase activity in canine macrophages at 48 h post-infection, indicating enhanced virulence of transgenic parasites expressing this protein. Nevertheless, this effect was not observed in infected murine macrophages where luciferase activity was similar to control parasites and the transgenic parasites expressing LinJ36.5780. Taken together, these results suggest that the secreted protein LinJ19.0410 from *L. infantum* increases its infectivity in cell lines derived from both human and dogs, the main natural mammalian hosts of *Leishmania* parasites.

EXAMPLE 3

Immunogenic Properties of Conserved Secreted Proteins from *Trypanosoma cruzi* Identified by a Genomic Based Approach 3.1. Material and Methods 3.1.1. Bacterial Strains and Plasmids

*Escherichia coli* TOP10 (Invitrogen) was used for primary cloning, and *E. coli* BL21 (DE3) for protein expression. Encoding sequence for the secreted protein Tc00.1047053509999.10 was cloned under the control of the T7lac promoter. The plasmid vector used was pET-21b (Novagen, Madison, Wis.) conferring resistance to ampicillin and allowing expression of the target protein fused to a C-terminal tail of six Histidine residues.

3.1.2. Cloning of *T. cruzi* Genes into the Expression Vector

*T. cruzi* gene encoding the secreted protein was amplified from genomic DNA (TcY7clone derived from the Y strain) by PCR using specific forward and reverse primers (table 1).

Tc00.1047053509999.10 gene (SEQ ID NO 85) was cloned without the amino-acid sequence corresponding to the predicted N-terminal signal peptide. PCR reactions were carried out in 20 μl using 0.5 μM of each primer, 0.2 mM dNTP, 0.4 U of Phusion high-fidelity polymerase (Finnzymes, Espoo, Finland) and the following cycling conditions: 98° C. for 30 s followed by 25 cycles of 98° C. for 10 s, 65° C. for 15 s, 72° C. for 45 s, and a 72° C. elongation for 5 min. Digested and purified fragments were inserted into the dephosphorylated pET-21b vector digested with the corresponding restriction enzymes. Cloned sequences were confirmed by restriction digestion and sequencing. Large scale preparations of the constructs were performed using the plasmid midi kit (Promega).

TABLE 1

Primers used for cloning into the pET21b expression vector

| Gene ID | Primer sequences[a] | Amplification product size (bp) | MW (kDa)[b] |
|---|---|---|---|
| Tc00.1047053509999.10 | F CATCGCAGC*ATATG*GCAGAAGAGGAGGACGTGAGG<br>R GCACTGAC*TCTCGAG*GCCGCACCAGCGCTCCAGAA | 1182 | 45.8 |

F, Forward primer and R, Reverse primer used for the amplification of the encoding sequence without the predicted secretion signal peptide.
[a]Restriction sites used for cloning in the pET21b vector are indicated in italics.
[b]Expected molecular weight of the protein.

3.1.3. Expression and Purification of *T. cruzi* Recombinant Proteins

The plasmid carrying the target protein was used to transform *E. coli* BL21(DE3) strain. Colonies were grown overnight at 37° C. with shaking in auto-inducing media ZYP-5052 (Studier F W, 2005) containing 100 μg/ml of ampicillin. Cleared *E. coli* lysates were obtained from cell pellets (50-ml cultures) re-suspended in 5 ml of buffer containing 100 mM $NaH_2PO_4$, 10 mM Tris-Cl and 8 M urea (pH 8.0). The clarified supernatant was applied to a Ni-NTA agarose column (Qiagen) and the recombinant protein was eluted in 8M Urea buffer at pH 4.5. To assess the purity of the proteins, eluted fractions were analyzed in SDS-PAGE gel by stained with Coomassie blue and/or by immunoblotting with an Anti-His (C-Term)-HRP antibody as detailed below.

3.1.4. SDS-PAGE

SDS-PAGE analysis was performed on a NuPAGE Bis-Tris gel (4-12%) in MOPS-SDS running buffer (Invitrogen) under reducing conditions (50 mM DTT). The gels were either stained with Coomassie blue or electroblotted onto PVDF membranes (Hybond-P, Amersham) for western blot analyses.

3.1.5. Western Blot Analysis

The PVDF membranes were rinsed twice in TBS and used for immuno-detection of the recombinant proteins with an Anti-His (C-Term)-HRP antibody (Invitrogen) according to the manufacturer's instructions. Membranes used for detection of anti-*T. cruzi* antibodies in patients' sera were rinsed twice in TBS and blocked overnight in TBS-Tween 0.1% (TBS-T) and 5% non-fat milk. Strips of paper (5 mm) were then cut and incubated separately in a 1:2,500 dilution of human serum for 2 h at room temperature. Strips were then washed five times (5 min) in TBS-T and incubated for 1 h at room temperature with HRP-conjugated anti-human IgG (heavy and light chain specific) (Nordic Immunology) diluted 20,000 times in TBS-T and 5% non-fat milk. The strips were washed as before, and the immune complexes were revealed by chemiluminescence emission using the ECL Plus Western blotting detection system and ECL Hyperfilms (GE Healthcare, UK).

3.1.6. Patients' Sera

Positive sera were obtained from infected chagasic individuals from an endemic region located in northeast Argentina (Chaco Province), a free-vector city located in northwestern Argentina (Salta-city) and from Bolivian children treated with Benznidazole (5 mg/kg/day) in the community of Tupiza (Potosi department), an area under controlled vector transmission. Negative sera were obtained from healthy blood donors of the same region respectively. The *T. cruzi* infection status was determined by using two conventional tests: commercial ELISA and IHA based on parasite homogenate antigens. Positive sera for both reactions were considered as true positives. Negative sera for both reactions were considered as true negatives.

3.2. Results

They are given in FIGS. 10 and 11.

3.2.1. Expression and Purification of Recombinant Protein rTc00.1047053509999.10 (SEQ ID NO 85)

In order to determine the antigenic properties of this *T. cruzi* secreted protein, the recombinant protein in *E. coli* was produced to subsequently analyse its reactivity with chagasic patient sera. Protein expression was assessed in transformed bacteria carrying the recombinant plasmid. The recombinant protein was expressed and purified under denaturing conditions in the *E. coli* BL21 (DE3) (FIG. 10).

3.2.2. Reactivity of Sera from Chagasic Patients with rTc00.1047053509999.10 (SEQ ID NO 85)

The ability of the recombinant protein rTc00.1047053509999.10 to detect chagasic infections was evaluated by Western Blot. As shown in FIG. 11 the recombinant protein rTc00.1047053509999.10 was recognized by sera from chagasic patients as a single band. Sera from healthy donors did not recognize the recombinant protein. Anti-Tc00.1047053509999.10 antibodies were detected in 80% (18/22) of sera from chagasic patients. The analysed sera belong to patients originating from different regions of Latin America. Six sera are from patients living in North-western Argentina (Salta-city) and presenting heart failure as detected by electrocardiogram and echocardiogram. Five out of these sera were positive by Western blot analyses. Among six sera of children from Northeast Argentina (Chaco-province), only 5 recognized the recombinant protein. The remaining sera correspond to five Bolivian children and five Mexican patients that recognized the *T. cruzi* protein in four out the five sera tested.

Furthermore, potential cross-reactivity with antibodies from five patients infected with *L. infantum* was evaluated. The recombinant protein was not recognized by these sera suggesting that the antibodies detected by chagasic patients are specific for *T. cruzi* infection.

In view of the antigenic properties of *T. cruzi* Tc00.1047053509999.10 (SEQ ID NO 85) said recombinant protein may represent an interesting antigen to specifically identify anti-*T. cruzi* antibodies in sera and may represent a new potential diagnostic tool for Chagas disease.

The invention claimed is:

1. A method of diagnosing Chagas disease caused by *Trypanosoma cruzi* in an in vitro assay comprising the steps of:

a. contacting a biological sample with a polypeptide comprising an amino acid sequence SEQ ID NO: 86 for a time and under conditions sufficient to form an immune complex; and b. detecting the presence or absence of the immune complex formed in a), where in the presence of an immune complex is indicative of Chagas disease.

* * * * *